(12) United States Patent
Moreau

(10) Patent No.: US 10,073,101 B2
(45) Date of Patent: Sep. 11, 2018

(54) METHODS FOR THE PREVENTION OR TREATMENT OF SCOLIOSIS

(71) Applicant: CHU Sainte-Justine, Montreal (CA)

(72) Inventor: Alain Moreau, Montreal (CA)

(73) Assignee: CHU SAINTE-JUSTINE, Montreal (CA)

( * ) Notice: Subject to any disclaimer, the term of this patent is extended or adjusted under 35 U.S.C. 154(b) by 78 days.

(21) Appl. No.: 14/807,450

(22) Filed: Jul. 23, 2015

(65) Prior Publication Data

US 2015/0323553 A1 Nov. 12, 2015

Related U.S. Application Data

(63) Continuation of application No. 13/775,069, filed on Feb. 22, 2013, now abandoned, which is a continuation of application No. 12/594,181, filed as application No. PCT/CA2008/000595 on Mar. 31, 2008, now abandoned.

(60) Provisional application No. 60/909,408, filed on Mar. 30, 2007, provisional application No. 61/025,571, filed on Feb. 1, 2008.

(51) Int. Cl.

| G01N 33/50 | (2006.01) |
| G01N 33/533 | (2006.01) |
| G01N 33/536 | (2006.01) |
| G01N 33/541 | (2006.01) |
| G01N 33/68 | (2006.01) |
| A61K 33/04 | (2006.01) |
| A61F 5/01 | (2006.01) |
| A23L 33/00 | (2016.01) |

(52) U.S. Cl.
CPC .......... G01N 33/6893 (2013.01); A23L 33/30 (2016.08); A61F 5/0102 (2013.01); A61K 33/04 (2013.01); G01N 33/6872 (2013.01); A23V 2002/00 (2013.01); G01N 2800/108 (2013.01); G01N 2800/50 (2013.01)

(58) Field of Classification Search
None
See application file for complete search history.

(56) References Cited

U.S. PATENT DOCUMENTS

| 5,434,183 | A | 1/1995 | Larsson-Backstrom |
| 6,010,865 | A | 1/2000 | Ponta et al. |
| 6,025,155 | A | 2/2000 | Hadlaczky et al. |
| 6,077,677 | A | 6/2000 | Hodgson et al. |
| 6,150,162 | A | 11/2000 | Bennett et al. |
| 6,204,023 | B1 | 3/2001 | Robinson et al. |
| 2001/0036921 | A1 | 11/2001 | Ashkar et al. |
| 2002/0160970 | A1 | 10/2002 | Hadlaczky et al. |
| 2003/0083293 | A1 | 5/2003 | Hadlaczky et al. |
| 2005/0130250 | A1 | 6/2005 | Moreau |
| 2005/0282163 | A1 | 12/2005 | Epstein |
| 2006/0002923 | A1 | 1/2006 | Toshimitsu et al. |
| 2006/0003327 | A1 | 1/2006 | Achiron et al. |
| 2013/0310261 | A1* | 11/2013 | Schramm ............. C12Q 1/6883 506/2 |

FOREIGN PATENT DOCUMENTS

| WO | WO 96/06622 | 3/1996 |
| WO | WO 98/08379 | 3/1998 |
| WO | WO 00/42216 | 7/2000 |
| WO | WO 01/71358 | 9/2001 |
| WO | WO 2004/024750 | 3/2004 |

OTHER PUBLICATIONS

Zhu et al. Effect of ulinastatin on expression of inflammatory cytokines during period of surgical correction of adolescent idiopathic scoliosis, Abstract, Dier Junyi Daxue Xuebao vol. 27(2):203-206 (2006).*
Sun et al. Association between circulating leptin level and anthropometric parameters in girls with adolescent idiopathic scoliosis. Abstract Zhonghua yi xue za zhi vol. 87(9):594-8 (Mar. 6, 2007).*
Giuliani et al. Osteopontin is produced by human multiple myeloma cells. Abstract. Blood, vol. 100, No. 11, Abstract No. 5077 (Nov. 16, 2002).*
Aherrahrou et al., "A locus on chromosome 7 determines dramatic up-regulation of osteopontin in dystrophic cardiac calcification in mice," *American J. of Pathology*, 164(4): 1379-1387, 2004.
Ando et al., "Determination of selenium in human serum by liquid chromatography/electron capture atmospheric pressure chemical ionization mass spectrometry after acid digestion and derivatization using 2,3-diaminonaphthalene," *Eur J Mass Spectrom*, 9(6): 619-622, 2003.
Ang et al., "Plasma osteopontin levels are predictive of disease stage in patients with transitional cell carcinoma of the bladder," *BJU International*, 96, 803-805, 2005.
Baba et al., "Remodeling of the Vertebral Body in Hereditary Lordoscoliotic Rabbits Revealed by In Situ Hybridization," *Bulletin of the Osaka Medical College*, 52(1): 37-44 (2006).
Bagnall et al, "Melatonin Levels in Idiopathic Scoliosis," *Spine*, 21(17): 1974-1978, 1996.

(Continued)

*Primary Examiner* — Elizabeth Kemmerer
*Assistant Examiner* — Regina M DeBerry
(74) *Attorney, Agent, or Firm* — Klarquist Sparkman, LLP

(57) ABSTRACT

A method for the prevention or treatment of scoliosis in a human subject comprising: (a)(i) measuring osteopontin (OPN) protein expression in a biological fluid sample from the subject over time; or (ii) measuring osteopontin (OPN) protein expression in a biological fluid sample from the subject and comparing the OPN protein expression to an OPN protein expression in a control biological fluid sample; (b) identifying the subject as being at risk of developing scoliosis when OPN protein expression increases in the subject sample over time; or when OPN protein expression is higher in the subject sample than that in the control sample; and (c) reducing OPN protein levels in the subject identified as being at risk of developing a scoliosis, thereby aiding in the prevention or treatment of scoliosis.

13 Claims, 54 Drawing Sheets
Specification includes a Sequence Listing.

(56) References Cited

OTHER PUBLICATIONS

Bennett et al., "Regulation of CD44 binding to hyaluronan by glycosylation of variably spliced exons," *J Cell Biology*, 131(6 Pt 1): 1623-1633, 1995.
Bertram et al., "Accelerated intervertebral disc degeneration in scoliosis versus physiological ageing develops against a background of enhanced anabolic gene expression," *Biochem. Biophys. Res. Comm.*, 342:963-972, 2006.
Boldrini et al., "Prognostic significance of osteopontin expression in early-stage non-small-cell lung cancer," *British Journal of Cancer*, 93, 453-457, 2005.
Brodner et al., "Melatonin and adolescent idiopathic scoliosis," *J Bone Joint Surg (Br)*, 82B(3): 399-403, 2000.
Buck et al., "Design Strategies and Performance of Custom DNA Sequencing primers," *BioTechniques*, 27(3): 528-536, 1999.
Chiocchetti et al., "High levels of osteopontin associated with polymorphisms in its gene are a risk factor for development of autoimmunity/lymphoproliferation," *Blood*, 103(4): 1376-1382, 2004.
Chiocchetti et al., "Osteopontin gene haplotypes correlate with multiple sclerosis development and progression," *J. Immunology*, 163: 172-178, 2005.
Coppola et al., "Correlation of Osteopontin Protein Expression and Pathological Stage across a Wide Variety of Tumor Histologies," *Clinical Cancer Research*, 10: 184-190, 2004.
Dastych et al., "Idiopathic scoliosis and concentrations of zinc, copper, and selenium in blood plasma," *Biological Trace Element Research*, 89: 105-110, 2002.
De George et al., "Idiopathic scoliosis: genetic and environmental aspects," *J Medical Genetics.*, 4, 251-257, 1967.
Denhardt et al., "Osteopontin as a means to cope with environmental insults: regulation of inflammation, tissue remodeling, and cell survival. *J Clinical Investigation*," 107(9): 1055-1061, 2001.
Drouin et al., "La famille Ptx des facteurs de transcription à homéodomaine," *Medicine/Science*, 14: 335-339, 1998.
Drouin et al., "The PTX family of homeodomain transcription factors during pituitary developments," *Molecular and Cellular Endocrinology*, 140: 31-36, 1998.
Eisterer et al., "Elevated levels of soluble CD44 are associated with advanced disease and in vitro proliferation of neoplastic lymphocytes in B-cell chronic lymphocytic leukaemia," *Leuk Res.* 28(10): 1043-51, 2004 (Abstract).
El-Bayoumy et al., "Molecular chemoprevention by selenium: a genomic approach. *Mutation Research*," 591: 224-236, 2005.
Extended Search Report, EP Patent Application 08733693.9, 9 pages, dated May 10, 2010.
Forootan et al., "Prognostic significance of osteopontin expression in human prostate cancer," *Int. J. Cancer*, 118: 2255-2261, 2006.
Franzmann et al., "Salivary soluble CD44: a potential molecular marker for head and neck cancer," *Cancer Epidemiol Biomarkers Prev.* 14(3): 735-9, 2005 (Abstract).
Garrett et al., "An introduction to the R Programming Environment," *The Plant Health Instructor*. DOI:10.1094/PHI-A-2007-1226-02.
Giacopelli et al., "Polymorphisms in the osteopontin promoter affect its transcriptional activity," *Physiol. Genomics*, 20: 87-96, 2004.
Goodison et al., "Clinical Implications of Anomalous Cd44 Gene Expression in Neoplasia," *Frontiers in Bioscience*, 3, e89-109: 1998.
Guarino et al., "Osteopontin Is Overexpressed in Human Papillary Thyroid Carcinomas and Enhances Thyroid Carcinoma Cell Invasiveness," *The Journal of Clinical Endocrinology & Metabolism*, 90(9): 5270-78, 2005.
Guo et al., Balance control in adolescents with idiopathic scoliosis and disturbed somatosensory function. *Spine*, 31(14): E437-E440, 2006.
He et al., "Therapeutic effects and molecular mechanisms of anti-fibrosis herbs and selenium on rats with hepatic fibrosis," *World J Gastroenterology*, 10(5): 703-706, 2004.
Ichiro et al., Remodeling of the vertebral body in hereditary lordoscoliotic rabbits revealed by in situ hybridization, *Bulletin of the Osaka Medical College*, 52, 37-44, 2006.
Ihaka et al., "R: A language for data analysis and graphics," *Journal of Computational and Graphical Statistics*, 5(3): 299-314, 1996.
International Search Report, PCT Application No. EP2006/064794, 2 pages, dated Jan. 31, 2008.
International Search Report, PCT Application No. PCT/CA2008/000595, 6 pages, dated Jul. 18, 2008.
Ito et al., "An Inducible Short-Hairpin RNA Vector against Osteopontin Reduces Metastatic Potential of Human Esophageal Squamous Cell Carcinoma in vitro and in vivo," *Clin. Cancer Res.*, 12(4): 1308-1316, 2006.
Iwasaki et al., "Thirteen single-nucleotide polymorphisms in the human osteopontin gene identified by sequencing of the entire gene in Japanese individuals," *J. Hum. Genet.*, 46: 544-546, 2001.
Jalkanen et al., "Lymphocyte CD44 binds the COOH-terminal heparin-binding domain of fibronectin," *J Cell Biology*, 116(3): 817-825, 1992.
Jenkins et al., Myofibroblastic differentiation leads to hyaluronan accumulation through reduced hyaluronan turnover, *J Biological Chemistry*, 279(40): 41453-460, 2004.
Kadkol et al, "Osteopontin Expression and Serum Levels in Metastatic Uveal Melanoma— A Pilot Study," *Investigative Ophthalmology & Visual Science*, 47(3): 802-806, 2006.
Karjalainen et al., "Reduced level of CD44 and hyaluronan associated with unfavorable prognosis in clinical stage I cutaneous melanoma," *American J. Pathology*, 157(3): 957-965, 2000.
Katagiri et al., "CD44 variants but not CD44s cooperate with beta1-containing integrins to permit cells to bind to osteopontin independently of arginine-glycine-aspartic acid, thereby stimulating cell motility and chemotaxis," *Cancer Research*, 59, 219-226, 1999.
Kim J. et al., "Elevated plasma osteopontin levels in patients with hepatocellular carcinoma," *American J Gastroenterology*, 101: 2051-2059, 2006.
Komura et al., "Elevated levels of circulating CD44 in patients with systemic sclerosis: association with a milder subset," *Rheumatology*, 41, 1149-1154, 2002.
Lackner et al., "Soluble CD44 v5 and v6 in serum of patients with breast cancer," *Breast Cancer Res Treat.*, 47(1): 29-40, 1998 (Abstract).
Lanctôt et al., "The bicoid-related homeoprotein Ptx1 defines the most anterior domain of the embryo and differentiates posterior from anterior lateral mesoderm," *Development*, 124: 2807-2817, 1997.
Lein et al., "Soluble CD44 variants in the serum of patients with urological malignancies," *Oncology*, 54(3): 226-230, 1997.
Lien et al., "Collagen, proteoglycan and hyaluronidase activity in cultures from normal and scoliotic chicken fibroblasts," *Biochim Biophys Acta*, 1034(3): 318-325, 1990.
Lopez et al., "Osteopontin expression detected in adult cochleae and inner ear fluids," *Hearing Research*, 85, 210-222, 1995.
Lorenzen et al., "The Role of Osteopontin in the Development of Albuminuria," *J Am Soc Nephrol* 19:884-890, 2008.
Lowe et al., "Etiology of idiopathic scoliosis: current trends in research," *J Bone Joint Surgery*, 82, 1157-1168, 2000.
Machida et al., Experimental scoliosis in melatonin-deficient C57BL/6J mice without pinealectomy, *J Pineal Research*, 41: 1-7, 2006.
Mazzali et al., "Osteopontin—a molecule for all seasons," *Q J Med.*, 95: 3-13, 2002.
Miller et al., "Cause and natural history of adolescent idiopathic scoliosis," *Orthopaedic Clin North Am.*, 30 (3): 343-52, vii, 1999.
Miller et al., "Characterization of Idiopathic Scoliosis in a Clinically Well-Defined Population," *Clinical Orthopaedics and Related Research*, 392: 349-357, 2001.
Miller, "Genetics of Familial Idiopathic Scoliosis," *Clinical Orthopaedics and Related Research*, 401: 60-64, 2002.
Mishima et al., "High plasma osteopontin levels in patients with inflammatory bowel disease," *J Clin Gastroenterol.*, 41(2):167-172, 2007.
Mor et al., "Serum protein markers for early detection of ovarian cancer," *PNAS*, 102(21): 7677-7682, 2005.
Moreau et al., "Melatonin Signaling Dysfunction in Adolescent Idiopathic Scoliosis," *Spine*, 29(16), 1772-81, 2004.

(56) References Cited

OTHER PUBLICATIONS

Naor et al., "CD44 in cancer," *Crit Rev Clin Lab Sci.*, 39(6): 527-79, 2002 (Abstract).
Naujokas et al., "The chondroitin sulfate form of invariant chain can enhance stimulation of T cell responses through interaction with CD44," *Cell*, 74: 257-268, 1993.
Notice of Reasons for Rejection [English Translation], Japanese Patent Application No. 2010-500039, 7 pages (dated Oct. 23, 2012).
Ogilvie et al., "The Search for Idiopathic Scoliosis Genes," *Spine*, 31(6): 679-681, 2006.
Panda et al., "Potential roles of osteopontin and alphaVbeta3 integrin in the development of coronary artery restenosis after angioplasty," *Proc Natl Acad Sci.*, 94: 9308-9313, 1997.
Ponta et al., "CD44: from Adhesion molecules to signalling regulators," *Nature Reviews Molecular Cell Biology*, 4: 33-45, 2003.
Rouschop et al., "Pre-transplant plasma and cellular levels of CD44 correlate with acute renal allograft rejection," *Nephrol Dial Transplant.*, 20(10): 2248-2254, 2005 (Abstract).
Rouschop et al., "Renal Expression of CD44 Correlates with Acute Renal Allograft Rejection," *Kidney Int.*, vol. 70:1127-1134, 2006.
Ruiz et al., "CD44 isoforms during differentiation and development," *BioEssays*, 17(1): 17-24, 1995.
Saito et al., "Serum concentration of CD44 variant 6 and its relation to prognosis in patients with gastric cancer," *Cancer.* 83(6): 1094-101, 1998 (Abstract).
Schlosser et al., "Low serum levels of CD44, CD44v6, and neopterin indicate immune dysfunction in chronic pancreatitis," *Pancreas*, 23(4), 335-340, 2001.
Schwarzler et al., Variant isoforms of CD44 are required in early thymocyte development. Eur. *J. Immunol.*, 31: 2997-3005, 2001.
Scott et al., "Plasma concentrations of reputed tumor-associated soluble CD44 isoforms (v5 and v6) in smokers are dose related and decline on smoking cessation," *Cancer Epidemiology Biomarkers Prevention*, 9: 1211-1214, 2000.
Sheehan et al., "Simplified fluorometric assay of total selenium in plasma and urine," *Clinical Chemistry*, 36(12): 2124-2126, 1990.
Shimada et al., "Clinical Significance of Osteopontin in Esophageal Squamous Cell Carcinoma: Comparison with Common Tumor Markers," *Oncology*, 68, 285-292, 2005.
Simoneau et al., "Sensory deprivation and balance control in idiopathic scoliosis adolescent," *Exp Brain Res.*, 170: 576-582, 2006.
Sjoberg et al., "Circulating soluble CD44 is higher among women than men and is not associated with cardiovascular risk factors or subclinical atherosclerosis," *Metabolism Clinical and Experimental*, 54: 139-141, 2005.
Stamenkovic et al., "The hematopoietic and epithelial forms of CD44 are distinct polypeptides with different adhesion potentials for hyaluronate-bearing cells," *EMBO J.*, 10(2): 343-348, 1991.
Supplementary Search Report, European Patent Application No. EP 08733693, 7 pages (dated May 10, 2010).
Uchio et al., "Tear osteopontin levels in patients with allergic conjunctival diseases," *Graefe's Arch Clin Exp Ophthalmology*, 240: 924-928, 2002.
Unni et al., "Osteopontin is a potential target gene in mouse mammary cancer chemoprevention by Semethylselenocysteine," *Breast Cancer Research*, 6(5): R586-R592, 2004.
Veldhuizen et al., "The aetiology of idiopathic scoliosis: biomechanical and neuromuscular factors," *Eur Spine J.*, 9: 178-184, 2000.
Von Gall et al., "Transcription factor dynamics and neuroendocrine signalling in the mouse pineal gland: a comparative analysis of melatonin-deficient C57BL mice and melatonin-proficient C3H mice," *European J. Neuroscience*, 12: 964-972, 2000.
Wang et al., "Characterization of the scoliosis that develops after pinealectomy in the chicken and comparison with adolescent idiopathic scoliosis in humans," *Spine*, 22(22): 2626-2635, 1997.
Weber et al., "Receptor-Ligand Interaction Between CD44 and Osteopontin (Eta-1)," *Science*, 271: 509-512, 1996.
Weber et al., "Transient expression of CD44 variant isoforms in the ontogeny of the rat: ectoderm-, endoderm- and mesoderm-derived cells express different exon combinations," *Differentiation*, 60: 17-29, 1996.
Wise et al., "Localization of susceptibility to familial idiopathic scoliosis," *Spine*, 25(18): 2372-2380, 2000.
Wong et al., "Elevation of plasma osteopontin concentration is correlated with disease activity in patients with systemic lupus erythematosus," *Rheumatology*, 44, 602-606, 2005.
Wynne-Davies R., "Familial (idiopathic) scoliosis. A family survey," *J Bone Joint Surgery (Br)*, 50B(1): 24-30, 1968.
Xu et al., "Overexpression of osteopontin in rheumatoid synovial mononuclear cells is associated with joint inflammation, not with genetic polymorphism," *The Journal of Rheumatology*, 32:410-6 (2005).
Yamaga et al., "Osteopontin Level in Synovial Fluid Is Associated with the Severity of Joint Pain and Cartilage Degradation after Anterior Cruciate Ligament Rupture," *PLoS ONE* 7(11):e49014, 2012.
Yamane et al., "Soluble CD44 variant 6 as a prognostic indicator in patients with colorectal cancer. *Oncology*," 56(3): 232-238, 1999 (Abstract).
Chan, "Integrating Transcriptomics and Proteomics," *Genomics and Proteomics*, Apr. 1, 2006 (6 pages).
Pascal et al., "Correlation of mRNA and protein levels: Cell type-specific gene expression of cluster designation antigens in the prostate," *BMC Genomics* 9:246, 2008 (13 pages).
Bulletin of the Osaka Medical College, Instructions to Authors (1 page).
Clemente et al., "Osteopontin Bridging Innate and Adaptive Immunity in Autoimmune Diseases," *J Immunol Res* 2016:7675437, 2016 (15 pages).
Ouellet and Odent, "Animal models for scoliosis research: state of the art, current concepts and future perspective applications," *Eur Spine J* 22(Suppl 2):S81-S95, 2013.

* cited by examiner

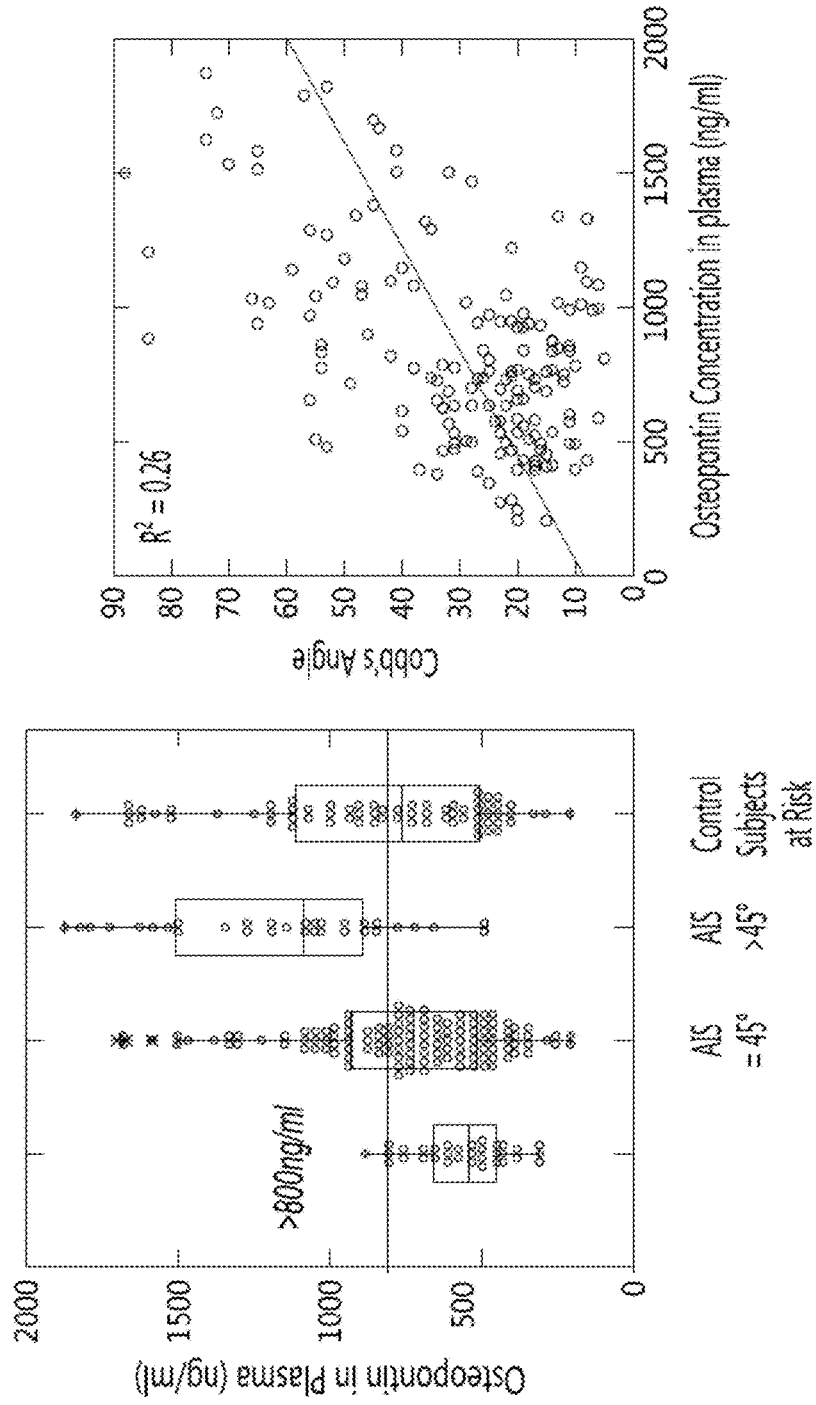

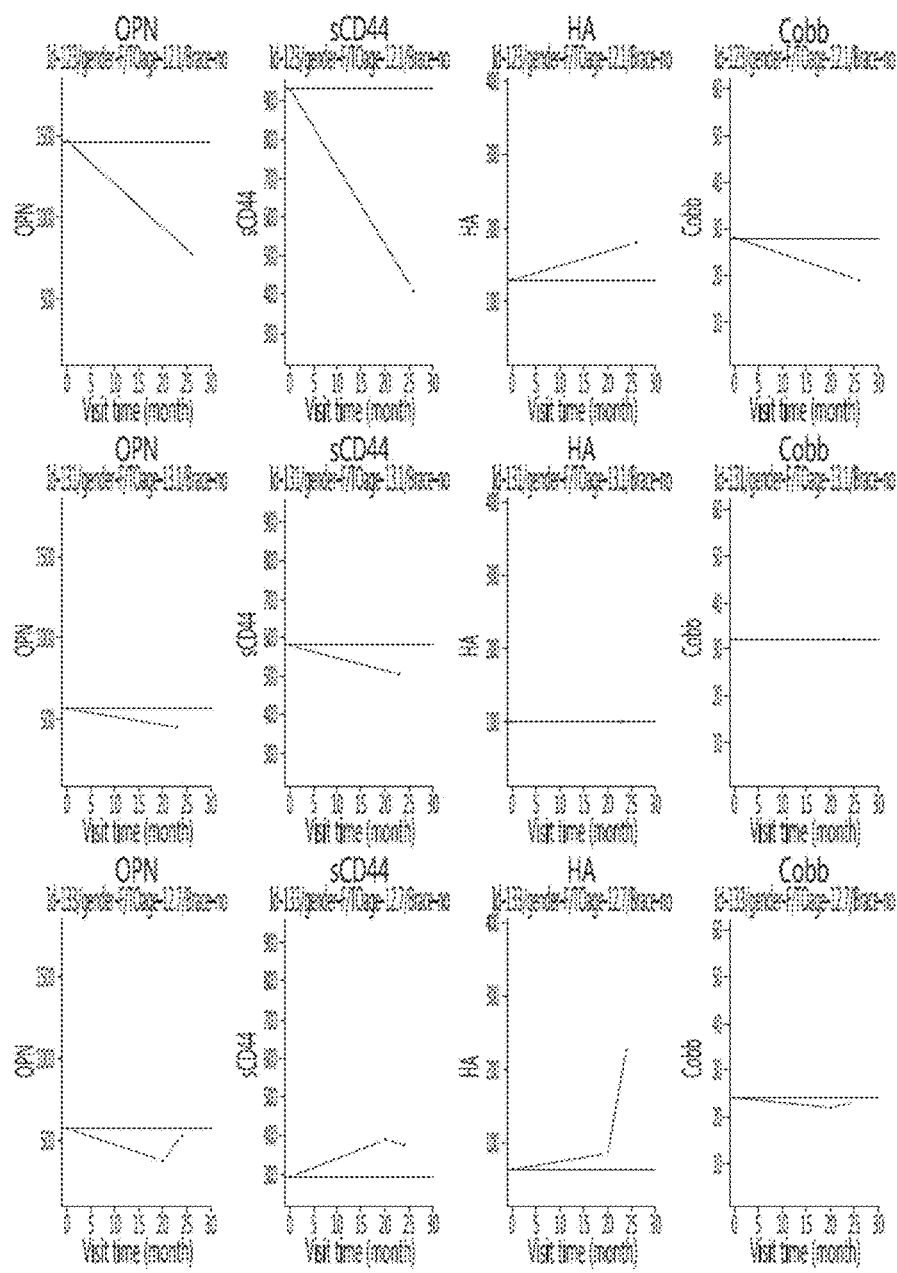

Brace patients: Prior to receiving bracing (n=8)

Brace patients: Having received bracing (n=8)

FIG. 20A

NM_001040058 transcript variant 1

```
   1 ctccctgtgt tggtggagga tgtctgcagc agcatttaaa ttctgggagg gcttggttgt
  61 cagcagcagc aggaggaggc agagcacagc atcgtcggga ccagactcgt ctcaggccag
 121 ttgcagcctt ctcagcaaa  cgccgaccaa ggaaaactca ctaccatgag aattgcagtg
 181 atttgctttt gcctcctagg catcacctgt gccataccag ttaaacaggc tgattctgga
 241 agttctgagg aaaagcagct ttacaacaaa tacccagatg ctgtggccac atggctaaac
 301 cctgaccat  ctcagaagca gaatctccta gcccacaga  atgctgtgtc ctctgaagaa
 361 accaatgact taaacaaga  gacccttcca agtaagtcca  cgaaagcca  tgaccacatg
 421 gatgatatgg atgatgaaga tgatgatgac catgtggaca gcaggactc  cattgactcg
 481 aacgactctg atgatgtaga tgcactgat  gattctcacc agtctgatga gtctcaccat
 541 tctgatgaat ctgatgaact ggtcactgat tttccacgg  acctgccagc aaccgaagtt
 601 ttcactccag ttgtccccac agtagacaca tatgatggcc gaggtgatag tgtggtttat
 661 ggactgaggt caaaatctaa gaagtttcgc agacctgaca tccagtaccc tgatgctaca
 721 gacgaggaca tcactcaca  catggaaagc gaggagttga atggtgcata caaggccatc
 781 ccgttgccc  aggactgaa  cgcgcctct  gattgggaca gccgtgggaa ggacagttat
 841 gaaacgagtc agctggatga ccagagtgct gaaacccaca gccacaagca gtccagatta
 901 tataagcgga aagccaatga tgagagcaat gagcattccg atgtgattga tagtcaggaa
 961 ctttccaaag tcagccgtga attccacagc catgaattca cagccatgaa agatatgctg
1021 gttgtagacc ccaaaagtaa ggaagaagat aaacacctga aatttcgtat ttctcatgaa
1081 ttagatagtg catcttctga ggtcaattaa aaggagaaaa aatacaattt ctcacttgc
1141 atttagtcaa aagaaaaaat gctttatagc aaaatgaaag agaacatgaa atgcttcttt
1201 ctcagtttat tggttgaatg tgtatctatt tgagtctgga aataactaat gtgtttgata
1261 attagtttag tttgtggctt catggaaact ccctgtaaac taaaagcttc agggttatgt
1321 ctatgttcat tctatagaag aaatgcaaac tatcactgta ttttaatatt tgttattctc
1381 tcatgaatag aaatttatgt agaagcaaac aaatacttt  taccaactta aaagagaat
1441 ataacatttt atgtcactat aatcttttgt tttttaagtt agtgtatatt ttgtgtgat
1501 tatcttttg  tggtgtgaat aaatctttta tcttgaatgt aataagaatt tggtggtgtc
1561 aattgcttat ttgttttccc acggttgtcc agcaattaat aaaacataac cttttttact
1621 gcctaaaaaa aaaaaaaaaa a
```

FIG. 20B

NM_000582 transcript variant 2

```
   1 ctcctgtgt tggtggagga tgtctgcagc agcatttaaa ttctgggagg gcttggttgt
  61 cagcagcagc aggaggaggc agagcacagc atcgtcggga ccagactcgt ctcaggccag
 121 ttgcagcctt ctcagccaaa cgccgaccaa ggaaaactca ctaccatgag aattgcagtg
 181 attttgctttt gcctcctagg catcacctgt gccataccag ttaaacaggc tgattctgga
 241 agtctgagg aaaagcagct ttacaacaaa taccagatg ctgtggccac atggctaaac
 301 cctgaccat ctcagaagca gaatctccta gcccacaga ccttccaag taagtccaac
 361 gaaagccatg accacatgga tgatatggat gatgaagatg atgatgacca tgtggacagc
 421 caggactcca ttgactcgaa cgactctgat gatgtagatg acactgatga ttctcaccag
 481 tctgatgagt ctcaccatc tgatgaatct gatgaactgg tcactgattt tccacggac
 541 ctgccagcaa ccgaagtttt cactccagtt gtcccacag tagacacata tgatggcga
 601 ggtgatagtg tggtttatgg actgaggtca aaatctaaga agtttcgcag acctgacatc
 661 cagtaccctg atgctacaga cgaggacatc acctcacaca tggaaagcga ggagttgaat
 721 gctgcataca aggccatccc cgttgcccag gacctgaacg cgcttctga ttgggacagc
 781 cgtgggaagg acagttatga aacgagtcag ctggatgacc agagtgctga accacagc
 841 cacaagcagt ccagattata taagcggaaa gccaatgatg agagcaatga gcattccgat
 901 gtgattgata gtcaggaact tccaaagtc agccgtgaat tccacagcca tgaatttcac
 961 agccatgaag atatgctggt tgtagacccc aaaagtaagg aagaagataa acacctgaaa
1021 tttcgtattt ctcatgaatt agatagtgca tcttctgagg tcaattaaaa ggagaaaaaa
1081 tacaatttct cacttgcat ttagtcaaaa gaaaaaatgc tttatagcaa aatgaaagag
1141 aacatgaaat gcttctttct cagtttattg gttgaatgtg tatctatttg agtctggaaa
1201 taactaatgt gtttgataat tagtttagtt tgtggcttca tggaaactcc ctgtaaacta
1261 aaagcttcag ggttatgtct atgttcattc tatagaagaa atgcaaacta tcactgtatt
1321 ttaatatttg ttattctctc atgaatagaa atttatgtag aagcaaacaa aatacttta
1381 cccacttaaa aagagaatat aacattttat gtcactataa tcttttgttt tttaagttag
1441 tgtatatttt gtgtgatta tcttttgtg gtgtgaataa atctttatc ttgaatgtaa
1501 taagaatttg gtggtgtcaa ttgcttattt gttttcccac ggttgtccag caattaataa
1561 aacataacct ttttactgc ctaaaaaaaa aaaaaaaaaa aaaaaaaaaa aaaaa
```

FIG. 20C

NM_001040060 transcript variant 3

```
   1 ctccctgtgt tggtggagga tgtctgcagc agcatttaaa ttctgggagg gcttggttgt
  61 cagcagcagc aggaggaggc agagcacagc atcgtcggga ccagactgt ctcaggcag
 121 ttgcagcctt ctcagccaaa cgccgaccaa ggaaaactca ctaccatgag aattgcagtg
 181 atttgctttt gctcctagg catcacctgt gcataccag taaacaggc tgattctgga
 241 agttctgagg aaaagcagaa tgctgtgtcc tctgaagaaa ccaatgactt taaacaagag
 301 acccttccaa gtaagtccaa cgaaagccat gaccacatgg atgatatgga tgatgaagat
 361 gatgatgacc atgtggacag ccaggactcc attgactcga acgactctga tgatgtagat
 421 gacactgatg atctccacca gtctgatgag tctcaccatt ctgatgaatc tgatgaactg
 481 gtcactgatt ttcccacgga cctgccagca acggaagttt tcactccagt tgtccccaca
 541 gtagacacat atgatggccg aggtgatagt gtggtttatg gactgaggtc aaaatctaag
 601 aagtttcgca gacctgacat ccagtaccct gatgctacag acgaggacat cacctcacac
 661 atggaaagcg aggagttgaa tggtgcatac aaggccatcc ccgttgccca ggacctgaac
 721 gcgccttctg attgggacag ccgtgggaag gacagttatg aaacgagtca gctggatgac
 781 cagagtgctg aaacccacag ccacaagcag tccagattat ataagcggaa agccaatgat
 841 gagagcaatg agcattccga tgtgattgat agtcaggaac tttccaaagt cagccgtgaa
 901 ttccacagcc atgaatttca cagccatgaa gatatgctgg ttgtagaccc caaaagtaag
 961 gaagaagata acaccctgaa atttcgtatt tctcatgaat tagatagtgc atcttctgag
1021 gtcaattaaa aggagaaaaa atacaatttc tcactttgca tttagtcaaa agaaaaaatg
1081 cttatagca aaatgaaaga gaacatgaaa tgcttcttc tcagtttatt ggttgaatgt
1141 gtatctattt gagtctggaa ataactaatg tgtttgataa ttagtttagt ttgtggcttc
1201 atggaaactc cctgtaaact aaaagcttca gggttatgtc tatgttcatt ctatagaaga
1261 aatgcaaact atcactgtat tttaatattt gtattctct catgaataga aatttatgta
1321 gaagcaaaca aaatacttt acccacttaa aaagagaata taacatttta tgtcactata
1381 atctttgtt ttttaagtta gtgtatattt tgtgtgatt atcttttgt ggtgtgaata
1441 aatcttttat cttgaatgta ataagaattt gtggtgtca attgcttatt tgttttccca
1501 cggttgtcca gcaattaata aaacataacc tttttactg cctaaaaaaa aaaaaaaaa
```

FIG. 20D

NP_001035147 isoform a

```
  1 mriavicfcl lgltcaipvk qadsqsseek qlynkypdav atxlnpdpsq kqillapqna
 61 vsseetndfk qetlpsksne shdmdmdd edddhvdsq dsidsndsd vddtdshqs
121 deshhsdesd elvtdfptdl patevftpvv ptvdtydgrg dsvvyglrsk skkfrrpdiq
181 ypdatdedit shmeseelng aykalpvaqd lnapsdwdsr gkdsyetsql ddqsaethsh
241 kqsrlykrka ndesnehsdv idsqelskvs refhshefhs hedmlvvdpk skeedkhlkf
301 risheldsas sevn
```

NP_000573 isoform b

```
  1 mriavicfcl lgltcaipvk qadsqsseek qlynkypdav atxlnpdpsq kqillapqtl
 61 psksneshdh mdmddeddd dhvdsqdsid sndsdvddt ddshqsdesh hsdesdelvt
121 dfptdlpate vftpvvptvd tydgrgdsvv yglrskskkf rrpdiqypda tdeditshme
181 seelngayka lpvaqdlnap sdwdsrgkds yetsqlddqs aethshkqsr lykrkandes
241 nehsdvidsq elskvsrefh shefhshedm lvvdpkskee dkhlkfrish eldsassevn
```

NP_001035149 isoform c

```
  1 mriavicfcl lgltcaipvk qadsqsseek qnavsseetn dfkqetlpsk sneshdmdd
 61 mddeddddhv dsqdsidsnd sddvddtdds hqsdeshhsd esdelvtdfp tdlpatevft
121 pvvptvdtyd grgdsvvygl rskskkfrrp diqypdatde ditshmesee lngaykalpv
181 aqdlnapsdw dsrgkdsyet sqlddqsaet hshkqsrlyk rkandesneh sdvidsqels
241 kvsrefhshe fhshedmlvv dpkskeedkh lkfrisheld sassevn
```

FIG. 21A

NM_000610 transcript variant 1

```
   1 gagaagaaag ccagtgcgtc tctgggcgca ggggccagtg gggctcggag gcacaggcac
  61 ccgcgacac tccaggttcc ccgaccacg tcctggcag cccgattat ttacagcctc
 121 agcagagcac gggcggggg cagagggcc cgccggag ggctgctact tcttaaaacc
 181 tctgcgggct gcttagtcac agccccctt gcttgggtgt gtcctcgct cgctccctcc
 241 ctccgtctta ggtcactgtt ttcaacctcg aataaaaact gcagccaact tccgaggcag
 301 cctcattgcc cagcggaccc cagcctctgc caggttcggt ccgccatcct cgtccgtcc
 361 tccgccggcc cctgcccgc gccagggat cctccagctc ctttcgccg cgcctccgt
 421 tcgctccgga caccatggac aagtttggt ggcacgcagc ctgggactc tgcctcgtgc
 481 cgctgagcct ggcgcagatc gatttgaata taacctgccg ctttgcaggt gtattccacg
 541 tggagaaaaa tggtcgctac agcatctctc ggacggaggc cgctgaccte tgcaaggctt
 601 tcaatagcac cttgccaca atggcccaga tggagaaagc tctgagcatc ggatttgaga
 661 cctgcaggta tgggttcata gaagggcacg tggtgattcc ccggatccac cccaactcca
 721 tctgtgcagc aaacaacaca ggggtgtaca tcctcacatc caacacctcc cagtatgaca
 781 catattgctt caatgcttca gctccacctg aagaagattg tacatcagtc acagacctgc
 841 ccaatgcctt tgatggacca attaccataa ctattgttaa ccgtgatggc accgctatg
 901 tccagaaagg agaatacaga acgaatcctg aagacatcta cccagcaac cctactgatg
 961 atgacgtgag cagcggctcc tccagtgaaa ggagcagcac ttcaggaggt tacatctttt
1021 acacctttc tactgtacac cccatccag acgaagacag tcctggatc acgacagca
1081 cagacagaat cctgctacc actttgatga gcactagtgc tacagcaact gagacagcaa
1141 ccaagaggca agaaacctgg gattggtttt catggttgtt tctaccatca gagtcaaaga
1201 atcatcttca cacaacaaca caaatggctg gtacgtcttc aaataccatc tcagcaggct
1261 gggagccaaa tgaagaaat gagatgaaa gagacagaca cctcagtttt tctggatcag
1321 gcattgatga tgatgaagat tttatctcca gcaccattc aaccacacca cgggcttttg
1381 accacacaaa acagaaccag gactggaccc agtggaaccc aagccattca aatcggaag
1441 tgctacttca gacaaccaca aggatgactg atgtagacag aaatggcacc actgcttatg
1501 aaggaaactg gaacccagaa gcacaccctc ccctcattca ccatgagcat catgaggaag
1561 aagagaccc acattctaca agcacaatcc aggcaactcc tagtagtaca acggaagaa
1621 cagctaccca gaaggaacag tggtttggca acagatggca tgagggatat cgccaaacac
1681 ccaaagaaga ctccattcg acaacaggga cagctgcagc ctcagctcat accagccatc
1741 caatgcaagg aaggacaaca ccaagcccag aggacagttc ctggactgat ttcttcaacc
1801 caatctcaca ccccatggga cgaggtcatc aagcaggaag aaggatggat atggactcca
```

FIG. 21B

```
1861 gtcatagtat aacgcttcag cctactgcaa atccaaacac aggtttggtg gaagatttgg
1921 acaggacagg acctctttca atgacaacgc agcagagtaa ttctcagagc ttctctacat
1981 cacatgaagg cttggaagaa gataaagacc atccaacaac ttctactctg acatcaagca
2041 ataggaatga tgtcacaggt ggaagaagag acccaaatca ttctgaaggc tcaactactt
2101 tactggaagg ttatacctct cattacccac acacgaagga aagcaggacc ttcatccag
2161 tgacctcagc taagactggg tcctttggag ttactgcagt tactgttgga gattccaact
2221 ctaatgtcaa tgttcctta tcaggagacc aagacacatt ccacccagt ggggggtccc
2281 ataccactca tggatctgaa tcagatggac actcacatgg gagtcaagaa ggtggagcaa
2341 acacaacctc tggtcctata aggacaccc aaattccaga atggctgatc atcttggcat
2401 ccctcttggc cttggctttg atcttgcag tttgcattgc agtcaacagt cgaagaagt
2461 gtgggcagaa gaaaaagcta gtgatcaaca gtggcaatgg agctgtggag gacagaaagc
2521 caagtggact caacggagag gccagcaagt ctcaggaaat ggtgcatttg gtgaacaagg
2581 agtcgtcaga aactccagac cagtttatga cagctgatga gacaaggaac ctgcagaatg
2641 tggacatgaa gattggggtg taacacctac accattatct tggaaagaaa caaccgttgg
2701 aaacataacc attacaggga gctggacac ttaacagatg caatgtgcta ctgattgttt
2761 cattgcgaat cttttttagc ataaatttt ctactcttt tgtttttgt gtttgttct
2821 ttaaagtcag gtccaattg taaaaacagc attgctttct gaaattaggg cccaattaat
2881 aatcagcaag aatttgatcg ttccagttcc cacttggagg cctttcatcc ctcgggtgtg
2941 ctatggatgg cttctaacaa aaactacaca tatgtattcc tgatcgccaa cctttccccc
3001 accagctaag gacatttccc aggttaata gggcctggtc cctgggagga aatttgaatg
3061 ggtccatttt gccttccat agcctaatcc ctgggcattg cttccactg aggttggggg
3121 tggggtgta ctagttacac atcttcaaca gacccctct agaaatttt cagatgcttc
3181 tgggagacac ccaaagggtg aagctattta tctgtagtaa actattatc tgtgttttg
3241 aaatattaaa ccctggatca gtccttgat cagtataatt ttaaagtt acttgtcag
3301 aggcacaaaa gggtttaaac tgattcataa taaatatctg tactcttcg atcttcacct
3361 tttgtgctgt gattcttcag tttctaaacc agcactgtct gggtcctac aatgtatcag
3421 gaagagctga gaatggtaag gagactcttc taagtcttca tctcagagac cctgagttcc
3481 cactcagacc cactcagcca aatctcatgg aagaccaagg agggcagcac tgttttgtt
3541 ttttgttttt tgtttttttt tttgacact gtccaaaggt ttccatcct gtcctggaat
3601 cagagttgga agctgaggag cttcagctc ttttatggtt taatggccac ctgttctctc
3661 ctgtgaaagg ctttgcaaag tcacattaag tttgcatgac ctgttatccc tgggcccta
3721 tttcatagag gctggcccta ttagtgattt ccaaaaacaa tatggaagtg cctttgatg
```

FIG. 21C

```
3781 tcttacaata agagaagaag ccaatggaaa tgaaagagat tggcaaaggg gaaggatgat
3841 gccatgtaga tcctgttga cattttatg gctgtatttg taaacttaaa cacaccagtg
3901 tctgttcttg atgcagttgc tatttaggat gagttaagtg cctggggagt ccctcaaaag
3961 gttaaaggga ttcccatcat tggaatctta tcaccagata ggcaagttta tgaccaaaca
4021 agagagtact ggcttatcc tctaacctca tatttctcc cacttggcaa gtcctttgtg
4081 gcattattc atcagtcagg gtgtccgatt ggtcctagaa cttcaaaggg ctgcttgtca
4141 tagaagccat tgcatctata aagcaacggc tcctgttaaa tggtatctcc ttctgaggc
4201 tcctactaaa agtcatttgt tacctaaact tatgtgctta acaggcaatg cttctcagac
4261 cacaaagcag aaagaagaag aaaagctcct gactaaatca gggctgggct tagacagagt
4321 tgatctgtag aatatcttta aaggagagat gtcaacttc tgcactattc ccagctctg
4381 ctcctcctg tctaccctct ccctccctc tctcctcca cttcaccca caatcttgaa
4441 aaacttcctt tctcttctgt gaacatcatt ggccagatcc attttcagtg gtctggattt
4501 cttttattt tcttttcaac ttgaaagaaa ctgacatta ggccactatg tgttgttact
4561 gccactagtg ttcaagtgcc tcttgttttc ccagagattt cctgggtctg ccagaggccc
4621 agacaggctc actcaagctc tttaactgaa aagcaacaag ccactccagg acaaggttca
4681 aaatggttac aacagcctct acctgtgcc ccagggagaa agggtagtg atacaagtct
4741 catagccaga gatggttttc cactccttct agatattccc aaaaagaggc tgagacagga
4801 ggttatttc aattttattt tggaattaaa tacttttc cctttattac tgttgtagtc
4861 cctcacttgg atataccctct gttttcacga tagaataag ggaggtctag agcttctatt
4921 cctggccat tgtcaacgga gagctggcca agtcttcaca aaccttgca acattgcctg
4981 aagttatgg aataagatgt attctcactc cctgatctc aagggcgtaa ctctggaagc
5041 acagcttgac tacacgtcat ttttaccaat gatttcagg tgacctgggc taagtcattt
5101 aaactgggtc tttataaaag taaaaggcca acatttaatt attttgcaaa gcaacctaag
5161 agctaaagat gtaattttc ttgcaattgt aaatctttg tgtctcctga agacttccct
5221 taaaattagc tctgagtgaa aaatcaaaag agacaaaaga catctcgaa tccatatttc
5281 aagcctggta gaattggctt ttctagcaga acctttccaa aagttttata ttgagattca
5341 taacaacacc aagaattgat tttgtagcca acattcattc aatactgtta tatcagagga
5401 gtaggagaga ggaacattt gactatctg gaaaagcaaa atgtacttaa gaataagaat
5461 aacatggtcc attcacctt atgttataga tatgtctttg tgtaaatcat ttgttttgag
5521 ttttcaaaga atagccatt gttcattctt gtgctgtaca atgaccactg ttattgttac
5581 tttgactttt cagagcacac ccttcctctg gtttttgtat atttattgat ggatcaataa
5641 taatgaggaa agcatgatat gtatattgct gagttgaaag cactttattgg aaaatattaa
5701 aaggctaaca ttaaaagact aaaggaaaca gaaaaaaaa aaaaaaa
```

FIG. 21D

NM_001001389 transcript variant 2

```
   1 gagaagaaag ccagtgcgtc tctgggcgca ggggccagtg gggctcggag gcacaggcac
  61 cccgcgacac tccaggttcc ccgaccacg tcctggcag cccgattat ttacagcctc
 121 agcagagcac gggcggggg cagaggcgcc cgccggag ggctgctact tcttaaaacc
 181 tctgcgggct gctagtcac agccccctt gttgggtgt gtcctcgct cgctccctcc
 241 ctccgtctta ggtcactgtt ttcaacctcg aataaaact gcagccaact tccgaggcag
 301 cctcattgcc cagggacca cagctctgc caggttcggt ccgccatct cgtcccgtcc
 361 tcgccggcc cctgcccgc gccaggggat cctccagctc ctttcgccg cgcctccgt
 421 tcgctccgga caccatggac aagtttggt ggcacgcagc ctggggactc tgcctcgtgc
 481 cgctgagcct ggcgcagatc gatttgaata taacctgccg ctttgcaggt gtattccacg
 541 tggagaaaaa tggtcgctac agcatctctc ggacggaggc cgctgacctc tgcaaggctt
 601 tcaatagcac cttgccaca atggccaga tggagaaagc tctgagcatc ggatttgaga
 661 cctgcaggta tgggttcata gaagggcacg tggtgattcc ccggatccac cccaactcca
 721 tctgtgcagc aaacaacaca gggtgtaca tcctcacatc caacacctcc cagtatgaca
 781 catattgctt caatgcttca gctccacctg aagaagattg tacatcagtc acagacctgc
 841 ccaatgcctt tgatggacca attaccataa ctattgttaa ccgtgatggc accgctatg
 901 tccagaaagg agaatacaga acgaatcctg aagcatcta cccagcaac cctactgatg
 961 atgacgtgag cagcggctcc tccagtgaaa ggagcagcac ttcaggaggt tacatctttt
1021 acaccttttc tactgtacac cccatccag acgaagacag tcctggatc accgacagca
1081 cagacagaat ccctgctacc agtacgtctt caaataccat ctcagcaggc tgggagccaa
1141 atgaagaaaa tgaagatgaa agagacagac acctcagttt ttctggatca ggcattgatg
1201 atgatgaaga tttatctcc agccacattt caaccacacc acgggctttt gaccacacaa
1261 aacagaacca ggactggacc cagtggaacc caagccattc aaatcggaa gtgctacttc
1321 agacaaccac aaggatgact gatgtagaca gaaatggcac cactgcttat gaaggaaact
1381 ggaacccaga agcacaccct cccctcattc accatgagca tcatgaggaa gagagacccc
1441 cacattctac aagcacaatc caggcaactc ctagtagtac aacggaagaa acagctaccc
1501 agaaggaaca gtggtttgc aacagatggc atgaggggata tgccaaaca cccaagaag
1561 actccattc gacaacaggg acagctgcag cctcagctca taccagccat ccaatgcaag
1621 gaaggacaac accaagccca gaggacagtt cctggactga tttcttcaac ccaatctcac
1681 acccatggg acgaggtcat caagcaggaa gaaggatgga tatggactcc agtcatagta
1741 taacgcttca gcctactgca aatccaaaca caggtttggt ggaagatttg gacaggacag
```

FIG. 21E

```
1801 gacctctttc aatgacaacg cagcagagta attctcagag cttctctaca tcacatgaag
1861 gcttggaaga agataaagac catccaacaa cttctactct gacatcaagc aataggaatg
1921 atgtcacagg tggaagaaga gaccaaatc attctgaagg ctcaactact ttactggaag
1981 gttatacctc tcattaccca cacacgaagg aaagcaggac cttcatccca gtgacctcag
2041 ctaagactgg gtcctttgga gttactgcag ttactgttgg agattccaac tctaatgtca
2101 atcgttcctt atcaggagac caagacacat tccacccag tgggggtcc cataccactc
2161 atggatctga atcagatgga cactcacatg ggagtcaaga agtggagca aacacaacct
2221 ctggtcctat aaggacaccc caaattccag aatggctgat catcctgca tccctcttgg
2281 cctggcttt gattcttgca gtttgcattg cagtcaacag tcgaagaagg tgtgggcaga
2341 agaaaaagct agtgatcaac agtggcaatg gagctgtgga ggacagaaag ccaagtggac
2401 tcaacggaga ggccagcaag tctcaggaaa tggtgcattt ggtgaacaag gagtcgtcag
2461 aaactccaga ccagtttatg acagctgatg agacaaggaa cctgcagaat gtggacatga
2521 agattggggt gtaacaccta caccattatc ttggaaagaa acaaccgttg gaaacataac
2581 cattacaggg agctgggaca cttaacagat gcaatgtgct actgattgtt tcattgcgaa
2641 tcttttttag cataaaattt tctactcttt ttgttttttg tgtttgttc tttaaagtca
2701 ggtccaattt gtaaaaacag cattgctttc tgaaattagg gcccaattaa taatcagcaa
2761 gaattgatc gttccagttc ccactggag gctttcatc cctcggtgt gctatggatg
2821 gcttctaaca aaaactacac atatgtattc ctgatcgcca accttcccc caccagctaa
2881 ggacatttcc caggttaat agggcctggt cctgggagg aaatttgaat ggtccattt
2941 tgccttcca tagcctaatc cctggcatt gcttccact gaggtgggg gttgggtgt
3001 actagttaca catcttcaac agacccctc tagaaatttt tcagatgctt ctgggagaca
3061 cccaaagggt gaagctattt atctgtagta aactatttat ctgtgttttt gaaatattaa
3121 acctggatc agtcctttga tcagtataat ttttaaagt tactttgtca gaggcacaaa
3181 agggtttaaa ctgattcata ataatatct gtacttcttc gatcttcacc tttgtgctg
3241 tgattcttca gtttctaaac cagcactgtc tgggtcccta caatgtatca ggaagagctg
3301 agaatggtaa ggagactctt ctaagtcttc atctcagaga ccctgagtc ccactcagac
3361 ccactcagcc aaatctcatg gaagacaag gagggcagca ctgttttgt ttttgtttt
3421 ttgttttttt ttttgacac tgtccaaagg tttccatcc tgtcctggaa tcagagttgg
3481 aagctgagga gcttcagcct ctttatggt ttaatggcca cctgttctct cctgtgaaag
3541 gctttgcaaa gtcacattaa gttgcatga cctgttatcc ctggggccct atttcataga
3601 ggctggccct attagtgatt tccaaaaaca atatggaagt gcctttgat gtcttacaat
3661 aagagaagaa gccaatggaa atgaaagaga ttggcaaagg ggaaggatga tgccatgtag
```

FIG. 21F

```
3721 atcctgtttg acatttttat ggctgtattt gtaaacttaa acacaccagt gtctgttctt
3781 gatgcagttg ctatttagga tgagttaagt gctggggag tccctcaaaa ggtaaaggg
3841 attcccatca ttggaatctt ataccagat aggcaagttt atgaccaaac aagagagtac
3901 tggctttatc ctctaacctc atattttctc ccacttggca agtcctttgt ggcatttatt
3961 catcagtcag ggtgtccgat tggtcctaga acttccaaag gctgttgtc atagaagcca
4021 ttgcatctat aaagcaacgg ctctgttaa atggtatctc cttctgagg ctcctactaa
4081 aagtcatttg ttacctaaac ttatgtgctt aacaggcaat gcttctcaga ccacaaagca
4141 gaagaagaa gaaaagctcc tgactaaatc agggctgggc ttagacagag ttgatctgta
4201 gaatatcttt aaggagaga tgtcaacttt ctgcactatt ccagcctct gtcctccct
4261 gtctaccctc tccctccct ctctcctcc acttcacccc acaatcttga aaaacttcct
4321 ttctcttctg tgaacatcat tggccagatc catttcagt ggtctggatt tcttttatt
4381 ttcttttcaa cttgaaagaa actggacatt aggccactat gtgttgttac tgccactagt
4441 gttcaagtgc ctcttgtttt ccagagatt tcctgggtct gcagaggcc cagacaggct
4501 cactcaagct ctttaactga aaagcaacaa gccactccag gacaaggttc aaaatggtta
4561 caacagcctc tactgtcgc ccagggaga aaggggtagt gatacaagtc tcatagccag
4621 agatggtttt ccactcctc tagatattcc caaaagagg ctgagacagg aggttatttt
4681 caatttatt ttggaattaa atacttttt cctttatta ctgttgtagt ccctcacttg
4741 gatataccctc tgttttcacg atagaaataa gggaggtcta gagcttctat tccttggcca
4801 ttgtcaacgg agagctggcc aagtcttcac aaacccttgc aacattgcct gaagttatg
4861 gaataagtg tattctcact ccttgatct caagggcgta actctggaag cacagcttga
4921 ctacacgtca ttttaccaa tgattttcag gtgacctggg ctaagtcatt taaactgggt
4981 ctttataaaa gtaaaggcc aacatttaat tatttgcaa agcaacctaa gagctaaaga
5041 tgtaatttt cttgcaattg taaatctttt gtgtctcctg aagacttccc ttaaaattag
5101 ctctgagtga aaaatcaaaa gagacaaaag acatcttcga atccatattt caagcctggt
5161 agaattggct ttctagcag aaccttcca aaagttttat attgagattc ataacaacac
5221 caagaattga ttttgtagcc aacattcatt caatactgtt atatcagagg agtaggagag
5281 aggaaacatt tgacttatct ggaaaagcaa aatgtactta agaataagaa taacatggtc
5341 cattcaccttt tatgttatag atatgtcttt gtgtaaatca tttgtttga gtttcaaag
5401 aatagcccat tgttcattct tgtgctgtac aatgaccact gttattgtta ctttgacttt
5461 tcagagcaca ccctcctct ggtttttgta tattattga tggatcaata ataatgagga
5521 aagcatgata tgtatattgc tgagttgaaa gcacttattg gaaatatta aaggctaac
5581 attaaaagac taaaggaaac agaaaaaaaa aaaaaaaa
```

FIG. 21G

NM_001001390 transcript variant 3

```
   1 gagaagaaag ccagtgcgtc tctgggcgca ggggccagtg gggctcggag gcacaggcac
  61 ccgcgacac tccaggttcc ccgaccacg tcctggcag cccgattat ttacagcctc
 121 agcagagcac ggggcggggg cagagggcc cgccgggag ggctgctact tcttaaaacc
 181 tctgcgggct gcttagtcac agccccctt gcttgggtgt gtcttcgct cgctccctcc
 241 ctccgtctta ggtcactgtt ttcaacctcg aataaaaact gcagccaact tccgaggcag
 301 cctcattgcc cagcggaccc cagctctgc caggttcggt ccgccatcct cgtccgtcc
 361 tccgcggcc cctgcccgc gccagggat cctccagctc ctttcgcccg cgcctccgt
 421 tcgctccgga caccatggac aagtttggt ggcacgcagc ctggggactc tgcctcgtgc
 481 cgctgagcct ggcgcagatc gatttgaata taacctgccg ctttgcaggt gtattccacg
 541 tggagaaaaa tggtcgctac agcatctctc ggacggaggc cgctgacctc tgcaggctt
 601 tcaatagcac cttgccaca atggcccaga tggagaaagc tctgagcatc ggatttgaga
 661 cctgcaggta tgggttcata gaagggcacg tggtgattcc ccggatccac cccaactcca
 721 tctgtgcagc aaacaacaca ggggtgtaca tcctcacatc caacacctcc cagtatgaca
 781 catattgctt caatgcttca gctccacctg aagaagattg tacatcagtc acagacctgc
 841 ccaatgcctt tgatggacca attaccataa ctattgttaa ccgtgatggc accgctatg
 901 tccagaaagg agaatacaga acgaatcctg aagacatcta cccagcaac ctactgatg
 961 atgacgtgag cagcggctcc tccagtgaaa ggagcagcac ttcaggaggt tacatctttt
1021 acaccttttc tactgtacac cccatcccag acgaagacag tcctggatc acggacagca
1081 cagacagaat cctgctacc aatatggact ccagtcatag tataacgctt cagcctactg
1141 caaatccaaa cacaggtttg gtggaagatt tggacaggac aggacctctt tcaatgacaa
1201 cgcagcagag taattctcag agcttctcta catcacatga aggcttggaa gaagataaag
1261 accatccaac aactctact ctgacatcaa gcaataggaa tgatgtcaca ggtggaagaa
1321 gagacccaaa tcattctgaa ggctcaacta ctttactgga aggttatacc tctcattacc
1381 cacacacgaa ggaaagcagg accttcatcc cagtgacctc agctaagact gggtcctttg
1441 gagttactgc agttactgtt ggagattcca actctaatgt caatcgttcc ttatcaggag
1501 accaagacac attccaccc agtgggggt cccataccac tcatggatct gaatcagatg
1561 gacactcaca tggagtcaa gaaggtggag caaacacaac ctctggtcct ataaggacac
1621 cccaaattcc agaatggctg atcatcttgg catccctctt ggcttggct ttgattcttg
```

FIG. 21H

```
1681 cagtttgcat tgcagtcaac agtcgaagaa ggtgtgggca gaagaaaaag ctagtgatca
1741 acagtggcaa tggagctgtg gaggacagaa agccaagtgg actcaacgga gaggccagca
1801 agtctcagga aatggtgcat ttggtgaaca aggagtcgtc agaaactcca gaccagttta
1861 tgacagctga tgagacaagg aacctgcaga atgtggacat gaagattggg gtgtaacacc
1921 tacaccatta tcttggaaag aaacaaccgt tggaaacata accattacag ggagctggga
1981 cacttaacag atgcaatgtg ctactgattg tttcattgcg aatcttttt agcataaaat
2041 tttctactct ttttgttttt tgtgttttgt tctttaaagt caggtccaat ttgtaaaaac
2101 agcattgctt tctgaaatta gggcccaatt aataatcagc aagaatttga tcgttccagt
2161 tccacttgg aggcctttca tccctcgggt gtgctatgga tggcttctaa caaaaactac
2221 acatatgtat tcctgatcgc caacttcc cccaccagt aaggacattt ccagggtta
2281 ataggcctg gtccctggga ggaaattga atgggtccat tttgccttc catagcctaa
2341 tcctgggca ttgctttcca ctgaggttgg gggttgggt gtactagtta cacatcttca
2401 acagacccc tctagaaatt tttcagatgc ttctggaga cacccaaagg gtgaagctat
2461 ttatctgtag taaactattt atctgtgttt ttgaaatatt aaccctgga tcagtcttt
2521 gatcagtata attttttaaa gttacttgt cagaggcaca aaagggttta aactgattca
2581 taataaatat ctgtacttct tcgatcttca ccttttgtgc tgtgattctt cagtttctaa
2641 accagcactg tctgggtccc tacaatgtat caggaagagc tgagaatggt aaggagactc
2701 ttctaagtct tcatctcaga gacctgagt tccactcag acccactcag ccaaatctca
2761 tggaagacca aggagggcag cactgtttt gttttttgtt ttttgttttt ttttttgac
2821 actgtccaaa ggttttccat cctgtcctgg aatcagagtt ggaagctgag gagcttcagc
2881 ctctttatg gtttaatgcc cacctgttct ctcctgtgaa aggctttgca aagtcacatt
2941 aagtttgcat gacctgttat ccctgggcc ctatttcata gaggctggcc ctattagtga
3001 ttccaaaaa caatatggaa gtgcctttg atgtcttaca ataagagaag aagccaatgg
3061 aaatgaaaga gattggcaaa ggggaaggat gatgccatgt agatcctgtt tgacatttt
3121 atggctgtat ttgtaaactt aaacacacca gtgtctgttc ttgatgcagt tgctatttag
3181 gatgagttaa gtgctggg agtccctcaa aaggttaaag ggattcccat cattggaatc
3241 ttatcaccag ataggcaagt ttatgaccaa acaagagagt actggcttta tcctctaacc
3301 tcatatttc tcccacttgg caagtccttt gtggcattta ttcatcagtc agggtgtccg
3361 attggtccta gaacttccaa aggctgcttg tcatagaagc cattgcatct ataagcaac
```

FIG. 21I

```
3421 ggctcctgtt aaatggtatc tccttctga ggctcctact aaaagtcatt tgttacctaa
3481 actatgtgc ttaacaggca atgcttctca gaccacaaag cagaagaag aagaaagct
3541 cctgactaaa tcaggyctgg gcttagacag agttgatctg tagaatatct ttaaaggaga
3601 gatgtcaact ttctgcacta ttcccagcct ctgtcctcc ctgtctaccc tctcccctcc
3661 ctctctcct ccacttcacc ccacaatctt gaaaaactc ctttctctc tgtgaacatc
3721 attggccaga tccattttca gtggtctgga tttcttttta ttttcttttc aacttgaaag
3781 aaactggaca ttaggccact atgtgttgtt actgccacta gtgttcaagt gcctcttgtt
3841 ttcccagaga tttcctgggt ctgccagagg cccagacagg ctcactcaag ctctttaact
3901 gaaaagcaac aagccactcc aggacaaggt tcaaaatggt tacaacagcc tctacctgtc
3961 gcccaggga gaaagggta gtgatacaag tctcatagcc agagatggtt ttccactcct
4021 tctagatatt cccaaaaga ggctgagaca ggaggttatt ttcaattta ttttggaatt
4081 aaatactttt ttcccttat tactgttgta gtccctcact tggatatacc tctgttttca
4141 cgatagaaat aagggaggtc tagagcttct attccttggc cattgtcaac ggagagctgg
4201 ccaagtcttc acaaacctt gcaacattgc ctgaagttta tgaataaga tgtattctca
4261 ctccttgat ctcaagggcg taactctgga agcacagctt gactacacgt cattttacc
4321 aatgatttc aggtgacctg ggctaagtca tttaaactgg gtctttataa aagtaaaagg
4381 ccaacattta attatttgc aaagcaacct aagagctaaa gatgtaattt ttcttgcaat
4441 tgtaaatctt ttgtgtctcc tgaagacttc ccttaaaatt agctctgagt gaaaaatcaa
4501 aagagacaaa agacatcttc gaatccatat ttcaagcctg gtagaattgg cttttctagc
4561 agaacttttc caaagtttt atattgagat tcataacaac accaagaatt gattttgtag
4621 ccaacattca ttcaatactg ttatatcaga ggagtaggag agaggaaaca tttgacttat
4681 ctggaaaagc aaaatgtact taagaataag aataacatgg tccattcacc tttatgttat
4741 agatatgtct ttgtgtaaat cattgtttt gagttttcaa agaatagccc attgttcatt
4801 cttgtgctgt acaatgacca ctgtattgt tactttgact ttcagagca cacccttcct
4861 ctggttttg tatatttatt gatggatcaa taataatgag gaaagcatga tatgtatatt
4921 gctgagttga aagcacttat tgaaaatat taaaaggcta acattaaaag actaaaggaa
4981 acagaaaaaa aaaaaaaaaa a
```

FIG. 21J

NM_001001391 transcript variant 4

```
   1 gagaagaaag ccagtgcgtc tctgggcgca ggggccagtg gggctcggag gcacaggcac
  61 ccgcgacac tccaggttcc ccgaccacg tccctggcag cccgattat ttacagcctc
 121 agcagagcac ggggcggggg cagaggggcc cgcccggag ggctgctact tcttaaaacc
 181 tctgcgggct gctagtcac agcccccct gcttgggtgt gtcctcgct cgctcctcc
 241 ctccgtctta ggtcactgtt ttcaacctcg aataaaaact gcagccaact tccgaggcag
 301 cctcattgcc cagcggacc cagctctgc caggttcggt ccgccatcct cgtcccgtcc
 361 tccgccggcc cctgcccgc gccaggat ctccagctc cttcgccg cgcctccgt
 421 tgctccgga ccaccatggac aagtttggt ggcacgcagc ctggggactc tgcctcgtgc
 481 cgctgagcct ggcgcagatc gatttgaata taacctgccg cttgcaggt gtattccacg
 541 tggagaaaaa tggtcgctac agcatctctc ggacggaggc cgctgacctc tgcaaggctt
 601 tcaatagcac cttgccaca atggcccaga tggagaaagc tctgagcatc ggatttgaga
 661 cctgcaggta tgggttcata gaaggcacg tggtgattcc ccggatccac cccaactcca
 721 tctgtgcagc aaacaacaca gggtgtaca tcctcacatc caacacctcc cagtatgaca
 781 catattgctt caatgcttca gctccacctg aagaagattg tacatcagtc acagacctgc
 841 ccaatgcctt tgatggacca attaccataa ctattgttaa ccgtgatggc accgctatg
 901 tccagaaagg agaatacaga acgaatcctg aagacatcta cccagcaac cctactgatg
 961 atgacgtgag cagggctcc tccagtgaaa ggagcagcac ttcaggaggt tacatctttt
1021 acaccttttc tactgtacac cccatcccag acgaagacag tcctggatc accgacagca
1081 cagacagaat ccctgctacc agagaccaag acacattcca cccagtggg gggtcccata
1141 ccactcatgg atctgaatca gatggacact cacatgggag tcagaaggt ggagcaaaca
1201 caacctctgg tcctataagg acacccaaa ttcagaatg gctgatcatc ttggcatccc
1261 tcttggcctt ggctttgatt cttgcagttt gcattgcagt caacagtcga agaaggtgtg
1321 ggcagaagaa aaagctagtg atcaacagtg gcaatggagc tgtggaggac agaaagccaa
1381 gtggactcaa cggagaggcc agcaagtctc aggaaatggt gcatttggtg aacaaggagt
```

FIG. 21K

```
1441 cgtcagaaac tccagaccag tttatgacag ctgatgagac aaggaacctg cagaatgtgg
1501 acatgaagat tgggtgtaa cacctacacc attatcttgg aaagaaacaa ccgttggaaa
1561 cataaccatt acagggagct gggacactta acagatgcaa tgtgctactg attgtttcat
1621 tgcgatctt tttagcata aaatttcta ctctttttgt ttttgtgtt ttgttcttta
1681 aagtcaggtc caattgtaa aaacagcatt gcttctgaa attagggcc aattaataat
1741 cagcaagaat tgatcgttc cagtcccac ttggaggcct ttcatccctc gggtgtgcta
1801 tggatggctt ctaacaaaaa ctacacatat gtattcctga tcgccaacct ttccccacc
1861 agctaaggac atttcccagg gttaataggg cctggtccct gggaggaaat ttgaatgggt
1921 ccatttgcc cttccatagc ctaatccctg ggcattgctt tccactgagg ttggggttg
1981 gggtgtacta gttacacatc ttcaacagac ccctctaga aattttcag atgcttctgg
2041 gagacaccca aaggtgaag ctattatct gtagtaaact attatctgt gttttgaaa
2101 tattaaaccc tggatcagtc ctttgatcag tataatttt taaagttact ttgtcagagg
2161 cacaaaaggg tttaaactga ttcataataa atatctgtac ttcttcgatc ttcaccttt
2221 gtgctgtgat tcttcagttt ctaaaccagc actgtctggg tcctacaat gtatcaggaa
2281 gagctgagaa tggtaaggag actcttctaa gtcttcatct cagagaccct gagttcccac
2341 tcagcccac tcagccaaat ctcatggaag accaaggagg gcagcactgt ttttgttttt
2401 tgttttttgt ttttttttt tgacactgtc caaaggtttt ccatcctgtc ctggaatcag
2461 agttggaagc tgaggagctt cagcctcttt tatggtttaa tgccacctg ttctctcctg
2521 tgaaaggctt tgcaaagtca cattaagttt gcatgacctg ttatccctgg ggcctattt
2581 catagaggct ggccctatta gtgatttcca aaaacaatat ggaagtgcct tttgatgtct
2641 tacaataaga gaagaagcca atggaaatga aagagattgg caaagggaa ggatgatgcc
2701 atgtagatcc tgtttgacat tttatggct gtatttgtaa acttaaacac accagtgtct
2761 gttcttgatg cagtgctat ttaggatgag ttaagtgcct ggggagtccc tcaaaaggtt
2821 aaagggatc ccatcattgg aatcttatca ccagatagc aagtttatga ccaaacaaga
2881 gagtactggc tttatcctct aacctcatat tttctcccac ttggcaagtc ctttgtggca
2941 tttattcatc agtcagggtg tccgattggt cctagaactt ccaaaggctg cttgtcatag
3001 aagccattgc atctataaag caacggctcc tgttaaatgg tatctccttt ctgaggctcc
```

FIG. 21L

```
3061 tactaaaagt catttgttac ctaaacttat gtgcttaaca ggcaatgctt ctcagaccac
3121 aaagcagaaa gaagaagaaa agctcctgac taaatcaggg ctgggcttag acagagttga
3181 tctgtagaat atctttaaag gagagatgtc aacttctgc actattccca gctctgctc
3241 ctcctgtct accctctcc ctccctctct cctccactt cacccacaa tcttgaaaaa
3301 cttcttct ctctgtgaa catcattggc cagatccatt ttcagtggtc tggatttctt
3361 tttatttct ttcaactg aaagaaactg gacattaggc cactatgtgt tgttactgcc
3421 actagtgttc aagtgcctct tgttttccca gagatttcct gggtctgcca gaggcccaga
3481 caggctcact caagctcttt aactgaaaag caacaagcca ctccaggaca aggtcaaaa
3541 tggttacaac agctctacc tgtcgcccca gggagaaagg ggtagtgata caagtctcat
3601 agccagagat ggttttccac tccttctaga tattcccaaa aagaggctga gacaggaggt
3661 tattttcaat tttatttgg aattaaatac tttttcctt ttattactgt tgtagtccct
3721 cacttggata tacctctgtt ttcacgatag aaataaggga ggtctagagc ttctattcct
3781 tggccattgt caacggagag ctggccaagt cttcacaaac cctgcaaca ttgcctgaag
3841 ttatggaat aagatgtatt ctcactcct tgatctcaag ggcgtaactc tggaagcaca
3901 gcttgactac acgtcatttt taccaatgat ttcaggtga cctgggctaa gtcatttaaa
3961 ctgggtcttt ataaaagtaa aaggccaaca tttaattatt ttgcaaagca acctaagagc
4021 taaagatgta attttttcttg caattgtaaa tcttttgtgt ctcctgaaga cttcccttaa
4081 aattagctct gagtgaaaaa tcaaaagaga caaaagacat cttcgaatcc atatttcaag
4141 cctggtagaa ttggcttttc tagcagaacc tttccaaaag ttttatattg agattcataa
4201 caacaccaag aattgatttt gtagccaaca ttcattcaat actgtatat cagaggagta
4261 ggagagagga aacatttgac ttatctggaa aagcaaaatg tacttaagaa taagataac
4321 atggtccatt cacctttatg ttatagatat gtctttgtgt aaatcatttg ttttgagttt
4381 tcaaagaata gccattgtt cattctgtg ctgtacaatg accactgtta ttgttactt
4441 gactttcag agcacacct tcctctggtt tttgtatatt tattgatgga tcaataataa
4501 tgaggaaagc atgatatgta tattgctgag ttgaagcac ttattggaaa atattaaaag
4561 gctaacatta aaagactaaa ggaaacagaa aaaaaaaaaa aaaaa
```

FIG. 21M

NM_001001392 transcript variant 5

```
   1 gagaagaaag ccagtgcgtc tctgggcgca ggggccagtg gggctggag gcacaggcac
  61 ccgcgacac tccaggttcc ccgacccacg tcctggcag cccgattat ttacagcctc
 121 agcagagcac gggcggggg cagaggggcc cgccgggag ggctgctact tcttaaaacc
 181 tctgcgggct gttagtcac agccccctt gcttgggtgt gtccttcgct cgtccctcc
 241 ctccgtctta ggtcactgtt ttcaacctcg aataaaaact gcagccaact tcgaggcag
 301 cctcattgcc cagcggaccc cagctctgc caggttcggt ccgccatcct cgtccgtcc
 361 tcgccggcc cctgcccgc gccaggat ctccagctc ctttcgccg cgcctccgt
 421 tgctccgga caccatggac aagtttggt ggcacgcagc ctggggactc tgcctgtgc
 481 cgctgagcct ggcgcagatc gatttgaata taacctgccg ctttgcaggt gtattccacg
 541 tggagaaaaa tgtcgctac agcatctctc ggacggagc cgctgacctc tgcaaggctt
 601 tcaatagcac cttgcccaca atggcccaga tggagaaagc tctgagcatc ggatttgaga
 661 cctgcagttt gcattgcagt caacagtcga agaaggtgtg ggcagaagaa aagctagtg
 721 atcaacagtg gcaatggagc tgtggaggac agaaagccaa gtggactcaa cgagaggcc
 781 agcaagtctc aggaaatggt gcatttggtg aacaaggagt cgtcagaaac tcagaccag
 841 tttatgacag ctgatgagac aaggaacctg cagaatgtgg acatgaagat tgggtgtaa
 901 cacctacacc attatcttgg aaagaaacaa ccgttggaaa cataaccatt acagggagct
 961 gggacactta acagatgcaa tgtgctactg attgtttcat tgcgaatctt tttagcata
1021 aaattttcta ctctttttgt ttttgtgtt ttgttcttta agtcaggtc caatttgtaa
1081 aaacagcatt gctttctgaa attagggccc aattaataat cagcaagaat tgatcgttc
1141 cagttccac ttggaggcct ttcatccctc gggtgtgcta tggatggctt ctaacaaaaa
1201 ctacatat gtattcctga tcgccaacct ttccccacc agctaaggac atttccagg
1261 gttaataggg cctggtcct gggaggaaat ttgaatgggt ccatttgcc cttccatagc
1321 ctaatccctg ggcattgctt tccactgagg ttggggttg gggtgtacta gttacacatc
1381 ttcaacagac ccctctaga aattttcag atgcttctgg gagacaccca aaggatgaag
```

FIG. 21N

```
1441 ctatttatct gtagtaaact atttatctgt gttttgaaa tattaaaccc tggatcagtc
1501 cttgatcag tataatttt taaagttact ttgtcagagg cacaaaaggg tttaaactga
1561 ttcataataa atatctgtac ttcttcgatc ttcacctttt gtgctgtgat tcttcagttt
1621 ctaaaccagc actgtctggg tcctacaat gtatcaggaa gagctgagaa tggtaaggag
1681 actcttctaa gtcttcatct cagagaccct gagttccac tcagaccac tcagccaaat
1741 ctcatggaag accaaggagg gcagcactgt tttgttttt tgtttttgt tttttttt
1801 tgacactgtc caaaggtttt ccatcctgtc ctggaatcag agttggaagc tgaggagctt
1861 cagcctcttt tatggtttaa tggccacctg ttctctcctg tgaaaggctt tgcaaagtca
1921 cattaagttt gcatgacctg tatccctgg ggcctattt catagaggct ggcctatta
1981 gtgatttcca aaacaatat ggaagtgcct tttgatgtct tacaataaga gaagaagcca
2041 atggaaatga aagagattgg caaggggaa ggatgatgcc atgtagatcc tgtttgacat
2101 ttttatggct gtatttgtaa acttaaacac accagtgtct gttcttgatg cagttgctat
2161 ttaggatgag ttaagtgcct ggggagtccc tcaaaaggtt aaagggattc ccatcattgg
2221 aatcttatca ccagataggc aagtttatga ccaaacaaga gagtactggc tttatctct
2281 aacctcatat tttctcccac ttggcaagtc ctttgtggca ttattcatc agtcagggtg
2341 tccgattggt cctagaactt ccaaaggctg cttgtcatag aagccattgc atctataaag
2401 caacggctcc tgttaaatgg tatctccttt ctgaggctcc tactaaaagt catttgttac
2461 ctaaacttat gtgcttaaca ggcaatgctt ctcagaccac aaagcagaaa gaagaagaaa
2521 agctcctgac taaatcaggg ctgggcttag acagagttga tctgtagaat atctttaaag
2581 gagagatgtc aacttctgc actattccca gcctctgctc ctccctgtct accctctccc
2641 ctccctctct ccctccactt caccccacaa tcttgaaaaa cttcctttct cttctgtgaa
2701 catcattggc cagatccatt ttcagtggtc tggattctt tttattttct tttcaactg
```

FIG. 21O

```
2761 aagaaactg gacattaggc cactatgtgt tgttactgcc actagtgttc aagtgcctct
2821 tgtttccca gagatttcct gggtctgcca gaggcccaga caggctcact caagctcttt
2881 aactgaaaag caacaagcca ctccaggaca aggttcaaaa tggttacaac agcctctacc
2941 tgtcgcccca gggagaaagg ggtagtgata caagtctcat agccagagat ggtttccac
3001 tcttctaga tattcccaaa aagaggctga gacaggaggt tatttcaat ttatttgg
3061 aattaaatac ttttttccct ttattactgt tgtagtcct cactggata tacctctgtt
3121 ttcacgatag aaataaggga ggtctagagc ttctattcct tgccattgt caacggagag
3181 ctggccaagt cttcacaaac ccttgcaaca ttgcctgaag tttatggaat aagatgtatt
3241 ctcactccct tgatctcaag gggtaactc tggaagcaca gcttgactac acgtcatttt
3301 taccaatgat tttcaggtga cctgggctaa gtcatttaaa ctgggtcttt ataaagtaa
3361 aaggccaaca tttaattatt tgcaaagca acctaagagc taagatgta atttttcttg
3421 caattgtaaa tctttgtgt ctcctgaaga cttcccttaa aattagctct gagtgaaaaa
3481 tcaaagaga caaagacat cttcgaatcc atatttcaag cctggtagaa ttggcttttc
3541 tagcagaacc tttccaaaag ttttatattg agattcataa caacaccaag aattgatttt
3601 gtagccaaca ttcattcaat actgttatat cagaggagta ggagagagga aacatttgac
3661 ttatctggaa aagcaaaatg tacttaagaa taagaataac atggtccatt caccttatg
3721 ttatagatat gtctttgtgt aaatcatttg ttttgagttt tcaaagaata gccattgtt
3781 cattcttgtg ctgtacaatg accactgtta ttgttacttt gactttcag agcacaccct
3841 tcctctggtt tttgtatatt tattgatgga tcaataataa tgaggaaagc atgatatgta
3901 tattgctgag ttgaaagcac ttattggaaa atattaaaag gctaacatta aagactaaa
3961 ggaaacagaa aaaaaaaaa aaaaa
```

FIG. 21P

X62739 Isoform identified in tumour cells

```
  1 gtacgtcttc aaataccatc tcagcaggct gggagccaaa tgaagaaaat gaagatgaaa
 61 gagacagaca cctcagtttt tctggatcag gcattgatga tgatgaagat tttatctcca
121 gcaccattc aaccacacca cgggcctttg accacacaaa acagaaccag gactggaccc
181 agtggaaccc aagccattca aatccggaag tgctacttca gacaaccaca aggatgactg
241 atgtagacag aaatggcacc actgcttatg aaggaaactg gaaccagaa gcacaccctc
301 ccctcattca ccatgagcat catgaggaag aagagaccc acattctaca agcacaatcc
361 aggcaactcc tagtagtaca acggaagaaa cagctaccca gaaggaacag tggtttggca
421 acagatggca tgagggatat cgccaaacac ccagagaaga ctccattcg acaacaggga
481 cagctgcagc ctcagctcat accagccatc caatgcaagg aagacaaca ccaagcccag
541 aggacagttc ctggactgat ttcttcaacc caatctcaca cccatggga cgaggtcatc
601 aagcaggaag aaggatggat atggactcca gtcatagtac aacgcttcag cctactgcaa
661 atccaaacac aggttggtg gaagatttgg acaggacag acctctttca atgacaacgc
721 agcagagtaa ttctcagagc ttctctacat cacatgaagg cttggaagaa gataaagacc
781 atccaacaac ttctactctg acatcaagca ataggaatga tgtcacaggt ggaagaagag
841 acccaaatca ttctgaaggc tcaactactt tactggaagg ttatacctct cattacccac
901 acaagaagga aagcaggacc ttcatcccag tgacctcagc taagactggg tcctttggag
961 ttactgcagt tactgttgga gattccaact ctaatgtcaa tcgttcctta tcag
```

FIG. 21Q

NP_000601 isoform 1 precursor

```
  1 mdkfwwhaaw glclvplsla qidlniterf agvfhvekng rysisrteaa dlckafnstl
 61 ptmagmekal sigfetcryg fleghvvipr ihpnsicaan ntgvyiltsn tsqydtycfn
121 asappeedct svtdlpnafd gpititivnr dgtryvqkge yrtnpedlyp snptdddvss
181 qsssersst s ggylfytfst vhpipdedsp witdstdrip attlmstsat atetatkrqe
241 twdwfswlfl pseskahlht ttqmagtssn tisagwepne enederdrhl sfsgsgiddd
301 edfisstist tprafdhtkg nqdwtqwmps hsnpevllqt ttrmtdvdrn gttayegnwn
361 peahpplihh enheeeetph ststiqatps stteetatqk eqwfqnrwhe gyzqtpkeds
421 hsttgtaaas ahtshpmggr ttpspedssw tdffnpishp mgrghqagrr mdmdsshsit
481 lqptanpntg lvedldrtgp lsmttqqsns qsfstshegl eedkdhptts tltssnrndv
541 tggrrdpnhs egsttllegy tshyphtkes rtfipvtsak tgsfgvtavt vqdsnsnvnr
601 slsgdqatfh psggshtthg sesdghshgs qegganttsg pirtpqipew lllaslial
661 alilavclav nsrrrcggkk klvinsgnga vedrkpsgln qeasksqemv hlvnkesset
721 pdgfmtadet mlgnvdnki gv
```

FIG. 21R

NP_001001389 isoform 2 precursor

```
  1 mdkfwwhaaw glclvplsla qidlnitcrf agvfhvekng rysisrteaa dlckafnstl
 61 ptmaqmekal slgfetcryg fleghvvipr lhpnslcaan ntgvylltsn tsqydtycfn
121 asappeedct svtdlpnafd qpititivnr dgtryvqkge yrtnpedlyp snptdddvss
181 gssserssts ggyifytfst vhplpdedsp witdstdrlp atstssntls agwepneene
241 derdrhlsfs qggidddedf isstlsttpr afdhtkqnqd wtqwnpshsn pevllqtttr
301 mtdvdrngtt ayegnwmpea hppllhhehh eeeetphsts tlqatpsstt eetatqkegw
361 fgnrwhegyr qtpkedshst tgtaaasaht shpmqgrttp spedsswtdf fnplshpmgr
421 ghcagrmdm dsshsitlqp tanpntglve dldrtqplsn ttqqsnsqsf stsheqleed
481 kdhpttstlt ssnrndvtgg rrdpnhseys ttllegytsh yphtkesrtf ipvtsaktgs
541 fgvtavtvgd snsnvnrsls qdqdtfhpsg gshtthgses dghshgsqeg qanttspir
601 tpqlpewlli lasllalali lavclavnsr rrcggkkklv lnsgngaved rkpsglngea
661 sksqemvhlv nkessetpdq fmtadetrnl qnvdmkigv
```

NP_001001390 isoform 3 precursor

```
  1 mdkfwwhaaw glclvplsla qidlnitcrf agvfhvekng rysisrteaa dlckafnstl
 61 ptmaqmekal slgfetcryg fleghvvipr lhpnslcaan ntgvylltsn tsqydtycfn
121 asappeedct svtdlpnafd qpititivnr dgtryvqkge yrtnpedlyp snptdddvss
181 gssserssts ggyifytfst vhplpdedsp witdstdrlp atnmdsshsl tlqptanpnt
241 glvedldrtq plsnttqqsn sqsfststsheg leedkdhptt stltssnrnd vtggrrdpnh
301 seqsttlleg ytshyphtke srtfipvtsa ktqsfgvtav tvgdsnsnvn rslsqdqdtf
361 hpsggshtth qsesdghshg sqeggantts qplrtpqlpe wlillaslla lalllavcla
421 vnsrrrcggk kklvlnsgng avedrkpsgl ngeasksqem vhlvnkesse tpdqfmtade
481 trnlqnvdmk igv
```

FIG. 21S

NP_001001391 Isoform 4 precursor

```
  1 mdkfwhaaw glclvplsla qidlnitcrf agvfhvekng rysisrteaa dlckafnstl
 61 ptmaqmekal sigfetcryg fleghvvipr ihpnslcaan ntgvyiltsn tsgydtycfn
121 asappeedct svtdlpnafd gpititivnr dgtryvqkge yrtnpedlyp snptdddvss
181 gssserssts ggyifytfst vhpipdedsp wltdstdrip atrdqgtfhp sggshtthgs
241 esdqhshgsq egganttsgp irtpqipewl iilasllala lilavciavn srrrcggkkk
301 lvinsgngav edrkpsglng easksqemvh lvnkessetp dqfntadetr nlgnvdnklg
361 v
```

NP_001001392 Isoform 5 precursor

```
  1 mdkfwhaaw glclvplsla qidlnitcrf agvfhvekng rysisrteaa dlckafnstl
 61 ptmaqmekal sigfetcslh csqgskkvwa eekasdqgwq wscggkakw tqrrgqqvsg
121 ngafgeqgvv rnsrpvyds
```

CAA44602 Isoform identified in tumour cells

```
  1 tssntisagw epneeneder drhlsfsgsg idddedfiss tisttprafd htkgnqdwtq
 61 wnpshsnpev llqtttrmtd vdrngttaye gnwnpeahpp lihhehheee etphststiq
121 atpsstteet atgkeqwfgn rwhegyrqtp redshsttgt aaasahtshp mggrttpspe
181 dsswtdffnp ishpmgrqhq agrmdmdss hsttlqptan pntglvedld rtgplsmttq
241 qsnsqsfsts hegleedkdh pttsltssn rndvtggrrd pnhseqsttl legytshyph
301 tkesrtfipv tsaktgsfgv tavtvgdsns nvnrsls
```

The sCD44std ELISA detects all circulating CD44 isoforms comprising the standard protein sequences (black area).

CD44 protein:  - standard protein sequences (black area)
               - Variant exons (open boxes numbered v2 - v10)

FIG. 22C

XLNITCRFAGVFHVEKNGRYSISRTEAADLCKAFNSTLPTMAQMEKALSIGFETCRYGFIEG
HVVIPRIHPNSICAANNTGVYILTSNTSQYDTYCFNASAPPEEDCTSVTDLPNAFDGPITIT
INNRDGTRYVQKGEYRTNPEDIYPSNPTDDDVSSGSSSERSSTSGGYIFYTFSTVHPIPDED
SPWLTDSTDRIPATTLMSTSATATETATKRQETNDWFSWLPLPSESKNHLHTTTQMAGTSSN
TISAGNEPNEENEDERDRHLSFSGSGIDDDEDFISSTISTTPRAFDHTKQNQDWTQWNPSHS
NPEVLLQTTTRMTDVDRNGTTAYEGNWNPEAHPPLHHEHHEEEETPHSTSTIQATPSSTTE
ETATQKEQWFGNRWHEGYRQTPKEDSHSTTGTAAASAHTSHPHQGRTTPSPEDSSWTDFFNP
ISHPMGRGHQAGRRMDMDSSHSTTLQPTANPNTGLVEDLDRTGPLSMTTQQSNSQSPSTSHE
GLEEDKDHPTTSTLTSSNRNDVTGGRRDPNHSEGSTTLLEGYTSHYPHTKESRTFIPVTSAK
TGSFGVTAVTVGDSNSNVNRSLSGDQDTFHPSGGSHTTHGSESDGHSHGSQEGGANTTSGPI
RTPQIPEWLIIIASLLALALLAVCIAVNSRRCGQKKKLVINSGNGAVEDRKPSGLNGEAS
KSQEMVHLVNKESSETPDQFMTADETRNLQNVDMKIGV

Cleavage site

SEQUENCE LISTING

```
<160> NUMBER OF SEQ ID NOS: 23

<210> SEQ ID NO 1
<211> LENGTH: 1641
<212> TYPE: DNA
<213> ORGANISM: Homo sapiens

<400> SEQUENCE: 1
ctccctgtgt tggtggagga tgtctgcagc agcatttaaa ttctgggagg gcttggttgt      60
cagcagcagc aggaggaggc agagcacagc atcgtcggga ccagactcgt ctcaggccag     120
ttgcagcctt ctcagccaaa cgccgaccaa ggaaaactca ctaccatgag aattgcagtg     180
atttgctttt gcctcctagg catcacctgt gccataccgt taaacaggc tgattctgga      240 agttctgagg aaaagcagct ttacaacaaa tacccagatg ctgtggccac atggctaaac     300
cctgacccat ctcagaagca gaatctccta gccccacaga atgctgtgtc ctctgaagaa     360
accaatgact ttaaacaaga gacccttcca agtaagtcca acgaaagcca tgaccacatg     420
gatgatatgg atgatgaaga tgatgatgac catgtggaca gccaggactc cattgactcg     480
aacgactctg atgatgtaga tgacactgat gattctcacc agtctgatga gtctcaccat     540
tctgatgaat ctgatgaact ggtcactgat tttcccacgg acctgccagc aaccgaagtt     600
ttcactccag ttgtccccac agtagacaca tatgatggcc gaggtgatag tgtggtttat     660
ggactgaggt caaaatctaa gaagtttcgc agacctgaca tccagtaccc tgatgctaca     720
gacgaggaca tcacctcaca catggaaagc gaggagttga atggtgcata caaggccatc     780
cccgttgccc aggacctgaa cgcgccttct gattgggaca gccgtgggaa ggacagttat     840
gaaacgagtc agctggatga ccagagtgct gaaacccaca gccacaagca gtccagatta     900
tataagcgga agccaatga tgagcaat gagcattccg atgtgattga tagtcaggaa      960
cttttccaaa g tcagccgtga attccacagc catgaatttc acagccatga agatatgctg    1020
```

<213> ORGANISM: Homo sapiens

<400> SEQUENCE: 2

| ctccctgtgt tggtggagga tgtctgcagc agcatttaaa ttctgggagg gcttggttgt | 60 |
| cagcagcagc aggaggaggc agagcacagc atcgtcggga ccagactcgt ctcaggccag | 120 |
| ttgcagcctt ctcagccaaa cgccgaccaa ggaaaactca ctaccatgag aattgcagtg | 180 |
| atttgctttt gcctcctagg catcacctgt gccataccag ttaaacaggc tgattctgga | 240 |
| agttctgagg aaaagcagct ttacaacaaa tacccagatg ctgtggccac atggctaaac | 300 |
| cctgacccat ctcagaagca gaatctccta gccccacaga cccttccaag taagtccaac | 360 |
| gaaagccatg accacatgga tgatatggat gatgaagatg atgatgacca tgtggacagc | 420 |
| caggactcca ttgactcgaa cgactctgat gatgtagatg acactgatga ttctcaccag | 480 |
| tctgatgagt ctcaccattc tgatgaatct gatgaactgg tcactgattt tcccacggac | 540 |
| ctgccagcaa ccgaagtttt cactccagtt gtccccacag tagacacata tgatggccga | 600 |
| ggtgatagtg tggtttatgg actgaggtca aaatctaaga agtttcgcag acctgacatc | 660 |
| cagtaccctg atgctacaga cgaggacatc acctcacaca tggaaagcga ggagttgaat | 720 |
| ggtgcataca aggccatccc cgttgcccag gacctgaacg cgccttctga ttgggacagc | 780 |
| cgtgggaagg acagttatga aacgagtcag ctggatgacc agagtgctga aacccacagc | 840 |
| cacaagcagt ccagattata aagcggaaa gccaatgatg agcaatga cattccgat | 900 |
| gtgattgata gtcaggaact ttccaaagtc agccgtgaat ccacagcca tgaatttcac | 960 |
| agccatgaag atatgctggt tgtagacccc aaaagtaagg aagaagataa acacctgaaa | 1020 |
| tttcgtattt ctcatgaatt agatagtgca tcttctgagg tcaattaaaa ggagaaaaaa | 1080 |
| tacaatttct cactttgcat ttagtcaaaa gaaaaaatgc tttatagcaa aatgaaagag | 1140 |
| aacatgaaat gcttctttct cagtttattg gttgaatgtg tatctatttg agtctggaaa | 1200 |
| taactaatgt gtttgataat tagtttagtt tgtggcttca tggaaactcc ctgtaaacta | 1260 |
| aaagcttcag ggttatgtct atgttcattc tatagaagaa atgcaaacta tcactgtatt | 1320 |
| ttaatatttg ttattctctc atgaatagaa atttatgtag aagcaaacaa aatactttta | 1380 |
| cccacttaaa aagagaatat aacatttttat gtcactataa tcttttgttt tttaagttag | 1440 |
| tgtatatttt gttgtgatta tcttttttgtg gtgtgaataa atcttttatc ttgaatgtaa | 1500 |
| taagaatttg gtggtgtcaa ttgcttattt gttttcccac ggttgtccag caattaataa | 1560 |
| aacataacct tttttactgc ctaaaaaaaa aaaaaaaaa aaaaaaaaaa aaaaaa | 1616 |

<210> SEQ ID NO 3
<211> LENGTH: 1560
<212> TYPE: DNA
<213> ORGANISM: Homo sapiens

<400> SEQUENCE: 3

| ctccctgtgt tggtggagga tgtctgcagc agcatttaaa ttctgggagg gcttggttgt | 60 |
| cagcagcagc aggaggaggc agagcacagc atcgtcggga ccagactcgt ctcaggccag | 120 |
| ttgcagcctt ctcagccaaa cgccgaccaa ggaaaactca ctaccatgag aattgcagtg | 180 |
| atttgctttt gcctcctagg catcacctgt gccataccag ttaaacaggc tgattctgga | 240 |
| agttctgagg aaaagcagaa tgctgtgtcc tctgaagaaa ccaatgactt taaacaagag | 300 |
| acccttccaa gtaagtccaa cgaaagccat gaccacatgg atgatatgga tgatgaagat | 360 |
| gatgatgacc atgtggacag ccaggactcc attgactcga acgactctga tgatgtagat | 420 |

```
gacactgatg attctcacca gtctgatgag tctcaccatt ctgatgaatc tgatgaactg    480
gtcactgatt ttcccacgga cctgccagca accgaagttt tcactccagt tgtcccaca    540 gtagacacat atgatggccg aggtgatagt gtggtttatg gactgaggtc aaaatctaag    600
aagtttcgca gacctgacat ccagtaccct gatgctacag acgaggacat cacctcacac    660
atggaaagcg aggagttgaa tggtgcatac aaggccatcc ccgttgccca ggacctgaac    720
gcgccttctg attgggacag ccgtgggaag gacagttatg aaacgagtca gctggatgac    780
cagagtgctg aaacccacag ccacaagcag tccagattat ataagcggaa agccaatgat    840
gagagcaatg agcattccga tgtgattgat agtcaggaac tttccaaagt cagccgtgaa    900
ttccacagcc atgaatttca gccatgaaga tatgctgg ttgtagaccc caaaagtaag    960
gaagaagata acaccctgaa atttcgtatt tctcatgaat tagatagtgc atcttctgag   1020
gtcaattaaa aggagaaaaa atacaatttc tcactttgca tttagtcaaa agaaaaaatg   1080
ctttatagca aaatgaaaga gaacatgaaa tgcttctttc tcagtttatt ggttgaatgt   1140
gtatctattt gagtctggaa ataactaatg tgtttgataa ttagtttagt ttgtggcttc   1200
atggaaactc cctgtaaact aaaagcttca gggttatgtc tatgttcatt ctatagaaga   1260
aatgcaaact atcactgtat tttaatattt gttattctct catgaataga aatttatgta   1320
gaagcaaaca aaatacttt acccacttaa aaagagaata taacatttta tgtcactata   1380
atcttttgtt ttttaagtta gtgtatattt tgttgtgatt atcttttttgt ggtgtgaata   1440 aatctttttat cttgaatgta ataagaattt ggtggtgtca attgcttatt tgttttccca   1500
cggttgtcca gcaattaata aaacataacc ttttttactg cctaaaaaaa aaaaaaaaaa   1560
```

<210> SEQ ID NO 4
<211> LENGTH: 314
<212> TYPE: PRT
<213> ORGANISM: Homo sapiens

<400> SEQUENCE: 4

```
Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
                20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Asn Ala Val Ser Ser Glu
        50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp His
                85                  90                  95

Val Asp Ser Gln Asp Ser Ile Asp Ser Asn Asp Ser Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175
```

```
Pro Asp Ile Gln Tyr Pro Asp Ala Thr Asp Glu Asp Ile Thr Ser His
                180                 185                 190

Met Glu Ser Glu Glu Leu Asn Gly Ala Tyr Lys Ala Ile Pro Val Ala
            195                 200                 205

Gln Asp Leu Asn Ala Pro Ser Asp Trp Asp Ser Arg Gly Lys Asp Ser
        210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
290                 295                 300

Glu Leu Asp Ser Ala Ser Ser Glu Val Asn
305                 310

<210> SEQ ID NO 5
<211> LENGTH: 300
<212> TYPE: PRT
<213> ORGANISM: Homo sapiens

<400> SEQUENCE: 5

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
                20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Thr Leu Pro Ser Lys Ser
        50                  55                  60

Asn Glu Ser His Asp His Met Asp Asp Met Asp Asp Glu Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Val Pro Thr Val Asp Thr Tyr Asp Gly
130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205

Asp Ser Tyr Glu Thr Ser Gln Leu Asp Asp Gln Ser Ala Glu Thr His
210                 215                 220

Ser His Lys Gln Ser Arg Leu Tyr Lys Arg Lys Ala Asn Asp Glu Ser
```

```
                225                 230                 235                 240
Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
                260                 265                 270

Val Asp Pro Lys Ser Lys Glu Asp Lys His Leu Lys Phe Arg Ile
                275                 280                 285

Ser His Glu Leu Asp Ser Ala Ser Ser Glu Val Asn
                290                 295                 300

<210> SEQ ID NO 6
<211> LENGTH: 287
<212> TYPE: PRT
<213> ORGANISM: Homo sapiens

<400> SEQUENCE: 6

Met Arg Ile Ala Val Ile Cys Phe Cys Leu Leu Gly Ile Thr Cys Ala
 1               5                  10                  15

Ile Pro Val Lys Gln Ala Asp Ser Gly Ser Ser Glu Glu Lys Gln Asn
                20                  25                  30

Ala Val Ser Ser Glu Glu Thr Asn Asp Phe Lys Gln Glu Thr Leu Pro
            35                  40                  45

Ser Lys Ser Asn Glu Ser His Asp His Met Asp Asp Met Asp Asp Glu
         50                  55                  60

Asp Asp Asp Asp His Val Asp Ser Gln Asp Ser Ile Asp Ser Asn Asp
65                  70                  75                  80

Ser Asp Asp Val Asp Thr Asp Asp Ser His Gln Ser Asp Glu Ser
                85                  90                  95

His His Ser Asp Glu Ser Asp Glu Leu Val Thr Asp Phe Pro Thr Asp
                100                 105                 110

Leu Pro Ala Thr Glu Val Phe Thr Pro Val Val Pro Thr Val Asp Thr
            115                 120                 125

Tyr Asp Gly Arg Gly Asp Ser Val Val Tyr Gly Leu Arg Ser Lys Ser
         130                 135                 140

Lys Lys Phe Arg Arg Pro Asp Ile Gln Tyr Pro Asp Ala Thr Asp Glu
145                 150                 155                 160

Asp Ile Thr Ser His Met Glu Ser Glu Glu Leu Asn Gly Ala Tyr Lys
                165                 170                 175

Ala Ile Pro Val Ala Gln Asp Leu Asn Ala Pro Ser Asp Trp Asp Ser
            180                 185                 190

Arg Gly Lys Asp Ser Tyr Glu Thr Ser Gln Leu Asp Asp Gln Ser Ala
         195                 200                 205

Glu Thr His Ser His Lys Gln Ser Arg Leu Tyr Lys Arg Lys Ala Asn
        210                 215                 220

Asp Glu Ser Asn Glu His Ser Asp Val Ile Asp Ser Gln Glu Leu Ser
225                 230                 235                 240

Lys Val Ser Arg Glu Phe His Ser His Glu Phe His Ser His Glu Asp
                245                 250                 255

Met Leu Val Val Asp Pro Lys Ser Lys Glu Glu Asp Lys His Leu Lys
            260                 265                 270

Phe Arg Ile Ser His Glu Leu Asp Ser Ala Ser Ser Glu Val Asn
         275                 280                 285

<210> SEQ ID NO 7
<211> LENGTH: 5748
```

```
<212> TYPE: DNA
<213> ORGANISM: Homo sapiens

<400> SEQUENCE: 7
gagaagaaag ccagtgcgtc tctgggcgca ggggccagtg gggctcggag gcacaggcac      60
cccgcgacac tccaggttcc ccgacccacg tccctggcag ccccgattat ttacagcctc     120
agcagagcac ggggcggggg cagaggggcc cgcccgggag ggctgctact tcttaaaacc     180
tctgcgggct gcttagtcac agccccccct tgcttgggtgt gtccttcgct cgctccctcc    240
ctccgtctta ggtcactgtt ttcaacctcg aataaaaact gcagccaact tccgaggcag     300
cctcattgcc cagcggaccc cagcctctgc caggttcggt ccgccatcct cgtcccgtcc     360
tccgccggcc cctgccccgc gcccagggat cctccagctc ctttcgcccg cgccctccgt     420
tcgctccgga caccatggac aagttttggt ggcacgcagc ctggggactc tgcctcgtgc     480
cgctgagcct ggcgcagatc gatttgaata taacctgccg ctttgcaggt gtattccacg     540
tggagaaaaa tggtcgctac agcatctctc ggacggaggc cgctgacctc tgcaaggctt     600
tcaatagcac cttgcccaca atggcccaga tggagaaagc tctgagcatc ggatttgaga     660
cctgcaggta tgggttcata gaagggcacg tggtgattcc ccggatccac cccaactcca     720
tctgtgcagc aaacaacaca ggggtgtaca tcctcacatc caacacctcc cagtatgaca     780
catattgctt caatgcttca gctccacctg aagaagattg tacatcagtc acagacctgc     840
ccaatgcctt tgatggacca attaccataa ctattgttaa ccgtgatggc acccgctatg     900
tccagaaagg agaatacaga acgaatcctg aagacatcta ccccagcaac cctactgatg     960
atgacgtgag cagcggctcc tccagtgaaa ggagcagcac ttcaggaggt tacatctttt    1020 acacccttttc tactgtacac cccatcccag acgaagacag tcctggatc accgacagca    1080 cagacagaat ccctgctacc actttgatga gcactagtgc tacagcaact gagacagcaa    1140
ccaagaggca agaaacctgg gattggtttt catggttgtt ctaccatcca gagtcaaaga    1200
atcatcttca cacaacaaca caaatggctg gtacgtcttc aaataccatc tcagcaggct    1260
gggagccaaa tgaagaaaat gaagatgaaa gagacagaca cctcagttttt tctggatcag    1320 gcattgatga tgatgaagat tttatctcca gcaccatttc aaccacacca cgggcttttg    1380
accacacaaa acagaaccag gactggaccc agtggaaccc aagccattca aatccggaag    1440
tgctacttca acaaccaca aggatgactg atgtagacag aaatggcacc actgcttatg    1500
aaggaaactg gaacccagaa gcacaccctc ccctcattca ccatgagcat catgaggaag    1560
aagagacccc acattctaca agcacaatcc aggcaactcc tagtagtaca cggaagaaa    1620 cagctaccca gaaggaacag tggtttggca acagatggca tgagggatat cgccaaacac    1680
ccaaagaaga ctcccattcg acaacaggga cagctgcagc ctcagctcat accagccatc    1740
caatgcaagg aaggacaaca ccaagcccag aggacagttc ctggactgat tcttcaacc    1800 caatctcaca ccccatggga cgaggtcatc aagcaggaag aaggatggat atggactcca    1860
gtcatagtat aacgcttcag cctactgcaa atccaaacac aggtttggtg aagatttgg    1920 acaggacagg acctctttca atgacaacgc agcagagtaa ttctcagagc ttctctacat    1980
cacatgaagg cttggaagaa gataaagacc atccaacaac ttctactctg acatcaagca    2040
ataggaatga tgtcacaggt ggaagaagag acccaaatca ttctgaaggc tcaactactt    2100
tactggaagg ttatacctct cattacccac acacgaagga aagcaggacc ttcatcccag    2160
tgacctcagc taagactggg tccttttggag ttactgcagt tactgttgga gattccaact    2220
```

```
ctaatgtcaa tcgttcctta tcaggagacc aagacacatt ccaccccagt ggggggtccc      2280
ataccactca tggatctgaa tcagatggac actcacatgg gagtcaagaa ggtggagcaa      2340
acacaacctc tggtcctata aggacacccc aaattccaga atggctgatc atcttggcat      2400
ccctcttggc cttggctttg attcttgcag tttgcattgc agtcaacagt cgaagaaggt      2460
gtgggcagaa gaaaaagcta gtgatcaaca gtggcaatgg agctgtggag acagaaagc       2520 caagtggact caacggagag gccagcaagt ctcaggaaat ggtgcatttg gtgaacaagg      2580
agtcgtcaga aactccagac cagtttatga cagctgatga gacaaggaac ctgcagaatg      2640
tggacatgaa gattggggtg taacaccctac accattatct ggaaagaaa caaccgttgg      2700 aaacataacc attacaggga gctgggacac ttaacagatg caatgtgcta ctgattgttt      2760
cattgcgaat cttttttagc ataaaatttt ctactctttt tgttttttgt gttttgttct      2820
ttaaagtcag gtccaatttg taaaaacagc attgctttct gaaattaggg cccaattaat      2880
aatcagcaag aatttgatcg ttccagttcc cacttggagg cctttcatcc ctcgggtgtg      2940
ctatggatgg cttctaacaa aaactacaca tatgtattcc tgatcgccaa cctttccccc      3000
accagctaag gacatttccc agggttaata gggcctggtc cctgggagga aatttgaatg      3060
ggtccatttt gccttccat agcctaatcc ctgggcattg cttccactg aggttggggg       3120 ttggggtgta ctagttacac atcttcaaca gacccctct agaaattttt cagatgcttc      3180
tgggagacac ccaaagggtg aagctattta tctgtagtaa actatttatc tgtgtttttg     3240
aaatattaaa ccctggatca gtcctttgat cagtataatt ttttaaagtt actttgtcag     3300
aggcacaaaa gggtttaaac tgattcataa taaatatctg tacttcttcg atcttcacct     3360
tttgtgctgt gattcttcag tttctaaacc agcactgtct gggtccctac aatgtatcag     3420 gaaagagctga gaatggtaag gagactcttc taagtcttca tctcagagac cctgagttcc    3480
cactcagacc cactcagcca aatctcatgg aagaccaagg agggcagcac tgttttgtt     3540 ttttgttttt tgtttttttt ttttgacact gtccaaaggt tttccatcct gtcctggaat     3600
cagagttgga agctgaggag cttcagcctc ttttatggtt taatggccac ctgttctctc     3660
ctgtgaaagg ctttgcaaag tcacattaag tttgcatgac ctgttatccc tggggcccta    3720
tttcatagag gctggcccta ttagtgattt ccaaaaacaa tatggaagtg ccttttgatg    3780
tcttacaata agagaagaag ccaatggaaa tgaaagagat tggcaaaggg gaaggatgat   3840
gccatgtaga tcctgtttga cattttttatg gctgtatttg taaacttaaa cacaccagtg   3900
tctgttcttg atgcagttgc tatttaggat gagttaagtg cctggggagt ccctcaaaag   3960
gttaaaggga ttcccatcat tggaatctta tcaccagata ggcaagttta tgaccaaaca   4020
agagagtact ggctttatcc tctaacctca tatttctcc cacttggcaa gtcctttgtg     4080
gcatttattc atcagtcagg gtgtccgatt ggtcctagaa cttccaaagg ctgcttgtca   4140
tagaagccat tgcatctata aagcaacggc tcctgttaaa tggtatctcc tttctgaggc   4200
tcctactaaa agtcattgt tacctaaact tatgtgctta acaggcaatg cttctcagac    4260
cacaaagcag aaagaagaag aaaagctcct gactaaatca gggctgggct tagacagagt   4320
tgatctgtag aatatcttta aaggagagat gtcaactttc tgcactattc ccagcctctg   4380
ctcctccctg tctaccctct cccctccctc tctccctcca cttcacccca caatcttgaa   4440
aaacttcctt tctcttctgt gaacatcatt ggccagatcc attttcagtg gtctggattt   4500
ctttttattt tcttttcaac ttgaaagaaa ctggacatta ggccactatg tgttgttact   4560
gccactagtg ttcaagtgcc tcttgttttc ccagagattt cctgggtctg ccagaggccc   4620
```

```
agacaggctc actcaagctc tttaactgaa aagcaacaag ccactccagg acaaggttca    4680
aaatggttac aacagcctct acctgtcgcc ccagggagaa aggggtagtg atacaagtct    4740
catagccaga gatggttttc cactccttct agatattccc aaaaagaggc tgagacagga    4800
ggttattttc aattttattt tggaattaaa tactttttc cctttattac tgttgtagtc     4860
cctcacttgg atatacctct gttttcacga tagaaataag ggaggtctag agcttctatt    4920
ccttggccat tgtcaacgga gagctggcca agtcttcaca aacccttgca acattgcctg    4980
aagtttatgg aataagatgt attctcactc ccttgatctc aagggcgtaa ctctggaagc    5040
acagcttgac tacacgtcat ttttaccaat gattttcagg tgacctgggc taagtcattt    5100
aaactgggtc tttataaaag taaaaggcca acatttaatt attttgcaaa gcaacctaag    5160
agctaaagat gtaattttc ttgcaattgt aaatcttttg tgtctcctga agacttccct     5220
taaaattagc tctgagtgaa aaatcaaaag agacaaaaga catcttcgaa tccatatttc    5280
aagcctggta gaattggctt ttctagcaga acctttccaa aagttttata ttgagattca    5340
taacaacacc aagaattgat tttgtagcca acattcattc aatactgtta tatcagagga    5400
gtaggagaga ggaaacattt gacttatctg gaaaagcaaa atgtacttaa gaataagaat    5460
aacatggtcc attcaccttt atgttataga tatgtctttg tgtaaatcat ttgttttgag    5520
ttttcaaaga atagcccatt gttcattctt gtgctgtaca atgaccactg ttattgttac    5580
tttgactttt cagagcacac ccttcctctg gtttttgtat atttattgat ggatcaataa    5640
taatgaggaa agcatgatat gtatattgct gagttgaaag cacttattgg aaaatattaa    5700
aaggctaaca ttaaaagact aaaggaaaca gaaaaaaaaa aaaaaaaa                 5748

<210> SEQ ID NO 8
<211> LENGTH: 5619
<212> TYPE: DNA
<213> ORGANISM: Homo sapiens

<400> SEQUENCE: 8
gagaagaaag ccagtgcgtc tctgggcgca ggggccagtg gggctcggag gcacaggcac      60
cccgcgacac tccaggttcc ccgacccacg tccctggcag ccccgattat ttacagcctc    120
agcagagcac ggggcggggg cagaggggcc cgcccgggag ggctgctact tcttaaaacc    180
tctgcgggct gcttagtcac agcccccctt gcttgggtgt gtccttcgct cgctccctcc    240
ctccgtctta ggtcactgtt ttcaacctcg aataaaaact gcagccaact tccgaggcag    300
cctcattgcc cagcggaccc cagcctctgc caggttcggt ccgccatcct cgtcccgtcc    360
tccgccggcc cctgccccgc gcccagggat cctccagctc ctttcgcccg cgccctccgt    420
tcgctccgga caccatggac aagttttggt ggcacgcagc tgggactc tgcctcgtgc       480 cgctgagcct ggcgcagatc gatttgaata taacctgccg cttttgcaggt gtattccacg    540 tggagaaaaa tggtcgctac agcatctctc ggacggaggc cgctgacctc tgcaaggctt    600
tcaatagcac cttgcccaca atggcccaga tggagaaagc tctgagcatc ggatttgaga    660
cctgcaggta tgggttcata gaagggcacg tggtgattcc ccggatccac cccaactcca    720
tctgtgcagc aaacaacaca ggggtgtaca tcctcacatc caacacctcc agtatgaca    780 catattgctt caatgcttca gctccacctg aagaagattg tacatcagtc acagacctgc    840
ccaatgcctt tgatggacca attaccataa ctattgttaa ccgtgatggc acccgctatg    900
tccagaaagg agaatacaga acgaatcctg aagcacatcta ccccagcaac cctactgatg    960
```

-continued

```
atgacgtgag cagcggctcc tccagtgaaa ggagcagcac ttcaggaggt tacatctttt    1020
acaccttttc tactgtacac cccatcccag acgaagacag tccctggatc accgacagca    1080
cagacagaat ccctgctacc agtacgtctt caaataccat ctcagcaggc tgggagccaa    1140
atgaagaaaa tgaagatgaa agagacagac acctcagttt ttctggatca ggcattgatg    1200
atgatgaaga tttatctcc agcaccattt caaccacacc acgggctttt gaccacacaa     1260
aacagaacca ggactggacc cagtggaacc caagccattc aaatccggaa gtgctacttc    1320
agacaaccac aaggatgact gatgtagaca gaaatggcac cactgcttat gaaggaaact    1380
ggaacccaga agcacaccct cccctcattc accatgagca tcatgaggaa gagagaccc     1440 cacattctac aagcacaatc caggcaactc ctagtagtac aacggaagaa acagctaccc    1500
agaaggaaca gtggtttggc aacagatggc atgagggata tcgccaaaca cccaaagaag    1560
actcccattc gacaacaggg acagctgcag cctcagctca taccagccat ccaatgcaag    1620
gaaggacaac accaagccca gaggacagtt cctggactga tttcttcaac ccaatctcac    1680
accccatggg acgaggtcat caagcaggaa gaaggatgga tatggactcc agtcatagta    1740
taacgcttca gcctactgca aatccaaaca caggtttggt ggaagatttg acaggacag    1800 gacctctttc aatgacaacg cagcagagta attctcagag cttctctaca tcacatgaag    1860
gcttggaaga agataaagac catccaacaa cttctactct gacatcaagc aataggaatg    1920
atgtcacagg tggaagaaga gacccaaatc attctgaagg ctcaactact ttactggaag    1980
gttatacctc tcattaccca cacacgaagg aaagcaggac cttcatccca gtgacctcag    2040
ctaagactgg gtcctttgga gttactgcag ttactgttgg agattccaac tctaatgtca    2100
atcgttcctt atcaggagac caagacacat tccaccccag tgggggtgcc cataccactc    2160
atggatctga atcagatgga cactcacatg ggagtcaaga aggtggagca acacaacct    2220 ctggtcctat aaggacaccc caaattccag aatggctgat catcttggca tccctcttgg    2280
ccttggcttt gattcttgca gtttgcattg cagtcaacag tcgaagaagg tgtgggcaga    2340
agaaaaagct agtgatcaac agtggcaatg gagctgtgga ggacagaaag ccaagtggac    2400
tcaacggaga ggccagcaag tctcaggaaa tggtgcattt ggtgaacaag gagtcgtcag    2460
aaactccaga ccagtttatg acagctgatg agacaaggaa cctgcagaat gtggacatga    2520
agattggggt gtaacaccta caccattatc ttggaaagaa acaaccgttg gaaacataac    2580
cattacaggg agctgggaca cttaacagat gcaatgtgct actgattgtt tcattgcgaa    2640
tcttttttag cataaaattt tctactcttt ttgtttttg tgtttgttc tttaaagtca     2700 ggtccaattt gtaaaaacag cattgctttc tgaaattagg gcccaattaa taatcagcaa    2760
gaatttgatc gttccagttc ccacttggag gcctttcatc cctcgggtgt gctatggatg    2820
gcttctaaca aaaactacac atatgtattc ctgatcgcca acctttcccc caccagctaa    2880
ggacatttcc cagggttaat agggcctggt ccctgggagg aaatttgaat gggtccattt    2940
tgcccttcca tagcctaatc cctgggcatt gctttccact gaggttgggg gttggggtgt    3000
actagttaca catcttcaac agaccccctc tagaaatttt tcagatgctt ctgggagaca    3060
cccaaagggt gaagctattt atctgtagta aactatttat ctgtgttttt gaaatattaa    3120
accctggatc agtcctttga tcagtataat tttttaaagt tactttgtca gaggcacaaa    3180
agggtttaaa ctgattcata ataaatatct gtacttcttc gatcttcacc ttttgtgctg    3240
tgattcttca gttctaaaac cagcactgtc tgggtccta caatgtatca ggaagagctg     3300
agaatggtaa ggagactctt ctaagtcttc atctcagaga ccctgagttc ccactcagac    3360
```

```
ccactcagcc aaatctcatg gaagaccaag gagggcagca ctgttttgt ttttgtttt      3420
ttgttttttt ttttgacac tgtccaaagg ttttccatcc tgtcctggaa tcagagttgg     3480
aagctgagga gcttcagcct cttttatggt ttaatggcca cctgttctct cctgtgaaag   3540
gctttgcaaa gtcacattaa gtttgcatga cctgttatcc ctggggccct atttcataga   3600
ggctggccct attagtgatt tccaaaaaca atatggaagt gccttttgat gtcttacaat   3660
aagagaagaa gccaatggaa atgaaagaga ttggcaaagg ggaaggatga tgccatgtag   3720
atcctgtttg acatttttat ggctgtattt gtaaacttaa acacaccagt gtctgttctt   3780
gatgcagttg ctatttagga tgagttaagt gcctggggag tccctcaaaa ggttaaaggg   3840
attcccatca ttggaatctt atcaccagat aggcaagttt atgaccaaac aagagagtac   3900
tggctttatc ctctaacctc atattttctc ccacttggca agtcctttgt ggcatttatt   3960
catcagtcag ggtgtccgat tggtcctaga acttccaaag gctgcttgtc atagaagcca   4020
ttgcatctat aaagcaacgg ctcctgttaa atggtatctc ctttctgagg ctcctactaa   4080
aagtcatttg ttacctaaac ttatgtgctt aacaggcaat gcttctcaga ccacaaagca   4140
gaaagaagaa gaaagctcc tgactaaatc agggctgggc ttagacagag ttgatctgta   4200
gaatatcttt aaaggagaga tgtcaacttt ctgcactatt cccagcctct gctcctccct   4260
gtctaccctc tccctccct ctctccctcc acttcacccc acaatcttga aaaacttcct    4320
ttctcttctg tgaacatcat tggccagatc cattttcagt ggtctggatt tcttttatt    4380
ttcttttcaa cttgaaagaa actggacatt aggccactat gtgttgttac tgccactagt   4440
gttcaagtgc ctcttgtttt cccagagatt tcctgggtct gccagaggcc cagacaggct   4500
cactcaagct ctttaactga aaagcaacaa gccactccag acaaggttc aaaatggtta    4560
caacagcctc tacctgtcgc cccagggaga aaggggtagt gatacaagtc tcatagccag   4620
agatggtttt ccactccttc tagatattcc caaaaagagg ctgagacagg aggttatttt   4680
caatttatt ttggaattaa atactttttt ccctttatta ctgttgtagt ccctcacttg    4740
gatatacctc tgttttcacg atagaaataa gggaggtcta gagcttctat tccttggcca   4800
ttgtcaacgg agagctggcc aagtcttcac aaacccttgc aacattgcct gaagtttatg   4860
gaataagatg tattctcact cccttgatct caagggcgta actctggaag cacagcttga   4920
ctacacgtca ttttaccaa tgattttcag gtgacctggg ctaagtcatt taaactgggt    4980
ctttataaaa gtaaaaggcc aacatttaat tattttgcaa agcaacctaa gagctaaaga   5040
tgtaattttt cttgcaattg taaatctttt gtgtctcctg aagacttccc ttaaaattag   5100
ctctgagtga aaaatcaaaa gagacaaaag acatcttcga atccatattt caagcctggt   5160
agaattggct tttctagcag aacctttcca aaagttttat attgagattc ataacaacac   5220
caagaattga ttttgtagcc aacattcatt caatactgtt atatcagagg agtaggagag   5280
aggaaacatt tgacttatct ggaaaagcaa aatgtactta agaataagaa taacatggtc   5340
cattcacctt tatgttatag atatgtcttt gtgtaaatca tttgttttga gttttcaaag   5400
aatagcccat tgttcattct tgtgctgtac aatgaccact gttattgtta ctttgacttt   5460
tcagagcaca cccttcctct ggttttgta tattattga tggatcaata ataatgagga    5520
aagcatgata tgtatattgc tgagttgaaa gcacttattg gaaaatatta aaaggctaac   5580
attaaaagac taaggaaac agaaaaaaaa aaaaaaaa                            5619
```

<210> SEQ ID NO 9

<211> LENGTH: 5001
<212> TYPE: DNA
<213> ORGANISM: Homo sapiens

<400> SEQUENCE: 9

| | | | | | |
|---|---|---|---|---|---|
| gagaagaaag | ccagtgcgtc | tctgggcgca | ggggccagtg | gggctcggag | gcacaggcac | 60 |
| cccgcgacac | tccaggttcc | ccgacccacg | tccctggcag | ccccgattat | ttacagcctc | 120 |
| agcagagcac | ggggcggggg | cagaggggcc | cgcccgggag | ggctgctact | tcttaaaacc | 180 |
| tctgcgggct | gcttagtcac | agccccccctt | gcttgggtgt | gtccttcgct | cgctccctcc | 240 |
| ctccgtctta | ggtcactgtt | ttcaacctcg | aataaaaact | gcagccaact | tccgaggcag | 300 |
| cctcattgcc | cagcggaccc | cagcctctgc | caggttcggt | ccgccatcct | cgtcccgtcc | 360 |
| tccgccggcc | cctgccccgc | gcccagggat | cctccagctc | ctttcgcccg | cgccctccgt | 420 |
| tcgctccgga | caccatggac | aagttttggt | ggcacgcagc | ctgggactc | tgcctcgtgc | 480 |
| cgctgagcct | ggcgcagatc | gatttgaata | taacctgccg | ctttgcaggt | gtattccacg | 540 |
| tggagaaaaa | tggtcgctac | agcatctctc | ggacggaggc | cgctgacctc | tgcaaggctt | 600 |
| tcaatagcac | cttgcccaca | atggcccaga | tggagaaagc | tctgagcatc | ggatttgaga | 660 |
| cctgcaggta | tgggttcata | gaagggcacg | tggtgattcc | ccggatccac | cccaactcca | 720 |
| tctgtgcagc | aaacaacaca | ggggtgtaca | tcctcacatc | caacacctcc | cagtatgaca | 780 |
| catattgctt | caatgcttca | gctccacctg | aagaagattg | tacatcagtc | acagacctgc | 840 |
| ccaatgcctt | tgatggacca | attaccataa | ctattgttaa | ccgtgatggc | acccgctatg | 900 |
| tccagaaagg | agaatacaga | acgaatcctg | aagcatcta | ccccagcaac | cctactgatg | 960 |
| atgacgtgag | cagcggctcc | tccagtgaaa | ggagcagcac | ttcaggaggt | tacatctttt | 1020 |
| acacctttc | tactgtacac | cccatcccag | acgaagacac | tccctggatc | accgacagca | 1080 |
| cagacagaat | ccctgctacc | aatatggact | ccagtcatag | tataacgctt | cagcctactg | 1140 |
| caaatccaaa | cacaggtttg | gtggaagatt | tggacaggac | aggacctctt | tcaatgacaa | 1200 |
| cgcagcagag | taattctcag | agcttctcta | catcacatga | aggcttggaa | gaagataaag | 1260 |
| accatccaac | aacttctact | ctgacatcaa | gcaataggaa | tgatgtcaca | ggtggaagaa | 1320 |
| gagacccaaa | tcattctgaa | ggctcaacta | ctttactgga | aggttatacc | tctcattacc | 1380 |
| cacacacgaa | ggaaagcagg | accttcatcc | cagtgacctc | agctaagact | gggtcctttg | 1440 |
| gagttactgc | agttactgtt | ggagattcca | actctaatgt | caatcgttcc | ttatcaggag | 1500 |
| accaagacac | attccacccc | agtgggggt | cccataccac | tcatggatct | gaatcagatg | 1560 |
| gacactcaca | tgggagtcaa | gaaggtggag | caaacacaac | ctctggtcct | ataaggacac | 1620 |
| cccaaattcc | agaatggctg | atcatcttgg | catccctctt | ggccttggct | ttgattcttg | 1680 |
| cagtttgcat | tgcagtcaac | agtcgaagaa | ggtgtgggca | gaagaaaaag | ctagtgatca | 1740 |
| acagtggcaa | tggagctgtg | gaggacagaa | agccaagtgg | actcaacgga | gaggccagca | 1800 |
| agtctcagga | aatggtgcat | ttggtgaaca | aggagtcgtc | agaaactcca | gaccagttta | 1860 |
| tgacagctga | tgagacaagg | aacctgcaga | atgtggacat | gaagattggg | gtgtaacacc | 1920 |
| tacaccatta | tcttggaaag | aaacaaccgt | tggaaacata | accattacag | ggagctggga | 1980 |
| cacttaacag | atgcaatgtg | ctactgattg | tttcattgcg | aatctttttt | agcataaaat | 2040 |
| tttctactct | ttttgttttt | tgtgttttgt | tctttaaagt | caggtccaat | ttgtaaaaac | 2100 |
| agcattgctt | tctgaaatta | gggcccaatt | aataatcagc | aagaatttga | tcgttccagt | 2160 |
| tcccacttgg | aggcctttca | tccctcgggt | gtgctatgga | tggcttctaa | caaaaactac | 2220 |

```
acatatgtat tcctgatcgc caacctttcc cccaccagct aaggacattt cccagggtta    2280
ataggcctg  gtccctggga ggaaatttga atgggtccat tttgcccttc catagcctaa    2340
tccctgggca ttgcttttca ctgaggttgg gggttggggt gtactagtta cacatcttca    2400
acagaccccc tctagaaatt tttcagatgc ttctgggaga cacccaaagg gtgaagctat   2460
ttatctgtag taaactattt atctgtgttt ttgaaatatt aaaccctgga tcagtccttt    2520
gatcagtata atttttaaa  gttactttgt cagaggcaca aaagggttta aactgattca    2580
taataaatat ctgtacttct tcgatcttca ccttttgtgc tgtgattctt cagtttctaa    2640
accagcactg tctgggtccc tacaatgtat caggaagagc tgagaatggt aaggagactc    2700
ttctaagtct tcatctcaga gaccctgagt tcccactcag acccactcag ccaaatctca    2760
tggaagacca aggagggcag cactgttttt gttttttgtt tttttgtttt tttttttgac    2820
actgtccaaa ggttttccat cctgtcctgg aatcagagtt ggaagctgag gagcttcagc    2880
ctcttttatg gttaatggc  cacctgttct ctcctgtgaa aggctttgca aagtcacatt    2940
aagtttgcat gacctgttat ccctggggcc ctatttcata gaggctggcc ctattagtga    3000
tttccaaaaa caatatggaa gtgccttttg atgtcttaca ataagagaag aagccaatgg    3060
aaatgaaaga gattggcaaa ggggaaggat gatgccatgt agatcctgtt tgacattttt    3120
atggctgtat ttgtaaactt aaacacacca gtgtctgttc ttgatgcagt tgctatttag    3180
gatgagttaa gtgcctgggg agtccctcaa aaggttaaag ggattcccat cattggaatc    3240
ttatcaccag ataggcaagt ttatgaccaa acaagagagt actggcttta tcctctaacc    3300
tcatattttc tcccacttgg caagtccttt gtggcattta ttcatcagtc agggtgtccg    3360
attggtccta gaacttccaa aggctgcttg tcatagaagc cattgcatct ataaagcaac    3420
ggctcctgtt aaatggtatc tccttttctga ggctcctact aaaagtcatt tgttacctaa    3480
acttatgtgc ttaacaggca atgcttctca gaccacaaag cagaaagaag aagaaaagct    3540
cctgactaaa tcagggctgg gcttagacag agttgatctg tagaatatct ttaaaggaga    3600
gatgtcaact ttctgcacta ttcccagcct ctgctcctcc ctgtctaccc tctcccctcc    3660
ctctctccct ccacttcacc ccacaatctt gaaaaacttc cttttctctttc tgtgaacatc    3720
attggccaga tccattttca gtggtctgga tttcttttta ttttcttttc aacttgaaag    3780
aaactggaca ttaggccact atgtgttgtt actgccacta gtgttcaagt gcctcttgtt    3840
ttcccagaga tttcctgggt ctgccagagg cccagacagg ctcactcaag ctctttaact    3900
gaaaagcaac aagccactcc aggacaaggt tcaaatggt  tacaacagcc tctacctgtc    3960
gccccaggga gaagggta  gtgatacaag tctcatagcc agagatggtt ttccactcct    4020
tctagatatt cccaaaaaga ggctgagaca ggaggttatt ttcaatttta ttttggaatt    4080
aaatactttt ttccctttat tactgttgta gtccctcact tggatatacc tctgttttca    4140
cgatagaaat aagggaggtc tagagcttct attccttggc cattgtcaac ggagagctgg    4200
ccaagtcttc acaaacccctt gcaacattgc ctgaagttta tggaataaga tgtattctca    4260
ctcccttgat ctcaagggcg taactctgga agcacagctt gactacacgt cattttttacc    4320
aatgattttc agtgacctg  ggctaagtca tttaaactgg gtcttataa  aagtaaaagg    4380
ccaacattta attattttgc aaagcaacct aagagctaaa gatgtaattt tcttgcaat     4440
tgtaaatctt ttgtgtctcc tgaagacttc ccttaaaatt agctctgagt gaaaaatcaa    4500
aagagacaaa agacatcttc gaatccatat ttcaagcctg gtagaattgg cttttctagc    4560
```

| | | | | | |
|---|---|---|---|---|---|
| agaaccttc | caaaagtttt | atattgagat | tcataacaac | accaagaatt | gattttgtag | 4620 |
| ccaacattca | ttcaatactg | ttatatcaga | ggagtaggag | agaggaaaca | tttgacttat | 4680 |
| ctggaaaagc | aaaatgtact | taagaataag | aataacatgg | tccattcacc | tttatgttat | 4740 |
| agatatgtct | ttgtgtaaat | catttgtttt | gagttttcaa | agaatagccc | attgttcatt | 4800 |
| cttgtgctgt | acaatgacca | ctgttattgt | tactttgact | tttcagagca | caccccttcct | 4860 |
| ctggttttg | tatattatt | gatggatcaa | taataatgag | gaaagcatga | tatgtatatt | 4920 |
| gctgagttga | aagcacttat | tggaaaatat | taaaaggcta | acattaaaag | actaaaggaa | 4980 |
| acagaaaaaa | aaaaaaaaaaa | a | | | | 5001 |

<210> SEQ ID NO 10
<211> LENGTH: 4605
<212> TYPE: DNA
<213> ORGANISM: Homo sapiens

<400> SEQUENCE: 10

| | | | | | |
|---|---|---|---|---|---|
| gagaagaaag | ccagtgcgtc | tctgggcgca | ggggccagtg | gggctcggag | gcacaggcac | 60 |
| cccgcgacac | tccaggttcc | ccgacccacg | tccctggcag | ccccgattat | ttacagcctc | 120 |
| agcagagcac | ggggcggggg | cagaggggcc | cgcccgggag | ggctgctact | tcttaaaacc | 180 |
| tctgcgggct | gcttagtcac | agccccccctt | gcttgggtgt | gtccttcgct | cgctccctcc | 240 |
| ctccgtctta | ggtcactgtt | ttcaacctcg | aataaaaact | gcagccaact | tccgaggcag | 300 |
| cctcattgcc | cagcggaccc | cagcctctgc | caggttcggt | ccgccatcct | cgtcccgtcc | 360 |
| tccgccggcc | cctgccccgc | gcccagggat | cctccagctc | ctttcgcccg | cgccctccgt | 420 |
| tcgctccgga | caccatggac | aagttttggt | ggcacgcagc | ctgggactc | tgcctcgtgc | 480 |
| cgctgagcct | ggcgcagatc | gatttgaata | taacctgccg | ctttgcaggt | gtattccacg | 540 |
| tggagaaaaa | tggtcgctac | agcatctctc | ggacggaggc | cgctgacctc | tgcaaggctt | 600 |
| tcaatagcac | cttgcccaca | atggcccaga | tggagaaagc | tctgagcatc | ggatttgaga | 660 |
| cctgcaggta | tgggttcata | gaagggcacg | tggtgattcc | ccggatccac | cccaactcca | 720 |
| tctgtgcagc | aaacaacaca | ggggtgtaca | tcctcacatc | caacacctcc | cagtatgaca | 780 |
| catattgctt | caatgcttca | gctccacctg | aagaagattg | tacatcagtc | acagacctgc | 840 |
| ccaatgcctt | tgatgaccca | attaccataa | ctattgttaa | ccgtgatggc | acccgctatg | 900 |
| tccagaaagg | agaatacaga | acgaatcctg | aagcatctca | ccccagcaac | cctactgatg | 960 |
| atgacgtgag | cagcggctcc | tccagtgaaa | ggagcagcac | ttcaggaggt | tacatctttt | 1020 |
| acaccttttc | tactgtacac | cccatcccag | acgaagacag | tccctggatc | accgacagca | 1080 |
| cagacagaat | ccctgctacc | agagaccaag | acacattcca | ccccagtggg | gggtcccata | 1140 |
| ccactcatgg | atctgaatca | gatggacact | cacatgggag | tcaagaaggt | ggagcaaaca | 1200 |
| caacctctgg | tcctataagg | acaccccaaa | ttccagaatg | gctgatcatc | ttggcatccc | 1260 |
| tcttggcctt | ggctttgatt | cttgcagttt | gcattgcagt | caacagtcga | agaaggtgtg | 1320 |
| ggcagaagaa | aaagctagtg | atcaacagtg | gcaatggagc | tgtggaggac | agaaagccaa | 1380 |
| gtggactcaa | cggagaggcc | agcaagtctc | aggaaatggt | gcatttggtg | aacaaggagt | 1440 |
| cgtcagaaac | tccagaccag | tttatgacag | ctgatgagac | aaggaacctg | cagaatgtgg | 1500 |
| acatgaagat | tgggggtgtaa | cacctacacc | attatcttgg | aaagaaacaa | ccgttggaaa | 1560 |
| cataaccatt | acagggagct | gggacactta | acagatgcaa | tgtgctactg | attgtttcat | 1620 |
| tgcgaatctt | ttttagcata | aaattttcta | ctcttttgt | ttttgtgtt | ttgttctta | 1680 |

```
aagtcaggtc caatttgtaa aaacagcatt gctttctgaa attagggccc aattaataat   1740
cagcaagaat ttgatcgttc cagttcccac ttggaggcct ttcatccctc gggtgtgcta   1800
tggatggctt ctaacaaaaa ctacacatat gtattcctga tcgccaacct ttcccccacc   1860
agctaaggac atttcccagg gttaataggg cctggtccct ggggaggaaat ttgaatgggt   1920 ccattttgcc cttccatagc ctaatccctg ggcattgctt tccactgagg ttggggttg    1980 gggtgtacta gttacacatc ttcaacagac cccctctaga aatttttcag atgcttctgg   2040
gagacaccca aagggtgaag ctatttatct gtagtaaact atttatctgt gttttttgaaa  2100 tattaaaccc tggatcagtc ctttgatcag tataatttt taaagttact ttgtcagagg    2160
cacaaaaggg tttaaactga ttcataataa atatctgtac ttcttcgatc ttcaccttttt  2220 gtgctgtgat tcttcagttt ctaaaccagc actgtctggg tccctacaat gtatcaggaa   2280
gagctgagaa tggtaaggag actcttctaa gtcttcatct cagagaccct gagttcccac   2340
tcagacccac tcagccaaat ctcatggaag accaaggagg gcagcactgt ttttgttttt    2400
tgttttttgt ttttttttt tgacactgtc caaaggtttt ccatcctgtc ctggaatcag    2460
agttggaagc tgaggagctt cagcctcttt tatggtttaa tggccacctg ttctctcctg   2520
tgaaaggctt tgcaaagtca cattaagttt gcatgacctg ttatccctgg ggccctattt   2580
catagaggct ggccctatta gtgatttcca aaaacaatat ggaagtgcct tttgatgtct   2640
tacaataaga gaagaagcca atggaaatga agagattgg caaggggaa ggatgatgcc     2700 atgtagatcc tgtttgacat ttttatggct gtatttgtaa acttaaacac accagtgtct   2760
gttcttgatg cagttgctat ttaggatgag ttaagtgcct ggggagtccc tcaaaaggtt   2820
aaagggattc ccatcattgg aatcttatca ccagataggc aagtttatga ccaaacaaga   2880
gagtactggc tttatcctct aacctcatat tttctcccac ttggcaagtc ctttgtggca   2940
tttattcatc agtcagggtg tccgattggt cctagaactt ccaaaggctg cttgtcatag   3000
aagccattgc atctataaag caacggctcc tgttaaatgg tatctccttt ctgaggctcc   3060
tactaaaagt catttgttac ctaaacttat gtgcttaaca ggcaatgctt ctcagaccac   3120 aaaagcagaaa gaagaagaaa agctcctgac taaatcaggg ctgggcttag acagagttga  3180
tctgtagaat atctttaaag gagagatgtc aactttctgc actattccca gcctctgctc   3240
ctccctgtct accctctccc ctccctctct ccctccactt caccccacaa tcttgaaaaa   3300
cttcctttct cttctgtgaa catcattggc cagatccatt ttcagtggtc tggatttctt   3360
tttattttct tttcaacttg aaagaaactg gacattaggc cactatgtgt tgttactgcc   3420
actagtgttc aagtgcctct tgtttttccca gagatttcct gggtctgcca gaggcccaga   3480
caggctcact caagctcttt aactgaaaag caacaagcca ctccaggaca aggttcaaaa   3540
tggttacaac agcctctacc tgtcgcccca gggagaaagg ggtagtgata caagtctcat   3600
agccagagat ggttttccac tccttctaga tattcccaaa aagaggctga acaggaggt    3660 tattttcaat tttatttttgg aattaaatac tttttttccct ttattactgt tgtagtccct  3720
cacttggata tacctctgtt ttcacgatag aaataaggga ggtctagagc ttctattcct   3780
tggccattgt caacggagag ctggccaagt cttcacaaac ccttgcaaca ttgcctgaag   3840
tttatggaat aagatgtatt ctcactccct tgatctcaag ggcgtaactc tggaagcaca   3900
gcttgactac acgtcatttt taccaatgat tttcaggtga cctgggctaa gtcatttaaa   3960
ctgggtcttt ataaaagtaa aaggccaaca tttaattatt ttgcaaagca acctaagagc   4020
```

| | |
|---|---|
| taaagatgta attttttcttg caattgtaaa tcttttgtgt ctcctgaaga cttcccttaa | 4080 |
| aattagctct gagtgaaaaa tcaaaagaga caaaagacat cttcgaatcc atatttcaag | 4140 |
| cctggtagaa ttggctttc tagcagaacc tttccaaaag ttttatattg agattcataa | 4200 |
| caacaccaag aattgatttt gtagccaaca ttcattcaat actgttatat cagaggagta | 4260 |
| ggagagagga acatttgac ttatctggaa aagcaaaatg tacttaagaa taagaataac | 4320 |
| atggtccatt caccttttatg ttatagatat gtctttgtgt aaatcatttg ttttgagttt | 4380 |
| tcaaagaata gcccattgtt cattcttgtg ctgtacaatg accactgtta ttgttacttt | 4440 |
| gacttttcag agcacaccct tcctctggtt tttgtatatt tattgatgga tcaataataa | 4500 |
| tgaggaaagc atgatatgta tattgctgag ttgaaagcac ttattggaaa atattaaaag | 4560 |
| gctaacatta aaagactaaa ggaaacagaa aaaaaaaaa aaaaa | 4605 |

<210> SEQ ID NO 11
<211> LENGTH: 3985
<212> TYPE: DNA
<213> ORGANISM: Homo sapiens

<400> SEQUENCE: 11

| | |
|---|---|
| gagaagaaag ccagtgcgtc tctgggcgca ggggccagtg gggctcggag gcacaggcac | 60 |
| cccgcgacac tccaggttcc ccgacccacg tccctggcag cccccgattat ttacagcctc | 120 |
| agcagagcac ggggcggggg cagaggggcc cgcccgggag gctgctact tcttaaaacc | 180 |
| tctgcgggct gcttagtcac agcccccctt gcttgggtgt gtccttcgct cgctccctcc | 240 |
| ctccgtctta ggtcactgtt ttcaacctcg aataaaaact gcagccaact tccgaggcag | 300 |
| cctcattgcc cagcggaccc cagcctctgc caggttcggt ccgccatcct cgtcccgtcc | 360 |
| tccgccggcc cctgccccgc gcccagggat cctccagctc ctttcgcccg cgccctccgt | 420 |
| tcgctccgga caccatggac aagttttggt ggcacgcagc ctggggactc tgcctcgtgc | 480 |
| cgctgagcct ggcgcagatc gatttgaata taacctgccg ctttgcaggt gtattccacg | 540 |
| tggagaaaaa tggtcgctac agcatctctc ggacggaggc cgctgacctc tgcaaggctt | 600 |
| tcaatagcac cttgcccaca atggcccaga tggagaaagc tctgagcatc ggatttgaga | 660 |
| cctgcagttt gcattgcagt caacagtcga agaaggtgtg ggcagaagaa aaagctagtg | 720 |
| atcaacagtg gcaatggagc tgtggaggac agaaagccaa gtggactcaa cggagaggcc | 780 |
| agcaagtctc aggaaatggt gcatttggtg aacaaggagt cgtcagaaac tccagaccag | 840 |
| tttatgacag ctgatgagac aaggaacctg cagaatgtgg acatgaagat tggggtgtaa | 900 |
| cacctacacc attatcttgg aaagaaacaa ccgttggaaa cataaccatt acagggagct | 960 |
| gggacactta acagatgcaa tgtgctactg attgtttcat tgcgaatctt ttttagcata | 1020 |
| aaatttctca ctcttttttgt tttttgtgtt ttgttctttta aagtcaggtc caatttgtaa | 1080 |
| aaacagcatt gctttctgaa attagggccc aattaataat cagcaagaat ttgatcgttc | 1140 |
| cagttcccac ttggaggcct ttcatccctc gggtgtgcta tggatggctt ctaacaaaaa | 1200 |
| ctacacatat gtattcctga tcgccaacct ttccccaccc agctaaggac atttcccagg | 1260 |
| gttaataggg cctggtccct gggaggaaat ttgaatgggt ccattttgcc cttccatagc | 1320 |
| ctaatccctg ggcattgctt tccactgagg ttgggggttg gggtgtacta gttacacatc | 1380 |
| ttcaacagac cccctctaga aatttttcag atgcttctgg gagacaccca aagggtgaag | 1440 |
| ctatttatct gtagtaaact atttatctgt gttttttgaaa tattaaaccc tggatcagtc | 1500 |
| ctttgatcag tataattttt taaagttact ttgtcagagg cacaaaaggg tttaaactga | 1560 |

```
ttcataataa atatctgtac ttcttcgatc ttcacctttt gtgctgtgat tcttcagttt    1620
ctaaaccagc actgtctggg tccctacaat gtatcaggaa gagctgagaa tggtaaggag    1680
actcttctaa gtcttcatct cagagaccct gagttcccac tcagacccac tcagccaaat    1740
ctcatggaag accaaggagg gcagcactgt ttttgttttt tgtttttgt ttttttttt    1800 tgacactgtc caaaggtttt ccatcctgtc ctggaatcag agttggaagc tgaggagctt    1860
cagcctcttt tatggtttaa tggccacctg ttctctcctg tgaaaggctt tgcaaagtca    1920
cattaagttt gcatgacctg ttatccctgg ggccctattt catagaggct ggccctatta    1980
gtgatttcca aaacaatat ggaagtgcct tttgatgtct tacaataaga gaagaagcca    2040
atggaaatga aagagattgg caaagggaa ggatgatgcc atgtagatcc tgtttgacat    2100
ttttatggct gtatttgtaa acttaaacac accagtgtct gttcttgatg cagttgctat    2160
ttaggatgag ttaagtgcct ggggagtccc tcaaaaggtt aaagggattc ccatcattgg    2220
aatcttatca ccagataggc aagtttatga ccaaacaaga gagtactggc tttatcctct    2280
aacctcatat tttctcccac ttggcaagtc ctttgtggca tttattcatc agtcagggtg    2340
tccgattggt cctagaactt ccaaaggctg cttgtcatag aagccattgc atctataaag    2400
caacggctcc tgttaaatgg tatctccttt ctgaggctcc tactaaaagt catttgttac    2460
ctaaacttat gtgcttaaca ggcaatgctt ctcagaccac aaagcagaaa gaagaagaaa    2520
agctcctgac taaatcaggg ctgggcttag acagagttga tctgtagaat atctttaaag    2580
gagagatgtc aactttctgc actattccca gcctctgctc ctccctgtct accctctccc    2640
ctccctctct ccctccactt caccccacaa tcttgaaaaa cttccttct cttctgtgaa    2700 catcattggc cagatccatt tcagtggtc tggatttctt tttatttct tttcaacttg    2760 aaagaaactg gacattaggc cactatgtgt tgttactgcc actagtgttc aagtgcctct    2820
tgttttccca gagatttcct gggtctgcca gaggcccaga caggctcact caagctcttt    2880
aactgaaaag caacaagcca ctccaggaca aggttcaaaa tggttacaac agcctctacc    2940
tgtcgcccca gggagaaagg ggtagtgata caagtctcat agccagagat ggttttccac    3000
tccttctaga tattcccaaa aagaggctga acaggaggt tattttcaat tttatttgg    3060 aattaaatac ttttttccct ttattactgt tgtagtccct cacttggata tacctctgtt    3120
ttcacgatag aaataaggga ggtctagagc ttctattcct tggccattgt caacggagag    3180
ctggccaagt cttcacaaac ccttgcaaca ttgcctgaag tttatggaat aagatgtatt    3240
ctcactccct tgatctcaag ggcgtaactc tggaagcaca gcttgactac acgtcatttt    3300
taccaatgat tttcaggtga cctgggctaa gtcatttaaa ctgggtcttt ataaaagtaa    3360
aaggccaaca tttaattatt ttgcaaagca acctaagagc taaagatgta atttttcttg    3420
caattgtaaa tcttttgtgt ctcctgaaga cttcccttaa aattagctct gagtgaaaaa    3480
tcaaaagaga caaagacat cttcgaatcc atatttcaag cctggtagaa ttggcttttc    3540
tagcagaacc tttccaaaag ttttatattg agattcataa caacaccaag aattgatttt    3600
gtagccaaca ttcattcaat actgttatat cagaggagta ggagagagga aacatttgac    3660
ttatctggaa aagcaaaatg tacttaagaa taagaataac atggtccatt caccttttatg    3720 ttatagatat gtcttttgtgt aaatcatttg ttttgagttt tcaaagaata gcccattgtt    3780
cattcttgtg ctgtacaatg accactgtta ttgttacttt gactttcag agcacaccct    3840 tcctctggtt tttgtatatt tattgatgga tcaataataa tgaggaaagc atgatatgta    3900
```

-continued

```
tattgctgag ttgaaagcac ttattggaaa atattaaaag gctaacatta aaagactaaa    3960
ggaaacagaa aaaaaaaaaa aaaaa                                          3985

<210> SEQ ID NO 12
<211> LENGTH: 1014
<212> TYPE: DNA
<213> ORGANISM: Homo sapiens

<400> SEQUENCE: 12
gtacgtcttc aaataccatc tcagcaggct gggagccaaa tgaagaaaat gaagatgaaa      60
gagacagaca cctcagtttt tctggatcag gcattgatga tgatgaagat tttatctcca     120
gcaccatttc aaccacacca cgggcctttg accacacaaa acagaaccag gactggaccc     180
agtggaaccc aagccattca aatccggaag tgctacttca gacaaccaca aggatgactg     240
atgtagacag aaatggcacc actgcttatg aaggaaactg gaacccagaa gcacaccctc     300
ccctcattca ccatgagcat catgaggaag aagagacccc acattctaca agcacaatcc     360
aggcaactcc tagtagtaca acggaagaaa cagctaccca gaaggaacag tggtttggca     420
acagatggca tgagggatat cgccaaacac ccagagaaga ctcccattcg acaacaggga     480
cagctgcagc ctcagctcat accagccatc aatgcaagg aaggacaaca ccaagcccag     540
aggacagttc ctggactgat ttcttcaacc caatctcaca ccccatggga cgaggtcatc     600
aagcaggaag aaggatggat atggactcca gtcatagtac aacgcttcag cctactgcaa     660
atccaaacac aggtttggtg aagatttgg acaggacagg acctctttca atgacaacgc     720
agcagagtaa ttctcagagc ttctctacat cacatgaagg cttggaagaa gataaagacc     780
atccaacaac ttctactctg acatcaagca ataggaatga tgtcacaggt ggaagaagag     840
acccaaatca ttctgaaggc tcaactactt tactggaagg ttatacctct cattacccac     900
acacgaagga agcaggacc ttcatcccag tgacctcagc taagactggg tcctttggag     960
ttactgcagt tactgttgga gattccaact ctaatgtcaa tcgttcctta tcag         1014

<210> SEQ ID NO 13
<211> LENGTH: 742
<212> TYPE: PRT
<213> ORGANISM: Homo sapiens

<400> SEQUENCE: 13

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
```

```
            130                 135                 140
Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
                260                 265                 270

Ser Ala Gly Trp Glu Pro Asn Glu Glu Asn Glu Asp Glu Arg Asp Arg
            275                 280                 285

His Leu Ser Phe Ser Gly Ser Gly Ile Asp Asp Glu Asp Phe Ile
        290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
                340                 345                 350

Thr Ala Tyr Glu Gly Asn Trp Asn Pro Glu Ala His Pro Pro Leu Ile
            355                 360                 365

His His Glu His His Glu Glu Glu Thr Pro His Ser Thr Ser Thr
        370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ser Ala His
                420                 425                 430

Thr Ser His Pro Met Gln Gly Arg Thr Thr Pro Ser Pro Glu Asp Ser
            435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560
```

```
Thr Ser His Tyr Pro His Thr Lys Glu Ser Arg Thr Phe Ile Pro Val
            565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
            595                 600                 605

Phe His Pro Ser Gly Ser His Thr Thr His Gly Ser Glu Ser Asp
            610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
            645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
            675                 680                 685

Gly Ala Val Glu Asp Arg Lys Pro Ser Gly Leu Asn Gly Glu Ala Ser
            690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
            725                 730                 735

Asp Met Lys Ile Gly Val
            740

<210> SEQ ID NO 14
<211> LENGTH: 699
<212> TYPE: PRT
<213> ORGANISM: Homo sapiens

<400> SEQUENCE: 14

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
            35                  40                  45

Ala Ala Asp Leu Cys Lys Ala Phe Asn Ser Thr Leu Pro Thr Met Ala
        50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
            85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
            115                 120                 125

Cys Thr Ser Val Thr Asp Leu Pro Asn Ala Phe Asp Gly Pro Ile Thr
            130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
            165                 170                 175

Asp Val Ser Ser Gly Ser Ser Ser Glu Arg Ser Ser Thr Ser Gly Gly
```

```
                180             185              190
Tyr Ile Phe Tyr Thr Phe Ser Thr Val His Pro Ile Pro Asp Glu Asp
            195                 200                 205
Ser Pro Trp Ile Thr Asp Ser Thr Asp Arg Ile Pro Ala Thr Ser Thr
    210                 215                 220
Ser Ser Asn Thr Ile Ser Ala Gly Trp Glu Pro Asn Glu Glu Asn Glu
225                 230                 235                 240
Asp Glu Arg Asp Arg His Leu Ser Phe Ser Gly Ser Gly Ile Asp Asp
                245                 250                 255
Asp Glu Asp Phe Ile Ser Ser Thr Ile Ser Thr Thr Pro Arg Ala Phe
            260                 265                 270
Asp His Thr Lys Gln Asn Gln Asp Trp Thr Gln Trp Asn Pro Ser His
        275                 280                 285
Ser Asn Pro Glu Val Leu Leu Gln Thr Thr Arg Met Thr Asp Val
    290                 295                 300
Asp Arg Asn Gly Thr Thr Ala Tyr Glu Gly Asn Trp Asn Pro Glu Ala
305                 310                 315                 320
His Pro Pro Leu Ile His His Glu His His Glu Glu Glu Glu Thr Pro
                325                 330                 335
His Ser Thr Ser Thr Ile Gln Ala Thr Pro Ser Ser Thr Thr Glu Glu
                340                 345                 350
Thr Ala Thr Gln Lys Glu Gln Trp Phe Gly Asn Arg Trp His Glu Gly
            355                 360                 365
Tyr Arg Gln Thr Pro Lys Glu Asp Ser His Ser Thr Thr Gly Thr Ala
        370                 375                 380
Ala Ala Ser Ala His Thr Ser His Pro Met Gln Gly Arg Thr Thr Pro
385                 390                 395                 400
Ser Pro Glu Asp Ser Ser Trp Thr Asp Phe Phe Asn Pro Ile Ser His
                405                 410                 415
Pro Met Gly Arg Gly His Gln Ala Gly Arg Arg Met Asp Met Asp Ser
                420                 425                 430
Ser His Ser Ile Thr Leu Gln Pro Thr Ala Asn Pro Asn Thr Gly Leu
            435                 440                 445
Val Glu Asp Leu Asp Arg Thr Gly Pro Leu Ser Met Thr Thr Gln Gln
        450                 455                 460
Ser Asn Ser Gln Ser Phe Ser Thr Ser His Glu Gly Leu Glu Glu Asp
465                 470                 475                 480
Lys Asp His Pro Thr Thr Ser Thr Leu Thr Ser Ser Asn Arg Asn Asp
                485                 490                 495
Val Thr Gly Gly Arg Arg Asp Pro Asn His Ser Glu Gly Ser Thr Thr
                500                 505                 510
Leu Leu Glu Gly Tyr Thr Ser His Tyr Pro His Thr Lys Glu Ser Arg
            515                 520                 525
Thr Phe Ile Pro Val Thr Ser Ala Lys Thr Gly Ser Phe Gly Val Thr
        530                 535                 540
Ala Val Thr Val Gly Asp Ser Asn Ser Asn Val Asn Arg Ser Leu Ser
545                 550                 555                 560
Gly Asp Gln Asp Thr Phe His Pro Ser Gly Gly Ser His Thr Thr His
                565                 570                 575
Gly Ser Glu Ser Asp Gly His Ser His Gly Ser Gln Glu Gly Gly Ala
                580                 585                 590
Asn Thr Thr Ser Gly Pro Ile Arg Thr Pro Gln Ile Pro Glu Trp Leu
            595                 600                 605
```

```
Ile Ile Leu Ala Ser Leu Leu Ala Leu Ile Leu Ala Val Cys
        610                 615                 620
Ile Ala Val Asn Ser Arg Arg Cys Gly Gln Lys Lys Leu Val
625                 630                 635                 640
Ile Asn Ser Gly Asn Gly Ala Val Glu Asp Arg Lys Pro Ser Gly Leu
                    645                 650                 655
Asn Gly Glu Ala Ser Lys Ser Gln Glu Met Val His Leu Val Asn Lys
                660                 665                 670
Glu Ser Ser Glu Thr Pro Asp Gln Phe Met Thr Ala Asp Glu Thr Arg
                675                 680                 685
Asn Leu Gln Asn Val Asp Met Lys Ile Gly Val
                690                 695

<210> SEQ ID NO 15
<211> LENGTH: 493
<212> TYPE: PRT
<213> ORGANISM: Homo sapiens

<400> SEQUENCE: 15

Met Asp Lys Phe Trp Trp His Ala Ala Trp Gly Leu Cys Leu Val Pro
1               5                   10                  15
Leu Ser Leu Ala Gln Ile Asp Leu Asn Ile Thr Cys Arg Phe Ala Gly
            20                  25                  30
Val Phe His Val Glu Lys Asn Gly Arg Tyr Ser Ile Ser Arg Thr Glu
        35                  40                  45
Ala Ala Asp Leu Cys Lys Ala Phe Asn Ser Thr Leu Pro Thr Met Ala
    50                  55                  60
Gln Met Glu Lys Ala Leu Ser Ile Gly Phe Glu Thr Cys Arg Tyr Gly
65                  70                  75                  80
Phe Ile Glu Gly His Val Val Ile Pro Arg Ile His Pro Asn Ser Ile
                85                  90                  95
Cys Ala Ala Asn Asn Thr Gly Val Tyr Ile Leu Thr Ser Asn Thr Ser
            100                 105                 110
Gln Tyr Asp Thr Tyr Cys Phe Asn Ala Ser Ala Pro Pro Glu Glu Asp
        115                 120                 125
Cys Thr Ser Val Thr Asp Leu Pro Asn Ala Phe Asp Gly Pro Ile Thr
    130                 135                 140
Ile Thr Ile Val Asn Arg Asp Gly Thr Arg Tyr Val Gln Lys Gly Glu
145                 150                 155                 160
Tyr Arg Thr Asn Pro Glu Asp Ile Tyr Pro Ser Asn Pro Thr Asp Asp
                165                 170                 175
Asp Val Ser Ser Gly Ser Ser Ser Glu Arg Ser Ser Thr Ser Gly Gly
            180                 185                 190
Tyr Ile Phe Tyr Thr Phe Ser Thr Val His Pro Ile Pro Asp Glu Asp
        195                 200                 205
Ser Pro Trp Ile Thr Asp Ser Thr Asp Arg Ile Pro Ala Thr Asn Met
    210                 215                 220
Asp Ser Ser His Ser Ile Thr Leu Gln Pro Thr Ala Asn Pro Asn Thr
225                 230                 235                 240
Gly Leu Val Glu Asp Leu Asp Arg Thr Gly Pro Leu Ser Met Thr Thr
                245                 250                 255
Gln Gln Ser Asn Ser Gln Ser Phe Ser Thr Ser His Glu Gly Leu Glu
            260                 265                 270
Glu Asp Lys Asp His Pro Thr Thr Ser Thr Leu Thr Ser Ser Asn Arg
```

```
                    275                 280                 285
Asn Asp Val Thr Gly Arg Arg Asp Pro Asn His Ser Glu Gly Ser
            290                 295                 300
Thr Thr Leu Leu Glu Gly Tyr Thr Ser His Tyr Pro His Thr Lys Glu
305                 310                 315                 320
Ser Arg Thr Phe Ile Pro Val Thr Ser Ala Lys Thr Gly Ser Phe Gly
                325                 330                 335
Val Thr Ala Val Thr Val Gly Asp Ser Asn Ser Asn Val Asn Arg Ser
            340                 345                 350
Leu Ser Gly Asp Gln Asp Thr Phe His Pro Ser Gly Gly Ser His Thr
        355                 360                 365
Thr His Gly Ser Glu Ser Asp Gly His Ser His Gly Ser Gln Glu Gly
370                 375                 380
Gly Ala Asn Thr Thr Ser Gly Pro Ile Arg Thr Pro Gln Ile Pro Glu
385                 390                 395                 400
Trp Leu Ile Ile Leu Ala Ser Leu Leu Ala Leu Ala Leu Ile Leu Ala
                405                 410                 415
Val Cys Ile Ala Val Asn Ser Arg Arg Arg Cys Gly Gln Lys Lys Lys
                420                 425                 430
Leu Val Ile Asn Ser Gly Asn Gly Ala Val Glu Asp Arg Lys Pro Ser
            435                 440                 445
Gly Leu Asn Gly Glu Ala Ser Lys Ser Gln Glu Met Val His Leu Val
        450                 455                 460
Asn Lys Glu Ser Ser Glu Thr Pro Asp Gln Phe Met Thr Ala Asp Glu
465                 470                 475                 480
Thr Arg Asn Leu Gln Asn Val Asp Met Lys Ile Gly Val
                485                 490

<210> SEQ ID NO 16
<211> LENGTH: 361
<212> TYPE: PRT
<213> ORGANISM: Homo sapiens

<400> SEQUENCE: 16

Met Asp Lys Phe Trp Trp His Ala Ala Trp Gly Leu Cys Leu Val Pro
1               5                   10                  15
Leu Ser Leu Ala Gln Ile Asp Leu Asn Ile Thr Cys Arg Phe Ala Gly
            20                  25                  30
Val Phe His Val Glu Lys Asn Gly Arg Tyr Ser Ile Ser Arg Thr Glu
        35                  40                  45
Ala Ala Asp Leu Cys Lys Ala Phe Asn Ser Thr Leu Pro Thr Met Ala
    50                  55                  60
Gln Met Glu Lys Ala Leu Ser Ile Gly Phe Glu Thr Cys Arg Tyr Gly
65                  70                  75                  80
Phe Ile Glu Gly His Val Val Ile Pro Arg Ile His Pro Asn Ser Ile
                85                  90                  95
Cys Ala Ala Asn Asn Thr Gly Val Tyr Ile Leu Thr Ser Asn Thr Ser
            100                 105                 110
Gln Tyr Asp Thr Tyr Cys Phe Asn Ala Ser Ala Pro Pro Glu Glu Asp
        115                 120                 125
Cys Thr Ser Val Thr Asp Leu Pro Asn Ala Phe Asp Gly Pro Ile Thr
    130                 135                 140
Ile Thr Ile Val Asn Arg Asp Gly Thr Arg Tyr Val Gln Lys Gly Glu
145                 150                 155                 160
```

```
Tyr Arg Thr Asn Pro Glu Asp Ile Tyr Pro Ser Asn Pro Thr Asp Asp
                165                 170                 175

Asp Val Ser Ser Gly Ser Ser Glu Arg Ser Ser Thr Ser Gly Gly
        180                 185                 190

Tyr Ile Phe Tyr Thr Phe Ser Thr Val His Pro Ile Pro Asp Glu Asp
            195                 200                 205

Ser Pro Trp Ile Thr Asp Ser Thr Asp Arg Ile Pro Ala Thr Arg Asp
        210                 215                 220

Gln Asp Thr Phe His Pro Ser Gly Gly Ser His Thr Thr His Gly Ser
225                 230                 235                 240

Glu Ser Asp Gly His Ser His Gly Ser Gln Glu Gly Gly Ala Asn Thr
                245                 250                 255

Thr Ser Gly Pro Ile Arg Thr Pro Gln Ile Pro Glu Trp Leu Ile Ile
                260                 265                 270

Leu Ala Ser Leu Leu Ala Leu Ala Leu Ile Leu Ala Val Cys Ile Ala
            275                 280                 285

Val Asn Ser Arg Arg Arg Cys Gly Gln Lys Lys Lys Leu Val Ile Asn
        290                 295                 300

Ser Gly Asn Gly Ala Val Glu Asp Arg Lys Pro Ser Gly Leu Asn Gly
305                 310                 315                 320

Glu Ala Ser Lys Ser Gln Glu Met Val His Leu Val Asn Lys Glu Ser
                325                 330                 335

Ser Glu Thr Pro Asp Gln Phe Met Thr Ala Asp Glu Thr Arg Asn Leu
                340                 345                 350

Gln Asn Val Asp Met Lys Ile Gly Val
            355                 360

<210> SEQ ID NO 17
<211> LENGTH: 139
<212> TYPE: PRT
<213> ORGANISM: Homo sapiens

<400> SEQUENCE: 17

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Ser Leu His
65                  70                  75                  80

Cys Ser Gln Gln Ser Lys Lys Val Trp Ala Glu Lys Ala Ser Asp
                85                  90                  95

Gln Gln Trp Gln Trp Ser Cys Gly Gly Gln Lys Ala Lys Trp Thr Gln
                100                 105                 110

Arg Arg Gly Gln Gln Val Ser Gly Asn Gly Ala Phe Gly Glu Gln Gly
            115                 120                 125

Val Val Arg Asn Ser Arg Pro Val Tyr Asp Ser
        130                 135

<210> SEQ ID NO 18
<211> LENGTH: 337
<212> TYPE: PRT
<213> ORGANISM: Homo sapiens
```

<400> SEQUENCE: 18

```
Thr Ser Ser Asn Thr Ile Ser Ala Gly Trp Glu Pro Asn Glu Asn
1               5                   10                  15

Glu Asp Glu Arg Asp Arg His Leu Ser Phe Ser Gly Ser Gly Ile Asp
            20                  25                  30

Asp Asp Glu Asp Phe Ile Ser Ser Thr Ile Ser Thr Thr Pro Arg Ala
            35                  40                  45

Phe Asp His Thr Lys Gln Asn Gln Asp Trp Thr Gln Trp Asn Pro Ser
50                  55                  60

His Ser Asn Pro Glu Val Leu Leu Gln Thr Thr Thr Arg Met Thr Asp
65                  70                      75                  80

Val Asp Arg Asn Gly Thr Thr Ala Tyr Glu Gly Asn Trp Asn Pro Glu
            85                  90                  95

Ala His Pro Pro Leu Ile His His Glu His His Glu Glu Glu Glu Thr
            100                 105                 110

Pro His Ser Thr Ser Thr Ile Gln Ala Thr Pro Ser Thr Thr Thr Glu
            115                 120                 125

Glu Thr Ala Thr Gln Lys Glu Gln Trp Phe Gly Asn Arg Trp His Glu
130                 135                 140

Gly Tyr Arg Gln Thr Pro Arg Glu Asp Ser His Ser Thr Thr Gly Thr
145                 150                 155                 160

Ala Ala Ala Ser Ala His Thr Ser His Pro Met Gln Gly Arg Thr Thr
            165                 170                 175

Pro Ser Pro Glu Asp Ser Ser Trp Thr Asp Phe Phe Asn Pro Ile Ser
            180                 185                 190

His Pro Met Gly Arg Gly His Gln Ala Gly Arg Arg Met Asp Met Asp
            195                 200                 205

Ser Ser His Ser Thr Thr Leu Gln Pro Thr Ala Asn Pro Asn Thr Gly
            210                 215                 220

Leu Val Glu Asp Leu Asp Arg Thr Gly Pro Leu Ser Met Thr Thr Gln
225                 230                 235                 240

Gln Ser Asn Ser Gln Ser Phe Ser Thr Ser His Glu Gly Leu Glu Glu
            245                 250                 255

Asp Lys Asp His Pro Thr Thr Ser Thr Leu Thr Ser Ser Asn Arg Asn
            260                 265                 270

Asp Val Thr Gly Gly Arg Arg Asp Pro Asn His Ser Glu Gly Ser Thr
            275                 280                 285

Thr Leu Leu Glu Gly Tyr Thr Ser His Tyr Pro His Thr Lys Glu Ser
            290                 295                 300

Arg Thr Phe Ile Pro Val Thr Ser Ala Lys Thr Gly Ser Phe Gly Val
305                 310                 315                 320

Thr Ala Val Thr Val Gly Asp Ser Asn Ser Asn Val Asn Arg Ser Leu
            325                 330                 335

Ser
```

<210> SEQ ID NO 19
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 19
acactttcac tccaatcgtc c          21

<210> SEQ ID NO 20
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 20
tgccctttcc gttgttgtcc                                                    20

<210> SEQ ID NO 21
<211> LENGTH: 18
<212> TYPE: DNA
<213> ORGANISM: Artificial sequence
<220> FEATURE:
<223> OTHER INFORMATION: Oligonucleotide primer

<400> SEQUENCE: 21
ggaaatcgtg cgtgacat                                                      18

<210> SEQ ID NO 22
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 22
tcatgatgga gttgaatgta gtt                                                23

<210> SEQ ID NO 23
<211> LENGTH: 720
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 23

Xaa Leu Asn Ile Thr Cys Arg Phe Ala Gly Val Phe His Val Glu Lys
1               5                   10                  15

Asn Gly Arg Tyr Ser Ile Ser Arg Thr Glu Ala Ala Asp Leu Cys Lys
            20                  25                  30

Ala Phe Asn Ser Thr Leu Pro Thr Met Ala Gln Met Glu Lys Ala Leu
        35                  40                  45

Ser Ile Gly Phe Glu Thr Cys Arg Tyr Gly Phe Ile Glu Gly His Val
    50                  55                  60

Val Ile Pro Arg Ile His Pro Asn Ser Ile Cys Ala Ala Asn Asn Thr
65                  70                  75                  80

Gly Val Tyr Ile Leu Thr Ser Asn Thr Ser Gln Tyr Asp Thr Tyr Cys
                85                  90                  95

Phe Asn Ala Ser Ala Pro Pro Glu Glu Asp Cys Thr Ser Val Thr Asp
            100                 105                 110

Leu Pro Asn Ala Phe Asp Gly Pro Ile Thr Ile Thr Ile Val Asn Arg
        115                 120                 125

Asp Gly Thr Arg Tyr Val Gln Lys Gly Glu Tyr Arg Thr Asn Pro Glu
    130                 135                 140

Asp Ile Tyr Pro Ser Asn Pro Thr Asp Asp Val Ser Ser Gly Ser
145                 150                 155                 160

-continued

```
Ser Ser Glu Arg Ser Ser Thr Ser Gly Gly Tyr Ile Phe Tyr Thr Phe
            165                 170                 175
Ser Thr Val His Pro Ile Pro Asp Glu Asp Ser Pro Trp Ile Thr Asp
            180                 185                 190
Ser Thr Asp Arg Ile Pro Ala Thr Thr Leu Met Ser Thr Ser Ala Thr
            195                 200                 205
Ala Thr Glu Thr Ala Thr Lys Arg Gln Glu Thr Trp Asp Trp Phe Ser
210                 215                 220
Trp Leu Phe Leu Pro Ser Glu Ser Lys Asn His Leu His Thr Thr Thr
225                 230                 235                 240
Gln Met Ala Gly Thr Ser Ser Asn Thr Ile Ser Ala Gly Trp Glu Pro
            245                 250                 255
Asn Glu Glu Asn Glu Asp Glu Arg Asp Arg His Leu Ser Phe Ser Gly
            260                 265                 270
Ser Gly Ile Asp Asp Asp Glu Asp Phe Ile Ser Ser Thr Ile Ser Thr
            275                 280                 285
Thr Pro Arg Ala Phe Asp His Thr Lys Gln Asn Gln Asp Trp Thr Gln
            290                 295                 300
Trp Asn Pro Ser His Ser Asn Pro Glu Val Leu Leu Gln Thr Thr Thr
305                 310                 315                 320
Arg Met Thr Asp Val Asp Arg Asn Gly Thr Thr Ala Tyr Glu Gly Asn
            325                 330                 335
Trp Asn Pro Glu Ala His Pro Pro Leu Ile His His Glu His His Glu
            340                 345                 350
Glu Glu Glu Thr Pro His Ser Thr Ser Thr Ile Gln Ala Thr Pro Ser
            355                 360                 365
Ser Thr Thr Glu Glu Thr Ala Thr Gln Lys Glu Gln Trp Phe Gly Asn
            370                 375                 380
Arg Trp His Glu Gly Tyr Arg Gln Thr Pro Lys Glu Asp Ser His Ser
385                 390                 395                 400
Thr Thr Gly Thr Ala Ala Ala Ser Ala His Thr Ser His Pro Met Gln
            405                 410                 415
Gly Arg Thr Thr Pro Ser Pro Glu Asp Ser Ser Trp Thr Asp Phe Phe
            420                 425                 430
Asn Pro Ile Ser His Pro Met Gly Arg Gly His Gln Ala Gly Arg Arg
            435                 440                 445
Met Asp Met Asp Ser Ser His Ser Ile Thr Leu Gln Pro Thr Ala Asn
450                 455                 460
Pro Asn Thr Gly Leu Val Glu Asp Leu Asp Arg Thr Gly Pro Leu Ser
465                 470                 475                 480
Met Thr Thr Gln Gln Ser Asn Ser Gln Ser Phe Ser Thr Ser His Glu
            485                 490                 495
Gly Leu Glu Glu Asp Lys Asp His Pro Thr Thr Ser Thr Leu Thr Ser
            500                 505                 510
Ser Asn Arg Asn Asp Val Thr Gly Gly Arg Arg Asp Pro Asn His Ser
            515                 520                 525
Glu Gly Ser Thr Thr Leu Leu Glu Gly Tyr Thr Ser His Tyr Pro His
            530                 535                 540
Thr Lys Glu Ser Arg Thr Phe Ile Pro Val Thr Ser Ala Lys Thr Gly
545                 550                 555                 560
Ser Phe Gly Val Thr Ala Val Thr Val Gly Asp Ser Asn Ser Asn Val
            565                 570                 575
Asn Arg Ser Leu Ser Gly Asp Gln Asp Thr Phe His Pro Ser Gly Gly
```

-continued

|  |  |  |  |  | 580 |  |  |  |  | 585 |  |  |  |  | 590 |  |  |
|---|---|---|---|---|---|---|---|---|---|---|---|---|---|---|---|---|---|
| Ser | His | Thr 595 | Thr | His | Gly | Ser | Glu 600 | Ser | Asp | Gly | His | Ser 605 | His | Gly | Ser |
| Gln | Glu 610 | Gly | Gly | Ala | Asn | Thr 615 | Thr | Ser | Gly | Pro | Ile 620 | Arg | Thr | Pro | Gln |
| Ile 625 | Pro | Glu | Trp | Leu | Ile 630 | Ile | Leu | Ala | Ser | Leu 635 | Leu | Ala | Leu | Ala | Leu 640 |
| Ile | Leu | Ala | Val | Cys 645 | Ile | Ala | Val | Asn | Ser 650 | Arg | Arg | Arg | Cys | Gly 655 | Gln |
| Lys | Lys | Lys | Leu 660 | Val | Ile | Asn | Ser | Gly 665 | Asn | Gly | Ala | Val | Glu 670 | Asp | Arg |
| Lys | Pro | Ser 675 | Gly | Leu | Asn | Gly | Glu 680 | Ala | Ser | Lys | Ser | Gln 685 | Glu | Met | Val |
| His | Leu | Val | Asn | Lys | Glu | Ser 695 | Ser | Glu | Thr | Pro | Asp 700 | Gln | Phe | Met | Thr |
|  | 690 |  |  |  |  |  |  |  |  |  |  |  |  |  |  |
| Ala 705 | Asp | Glu | Thr | Arg | Asn 710 | Leu | Gln | Asn | Val | Asp 715 | Met | Lys | Ile | Gly | Val 720 |

METHODS FOR THE PREVENTION OR TREATMENT OF SCOLIOSIS

CROSS REFERENCE TO RELATED APPLICATIONS

This Application is a Continuation Application of U.S. patent application Ser. No. 13/775,069, filed Feb. 22, 2013, now abandoned, which is a Continuation Application of U.S. patent application Ser. No. 12/594,181, filed Sep. 30, 2009, now abandoned, which is a National Entry Application of PCT Application Serial No. PCT/CA2008/000595 filed on Mar. 31, 2008 and published in English under PCT Article 21(2), which itself claims the benefit of U.S. Provisional Application Ser. No. 60/909,408, filed on Mar. 30, 2007 and on U.S. Provisional Application Ser. No. 61/025,571, filed on Feb. 1, 2008. All documents above are incorporated herein in their entirety by reference.

STATEMENT REGARDING FEDERALLY SPONSORED RESEARCH OR DEVELOPMENT

N/A.

FIELD OF THE INVENTION

The present invention relates to methods of determining the risk of developing scoliosis, methods of stratifying a subject having a scoliosis, methods for assessing the efficacy of a brace on a subject having a scoliosis, and kits therefor.

SEQUENCE LISTING

The nucleic acid and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file created Jul. 13, 2015, 78.3 KB, which is incorporated by reference herein.

BACKGROUND OF THE INVENTION

Spinal deformities and scoliosis in particular, represent the most prevalent type of orthopedic deformities in children and adolescents, while adolescent idiopathic scoliosis (AIS) represents the most common form of scoliosis.

The etiology of adolescent idiopathic scoliosis (AIS) remains poorly understood resulting in the traditional paradigm that AIS is a multi-factorial disease with a genetic predisposition.[1-7] The occurrence of a melatonin signaling dysfunction in cells derived from biopsies obtained intraoperatively from affected AIS patients has been reported.[8]

Unfortunately, there is no proven method or test available to identify children or adolescents at risk of developing AIS or to identify, which of the affected individuals may require treatment due to the risk of progression. Consequently, the application of current treatments, such as bracing or surgical correction, is delayed until a significant deformity is detected or until a significant progression is clearly demonstrated, resulting in a delayed and less optimal treatment.[29]

The present description refers to a number of documents, the content of which is herein incorporated by reference in their entirety.

SUMMARY OF THE INVENTION

More specifically, in accordance with the present invention, there is provided a method for determining the risk for developing a scoliosis comprising monitoring osteopontin (OPN) expression in a sample from a subject over time; wherein an OPN expression that increases in the subject sample over time is indicative that the subject is at risk for developing a scoliosis.

In a specific embodiment, the monitoring begins when the subject is about three years old. In another specific embodiment, the monitoring is performed by measuring OPN expression at a frequency of at least about once per month. In another specific embodiment, the monitoring is performed by measuring OPN expression at a frequency of at least about once per six month. In another specific embodiment, the method further comprises measuring sCD44 expression in a sample from the subject. In another specific embodiment, the monitoring OPN expression is performed using an enzyme-linked immunosorbent assay (ELISA) or radioimmunoassay (RIA).

In accordance with the present invention, there is provided a method for determining the risk for developing a scoliosis comprising measuring osteopontin (OPN) expression in a sample from a subject; wherein an OPN expression that is higher in the subject sample than that in a control sample is indicative that the subject is at risk for developing a scoliosis.

In another specific embodiment, the subject is a likely candidate for developing a scoliosis. In another specific embodiment, the subject is a likely candidate for developing adolescent idiopathic scoliosis. In another specific embodiment, the subject is pre-diagnosed as having a scoliosis.

In another specific embodiment, the subject is pre-diagnosed with adolescent idiopathic scoliosis.

In accordance with another aspect of the present invention, there is provided a method of stratifying a subject having a scoliosis comprising measuring osteopontin (OPN) expression in a sample from the subject; whereby the measuring step enables the stratification of the subject into a scoliosis subgroup.

In accordance with another aspect of the present invention, there is provided a method for assessing the efficacy of a brace on a subject having a scoliosis comprising measuring osteopontin (OPN) expression in a sample from the subject prior to and at least once after bracing the subject, wherein an increase in the OPN expression after as compared to prior to bracing the subject is indicative that the brace is ineffective.

In a specific embodiment, the determining the OPN expression after the bracing is performed at least one month after the bracing. In another specific embodiment, the determining the OPN expression after bracing the subject is performed at least 2 months hours after the bracing. In another specific embodiment, the determining the OPN expression after bracing the subject is performed at least three months after the bracing. In another specific embodiment, the determining the OPN expression after bracing the subject is performed at least six months after the bracing.

In another specific embodiment, the method further comprises measuring soluble CD44 receptor (sCD44) expression in the sample from the subject.

In another specific embodiment, the sample from the subject is a biological fluid from the subject. In another specific embodiment, the biological fluid is selected from the group consisting of blood, urine, tear and saliva. In another specific embodiment, the biological fluid is plasma.

In another specific embodiment, the OPN expression is OPN protein. In another specific embodiment, the determining of the OPN expression is performed with an antibody that specifically binds to OPN. In another specific embodiment, the measuring OPN expression is performed using an enzyme-linked immunosorbent assay (ELISA). In another specific embodiment, the sample is a plasma sample and an OPN expression that is higher than 700 nanograms per milliliter of plasma is indicative that the subject is at risk for developing a scoliosis. In another specific embodiment, the sample is a plasma sample and an OPN expression that is higher than 800 nanograms per milliliter of plasma is indicative that the subject is at risk for developing a scoliosis.

In another specific embodiment, the OPN expression is OPN RNA. In another specific embodiment, the sample from the subject is a paraspinal muscle biopsy and the OPN expression is OPN RNA.

In accordance with another aspect of the present invention, there is provided a method of selecting an agent as a potential candidate for the reduction or prevention of scoliosis comprising contacting a candidate agent with a cell expressing osteopontin (OPN), and detecting the expression of OPN, wherein when the expression of OPN is lower in the presence of the candidate agent as compared to in the absence thereof, the candidate agent is selected.

In accordance with another aspect of the present invention, there is provided a method of selecting an agent as a potential candidate for the reduction or prevention of scoliosis comprising contacting a candidate agent with a cell expressing sCD44, and detecting the expression of sCD44, wherein when the expression of OPN is higher in the presence of the candidate agent as compared to in the absence thereof, the candidate agent is selected.

In another specific embodiment, the cell is a cell derived from a scoliotic patient.

In accordance with another aspect of the present invention, there is provided a method of selecting an agent as a potential candidate for the prevention or reduction of scoliosis comprising administering a candidate agent to a scoliosis model animal before scoliosis has developed in the animal, whereby the candidate is selected when the scoliosis is prevented or reduced in the model animal as compared to in a control animal who was not administered the candidate agent.

In accordance with another aspect of the present invention, there is provided a method of preventing or reducing scoliosis comprising administering to a subject having scoliosis a therapeutically effective amount of an osteopontin inhibitor (OPN) or a selenium rich diet, whereby scoliosis is thereby prevented or treated.

In accordance with another aspect of the present invention, there is provided a method of preventing or reducing scoliosis comprising administering to a subject having scoliosis a therapeutically effective amount of a CD44 inhibitor, whereby scoliosis is thereby prevented or treated.

In accordance with another aspect of the present invention, there is provided a method of preventing or reducing scoliosis comprising administering to a subject having scoliosis a therapeutically effective amount of a sCD44 stimulator, whereby scoliosis is thereby prevented or treated.

In a specific embodiment of the methods of the present invention, the subject is human. In another specific embodiment of the methods of the present invention, the subject is human female. In another specific embodiment of the methods of the present invention, the subject is human male.

In accordance with another aspect of the present invention, there is provided an osteopontin inhibitor for use in the treatment or prevention of scoliosis.

In accordance with another aspect of the present invention, there is provided a CD44 inhibitor for use in the treatment or prevention of scoliosis.

In accordance with another aspect of the present invention, there is provided a sCD44 stimulator for use in the treatment or prevention of scoliosis.

In accordance with another aspect of the present invention, there is provided a use of an osteopontin inhibitor in the manufacture of a medicament for the prevention or the treatment of scoliosis.

In accordance with another aspect of the present invention, there is provided a use of an osteopontin inhibitor for the prevention or the treatment of scoliosis.

In accordance with another aspect of the present invention, there is provided a use of a CD44 inhibitor in the manufacture of a medicament for the prevention or the treatment of scoliosis.

In accordance with another aspect of the present invention, there is provided a use of a CD44 inhibitor for the prevention or the treatment of scoliosis.

In accordance with another aspect of the present invention, there is provided a use of a sCD44 stimulator in the manufacture of a medicament for the prevention or the treatment of scoliosis.

In accordance with another aspect of the present invention, there is provided a use of a sCD44 stimulator for the prevention or the treatment of scoliosis.

In a specific embodiment of the uses of the present invention, the scoliosis is adolescent idiopathic scoliosis.

In accordance with another aspect of the present invention, there is provided a kit for predicting the risk of developing a scoliosis comprising a ligand specific to osteopontin (OPN) and instructions to use the kit for predicting the risk of developing a scoliosis. In a specific embodiment, the kit further comprises a ligand specific to soluble CD44 (sCD44).

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIGS. 5A-5D graphically present the sensitivity and specificity of plasma osteopontin in healthy control subjects, AIS patients and at risk asymptomatic subjects. In FIG. 5A, an analysis that included 33 healthy control subjects and 32 AIS patients with severe Cobb's Angle)(≥45°) revealed an area under the curve (AUC) of 0.94 with a standard error of 0.03 (95 percent confidence interval [CI], 0.88 to 1.000). In FIG. 5B, the use of a cut-off value of 700 nanograms per ml of osteopontin showed a high sensitivity (90.6%) and a very good specificity (81.8%) for the early detection of AIS and for detecting the risk of scoliosis progression. In FIG. 5C, the use of a cut-off value of 800 nanograms/ml of osteopontin also showed a high sensitivity (84.9%) and a higher specificity (90.9%) for the early detection of AIS and for detecting the risk of scoliosis progression. In FIG. 5D, a clear correlation between the levels of plasma osteopontin and the Cobb's angle is demonstrated using all AIS patients, yielding a p-value <0.001 and $r^2$=0.26;

FIGS. 10A-10H present graphs showing OPN regression or stabilization correlated with Cobb's angle regression or stabilization in AIS patients;

FIGS. 20A-20D present the nucleotide sequences of the three human OPN isoforms (transcript variant 1, mRNA NM_001040058 (SEQ ID NO: 1); transcript variant 2, mRNA NM_000582 (SEQ ID NO: 2); transcript variant 3, mRNA NM_001040060 (SEQ ID NO: 3) and the amino acid sequences of the three human OPN isoforms (isoform a NP_001035147 (SEQ ID NO: 4); isoform b NP_000573 (SEQ ID NO: 5); and isoform c NP_001035149 (SEQ ID NO: 6));

FIGS. 21A-21S present the nucleotide sequences (mRNA) of six isoforms of human CD44 (NM_000610 transcript variant 1 (SEQ ID NO: 7); NM_001001389 transcript variant 2 (SEQ ID NO: 8); NM_001001390 transcript variant 3 (SEQ ID NO: 9); NM_001001391 transcript variant 4 (SEQ ID NO: 10); NM_001001392 transcript variant 5 (SEQ ID NO: 11); X62739 Isoform identified in tumour cells (SEQ ID NO: 12)) and amino acid sequences of six isoforms of human sCD44 (NP_000601 isoform 1 precursor (SEQ ID NO: 13); NP_001001389 isoform 2 precursor (SEQ ID NO: 14); NP_001001390 isoform 3 precursor (SEQ ID NO: 15); NP_001001391 isoform 4 precursor (SEQ ID NO: 16); NP_001001392 isoform 5 precursor (SEQ ID NO: 17); and CAA44602 Isoform identified in tumour cells (SEQ ID NO: 18)); and FIGS. 22A-22C show the structure of sCD44 (FIG. 22A), the origin of the various CD44 isoforms (FIG. 22B) and the cleavage site in one sCD44 isoform (SEQ ID NO: 23; FIG. 22C).

DESCRIPTION OF ILLUSTRATIVE EMBODIMENTS

Figure 1:
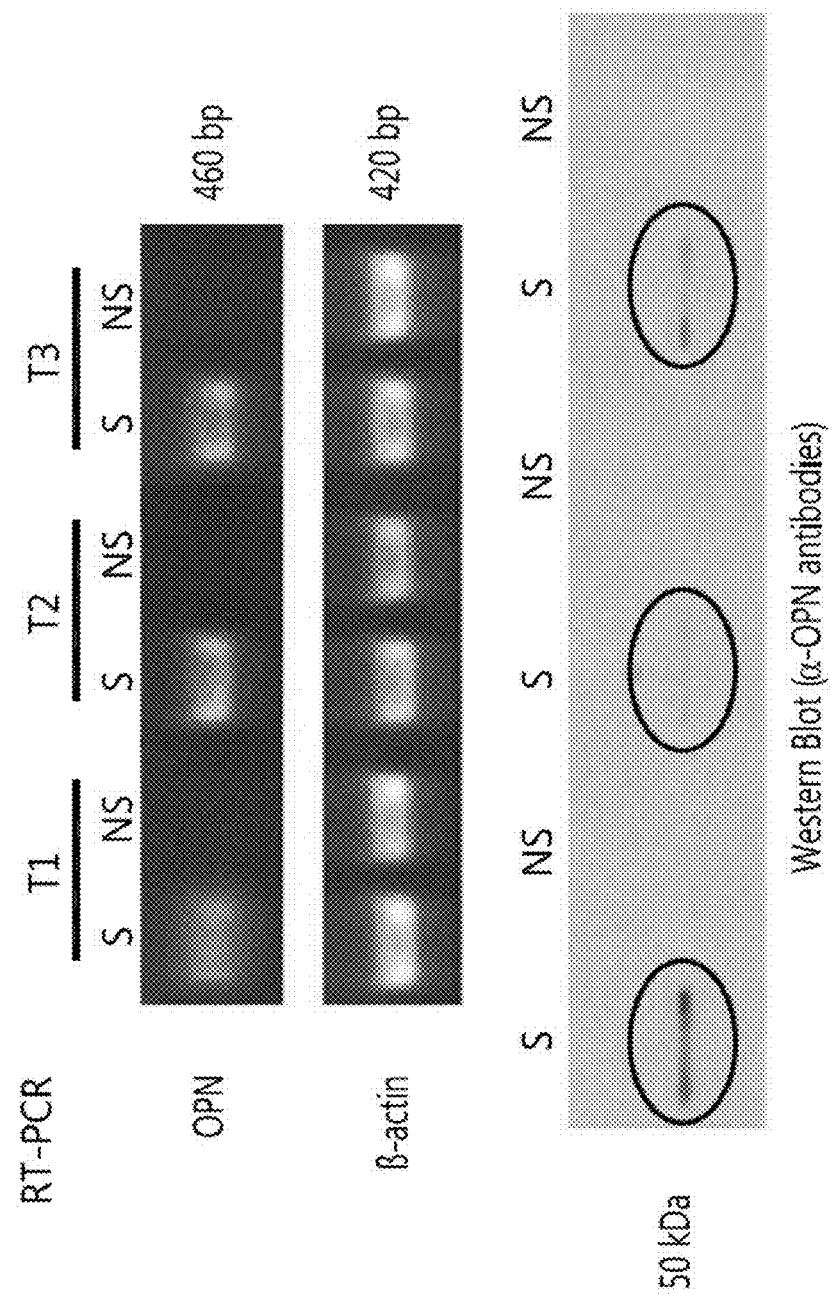
FIG. 1 presents OPN detection in pinealectomized chicken and corresponding scoliosis. Upper and lower panels illustrates the up regulation of OPN expression detected in paraspinal muscles of pinealectomized chicken developing a scoliosis (S) vs. those remaining unaffected (NS) at the mRNA and protein levels respectively.

The involvement of osteopontin (OPN) (also called secreted phosphoprotein 1, bone sialoprotein I, early T-lymphocyte activation 1), a multifunctional cytokine, was investigated in adolescent idiopathic scoliosis (AIS) and plasma OPN concentrations were determined in three populations: patients with AIS, healthy controls without any family antecedent for scoliosis and asymptomatic offspring, born from at least one scoliotic parent, who are considered as at risk ("children at risk").

A group of 252 consecutive patients with AIS were compared with 35 healthy control subjects without any family history of scoliosis and 70 asymptomatic at risk subjects. All subjects were Caucasians and demographic characteristics are shown in Table 2 below. Plasma OPN, soluble CD44 receptor (sCD44), and hyaluronan (HA) levels were measured by enzyme-linked immunosorbent assays. Pinealectomized chicken and genetically modified bipedal C57Bl/6j mice devoid of either OPN or CD44 receptor, a known OPN receptor, were also studied.

Mean plasma OPN concentration in patients with AIS were significantly higher (p-value <0.001) in patients with AIS having a Cobb's angle >45° (965±414 nanograms per milliliter) than that in healthy controls (570±156 nanograms per milliliter) and that in AIS patients with a Cobb's angle <45° (799±284 nanograms per milliliter). Diagnostic sensitivity and specificity of OPN for AIS was 84.4 percent and 90.6 percent respectively (cut-off value ≥800 nanograms per milliliter). Subgroup analysis showed that 47.9 percent of children at risk had OPN values higher than 800 nanograms per milliliter as opposed to only 8.6 percent for the controls indicating that elevated plasma OPN levels precede scoliosis formation. There were no significant differences in mean plasma sCD44 levels and HA levels between all groups. In respect to pathophysiology of scoliosis, the bipedal C57Bl/6j mouse model demonstrated that the development of scoliosis requires OPN interactions with CD44 receptors since none of the genetically modified bipedal mice developed a scoliosis. Cut-off values for OPN disclosed herein were calculated using the commercial Elisa kit specific to human OPN from IBL. They may vary when a OPN expression (mRNA or protein) is measured differently (e.g. measuring OPN expression in a different biological sample through OPN RNA or OPN protein but using a different antibody).

OPN (also called secreted phosphoprotein-1, minopontin, or Eta-1) is a phosphorylated glycoprotein containing an arginine-glycine-aspartate (RGD) sequence present in mineralized tissues such as extracellular matrices. This multifunctional cytokine is involved in many pathological conditions.[9,10] The presence of OPN transcripts and proteins in postural control centers such as the cerebellum, skeletal muscle proprioceptive sensory organs, and inner ear structures that control of equilibrium[11] is of interest, since AIS patients also exhibit defects in postural control, proprioception and equilibrium.[12,13] High plasma OPN levels have been found in different adult cancers and inflammatory conditions[30-33].

OPN signaling action: The OPN signaling pathways are not well understood, although it is known that aside from interacting with integrins, OPN can interact with CD44 receptor at the cell surface[14,15]. Although CD44 is a major receptor for hyaluronan (HA), it also acts as a receptor for OPN and has multiple RGD binding sites. All human isoforms of the CD44 family of adhesion molecules are encoded by a single gene. Alternate splicing of 12 of the 19 exons in the human CD44 gene leads to the production of multiple variant isoforms[16,17] and such structural heterogeneity is responsible of the ligand repertoire of CD44, which includes fibronectin[18], chondroitine sulphate[19], osteopontin[20], at least two heparin binding growth hormones and hyaluronan.[21,22] Soluble variant isoforms of sCD44 (sCD44var) have been associated with several pathological conditions[16,18,23,24]. It has been proposed that sCD44 isoforms are either generated through proteolytic cleavage of cell surface CD44 or by de novo synthesis due to alternative splicing. Functional diversity among CD44 molecules, unrelated to variant exon usage, is demonstrated by observations that CD44H, or any particular splice-variant, can be active for hyaluronan (HA) binding when expressed in some cell types but inactive in others. Many CD44 isoforms are tissue specific, but the full range of soluble variant isoform(s) of sCD44 has been associated with some pathological conditions. Indeed, circulating levels of total sCD44 and specific soluble CD44 isoforms have been shown to correlate with tumor metastasis in some malignancies, including non-Hodgkin's lymphoma and breast, gastric, and colon carcinomas. The level of soluble CD44 is also known to be higher in the body fluids of subjects with particular inflammatory conditions, such as rheumatoid arthritis, pouchitis and colitis, and bronchitis. Hyaluronan (HA), also called hyaluronate or hyaluronic acid, is a mucopolysaccharide widely distributed throughout the body and produced by a variety of cells including fibroblasts and other specialized connective tissue cells.

As used herein the term "subject" is meant to refer to any mammal including human, mice, rat, dog, cat, pig, monkey, horse, etc. In a particular embodiment, it refers to a human.

As used herein the term "brace" is meant to include dental and orthopedic brace and "bracing" thus refers to the action of placing the braces on the subject. In a specific embodiment, it is meant to refer to braces for scoliotic subjects.

As used herein the terminology "spinal disorders and disorders causing scoliosis" refers to disorders that may involve development of a scoliosis. Without so limited, it includes AIS, congenital scoliosis, congenital cyphose scoliosis, neurological scoliosis, dysplasic scoliosis, neurofibromatosis, cerebral palsy, muscular dystrophies, neuromuscular scoliosis, spondylolesthesis and Noonan syndrome. Scoliosis that may be stratified or predicted excludes those caused by an accident and certain congenital malformations.

As used herein the terms "likely candidate for developing adolescent idiopathic scoliosis" include children of which at least one parent has adolescent idiopathic scoliosis. Among other factors, age (adolescence), gender and heredity (i.e. born from a mother or father having a scoliosis) are factors that are known to contribute to the risk of developing a scoliosis and are used to a certain degree to assess the risk of developing AIS. In certain subjects, scoliosis develops rapidly over a short period of time to the point of requiring a corrective surgery. Current courses of action available from the moment AIS is diagnosed (when scoliosis is apparent) include observation (when Cobb's angle is around 10-25°), orthopaedic devices (when Cobb's angle is around 25-30°), and surgery (over 45°). The more reliable methods of determining the risk of progression and of monitoring treatment efficiency in accordance of the present invention may assist in 1) selecting an appropriate diet to remove certain food products identified as contributors to scoliosis; 2) selecting the best therapeutic agent; 3) selecting the least invasive preventive action and/or available treatment such as postural exercises, orthopaedic device, and/or less invasive surgeries or surgeries without fusions (a surgery that does not fuse vertebra and preserves column mobility).

As used herein, the terms "severe AIS" refers to a scoliosis characterized by Cobb's angle of 45° or more.

As used herein the terms "risk of developing scoliosis" refer to a genetic or metabolic predisposition of a subject to develop a scoliosis (i.e. spinal deformity) and/or to develop a more severe scoliosis at a future time. For instance, an increase of the Cobb's angle of a subject (e.g. from 40° to 50°, or from 18° to 25°) is a "development" of scoliosis.

As used herein the terminology "biological sample" refers to any solid or liquid sample isolated from a living being. In a particular embodiment, it refers to any solid or liquid sample isolated from a human. Without being so limited it includes a biopsy material, blood, tears (48), saliva, maternal milk, synovial fluid, urine, ear fluid, amniotic fluid and cerebrospinal fluid. In a specific embodiment it refers to a blood sample.

As used herein the terminology "blood sample" is meant to refer to blood, plasma or serum. In a preferred embodiment, plasma is used. In a more specific embodiment it refers to a plasma sample.

As used herein the terminology "control sample" is meant to refer to a sample that does not come from a subject known to have scoliosis or known to be a likely candidate for developing a scoliosis. In methods for determining the risk of developing scoliosis in a subject that is pre-diagnosed with scoliosis, the sample may however also come from the subject under scrutiny at an earlier stage of the disease or disorder.

As used herein the term "treating" or "treatment" in reference to scoliosis is meant to refer to at least one of a reduction of Cobb's angle in a preexisting spinal deformity, improvement of column mobility, preservation/maintenance of column mobility, improvement of equilibrium and balance in a specific plan; maintenance/preservation of equilibrium and balance in a specific plan; improvement of functionality in a specific plan, preservation/maintenance of functionality in a specific plan, cosmetic improvement, and combination of any of the above.

As used herein the term "preventing" or "prevention" in reference to scoliosis is meant to refer to a at least one of a reduction in the progression of a Cobb's angle in a patient having a scoliosis or in an asymptomatic patient, a complete prevention of apparition of a spinal deformity, including changes affecting the rib cage and pelvis in 3D, and a combination of any of the above.

As used herein the term "osteopontin inhibitor" refers to an agent able to reduce or block expression (transcription or translation) of OPN (gene called sspi1), an agent able to reduce or block OPN secretion or an agent able to reduce or block OPN binding to its receptor CD44. Without being so limited, the agent can be natural or synthetic and can be a protein such as but not limited to an antibody that specifically binds to OPN, a peptide, a small molecule, a nucleotide such as but not limited to an antisense or a siRNA specific to OPN.

As used herein the term "CD44 inhibitor" refers to an agent able to reduce expression (transcription or translation) of CD44, or an agent able to reduce CD44 localization at the cellular membrane. Without being so limited, the agent can be natural or synthetic and can be a protein such as but not limited to an antibody that specifically binds to CD44, a peptide, a small molecule, a nucleotide such as but not limited to an antisense or a siRNA specific to CD44.

As used herein the term "sCD44 stimulator" refers to an agent able to increase expression (transcription or translation) of sCD44, an agent able to increase sCD44 secretion or an agent able to increase sCD44 affinity toward OPN. Without being so limited, the agent can be a protein, a peptide, a small molecule or a nucleotide.

The articles "a," "an" and "the" are used herein to refer to one or to more than one (i.e., to at least one) of the grammatical object of the article.

The term "including" and "comprising" are used herein to mean, and re used interchangeably with, the phrases "including but not limited to" and "comprising but not limited to".

The terms "such as" are used herein to mean, and is used interchangeably with, the phrase "such as but not limited to".

The present invention also relates to methods for the determination of the level of expression (i.e. transcript or translation product) of OPN, HA or sCD44. The present invention therefore encompasses any known method for such determination including Elisa (Enzyme Linked Immunosorbent Assay), RIA (Radioimmunoassay), real time PCR and competitive PCR, Northern blots, nuclease protection, plaque hybridization and slot blots.

The present invention also concerns isolated nucleic acid molecules including probes and primers to detect OPN, sCD44 or CD44. In specific embodiments, the isolated nucleic acid molecules have no more than 300, or no more than 200, or no more than 100, or no more than 90, or no more than 80, or no more than 70, or no more than 60, or no more than 50, or no more than 40 or no more than 30 nucleotides. In specific embodiments, the isolated nucleic acid molecules have at least 17, or at least 18, or at least 19, or at least 20, or at least 30, or at least 40 nucleotides. In other specific embodiments, the isolated nucleic acid molecules have at least 20 and no more than 300 nucleotides. In other specific embodiments, the isolated nucleic acid molecules have at least 20 and no more than 200 nucleotides. In other specific embodiments, the isolated nucleic acid molecules have at least 20 and no more than 100 nucleotides. In other specific embodiments, the isolated nucleic acid molecules have at least 20 and no more than 90 nucleotides. In other specific embodiments, the isolated nucleic acid molecules have at least 20 and no more than 80 nucleotides. In other specific embodiments, the isolated nucleic acid molecules have at least 20 and no more than 70 nucleotides. In other specific embodiments, the isolated nucleic acid molecules have at least 20 and no more than 60 nucleotides. In other specific embodiments, the isolated nucleic acid molecules have at least 20 and no more than 50 nucleotides. In other specific embodiments, the isolated nucleic acid molecules have at least 20 and no more than 40 nucleotides. In other specific embodiments, the isolated nucleic acid molecules have at least 17 and no more than 40 nucleotides. In other specific embodiments, the isolated nucleic acid molecules have at least 20 and no more than 30 nucleotides. In other specific embodiments, the isolated nucleic acid molecules have at least 17 and no more than 30 nucleotides. In other specific embodiments, the isolated nucleic acid molecules have at least 30 and no more than 300 nucleotides. In other specific embodiments, the isolated nucleic acid molecules have at least 30 and no more than 200 nucleotides. In other specific embodiments, the isolated nucleic acid molecules have at least 30 and no more than 100 nucleotides. In other specific embodiments, the isolated nucleic acid molecules have at least 30 and no more than 90 nucleotides. In other specific embodiments, the isolated nucleic acid molecules have at least 30 and no more than 80 nucleotides. In other specific embodiments, the isolated nucleic acid molecules have at least 30 and no more than 70 nucleotides. In other specific embodiments, the isolated nucleic acid molecules have at least 30 and no more than 60 nucleotides. In other specific embodiments, the isolated nucleic acid molecules have at least 30 and no more than 50 nucleotides. In other specific embodiments, the isolated nucleic acid molecules have at least 30 and no more than 40 nucleotides. It should be understood that in real-time PCR, primers also constitute probe without the traditional meaning of this term. Primers or probes appropriate to detect OPN sCD44 and CD44 in the methods of the present invention can be designed with known methods using sequences distributed across their respective nucleotide sequence (49).

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally known. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds. Other detection methods include kits containing probes on a dipstick setup and the like.

As used herein the terms "detectably labeled" refer to a marking of a probe or an antibody in accordance with the presence invention that will allow the detection of OPN, HA and/or sCD44 in accordance with the present invention. Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods. Non-limiting examples of labels include 3H, 14C, 32P, and 35S. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma 32P ATP and polynucleotide kinase, using the Klenow fragment of Pol I of E. coli in the presence of radioactive dNTP (e.g. uniformly labeled DNA probe using random oligonucleotide primers in low-melt gels), using the SP6/T7 system to transcribe a DNA segment in the presence of one or more radioactive NTP, and the like.

The present invention also relates to methods of selecting compounds. As used herein the term "compound" is meant to encompass natural, synthetic or semi-synthetic compounds, including without being so limited chemicals, macromolecules, cell or tissue extracts (from plants or animals), nucleic acid molecules, peptides, antibodies and proteins.

The present invention also relates to arrays. As used herein, an "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

As used herein "array of nucleic acid molecules" is an intentionally created collection of nucleic acids which can be prepared either synthetically or biosynthetically in a variety of different formats (e.g., libraries of soluble molecules; and libraries of oligonucleotides tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

As used herein "solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Any known nucleic acid arrays can be used in accordance with the present invention. For instance, such arrays include those based on short or longer oligonucleotide probes as well as cDNAs or polymerase chain reaction (PCR) products. Other methods include serial analysis of gene expression (SAGE), differential display, as well as subtractive hybridization methods, differential screening (DS), RNA arbitrarily primer (RAP)-PCR, restriction endonucleolytic analysis of differentially expressed sequences (READS), amplified restriction fragment-length polymorphisms (AFLP).

Antibodies

The present invention encompasses using antibodies for detecting or determining OPN, sCD44 or CD44 levels for instance in the samples of a subject and for including in kits of the present invention. Antibodies that specifically bind to these biological markers can be produced routinely with methods further described below. The present invention also encompasses using antibodies commercially available. Without being so limited antibodies that specifically bind to OPN include those listed in Table 1 below.

TABLE 1 commercially available human OPN Elisa kits.

| Company | Kit name | Catalogue number | Sensitivity |
| --- | --- | --- | --- |
| IBL Hambourg | Human Osteopontin ELISA | JP 171 58 | 3.33 ng/ml |
| IBL America | Human Osteopontin N-Half Assay Kit-IBL | 27258 | 3.90 pmol/L |
| IBL-America | Human Osteopontin Assay Kit-IBL | 27158 | 3.33 ng/ml |
| Assay designs | Osteopontin (human) EIA Kit | 900-142 | 0.11 ng/ml |
| American Research Products, Inc. | Osteopontin, human kit | 17158 | ? |
| R&D Systems | Human Osteopontin (OPN) ELISA Kit | DOST00 | 0.024 ng/mL |
| Promokine | Human Osteopontin ELISA | PK-EL-KA4231 | 3.6 ng/ml |
| Uscnlife | Human Osteopontin, OPN ELISA Kit | E0899h | ? |

Both monoclonal and polyclonal antibodies directed to OPN are included within the scope of this invention as they can be produced by well established procedures known to those of skill in the art. Additionally, any secondary antibodies, either monoclonal or polyclonal, directed to the first antibodies would also be included within the scope of this invention.

As used herein, the term "anti-OPN antibody" or "immunologically specific anti-OPN antibody" refers to an antibody that specifically binds to (interacts with) an OPN protein and displays no substantial binding to other naturally occurring proteins other than the ones sharing the same antigenic determinants as the OPN protein. The term antibody or immunoglobulin is used in the broadest sense, and covers monoclonal antibodies (including full length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')$_2$, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions ($V_H$, $V_H$-$V_H$), anticalins, PEPBODIES™, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody encompasses herein polyclonal, monoclonal antibodies and antibody variants such as single-chain antibodies, humanized antibodies, chimeric antibodies and immunologically active fragments of antibodies (e.g. Fab and Fab' fragments) which inhibit or neutralize their respective interaction domains in Hyphen and/or are specific thereto.

Polyclonal antibodies are preferably raised in animals by multiple subcutaneous (sc), intravenous (iv) or intraperitoneal (ip) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl2, or $R^1N$=C=NR, where R and $R^1$ are different alkyl groups.

Animals may be immunized against the antigen, immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to 1/10 of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293 (see also, e.g., Lindenbaum et al., 2004).

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

As used herein, the term "purified" in the expression "purified antibody" is simply meant to distinguish man-made antibody from an antibody that may naturally be produced by an animal against its own antigens. Hence, raw serum and hybridoma culture medium containing anti-OPN antibody are "purified antibodies" within the meaning of the present invention.

The present invention also encompasses arrays to detect and/or quantify the translation products of OPN, HA or sCD44. Such arrays include protein micro- or macroarrays, gel technologies including high-resolution 2D-gel methodologies, possibly coupled with mass spectrometry imaging system at the cellular level such as microscopy combined with a fluorescent labeling system.

The present invention also encompasses methods for identifying specific mutation(s) directly or indirectly affecting the transcription, translation, post-translational modification or activity of OPN. Without being so limited, mutations of interest include any mutation affecting the interactions between OPN and any soluble or non-soluble isoform of CD44 or the binding of HA to any soluble or non-soluble isoform of CD44.

The present invention also encompasses the monitoring of the biomarkers disclosed herein to assess the efficacy of numerous approaches to prevent scoliosis and curve progression such as any physical therapies (e.g. postural exercises, physiotherapies, biomechanical stimulations by manipulation or using specific devices e.g. vibrant plates); the monitoring of bracing efficacy or development of novel braces; the monitoring of new surgical devices with or without fusion of vertebrae, and the monitoring of the efficacy of specific diet, nutraceutical and/or pharmacological treatments. Without being so limited, the first measure after the braces have been applied could be performed 1 month later to determine for instance whether the braces are well adjusted and determine whether the patient is compliant to the treatment. Thereafter, the monitoring could be performed every three to six months depending on whether high OPN levels are detected or not. This method of the present invention may advantageously reduce the requirement for x-rays. X-rays could be performed for instance only at visits where OPN levels detected are too high.

The present invention also encompasses the monitoring of the biomarkers disclosed herein to identify patients having a risk of progression for early bracing or for less-invasive surgeries with novel fusionless devices, for pharmacological treatments and to monitor responses to treatment in patients with AIS. Of note, fusionless devices are particularly useful for patients still possessing a growth potential so that identification of the risk of developing a scoliosis as early as possible in the life of the subject is beneficial. In a specific embodiment, monitoring begins when the subject is about 5 years old or less in subjects having a scoliosis family antecedent/history. The frequency of the testing could typically be every six months. In case where OPN values are above the cut-off value (i.e. >800 ng/ml when the OPN IBL ELISA kit code No. 27158 is used), the frequency would be advantageously significantly increased (e.g. every month, every two months, every three months . . . ).

The present invention also encompasses methods to screen/select for potential useful therapeutic agents using whole cells assays, the therapeutic compound being able to repress the transcription and/or synthesis of OPN (encoded by ssp1 gene), and/or able to increase the production of sCD44 which could sequester circulating OPN, and/or able to interfere with OPN liaison with the CD44 receptor, and/or able to block the CD44 receptor. Cells for use in such methods includes cells of any source (including in house or commercially available cell lines) and type (any tissue). In house cell lines could be made for instance by immortalizing cells from AIS subjects. In specific embodiments, methods of screening of the invention seek to identify agents that inhibit OPN expression (transcription and/or translation) and agents that increase sCD44 expression (transcription and/or translation). Useful cell lines for these embodiments include those producing high levels of OPN and/or low levels of sCD44. Such useful cell lines are described in references 43-56.

In a particular embodiment, it includes cells of any cell type derived from a scoliotic patient. In specific embodiments, it includes osteoblasts, chondrocytes, myoblasts or blood cells including lymphocytes. As used herein, the term "cell derived from a scoliotic patient" refers to cells isolated directly from scoliotic patients, or immortalized cell lines originating from cells isolated directly from scoliotic patients. In specific embodiments, the cells are paraspinal muscle cells. Such cells may be isolated by a subject through needle biopsies for instance.

Pharmaceutical compositions can also be administered by routes such as the nasal, intravenous, intramuscular, subcutaneous, sublingual, intrathecal, or intradermal route. The route of administration can depend on a variety of factors, such as the environment and therapeutic goals.

Dosage

Any amount of a pharmaceutical and/or nutraceutical and/or dietary supplement compositions can be administered to a subject. The dosages will depend on many factors including the mode of administration. Typically, the amount of anti-scoliosis composition (e.g. osteopontin inhibitor or selenium compound) contained within a single dose will be an amount that effectively prevents, delays or reduces scoliosis without inducing significant toxicity "therapeutically effective amount".

In some embodiments, the therapeutically effective amount of the neutraceutical anti-scoliosis composition (e.g. selenium supplement) can be altered. Useful effective amount concentrations include amounts ranging from about 0.01% to about 10% of a total diet on a weight by weight basis, from about 1% to about 6% of a total diet on a weight by weight basis, or from about 02% to about 6% of a total diet on a weight by weight basis.

The effective amount of the osteopontin inhibitor or selenium compound may also be measured directly. The effective amount may be given daily or weekly or fractions thereof. Typically, a pharmaceutical and/or nutraceutical and/or dietary supplement composition of the invention can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount is a dose that ranges from about 1 mg to about 25 grams of the anti-scoliose preparation per day, about 50 mg to about 10 grams of the anti-scoliose preparation per day, from about 100 mg to about 5 grams of the anti-scoliose preparation per day, about 1 gram of the anti-scoliose preparation per day, about 1 mg to about 25 grams of the anti-scoliose preparation per week, about 50 mg to about 10 grams of the anti-scoliose preparation per week, about 100 mg to about 5 grams of the anti-scoliose preparation every other day, and about 1 gram of the anti-scoliose preparation once a week.

By way of example, a pharmaceutical (e.g. containing an osteopontin inhibitor) and/or nutraceutical (e.g. containing selenium) and/or dietary supplement (e.g. containing selenium) composition of the invention can be in the form of a liquid, solution, suspension, pill, capsule, tablet, gelcap, powder, gel, ointment, cream, nebulae, mist, atomized vapor, aerosol, or phytosome. For oral administration, tablets or capsules can be prepared by conventional means with at least one pharmaceutically acceptable excipient such as binding agents, fillers, lubricants, disintegrants, or wetting agents. The tablets can be coated by methods known in the art. Liquid preparations for oral administration can take the form of, for example, solutions, syrups, or suspension, or they can be presented as a dry product for constitution with saline or other suitable liquid vehicle before use. Dietary supplements of the invention also can contain pharmaceutically acceptable additives such as suspending agents, emulsifying agents, non-aqueous vehicles, preservatives, buffer salts, flavoring, coloring, and sweetening agents as appropriate. Preparations for oral administration also can be suitably formulated to give controlled release of the active ingredients.

In addition, a pharmaceutical (e.g. containing an osteopontin inhibitor) and/or nutraceutical (e.g. containing selenium) and/or dietary supplement (e.g. containing selenium) composition of the invention can contain a pharmaceutically acceptable carrier for administration to a mammal, including, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Pharmaceutically acceptable carriers also can include physiologically acceptable aqueous vehicles (e.g., physiological saline) or other known carriers appropriate to specific routes of administration.

An osteopontin inhibitor or selenium may be incorporated into dosage forms in conjunction with any of the vehicles which are commonly employed in pharmaceutical preparations, e.g. talc, gum arabic, lactose, starch, magnesium searate, cocoa butter, aqueous or non-aqueous solvents, oils, paraffin derivatives or glycols. Emulsions such as those described in U.S. Pat. No. 5,434,183, may also be used in which vegetable oil (e.g., soybean oil or safflower oil), emulsifying agent (e.g., egg yolk phospholipid) and water are combined with glycerol. Methods for preparing appropriate formulations are well known in the art (see e.g., Remington's Pharmaceutical Sciences, 16th Ed., 1980, A. Oslo Ed., Easton, Pa.).

In cases where parenteral administration is elected as the route of administration, preparations containing osteopontin inhibitor or selenium may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

These are simply guidelines since the actual dose must be carefully selected and titrated by the attending physician based upon clinical factors unique to each patient or by a nutritionist. The optimal daily dose will be determined by methods known in the art and will be influenced by factors such as the age of the patient and other clinically relevant factors. In addition, patients may be taking medications for other diseases or conditions. The other medications may be continued during the time that the osteopontin inhibitor or selenium compound is given to the patient, but it is particularly advisable in such cases to begin with low doses to determine if adverse side effects are experienced.

The present invention also relates to kits. Without being so limited, it relates to kits for stratifying scoliotic subjects and/or predicting whether a subject is at risk of developing a scoliosis comprising an isolated nucleic acid, a protein or a ligand such as an antibody in accordance with the present invention as described above. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the subject sample (DNA genomic nucleic acid, cell sample or blood samples), a container which contains in some kits of the present invention, the probes used in the methods of the present invention, containers which contain enzymes, containers which contain wash reagents, and containers which contain the reagents used to detect the extension products. Kits of the present invention may also contain instructions to use these probes and or antibodies to stratify scoliotic subjects or predict whether a subject is at risk of developing a scoliosis.

The present invention is illustrated in further details by the following non-limiting examples.

Example 1

Material and Methods

Generation of Bipedal C57BL/6J OPN-Null and CD44-Null Mice.

Experiments in mice were conducted according to protocols approved by The Ste-Justine Hospital's Animal Health Care Review Committee. Breeding pairs of C57Bl/6 devoid of either OPN (OPN-null mice) or CD44 receptor (CD44-null mice) backcrossed for more than 10 generations in C57Bl/6j mice were graciously obtained from Dr. Susan Rittling, (Rutger University, NJ, USA) and Dr. Tak Mak (University of Toronto, ON, Canada), respectively, to establish new colonies, while C57Bl/6j mice served as wild-type control mice (Charles-River, Wilmington, Mass., USA). The C57Bl6/6j mouse strain was used because it is naturally deficient in melatonin[26], exhibits high circulating OPN levels[27] and develops scoliosis when they are maintained in a bipedal state.[28] It is a well-known scoliosis animal model. Bipedal surgeries were performed after weaning by amputation of the forelimbs and tail under anesthesia as reported previously.[28] All mice underwent complete radiographic examination under anesthesia using a FAXITRON™ X-rays apparatus (Faxitron X-rays Corp. Wheeling, Ill., USA) every two weeks starting at the age of six weeks. Anteroposterior X-rays were taken and each digital image was evaluated subsequently for the presence of scoliosis. Cobb's angle threshold value of 10° or higher was retained as a significant scoliotic condition.

Immunodetection of Mouse OPN

Mouse serum was obtained from peripheral blood samples for the determination of serum levels of OPN and were collected in serum separator tubes containing silica gel (BD Microtainer, BD New Jersey, USA) and then centrifuged. Derived serum samples were aliquoted and kept frozen at −80° C. until thawed and analyzed. Serum concentrations of OPN were measured by capture enzyme-linked immunosorbent assays (ELISA) according to the protocol provided by the manufacturer (IBL, Hamburg, Germany). The OPN ELISA kit measured total concentration of both phosphorylated and non-phosphorylated of all isoforms of OPN in serum. ELISA tests were performed in duplicate and the optical density was measured at 450 nm using an ASYSHITECH™ Expert-96 microplate reader (Biochrom, Cambridge, UK). Although serum was used in mice herein, the present invention also encompasses measuring OPN in mice plasma.

Generation of Pinealectomized Chickens.

A percentage of pinealectomized chickens develop a scoliosis and they are thus used as a scoliosis model. For this study, 145 newly hatched chickens (Mountain Hubbard) were purchased at a local hatchery and pinealectomy were performed as previously described[25].

Expression Analysis and Immunodetection of Chicken OPN.

Total cellular RNA was prepared from paraspinal muscles of pinealectomized chickens by phenol/chloroform extraction. For RT-PCR, 1 microgram total RNA was reversed transcribed using THERMOSCRIPT™ reverse transcriptase (Invitrogen), and the equivalent of 0.1 microgram of reverse-transcribed RNA used for PCR reactions. These were carried out in a final volume of 50 microliters containing 200 micromolar dNTPs, 1.5 millimolar $MgCl_2$, 10 picomolar of each primer, and 1 U Pfu DNA-polymerase (Stratagene, La Jolla, Calif., USA). PCR reactions were performed using the following primers and conditions: chicken OPN (420 bp PCR product): 5'-ACACTTTCACTC-CAATCGTCC-3' (SEQ ID NO: 19) (forward), 5'-TGC-CCTTTCCGTTGTTGTCC-3' (SEQ ID NO: 20) (reverse) 35 cycles: 95° C./45 seconds, 66° C./45 seconds, 72° C./1 minute. For quantitative analysis, all amplifications were normalized against that of the housekeeping gene β-actin; chicken β-actin (460 bp PCR product) 5'-GGAAATCGTcontrols were recruited in elementary schools of Montreal. Each subject was examined by the same orthopedic surgeon using Adam's forward bending-test with a scoliometer.

Three populations were investigated: patients with AIS, healthy controls without any family antecedent/history for scoliosis and asymptomatic offspring, born from at least one scoliotic parent, who are considered as at risk of developing a scoliosis. A group of 252 consecutive patients with AIS, 35 healthy control subjects and 70 asymptomatic children at risk of developing a scoliosis were recruited. All subjects were Caucasians and demographic characteristics are shown in Table 2 below).

TABLE 2

Demographic and clinical characteristics of patients with AIS, healthy control and at risk control subjects.

| Characteristics | AIS | | | | Healthy Control Subjects | | At Risk Control Subjects | |
|---|---|---|---|---|---|---|---|---|
| | Female | | Male | | Female | Male | Female | Male |
| Number | | 215 | | 37 | 19 | 16 | 45 | 25 |
| Mean Age (Years) | | 141 ± 2.1 | | 14.8 ± 22 | 10.6 ± 0.6 | 10.9 ± 0.6 | 9.8 ± 3.7 | 10.0 ± 2.9 |
| Patient percentage & Mean Cobb's Angle | | | | | | | | |
| Thoracolumbar | 35.8% | 22.5 ± 15.2 | 29.7% | 28.3 ± 22.8 | — | — | — | — |
| Thoracic | 20.5% | 39.7 ± 20.4 | 29.7% | 34.1 ± 22.3 | — | — | — | — |
| Double Scoliosis | 30.2% | | 24.3% | | — | — | — | — |
| (Thoracic + Lumbar) | | | | | | | | |
| Thoracic Curvature | | 34.8 ± 19.0 | | 38.9 ± 21.2 | | | | |
| Lumbar Curvature | | 31.0 ± 17.3 | | 33.0 ± 18.7 | | | | |
| Lumbar | 4.7% | 25.4 ± 10.7 | 8.1% | 20.3 ± 3.5 | — | — | — | — |
| Double Scoliosis | 6.0% | | 5.4% | | — | — | — | — |
| (Thoracic + Thoracolumbar) | | | | | | | | |
| Thoracic Curvature | | 25.4 ± 13.5 | | 36.0 ± 19.8 | | | | |
| Lumbar Curvature | | 25.2 ± 15.5 | | 41.0 ± 29.7 | | | | |
| Triple Scoliosis | 1.9% | 36.8 ± 18.5 | 2.7% | 8.0 | — | — | — | — |
| | | 41.0 ± 14.3 | | 11.0 | | | | |
| | | 30.5 ± 7.7 | | 11.0 | | | | |
| Double Scoliosis | 0.9% | | — | | — | — | — | — |
| (Thoracic + Thoracic) | | | | | | | | |
| | | 29.0 ± 5.7 | | — | | | | |
| | | 16.5 ± 3.5 | | — | | | | |
| Heredity | | 36.3% | | 37.8% | 0.0% | 0.0% | 100.0% | 100.0% |

* Plus-minus values are means ± standard deviations.
† Mean Cobb's Angles for double scoliosis are represented by the curvatures on the thoracic and lumbar levels separately.
‡ Mean Cobb's Angle for the triple scoliosis represents two thoracic curvatures and one lumbar curvature.

GCGTGACAT-3' (SEQ ID NO: 21) (forward), 5'-TCAT-GATGGAGTTGAATGTAGTT-3' (SEQ ID NO: 22) (reverse) 32 cycles: 94° C./45 seconds, 55° C./45 seconds, 72° C./1 minute. PCR amplified products were analyzed on 1.5% agarose gel containing ethidium bromide. Total protein extracts of paraspinal muscles were used to detect chicken OPN by Western blot using anti-human OPN antibodies cross-reacting with chicken OPN (clone 8E5, Kamiya Biomedial, WA, USA).

Human Populations

The institutional review boards of The Sainte-Justine Hospital, The Montreal Children's Hospital, The Shriners Hospital for Children in Montreal, McGill University and The Affluent School Board, approved the study. Parents or legal guardians of all participants gave written informed consent, and minors gave their assent.

Figure 22A:
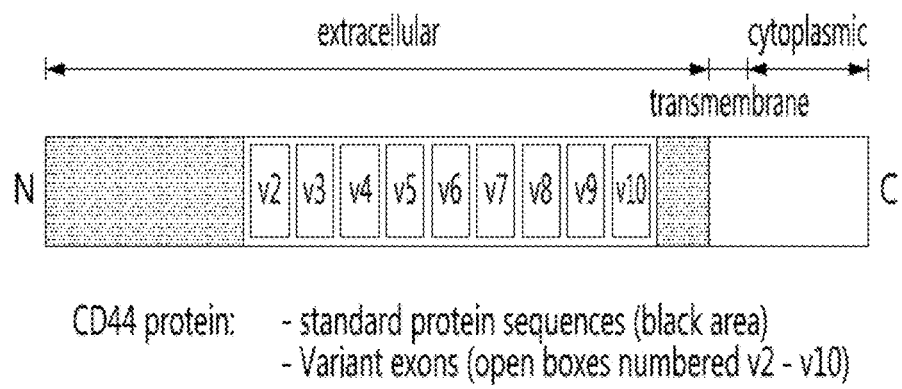
Figure 22B:
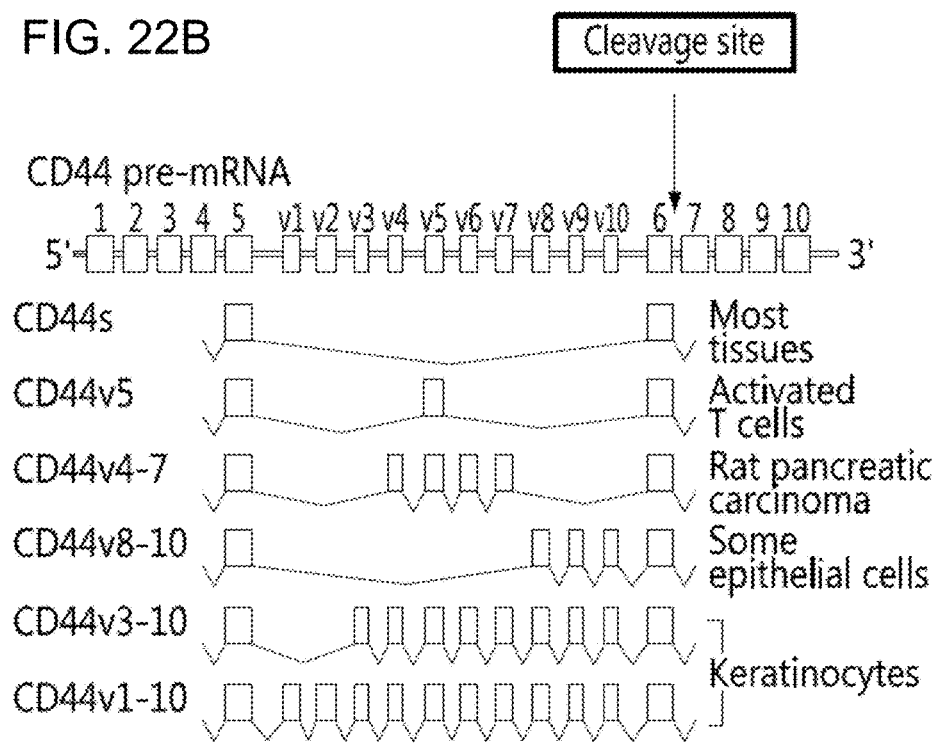

All patients with AIS were examined by one of six orthopedic surgeons. A person was deemed to be affected if history and physical examination were consistent with the diagnosis of idiopathic scoliosis and a minimum of a ten degree curvature in the coronal plane with vertebral rotation was found on a standing radiograph of the spine. Healthy Osteopontin, sCD44 and HA Enzyme-Linked Immunosorbent Assays Peripheral blood samples for AIS patients, asymptomatic children and control groups were collected in EDTA-containing tubes and then centrifuged. Derived plasma samples were aliquoted and kept frozen at −80° C. until thawed and analyzed. Plasma concentrations of OPN and sCD44 were measured by capture enzyme-linked immunosorbent assays (ELISA) according to protocols provided by the manufacturer (IBL, Hamburg, Germany). The sCD44 Elisa kit (sCD44std) measured all circulating (soluble) CD44 isoforms comprising the standard protein sequences but not the rare isoforms associated with alternative splicing between exons V2 and V10 (50) (see also FIG. 22). The OPN IBL ELISA kit (code No. 27158) measures total concentration of both phosphorylated and non-phosphorylated of all isoforms of OPN in plasma. Circulating levels of HA were measured in all plasma samples using an ELISA kit (HA-Elisa (K-1200), Echelon Biosciences, Salt Lake City, Utah). All ELISA tests were performed in duplicate and the optical density was measured at 450 nm (for OPN and sCD44) and 405 nm (for HA) using an AsysHiTech Expert-96™ microplate reader (Biochrom, Cambridge, UK). Other Elisa kits available commercially or house made can be used in methods of the present invention. The cut-off value that statistically distinguishes non-scoliotic subjects from scoliotic subjects that will help predict the risk of scoliosis progression as determined with these other kits will likely differ from that calculated with the kit used herein. It may however be calculated for each new antibody used as described herein.

Statistical Analysis

Age and gender differences among the different AIS and control groups were assessed using Pearson's Chi-square and Student's t tests, respectively. Multiple linear regression models were used to test for association between groups and levels of OPN, sCD44, and HA. Values were adjusted for age, gender, and age-gender interaction when these potential confounders were associated with the biomarker levels at $p<0.1$. Interactions between group and gender were also investigated. It was first tested for an overall group effect using a global F test comparing models with and without group effects. Were then tested specific differences between groups, applying a Bonferroni correction for multiple testing. Receiver-operating characteristics (ROC) curves were used to evaluate the diagnostic value of OPN, and to identify the optimal threshold values. The sensitivity (proportion of true-positive results when the assay was applied to patients known to have AIS) and specificity (proportion of true-negative results when the assay was applied to healthy controls) of OPN were profiled by curves. The area under ROC curve (AUC) and associated 95% confidence interval were calculated. The test of the hypothesis that the theoretical AUC is 0.5 was based on the confidence interval. Statistical analysis was performed with the SAS software, version 9.1, with the exception of the ROC curve analysis, which was performed with the ROCR package for R[51,52]. In all analyses except when otherwise mentioned a p-value <0.05 was considered statistically significant.

Example 2 mRNA and Protein OPN Levels Pinealectomized Chicken

Expression analysis and immunodetection analysis of OPN in pinealectomized chicken were performed as described in Example 1 above. OPN at the mRNA and protein levels occurring in pinealectomized chicken were measured. FIG. 1 shows a strong increase of OPN at the mRNA and protein levels only in pinealectomized chicken that developed a scoliosis.

Example 3

OPN Protein Levels in C57Bl/6j Mice

Bipedal C57Bl/6j mice were generated and their OPN level was determined as described in Example 1 above. Bipedal ambulation for 8 weeks in C57Bl/6j mice induced scoliosis at a rate of 46 percent in females and 24 percent in males which correlated well with higher plasma OPN levels found in females (Table 3 below). The relevance of this animal model is strengthened by the fact that scoliosis are more frequently seen in number and severity in bipedal C57Bl/6j females (46%) when compared to bipedal males (24%) as is also observed in humans.

TABLE 3

Scoliosis frequency in naturally melatonin deficient mouse strain C57Bl/6j mice and genetically modified C57Bl mice devoid of OPN or CD44.

|  |  | n | % of scoliosis | Mean period of follow-up |
|---|---|---|---|---|
| C57Bl/6j | ♂ | 21 | 24% | 57 weeks +/− 3 |
|  | ♀ | 28 | 46% | 57 weeks +/− 3 |
| C57Bl/6j OPN-null | ♂ | 30 | 0% | 54 weeks +/− 2 |
|  | ♀ | 24 | 0% | 54 weeks +/− 2 |
| C57Bl/6j CD44-null | ♂ | 29 | 0% | 52 weeks +/− 2 |
|  | ♀ | 31 | 0% | 52 weeks +/− 2 |

Figure 2:
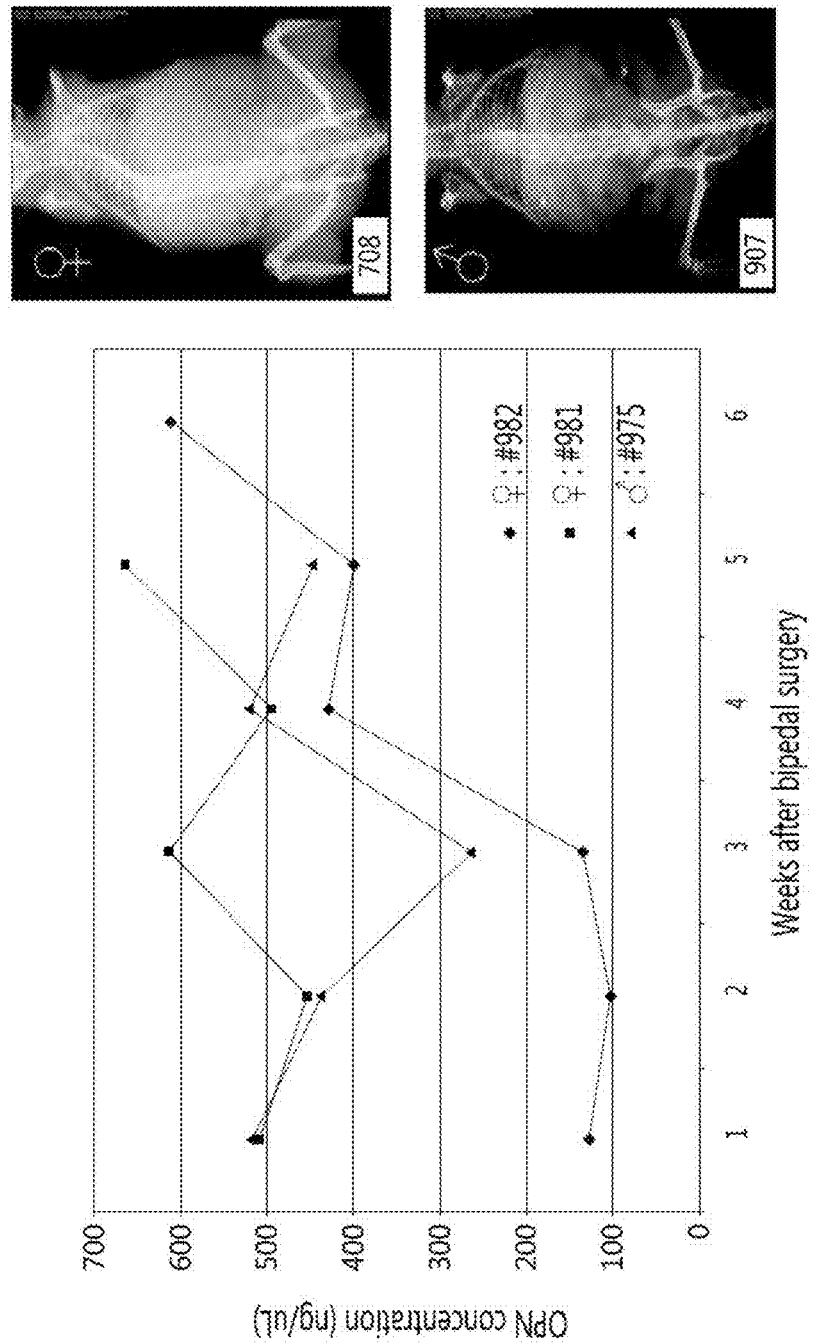
FIG. 2 graphically presents in the left panel the dynamic variation of circulating OPN levels in scoliotic bipedal C57Bl/6j mice after surgery, and in the right panel presents typical x-rays of scoliotic deformities observed in bipedal C57Bl/6j mice, where females (708) are more severely affected than males (907)

FIG. 2 shows that the OPN protein level strongly increases after bipedal surgery (i.e. during scoliosis development) in scoliotic C57Bl/6j mice.

Example 4

Observation of Effect of Absence of OPN or CD44 Bipedal C57Bl/6j Mice on Scoliosis The contribution of OPN and CD44 receptor as an integral part of the pathophysiology cascade in scoliosis formation and curve progression was also examined by studying genetically modified bipedal C57Bl/6j mice by conducting experiments as described in Example 1 above. As shown in Table 3 above, it was found that none of the bipedal C57Bl/6j OPN-null (n=54) and C57Bl/6j CD44-null mice (n=60) respectively, developed a scoliosis even if their analysis was extended over 52 weeks. Scoliosis development is detected 8 weeks after the surgery. A longer follow-up was performed to demonstrate that scoliosis development was not simply delayed in OPN-null and CD44-null mice.

In parallel, melatonin circulating levels were measured in wild-type and OPN-KO mice to exclude the possibility that absence of scoliosis in bipedal C57Bl/6 OPN-KO mice was due to an increased production of melatonin.

Figure 3:
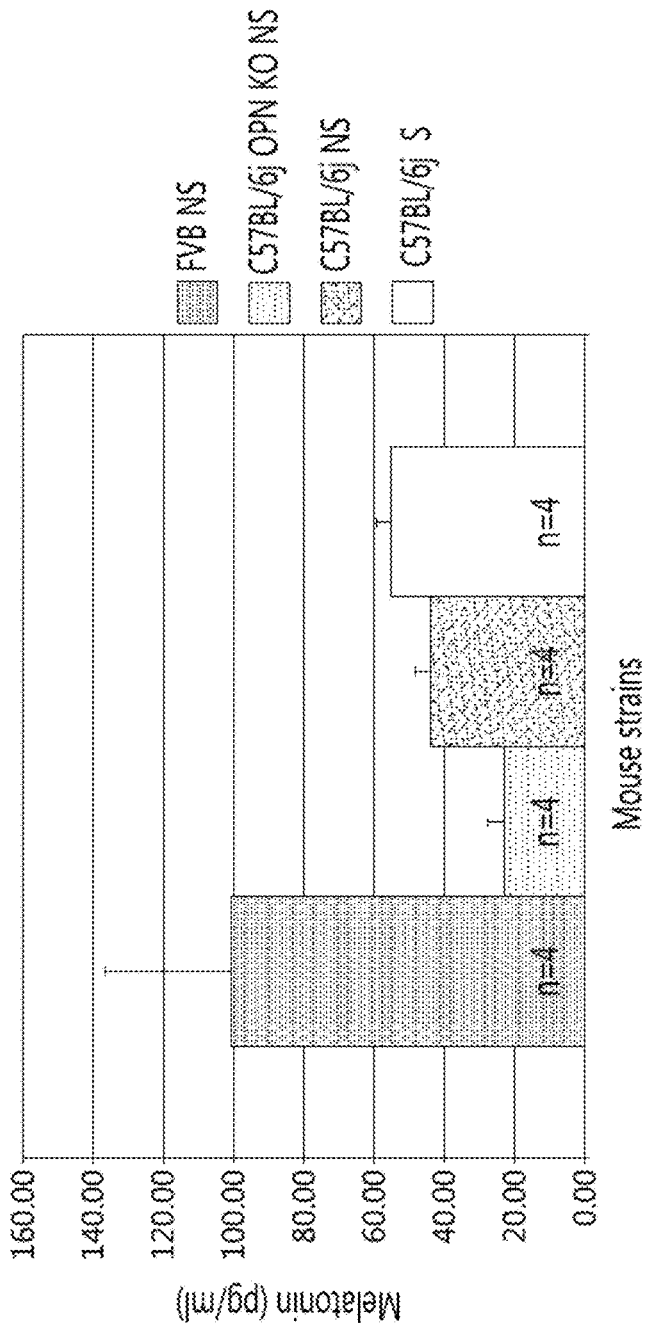
FIG. 3 shows a variation in plasma melatonin concentrations in different mouse strains. S=scoliotic; NS=non-scoliotic.

FIG. 3 shows a two-fold decrease in circulating melatonin level of bipedal C57Bl/6j OPN KO mice when compared to wild-type ones (C57Bl/6j, C57Bl/6j and FVB).

As indicated above, C57Bl/6j mice are melatonin deficient and may develop a scoliosis (S) in contrast to the FVB strain, which produces high melatonin levels. OPN-knockout mice do not develop a scoliosis (NS) even if they are in the same genomic background (C57Bl6/j), although melatonin is markedly decreased, suggesting that melatonin negatively regulates OPN expression and synthesis in vivo. Without being bound by this hypothesis, it is also suggested that in absence of OPN in genetically modified mice, the melatonin level will be further decreased accordingly as an adaptive physiological response to enhance OPN expression and synthesis.

Example 5

Effect of OPN Inhibitors on Scoliosis Prevention

Two compounds suspected of having an effect on OPN transcription or synthesis were injected intraperitoneally at a dosage of 500 µg/kg of body weight/day to chicken 24-48 h prior pinealectomy.

Figure 4:
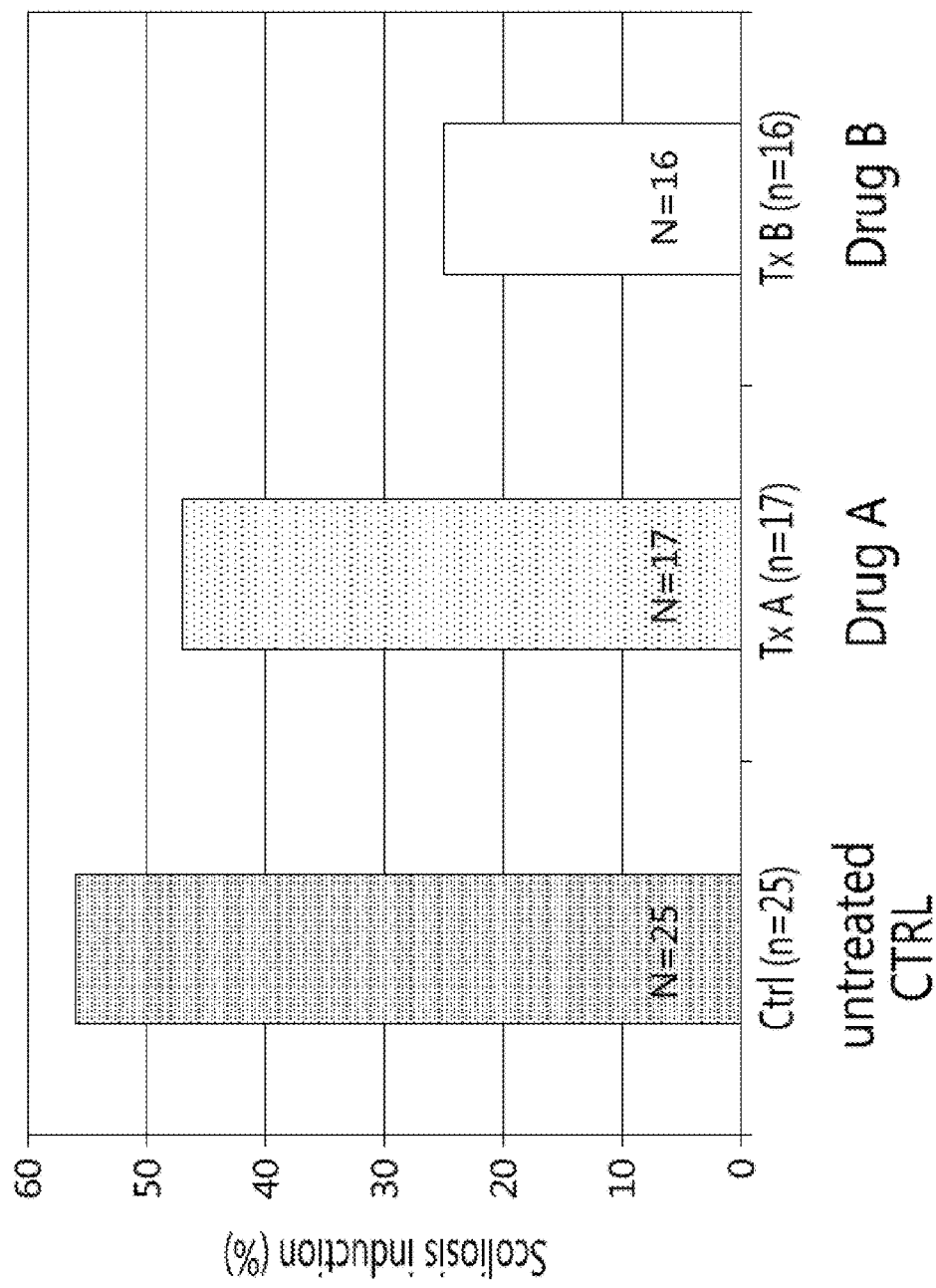
FIG. 4 shows the effect of the pharmacological inhibition of OPN transcription on scoliotic pinealectomized chicken.

As is apparent in FIG. 4, fewer pinealectomized chicken pre-treated with the drugs developed scoliosis (a reduction of 50%) than untreated pinealectomized chickens.

Example 6

Comparing the Level of Circulating OPN in AIS Patients Classified in Two Groups and Healthy Controls

A group of 252 patients with AIS and 35 healthy control subjects were tested as described in Example 1 above. Patients with AIS were divided into two subgroups according to their spinal curve severity (10°-44° vs. ≥45°) In the most severely affected AIS subgroup, none of the patients had corrective surgery at the time of the tests. Consistent with literature reporting increased AIS prevalence in teenage girls when compared to boys for moderate curves (ratio 10:1 for curve with a Cobb's angle ≥30°), a greater proportion of girls in the AIS groups (86% and 84% in the 10°-44° and ≥45° subgroups, respectively were observed compared to the control groups (54% and 64% in healthy and at risk control groups, respectively, p≤0.0001 when comparing the control groups). There was no significant gender difference between the two AIS subgroups (p=0.76) or between the two control groups (p=0.32). Mean age was significantly higher in AIS patients with Cobb's angle ≥45° compared to those with 10-44° angle (15.2±1.8 vs. 13.8±2.1, p<0.0001). Both AIS groups had higher mean age compared to control groups (10.7±0.6 for the healthy and 9.9±3.4 for the at risk group, p<0.0001 when comparing to either AIS group).

Figure 5B:
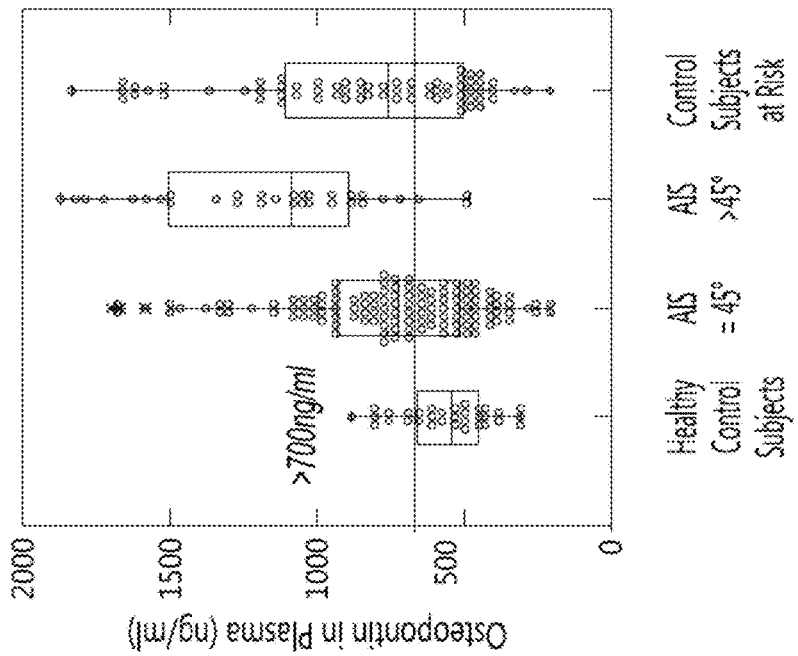

The plasma OPN levels in patients with AIS exhibiting a severe deformity (Cobb's angle ≥45°), low to moderate curve (Cobb's angle between 10° and 44°) and healthy controls are summarized in Table 4 below according to various clinical parameters. The mean plasma OPN levels were significantly higher in both AIS groups when compared to healthy control group although plasma OPN levels were more elevated in patients with the most severe deformities (Cobb's angle ≥45°) (Bonferroni-corrected p<0.001 after adjustment for age, gender, and age-gender interaction). Plasma OPN levels in AIS patients were correlated with the severity of curve deformity (FIG. 5D) in girls and boys (Partial Pearson correlation coefficient adjusted for age=0.29, p<0.001, and 0.33, p=0.04, respectively). Mean plasma OPN levels in the group at risk of developing scoliosis (846±402 ng/ml) differed significantly (Bonferroni-corrected p<0.001) from the healthy controls (570±156 ng/ml).

Figure 5A:
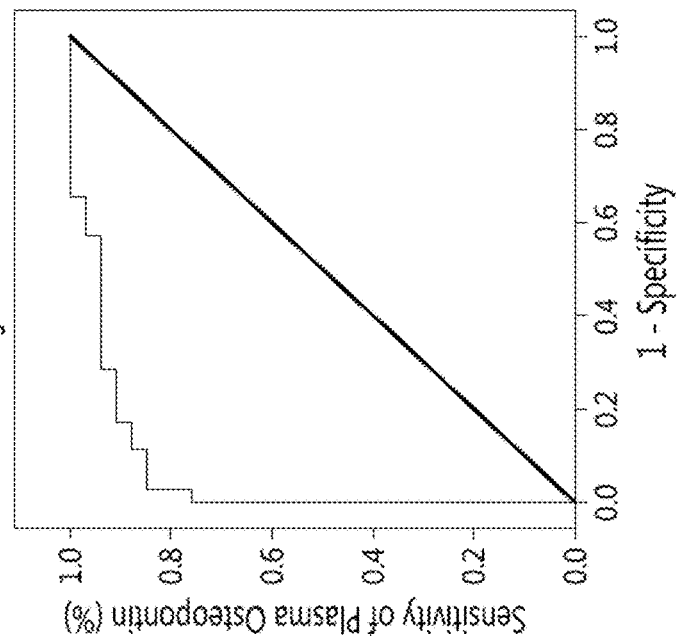
Figure 6:
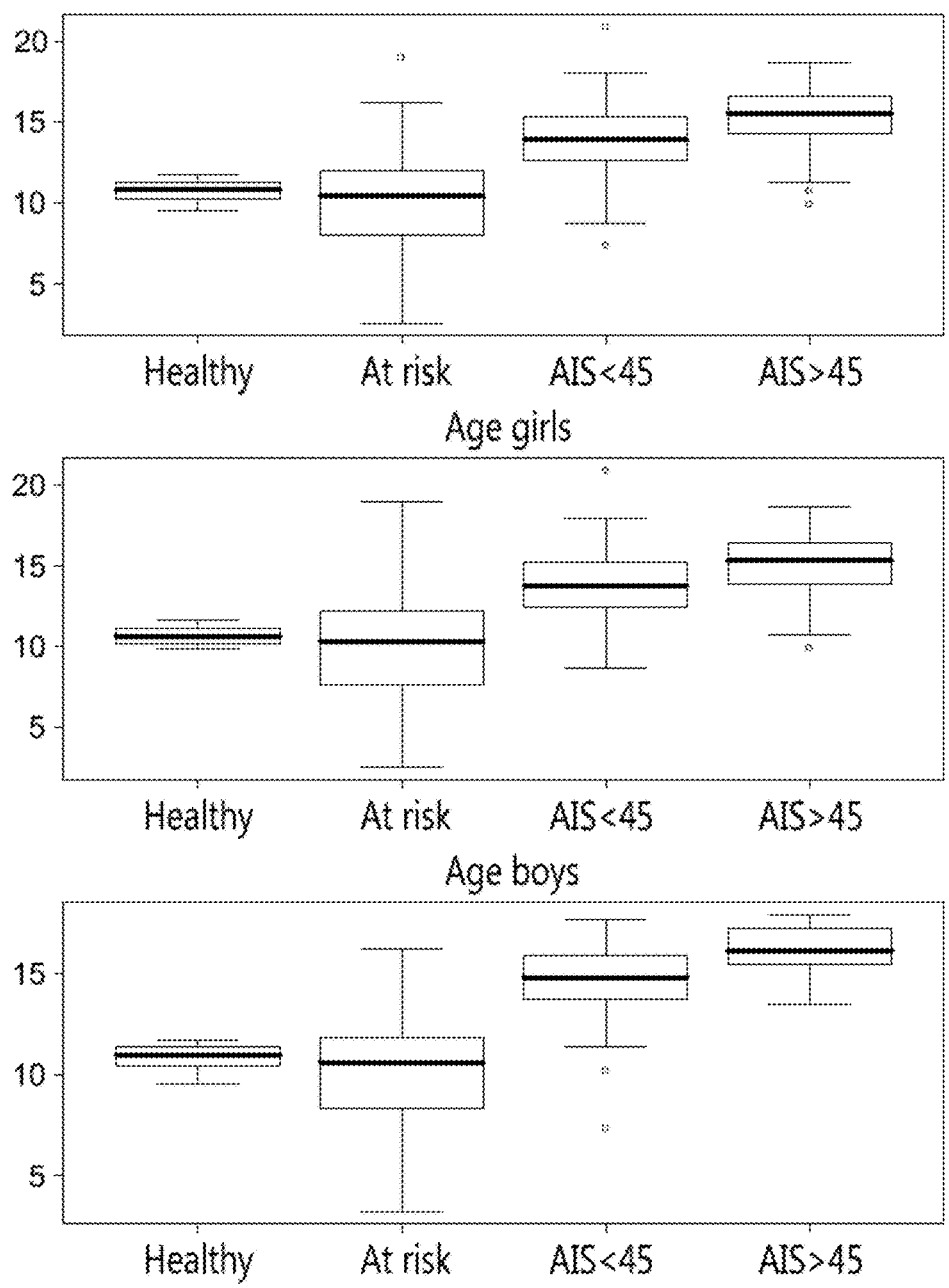
FIG. 6 presents graphs showing the distribution of age in the different groups for male and female combined (control, at risk, AIS<45 and AIS≥45) (top), and separated by sex female (middle) and male (bottom)

Receiver-operating characteristics (ROC) curves analyzes of plasma OPN comparing the patients with AIS more severely affected (Cobb's angle ≥45°) with healthy controls showed an AUC of 0.94 with a standard error of 0.03 (95 percent confidence interval 0.88 to 0.99) (see FIG. 5A). A cut-off value >700 nanograms per milliliter gave a sensitivity of 90.6 percent and a specificity of 81.8 percent with (see FIG. 5B). A cut-off value >800 nanograms per milliliter had the highest accuracy with a sensitivity of 84.4 percent and specificity of 90.6 percent for confirming scoliosis (minimal false negative and false positive results) (see FIG. 5C).

Although as indicated above, high levels of OPN are found in other adult diseases, high plasma OPN levels found in patients with scoliosis are unique in the pediatric population. The detection of OPN level can thus be used to identify within asymptomatic children those who are at risk of developing a scoliosis (AIS or other spinal disorders and disorders causing scoliosis) and identify among scoliotic subjects, those or are at risk of experiencing a progression of scoliosis. Moreover, plasma OPN levels found in AIS patients were often higher than those measured in adult diseases. OPN levels can also be used to predict the risk in adults (e.g. degenerative scoliosis and idiopathic scoliosis that progress through adulthood). Certain mutations have already been associated with other disorders that may lead to scoliosis. In a particular embodiment, the OPN levels could be used in combination with the detection of these mutations.

Example 7

Comparing the Level of Circulating OPN in Asymptomatic Children at Risk and Healthy Controls

A group of 70 asymptomatic children at risk of developing a scoliosis and 35 healthy control subjects were tested as described in Example 1 above. The mean plasma OPN levels in the group at risk of developing a scoliosis (846.30±402 nanograms per milliliter) differed significantly (p=0.001) from the healthy controls (570±156 nanograms per milliliter) and both groups were age- and gender-matched. No significant gender difference was observed (see Table 4 above).

TABLE 4

Mean biochemical values of patients with AIS, healthy control subjects and asymptomatic at risk control subjects*.

| | | Female | | | Male | | | Female + Male | | | |
| --- | --- | --- | --- | --- | --- | --- | --- | --- | --- | --- | --- |
| | Subject Type | N | Mean biomarker level (ng/ml) | Range | N | Mean biomarker level (ng/ml) | Range | N | Mean biomarker level (ng/ml) | Range | P-value† |
| OPN | Healthy controls | 19 | 580 ± 150 | 318-882 | 16 | 558 ± 168 | 308-856 | 35 | 570 ± 156 | 308-882 | — |
| | At risk control | 45 | 829 ± 419 | 208-1834 | 25 | 877 ± 378 | 391-1629 | 70 | 846 ± 402 | 208-1834 | <0.001 |
| | AIS < 45° | 162 | 774 ± 268 | 373-1585 | 27 | 948 ± 335 | 445-1668 | 189 | 799 ± 284 | 373-1668 | <0.001 |
| | AIS ≥ 45° | 53 | 913 ± 398 | 201-1821 | 10 | 1238 ± 409 | 575-1872 | 63 | 965 ± 414 | 201-1872 | <0.001 |
| sCD44 | Healthy controls | 19 | 522 ± 99 | 373-829 | 16 | 575 ± 92 | 404-800 | 35 | 546 ± 98 | 373-829 | — |
| | At risk controls | 45 | 508 ± 96 | 316-760 | 25 | 533 ± 98 | 304-510 | 70 | 517 ± 97 | 304-760 | >0.5 |
| | AIS < 45° | 162 | 503 ± 161 | 194-1253 | 27 | 527 ± 110 | 364-793 | 189 | 506 ± 155 | 194-1253 | >0.5 |
| | AIS ≥ 45° | 53 | 436 ± 251 | 87-882 | 10 | 402 ± 216 | 147-962 | 63 | 431 ± 245 | 87-962 | 0.066 |
| HA | Healthy control | 19 | 128 ± 38 | 72-236 | 16 | 132 ± 49 | 80-255 | 35 | 130 ± 43 | 72-255 | — |
| | At risk controls | 45 | 119 ± 51 | 36-257 | 25 | 117 ± 52 | 33-226 | 70 | 118 ± 51 | 33-257 | >0.5 |
| | AIS < 45° | 162 | 112 ± 60 | 18-356 | 27 | 124 ± 60 | 27-283 | 189 | 114 ± 60 | 18-356 | >0.5 |
| | AIS ≥ 45° | 53 | 93 ± 40 | 32-222 | 10 | 128 ± 71 | 41-25435 | 63 | 98 ± 48 | 32-254 | 0.140 |

*SD is standard deviation

†P-value is from the comparison with healthy control group in all subjects after Bonferroni correction and adjustment for age, gender, and age-gender interaction (OPN and HA) or age (sCD44). After the same adjustments, overall F test p-values for association between group and biomarker levels were < 0.001 (OPN), 0.035 (sCD44), and 0.163 (HA).

Using a cut-off value of 800 nanograms per milliliter, it was observed that 47.9 percent of asymptomatic children in that group were above this plasma OPN value while only 8.6 percent of healthy controls were above this value. These results are in agreement with previous reports showing that the offspring of at least one affected parent develops more often a scoliosis than ones born from unaffected parents (34, 35).

An enzyme-linked immunosorbent assay (ELISA) or RIA for OPN for instance can thus be used for early identification of subjects at risk of developing a scoliosis for purposes of prognosis and/or scoliotic patients stratification for early bracing and less-invasive surgeries with novel fusionless devices, for pharmacological treatments and to monitor responses to treatment in patients with AIS.

Example 8

Comparing the Level of Circulating sCD44 in AIS Patients Classified Two Groups and Healthy Controls Experiments were conducted as described in Example 1 above. The plasma sCD44 and HA levels in healthy controls, both AIS groups and asymptomatic at risk children are displayed in Table 4 above. Comparison among all groups showed no significant change in mean plasma sCD44 and HA values. However, AIS patients exhibiting the most severe spinal deformities (≥45°) had also the lowest mean plasma sCD44 level when compared to the other three groups (p=0.066).

Figure 17:
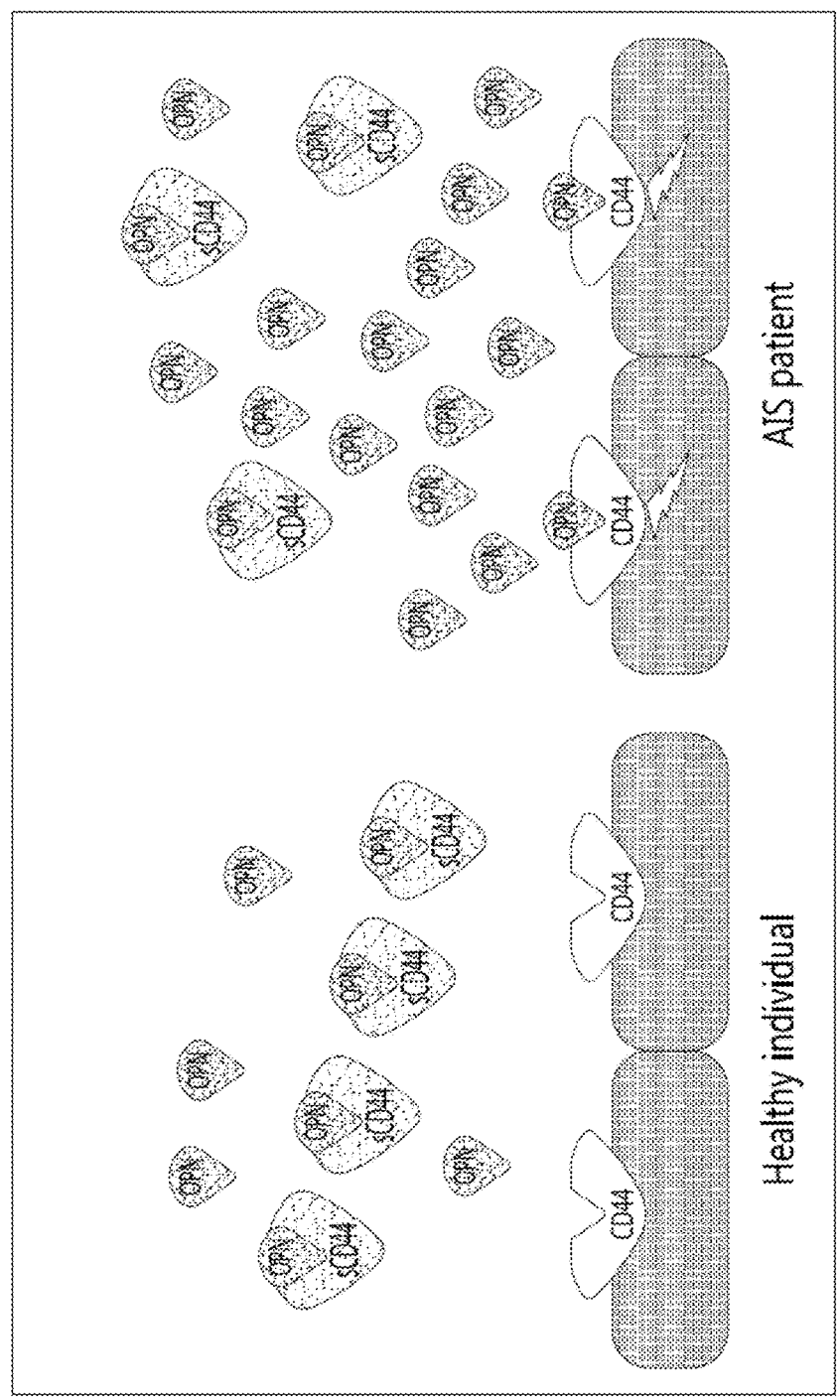
FIG. 17 illustrates a hypothetic molecular concept underlying spinal deformity progression in AIS.

CD44 and sCD44 can act as a receptor and decoy receptor for OPN respectively. In spite that no significant changes were measured among all groups tested, the most severely affected AIS patients (≥45°) showed the lowest mean sCD44 value among all groups tested. Interestingly, decreased plasma sCD44 levels were found in immunodeficiency and autoimmune diseases[35-37], but none of these conditions normally lead to scoliosis in absence of high plasma OPN levels, suggesting that sCD44 could play a role in AIS as disease-modifying factor by interfering with the action of OPN (see FIG. 17).

Example 9

Figure 7:
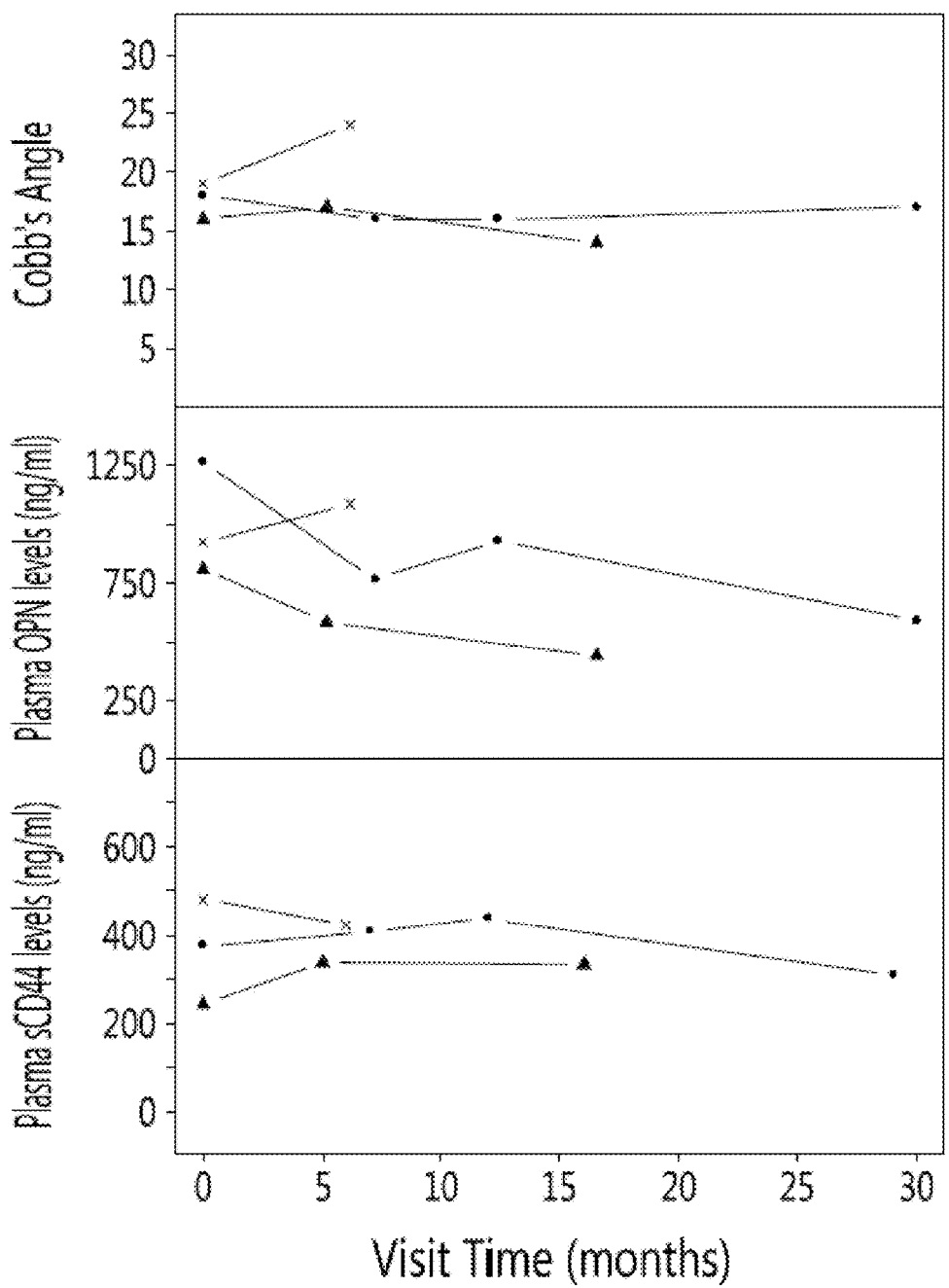
FIG. 7 shows profiles of change in OPN levels, sCD44 levels, and Cobb's angle over follow up time in 4 selected AIS female patients (not under brace treatment) aged 12 (red), 14 (green and blue), and 17 (yellow) at baseline visit.

Profiles of Change in OPN Levels, sCD44 Levels, and Cobb's Angle of AIS Patients Over Time The progression of biomarkers (OPN and sCD44 levels) and Cobb's angle was measured over follow up time in AIS patients. FIG. 7 presents these progression in 4 selected AIS female patients (not under brace treatment) aged 12 (red), 14 (green and blue), and 17 (yellow) at baseline visit.

Figure 8:
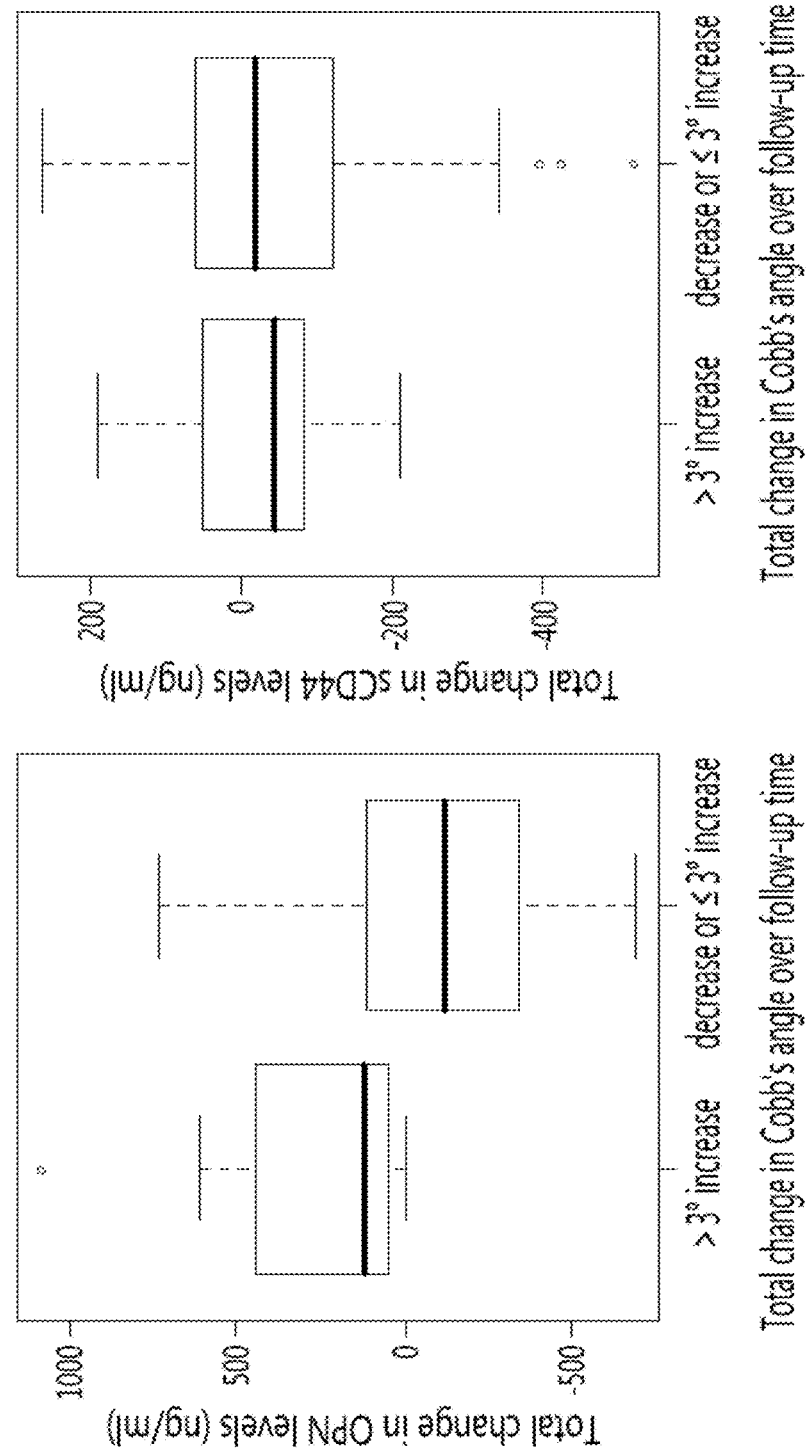
FIG. 8 shows the distribution of total change in OPN (left panel) and sCD44 (left panel) levels over follow-up time in AIS patients with worsened curve deformity (total increase in Cobb's angle greater than 3°; n=14) and in those without significant change in curve (no change in Cobb's angle, decrease, or increase smaller than 3°; n=36)

FIG. 8 presents the distribution of total change in OPN (left panel) and sCD44 (right panel) levels over follow-up time in AIS patients with worsened curve deformity (total increase in Cobb's angle greater than 3°) and in those without significant change in curve (no change in Cobb's angle, decrease, or increase smaller than 3°; also presents for all Average change in OPN levels was significantly higher in the group with worsened curve deformity (Wilcoxon rank sum test p<0.01). No significant difference was detected for sCD44 (p>0.5). Length of follow-up time was similar between the 2 groups (p>0.5).

Figure 9A:
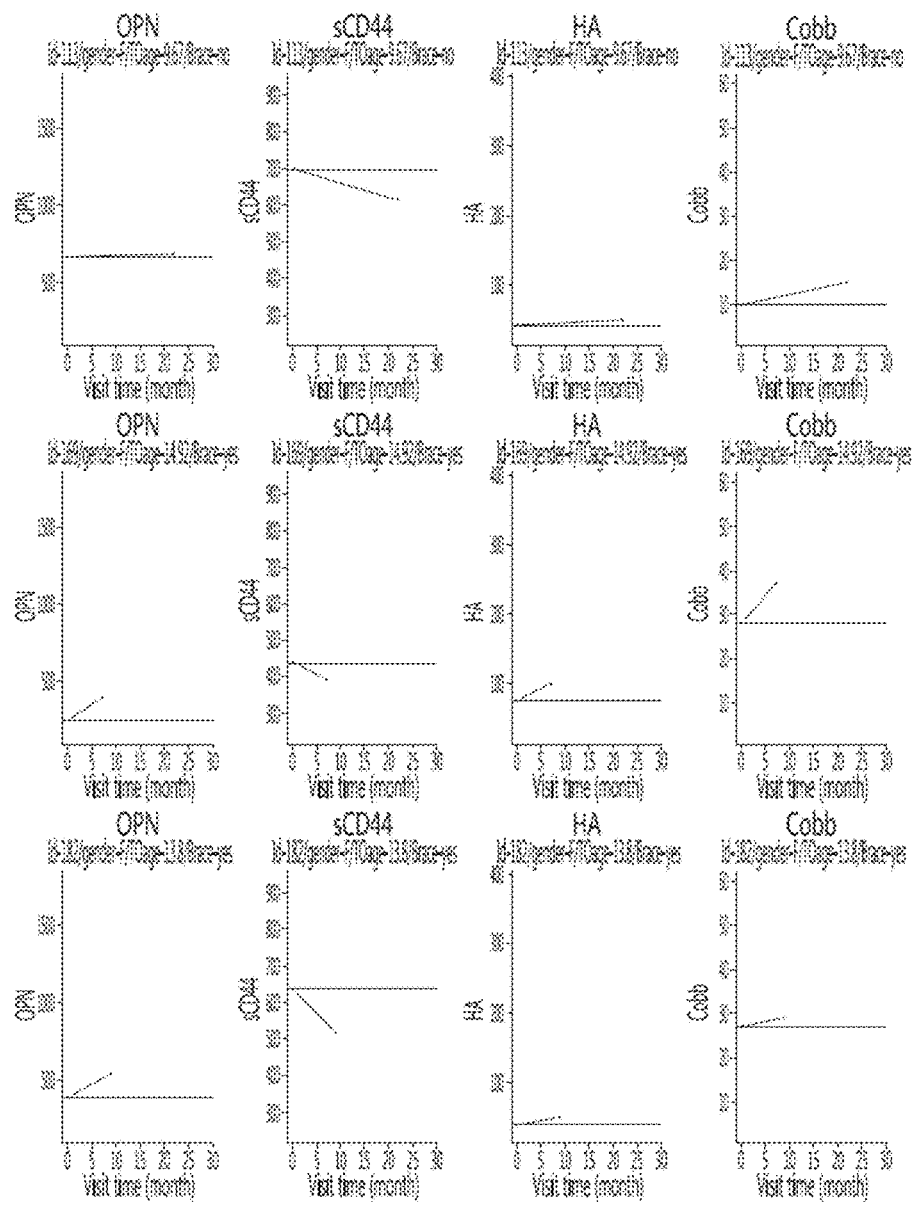
FIGS. 9A-9C present graphs showing OPN progression correlated with Cobb's angle progression in AIS patients.
Figure 9B:
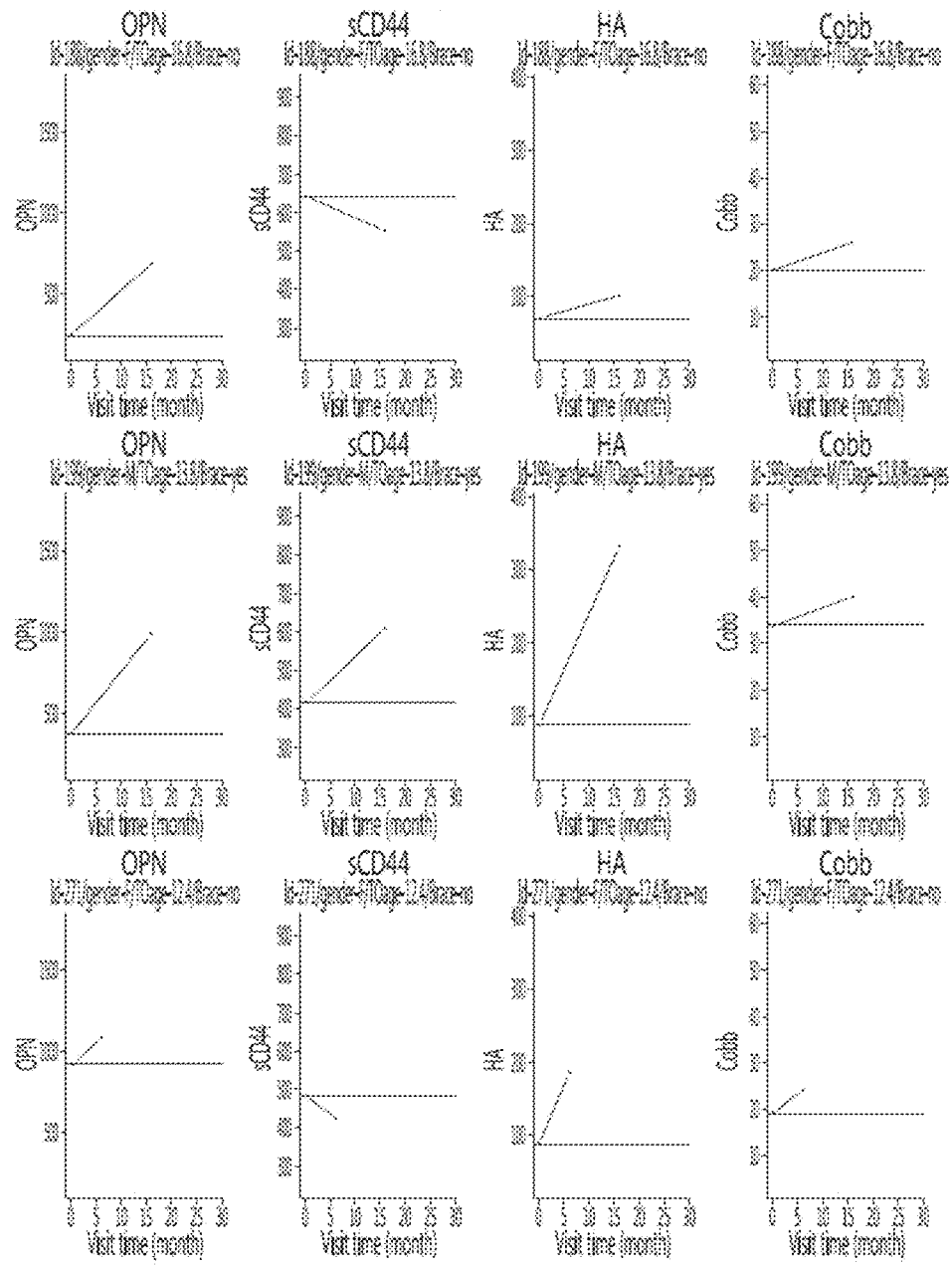
Figure 9C:
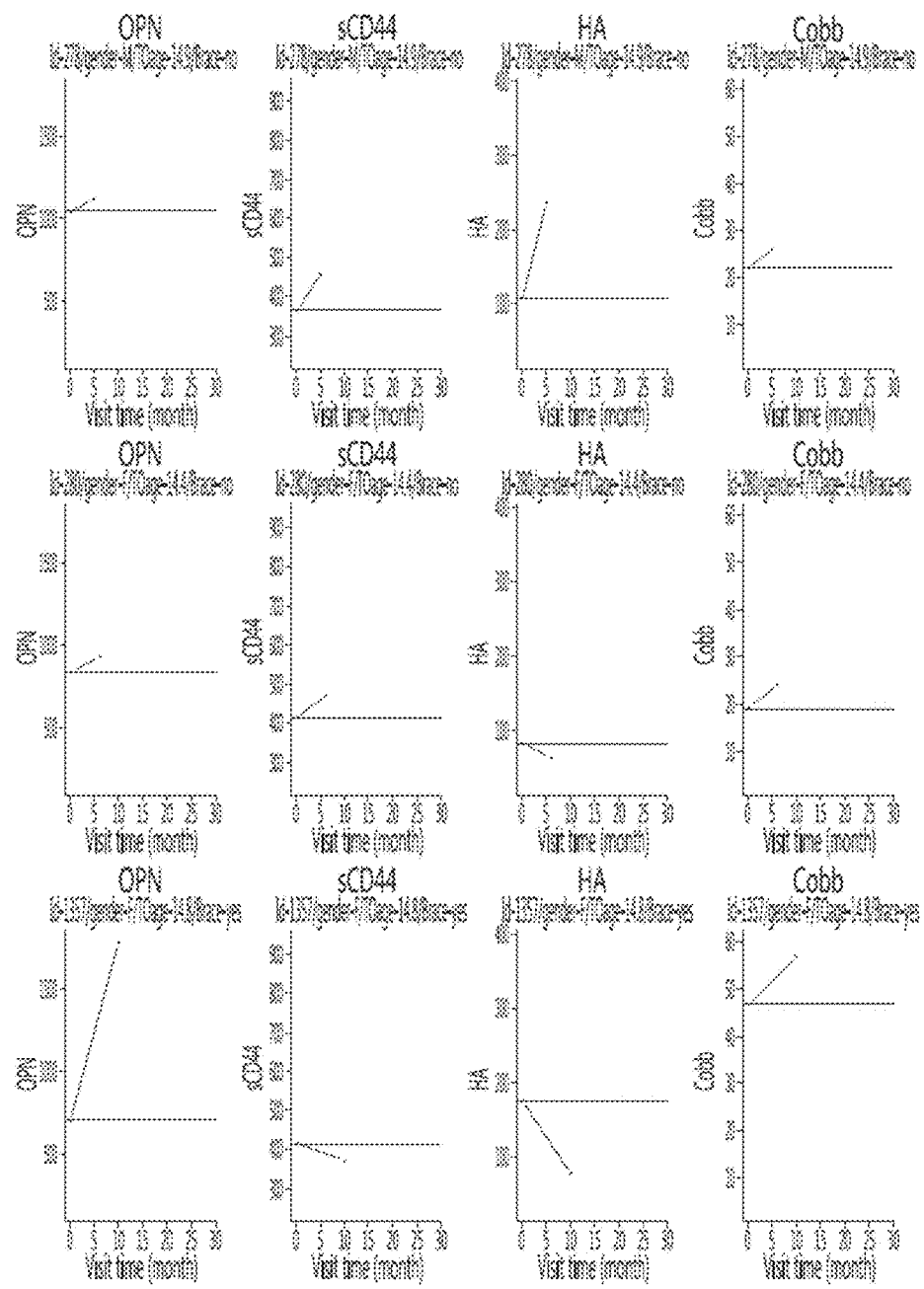
Figure 10A:
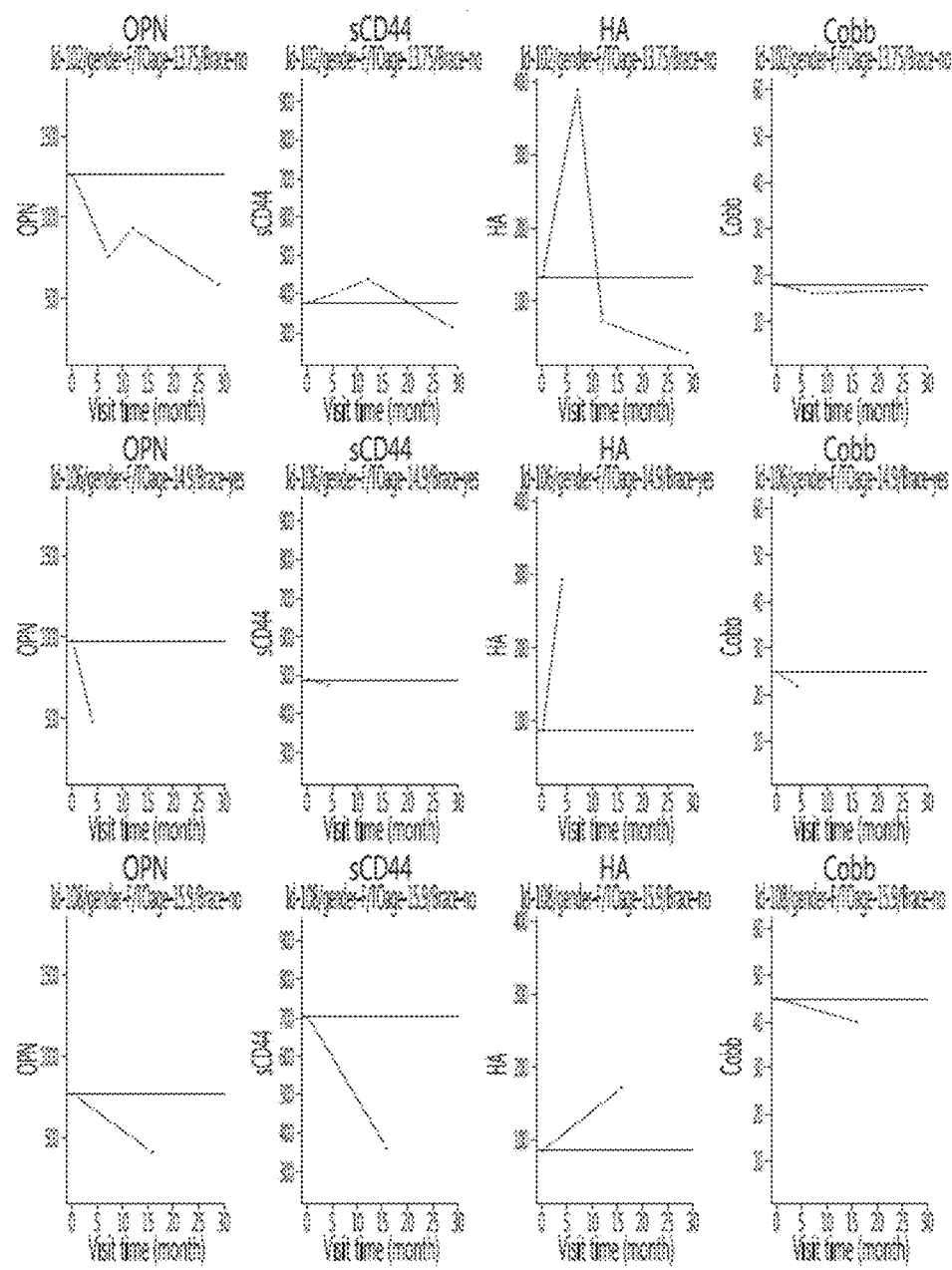
Figure 10C:
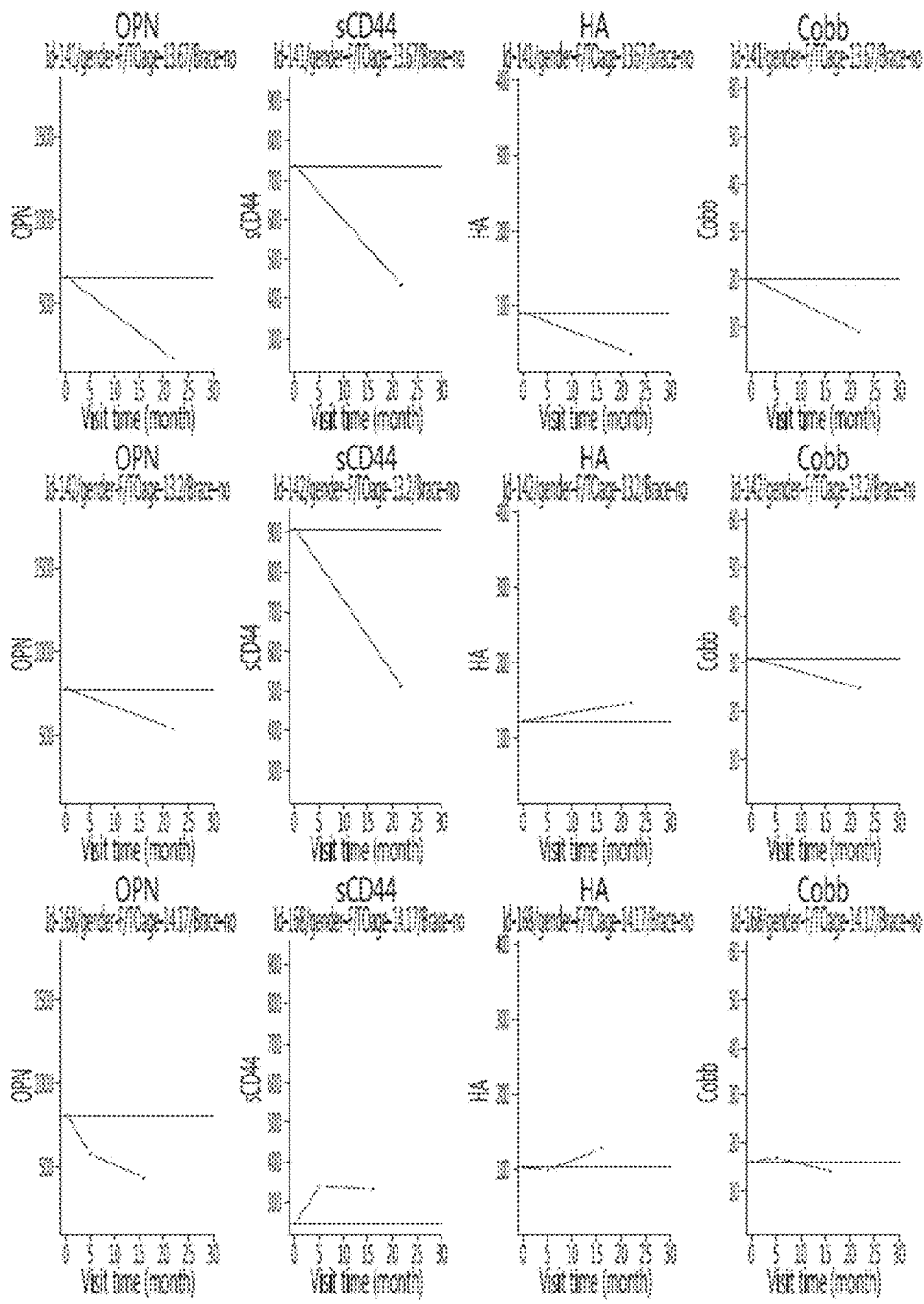
Figure 10D:
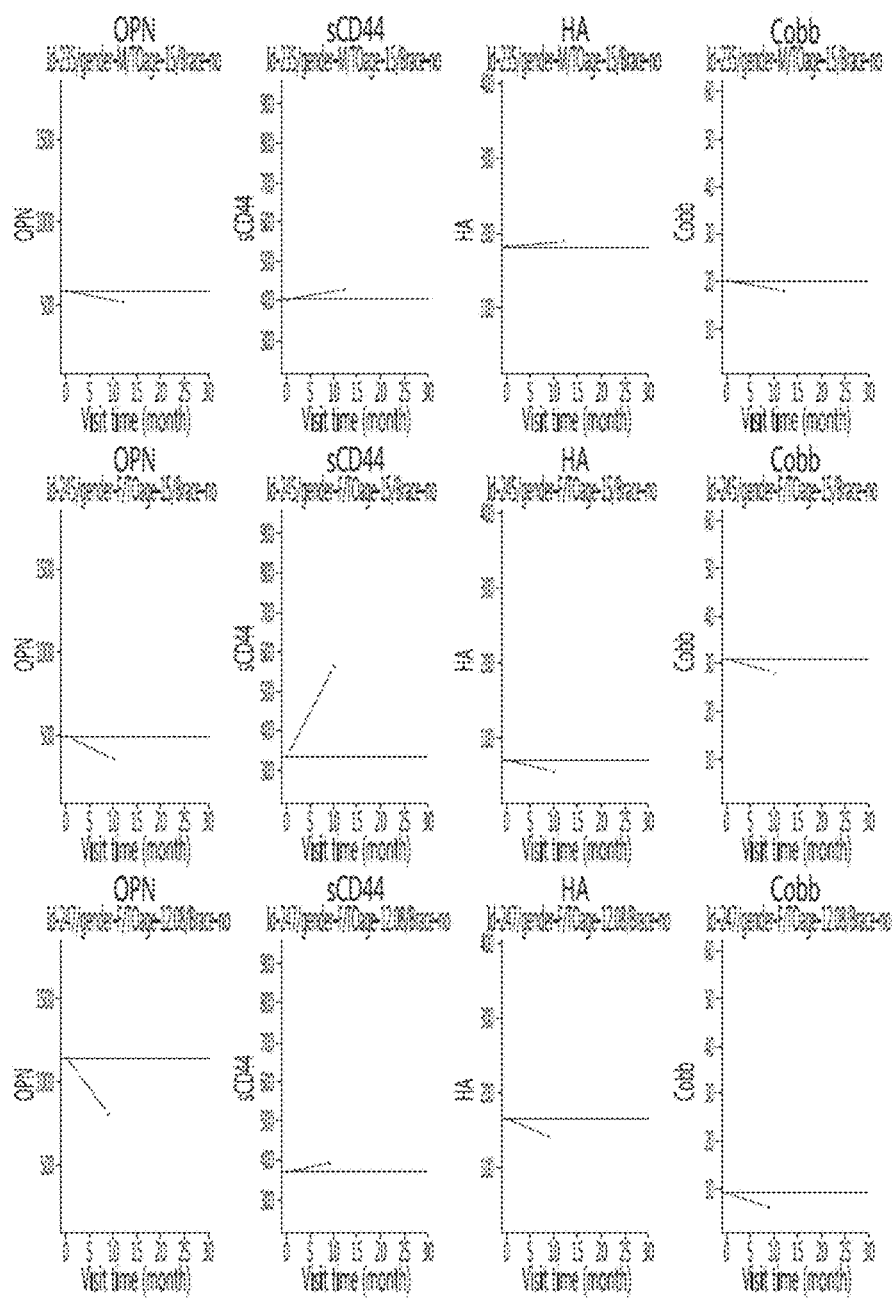
Figure 10E:
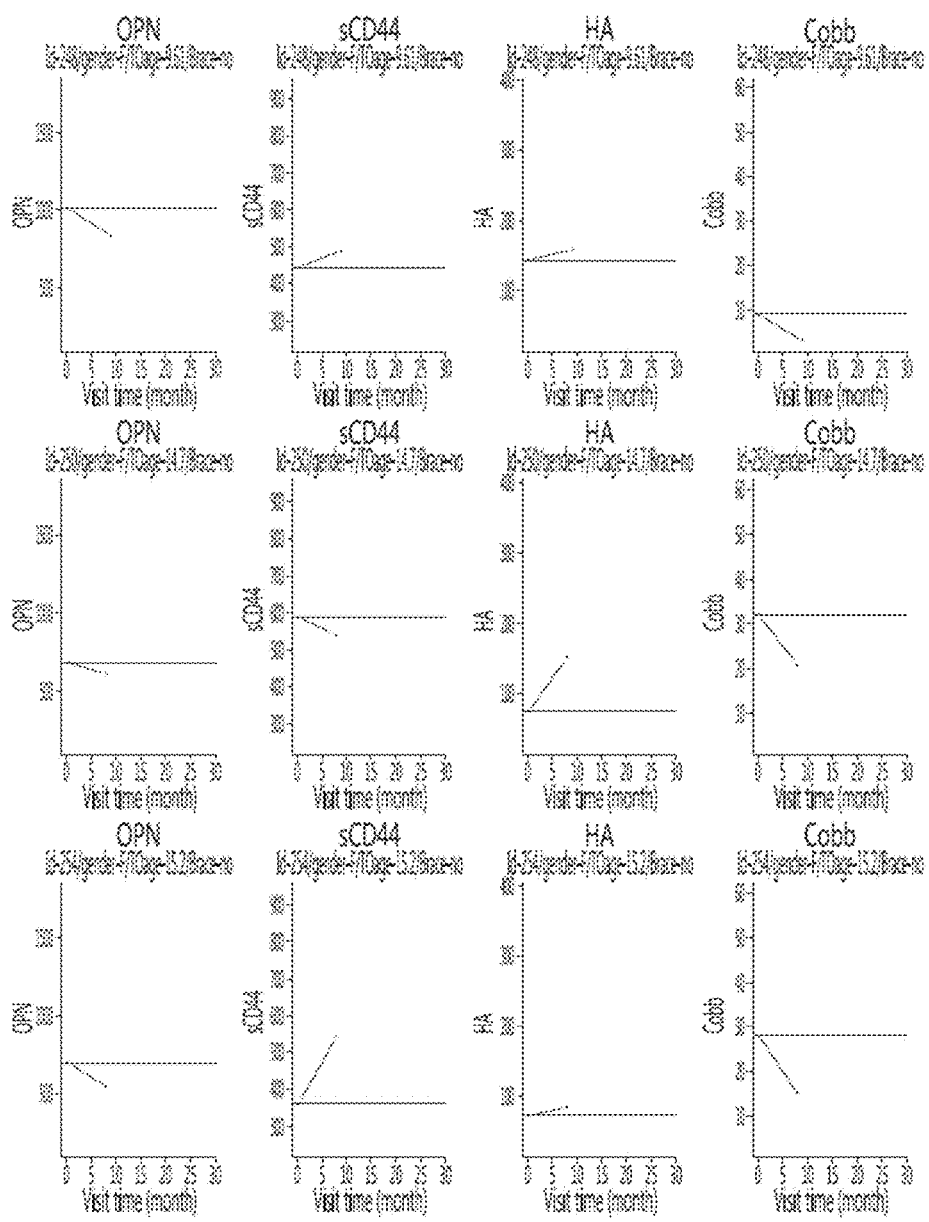
Figure 10F:
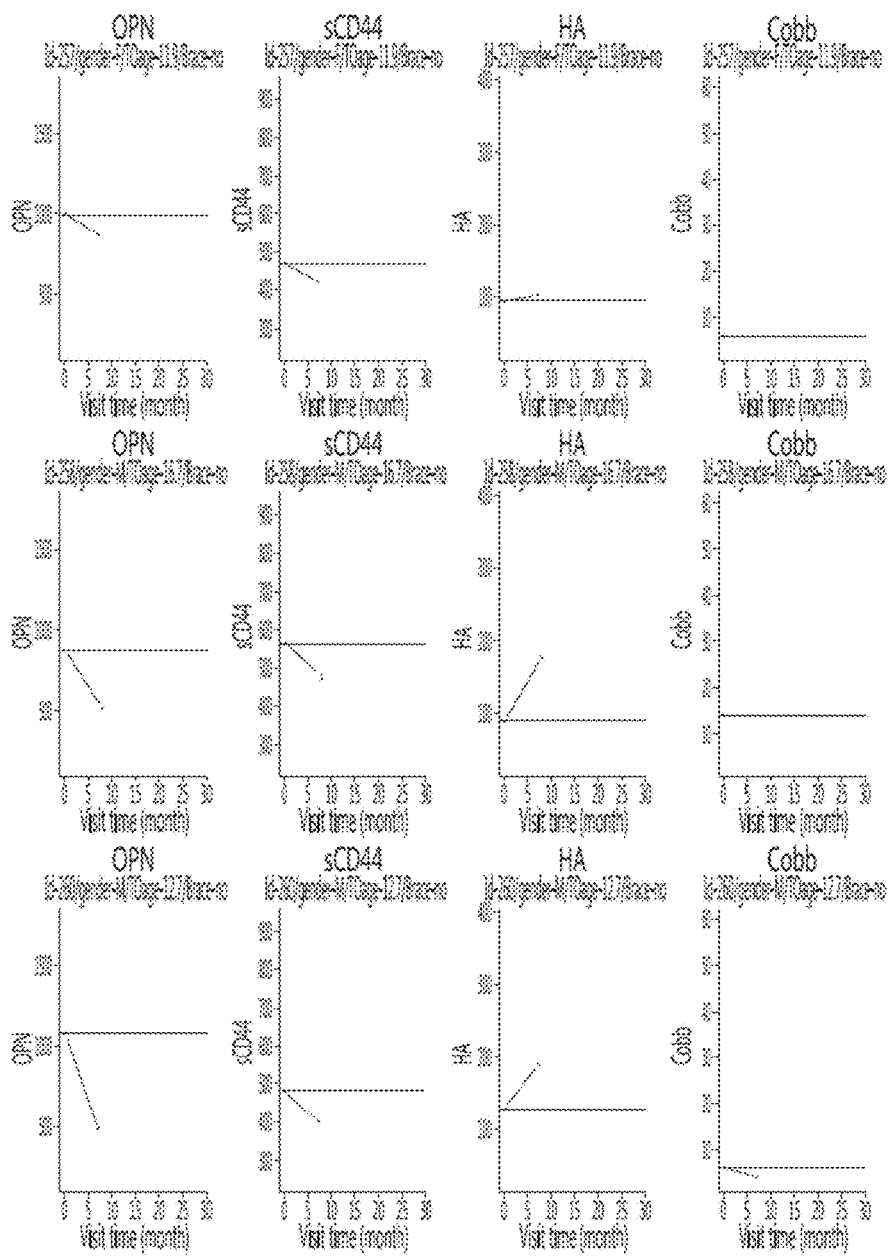
Figure 10G:
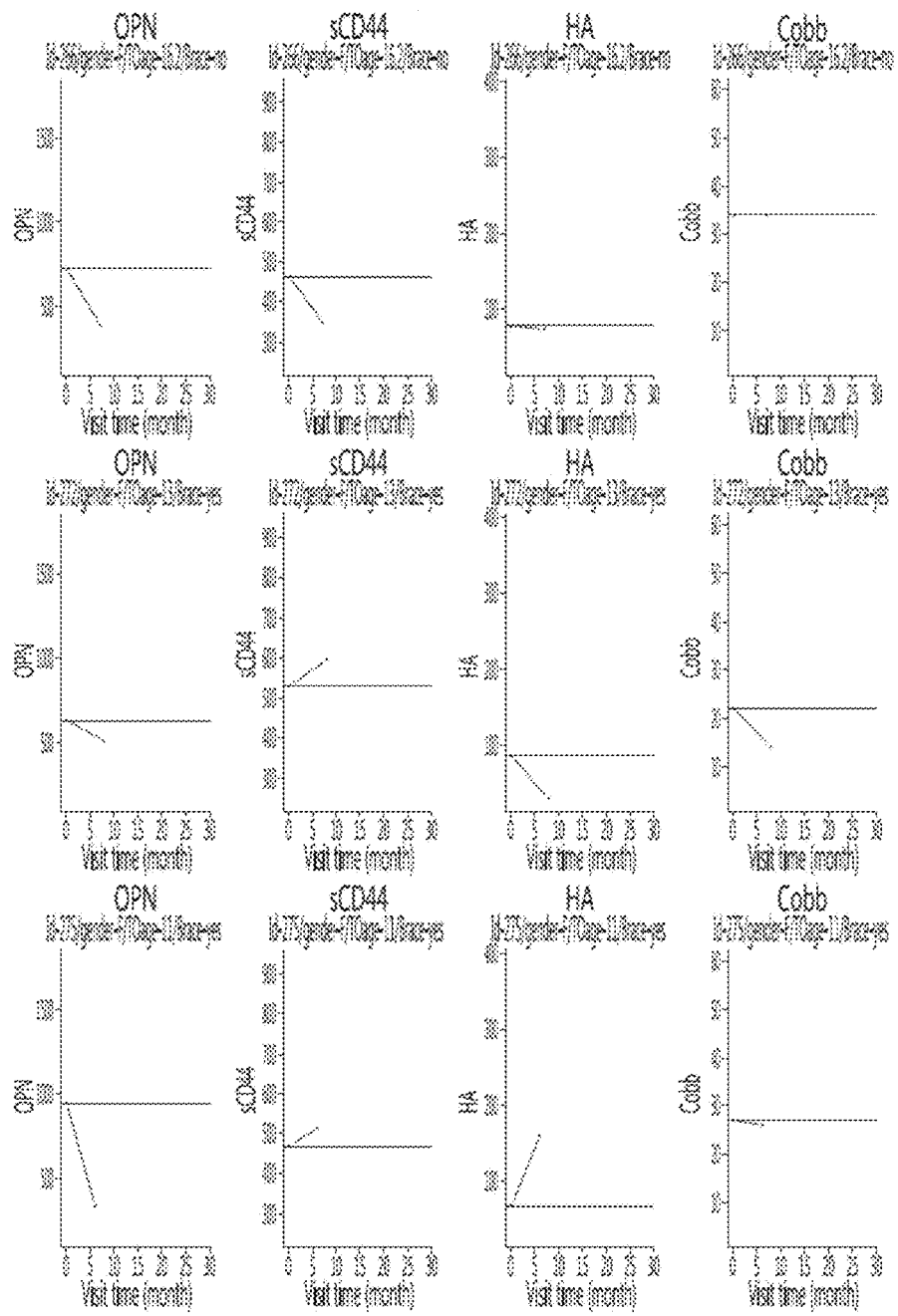
Figure 10H:
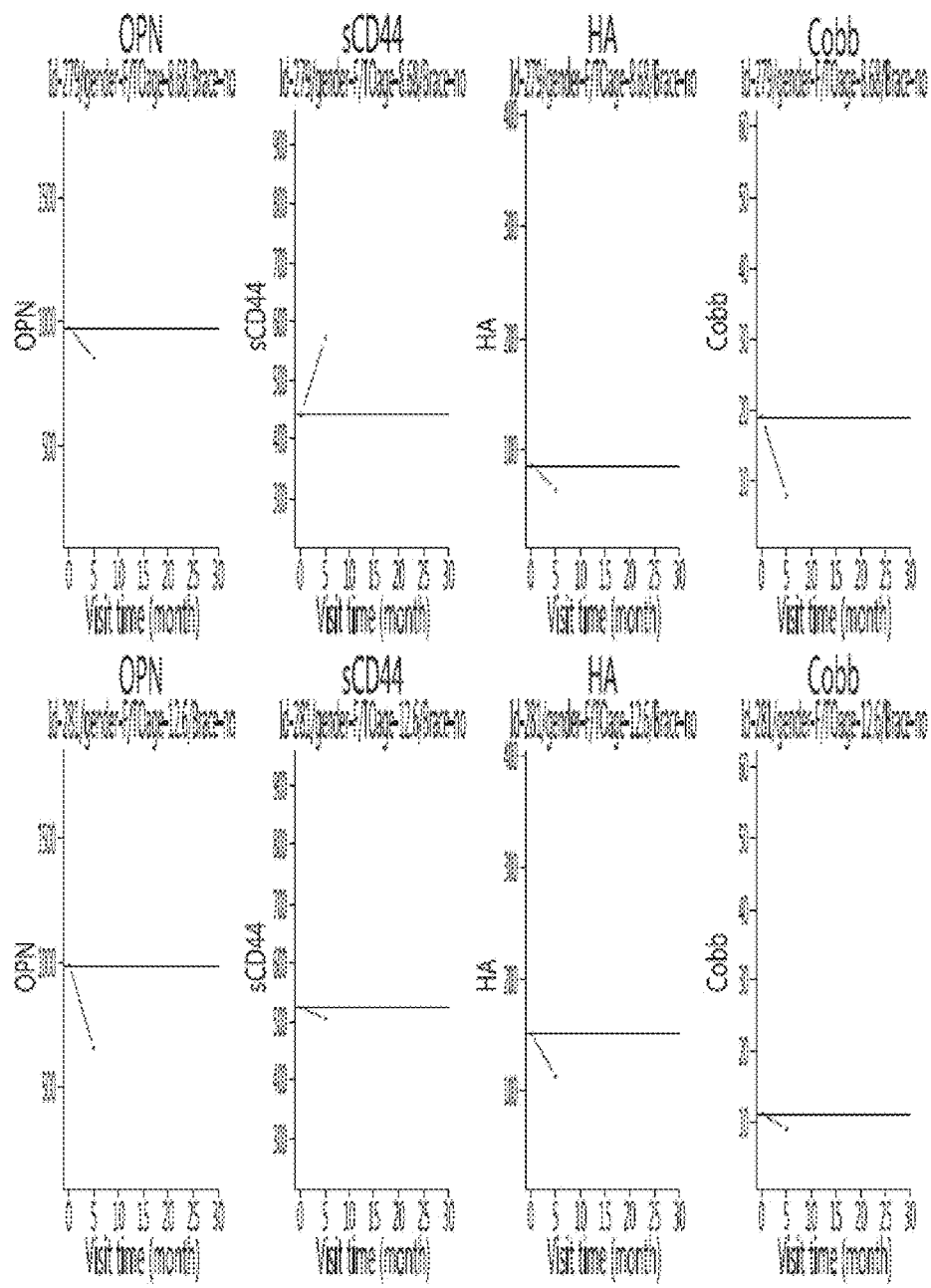

FIG. 9 shows OPN progression correlated with Cobb's angle progression in a group of AIS patients while FIG. 10 shows OPN regression or stabilization correlated with Cobb's angle regression or stabilization in other AIS patients;

OPN level can be used to identify among pre-diagnosed patients those in which scoliosis will progress.

Example 10

Figure 11:
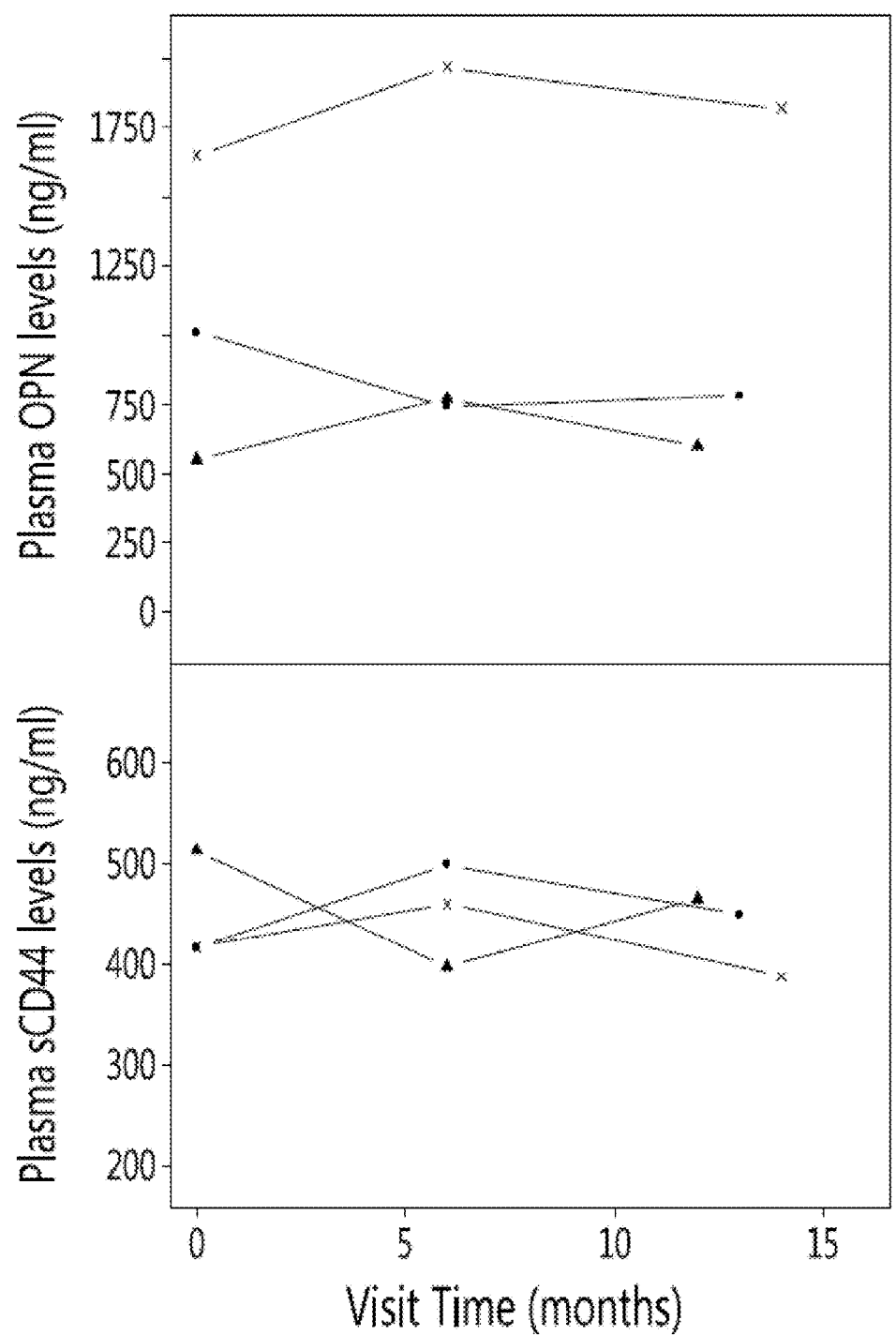
FIG. 11 shows profiles of change in OPN and sCD44 levels over follow up time in 4 selected at risk subjects without scoliosis: one male aged 13 (green), and 3 female aged 5 (gold), 11 (blue), and 9 (red) at baseline visit.

Profiles of Change in OPN Levels, sCD44 Levels, and Cobb's Angle of Asymptomatic at Risk Patients Over Time FIG. 11 shows profiles of change in OPN and sCD44 levels angle in 4 selected at risk subjects without scoliosis: one male aged 13 (green), and 3 female aged 5 (gold), 11 (blue), and 9 (red) at baseline visit. Significant inter-subject variability was observed in the baseline levels of biomarkers and change over time among at risk subjects (especially for OPN), indicating the potential of using this biomarker as a tool to monitor onset of scoliosis in at risk subjects.

Tables 5 to 8 below present the clinical and biochemical profiles in detail for each of the healthy control subjects (Table 5), of the AIS patients with Cobb's angles of less than 45 degrees (Table 6), of the AIS patients with Cobb's angles 45° or more (Table 7), and of the asymptomatic at risk children (Table 8).

TABLE 5

Clinical and biochemical profile of healthy control subjects.

| Random | Date of Birth | Gender | Age | Collection Date | Time point (months) | [OPN] (ng/ml) | [sCD44] (ng/ml) | [HA] (ng/ml) |
|---|---|---|---|---|---|---|---|---|
| 1 | 1996 Mar. 21 | M | 11.2 | 2007 May 22 | T0 | 663.92 ± 26.03 | 533.4 | 164.87 ± 6.05 |
| 2 | 1996 Jun. 26 | M | 10.9 | 2007 May 22 | T0 | 418.23 ± 12.49 | 504.38 | 120.49 ± 2.06 |
|   |   |   | 11.6 | 2008 Jan. 16 | T8 | 593.64 ± 28.77 | 555.88 | 150.02 ± 15.74 |
| 3 | 1996 May 28 | F | 11.0 | 2007 May 22 | T0 | 629.52 ± 0.64 | 829.35 | 140.89 ± 3.90 |
|   |   |   | 11.7 | 2008 Jan. 16 | T8 | 892.76 ± 1.54 | 507.54 | 146.71 ± 24.69 |
| 4 | 1996 Jun. 22 | M | 10.9 | 2007 May 22 | T0 | 458.68 ± 11.40 | 799.57 | 100.98 ± 6.89 |
| 5 | 1996 Oct. 13 | F | 10.6 | 2007 May 22 | T0 | 459.33 ± 2.90 | 525.76 | 139.84 ± 2.89 |
|   |   |   | 11.3 | 2008 Jan. 16 | T8 | 464.48 ± 2.29 | 476.43 | 157.36 ± 20.10 |
| 7 | 1998 Aug. 8 | F | 10.8 | 2007 May 22 | T0 | 691.18 ± 2.50 | 664.38 | 120.69 ± 2.79 |
|   |   |   | 11.5 | 2008 Jan. 16 | T8 | 825.38 ± 1.16 | 545.85 | 180.39 ± 42.55 |
| 8 | 1996 Feb. 1 | M | 11.3 | 2007 May 22 | T0 | 498.86 ± 0.66 | 643.38 | 99.24 ± 2.35 |
|   |   |   | 12.0 | 2008 Jan. 16 | T8 | 469.87 ± 11.47 | 440.44 | 154.20 ± 2.53 |
| 9 | 1997 Jun. 28 | M | 9.9 | 2007 May 22 | T0 | 517.11 ± 53.44 | 582.66 | 134.43 ± 6.42 |
| 10 | 1997 Jul. 23 | F | 9.8 | 2007 May 22 | T0 | 756.24 ± 23.61 | 499.03 | 131.04 ± 1.98 |
|   |   |   | 10.5 | 2008 Jan. 16 | T8 | 1039.80 ± 3.10 | 337.33 | 167.84 ± 2.48 |

TABLE 5-continued

Clinical and biochemical profile of healthy control subjects.

| Random | Date of Birth | Gender | Age | Collection Date | Time point (months) | [OPN] (ng/ml) | [sCD44] (ng/ml) | [HA] (ng/ml) |
|---|---|---|---|---|---|---|---|---|
| 11 | 1996 Feb. 22 | M | 11.3 | 2007 Jun. 6 | T0 | 653.09 ± 15.14 | 581.14 | 191.13 ± 17.98 |
| | | | 11.8 | 2007 Dec. 4 | T6 | 521.00 ± 5.82 | 861.46 | 265.54 ± 6.97 |
| 12 | 1996 Feb. 9 | F | 11.3 | 2007 Jun. 6 | T0 | 449.97 ± 11.21 | 490.25 | 112.71 ± 17.95 |
| | | | 11.8 | 2007 Dec. 4 | T6 | 923.12 ± 1.03 | 476.09 | 188.80 ± 15.17 |
| 13 | 1996 May 17 | F | 11.1 | 2007 Jun. 6 | T0 | 488.30 ± 0.80 | 428.77 | 168.61 ± 9.49 |
| | | | 11.6 | 2007 Dec. 4 | T6 | 659.35 ± 1.68 | 584.96 | 182.09 ± 13.74 |
| 14 | 1995 Oct. 20 | M | 11.6 | 2007 Jun. 6 | T0 | 610.77 ± 8.93 | 573.88 | 128.40 ± 6.58 |
| | | | 12.1 | 2007 Dec. 4 | T6 | 469.87 ± 19.12 | 527.07 | 167.16 ± 44.48 |
| 16 | 1997 Mar. 7 | F | 10.2 | 2007 Jun. 6 | T0 | 544.82 ± 7.91 | 516.6 | 132.83 ± 2.07 |
| | | | 10.7 | 2007 Dec. 4 | T6 | 723.88 ± 8.56 | 503.74 | 65.43 ± 9.60 |
| 17 | 1996 May 9 | M | 11.1 | 2007 Jun. 6 | T0 | 450.87 ± 6.41 | 553.26 | 255.19 ± 14.61 |
| | | | 11.6 | 2007 Dec. 4 | T6 | 530.37 ± 16.78 | 267.86 | 42.33 ± 7.47 |
| 18 | 1997 Sep. 2 | F | 9.8 | 2007 Jun. 6 | T0 | 555.41 ± 32.17 | 498.65 | 127.24 ± 10.65 |
| 19 | 1996 Nov. 4 | M | 10.6 | 2007 Jun. 6 | T0 | 314.85 ± 9.93 | 682.71 | 175.92 ± 16.20 |
| 20 | 1997 May 30 | F | 10.0 | 2007 Jun. 6 | T0 | 381.57 ± 4.61 | 373.01 | 87.65 ± 3.71 |
| | | | 10.5 | 2007 Dec. 4 | T6 | 434.48 ± 5.73 | 497.7 | 142.61 ± 8.42 |
| 21 | 1997 Jan. 7 | F | 10.4 | 2007 Jun. 6 | T0 | 318.19 ± 6.62 | 474.59 | 235.76 ± 3.68 |
| | | | 10.9 | 2007 Dec. 4 | T6 | 393.98 ± 3.87 | 571.14 | 209.26 ± 2.40 |
| 22 | 1997 Feb. 9 | F | 10.3 | 2007 Aug. 6 | T0 | 882.15 ± 18.31 | 542.95 | 131.86 ± 1.13 |
| | | | 10.8 | 2007 Dec. 4 | T6 | 804.46 | 593.61 | 120.43 ± 14.60 |
| 23 | 1997 Mar. 2 | M | 10.3 | 2007 Jun. 6 | T0 | 307.71 ± 4.88 | 621.23 | 157.12 ± 2.29 |
| 24 | 1997 Jun. 19 | F | 10.0 | 2007 Jun. 6 | T0 | 423.06 ± 13.90 | 561.28 | 149.88 ± 5.65 |
| 25 | 1997 Apr. 12 | F | 10.1 | 2007 Jun. 6 | T0 | 758.88 ± 5.74 | 478.79 | 169.32 ± 8.25 |
| 26 | 1997 Dec. 2 | M | 9.5 | 2007 Jun. 6 | T0 | 441.36 ± 8.32 | 645.84 | 148.32 ± 16.36 |
| 27 | 1996 Apr. 3 | F | 11.2 | 2007 Jun. 6 | T0 | 794.21 ± 5.50 | 545.62 | 77.58 ± 8.87 |
| | | | 11.7 | 2007 Dec. 4 | T6 | 748.79 ± 7.61 | 575.46 | 228.08 ± 27.64 |
| 28 | 1995 Sep. 30 | F | 11.7 | 2007 Jun. 12 | T0 | 503.25 ± 8.16 | 451.68 | 71.91 ± 4.23 |
| 29 | 1996 Sep. 15 | M | 10.7 | 2007 Jun. 12 | T0 | 576.62 ± 5.29 | 554.79 | 80.24 ± 3.69 |
| | | | 11.2 | 2007 Dec. 4 | T6 | 552.15 | 598.79 | 108.09 ± 16.44 |
| 30 | 1996 Jan. 18 | F | 11.4 | 2007 Jun. 12 | T0 | 578.62 ± 0.24 | 634.22 | 126.21 ± 4.18 |
| | | | 11.9 | 2007 Dec. 4 | T6 | 498.67 ± 8.60 | 606.57 | 192.18 ± 31.90 |
| 31 | 1996 Aug. 24 | F | 10.8 | 2007 Jun. 12 | T0 | 531.91 ± 4.36 | 432.2 | 132.19 ± 5.06 |
| | | | 11.3 | 2007 Dec. 4 | T6 | 455.46 ± 4.85 | 660.14 | 244.46 ± 3.49 |
| 32 | 1997 Apr. 19 | F | 10.1 | 2007 Jun. 12 | T0 | 611.32 ± 6.46 | 481.47 | 92.69 ± 2.87 |
| | | | 10.6 | 2007 Dec. 4 | T6 | 406.38 ± 19.28 | 415.61 | 142.80 ± 25.25 |
| 33 | 1997 Apr. 21 | M | 10.1 | 2007 Jun. 12 | T0 | 543.15 ± 7.32 | 403.56 | 91.82 ± 4.49 |
| | | | 10.6 | 2007 Dec. 4 | T6 | 360.77 ± 9.93 | 544.36 | 81.68 ± 23.85 |
| 34 | 1995 Nov. 15 | M | 11.6 | 2007 Jun. 12 | T0 | 856.07 ± 3.82 | 501.71 | 96.3 ± 4.15 |
| | | | 12.1 | 2007 Dec. 4 | T6 | 922.12 ± 20.68 | 535.71 | 56.34 ± 1.86 |
| 35 | 1996 Apr. 22 | F | 11.1 | 2007 Jun. 12 | T0 | 659.81 ± 5.54 | 502.09 | 87.90 ± 4.85 |
| | | | 11.6 | | T6 | 596.77 ± 10.14 | 378.46 | 242.42 ± 36.30 |
| 38 | 1995 Dec. 9 | M | 11.5 | 2007 Jun. 12 | T0 | 818.84 ± 14.56 | 502.85 | 83.26 ± 0.12 |
| 37 | 1995 Oct. 7 | M | 11.7 | 2007 Jun. 12 | T0 | 805.92 ± 14.01 | 511.63 | 80.24 ± 3.69 |
| | | | 12.2 | 2007 Dec. 4 | T6 | 304.61 ± 14.94 | 489.06 | 141.51 ± 21.50 |

\* Plus-minus values are means ± standard deviations.
† Healthy control subjects have no family history of scoliosis and are examined before sample collection by an orthopaedic surgeon.

TABLE 6

Clinical and biochemical profiles of AIS patients with Cobb's angles less than 45°.

| Patient ID | Date of Birth | Gender | Age | Collection Date | Time point (mths) | Cobb's Angle Pre-op | Curve Type | Date of surgery | Family history | [OPN] (ng/ml) | [sCD44] (ng/ml) | [HA] (ng/ml) |
|---|---|---|---|---|---|---|---|---|---|---|---|---|
| 102 | 1991 Sep. 12 | F | 13.8 | 2005 Jun. 10 | T0 | 18 | rT | — | Cousin | 1265.10 | 375.56 | 132.06 ± 39.35 |
|  |  |  | 14.3 | 2006 Jan. 13 | T7 | 16 | rT | — |  | 766.80 | 408.06 | 368.93 ± 23.42 |
|  |  |  | 15.8 | 2007 Jun. 1 | T12 | 16 | rT | — |  | 933.77 ± 13.23 | 437.55 | 71.91 ± 4.23 |
|  |  |  | 16.2 | 2007 Nov. 30 | T29 | 17 | rT | — |  | 591.72 ± 66.49 | 311.40 | 27.92 ± 1.72 |
| 103 |  | M | 13.8 | 2005 Jun. 10 | T0 | 13 | lT | — | Father (cyphose) | 1338.32 | 792.62 | 207.12 |
| 104 | 1991 Sep. 4 | F | 13.4 | 2005 Jun. 10 | T0 | 21-22 | rflL | — | — | 1221.83 | 742.48 | 132.24 |
| 106 | 1992 Jan. 29 | F | 14.8 | 2007 Jun. 5 | T0 | 25-24 | rflL | — | — | 972.87 ± 16.73 | 488.72 | 86.78 ± 6.34 |
|  | 1992 Aug. 10 |  | 15.2 | 2007 Oct. 5 | T4 | 22-18 | rflL | — |  | 485.82 ± 34.70 | 475.13 | 293.05 ± 40.93 |
| 107 | 1991 Sep. 9 | F | 13.8 | 2005 Jun. 20 | T0 | 31-32 | rT | — | Mother | 739.61 | 1253.3 | 109.39 ± 26.70 |
| 113 | 1995 Nov. 21 | F | 9.7 | 2005 Jul. 22 | T0 | 10 | rT | — | — | 670.49 ± 5.45 | 695.21 | 41.10 ± 8.51 |
|  |  |  | 11.5 | 2007 May 18 | T22 | 15 | rT | — |  | 688.49 ± 23.78 | 613.79 | 49.16 ± 9.14 |
| 118 | 1991 Jun. 4 | F | 16.6 | 2008 Jan. 18 | T0 | 22-22 | rflTL | — | Both parents | 372.79 ± 10.86 | 273.31 | 70.42 ± 4.85 |
| 123 | 1993 Sep. 23 | F | 12.1 | 2005 Nov. 4 | T0 | 28 | rfL | — | Both parents | 1466.97 | 931.05 | 128.78 ± 4.22 |
|  |  |  | 14.3 | 2008 Jan. 18 | T26 | 19-31 | lTrfL | — |  | 779.90 ± 16.68 | 410.10 | 179.52 ± 21.17 |
| 124 | 1990 Dec. 9 | F | 14.9 | 2005 Nov. 4 | T0 | 33-32 | rflTL | — | Cousins | 625.97 | 816.60 | 96.08 |
| 127 | 1992 Jan. 18 | F | 13.9 | 2005 Dec. 2 | T0 | 33-19 | rrT | — | — | 786.71 | 755.60 | 131.36 ± 22.43 |
| 128 | 1997 Mar. 18 | F | 8.8 | 2005 Dec. 2 | T0 | 10 | lTL | — | — | 837.64 | 628.74 | 118.73 ± 10.43 |
| 130 | 1991 Jun. 5 | F | 14.5 | 2005 Dec. 9 | T0 | 19 | rfL | — | — | 559.85 | 552.78 | 75.09 ± 7.11 |
| 131 | 1992 Nov. 9 | F | 13.1 | 2005 Dec. 9 | T0 | 32-24 | rflL | — | — | 568.01 | 578.96 | 101.00 ± 11.04 |
|  |  |  | 15.0 | 2007 Nov. 12 | T23 | 32-24 | rflL | — |  | 450.45 ± 9.36 | 505.94 | 100.03 ± 9.68 |
| 136 | 1969 Oct. 10 | F | 16.3 | 2006 Jan. 13 | T0 | 14 | rflL | — | — | 411.02 | 670.31 | 84.81 ± 2.56 |
| 138 | 1993 Jun. 4 | F | 12.7 | 2008 Feb. 17 | T0 | 24-26 | rflL | — | Cousin | 577.78 | 293.51 | 63.86 ± 4.11 |
|  |  |  | 14.3 | 2007 Oct. 24 | T20 | 22-25 | rflL | — |  | 379.04 ± 18.07 | 388.16 | 86.23 ± 11.26 |
|  |  |  | 14.7 | 2008 Feb. 4 | T24 | 23-26 | rflTL | — |  | 529.70 ± 4.86 | 378.03 | 227.26 ± 0.94 |
|  |  |  | 12.2 | 2006 Feb. 24 | T0 | 12-14 | rflL | — |  | 847.98 | 868.95 | 136.19 ± 7.83 |
| 139 | 1993 Dec. 6 | F | 14.2 | 2008 Feb. 8 | T24 | 12-6 | rflL | — | — | 1192.61 ± 10.71 | 444.33 | 73.88 ± 19.39 |
| 141 | 1992 Jul. 20 | F | 13.7 | 2006 Mar. 10 | T0 | 20-18 | rflL | — | Grand-mother, cousins, uncle | 658.28 | 735.50 | 90.51 |
| 142 | 1992 Dec. 19 | F | 15.5 | 2008 Jan. 22 | T22 | 9-13 | rflTL | — | Mother, cousin | 172.67 ± 8.59 | 433.6 | 37.31 ± 7.61 |
|  |  |  | 13.2 | 2006 Mar. 10 | T0 | 31 | lTL | — |  | 776.43 | 907.96 | 122.73 ± 7.61 |
|  |  |  | 15.1 | 2008 Jan. 23 | T22 | 25 | lTL | — |  | 542.85 ± 1.41 | 511.4 | 146.43 ± 63.23 |
| 146 | 1990 May 13 | F | 16.0 | 2006 May 26 | T0 | 32-22 | lTL | — | — | 1501.42 | 475.91 | 75.68 ± 10.22 |
| 148 | 1993 Aug. 12 | F | 14.3 | 2007 Dec. 7 | T0 | 11 | lTL | — | Mother | 1416.91 ± 41.50 | 550.4 | 37.79 ± 6.19 |
| 149 | 1988 Sep. 28 | M | 17.7 | 2006 Jun. 2 | T0 | 31-26 | lTL | — | — | 472.61 | 559.97 | 138.95 ± 7.42 |
| 150 | 1992 Oct. 16 | F | 13.6 | 2006 Jun. 2 | T0 | 25 | rT | — | Sister | 805.88 | 543.22 | 71.24 ± 1.52 |
| 151 | 1993 Apr. 11 | F | 14.7 | 2007 Dec. 3 | T0 | 28-20 | rflL | — | — | 732.19 ± 2.30 | 403.51 | 20.80 ± 3.30 |
| 152 | 1990 Oct. 4 | F | 15.7 | 2006 Jun. 2 | T0 | 34 | lL | — | Father | 655.10 | 551.24 | 122.69 ± 0.10 |
| 154 | 1989 Nov. 24 | F | 16.6 | 2006 Jun. 8 | T0 | 40 | rflL | — | Cousin | 541.07 | 639.52 | 104.09 ± 13.96 |
|  |  |  | 18.1 | 2007 Dec. 7 | T18 | 38 | lTL | — |  | 1101.07 ± 38.84 | 342.17 | 35.08 ± 5.40 |
| 155 | 1991 Jan. 1 | F | 15.4 | 2006 Jun. 8 | T0 | 26 | lTL | — | Aunt | 738.59 | 796.06 | 121.33 ± 17.72 |
| 159 | 1998 Mar. 4 | F | 9.7 | 2007 Nov. 6 | T0 | 3 | lTL | — | Mother | 769.50 ± 21.57 | 831.18 | 107.5 ± 1.08 |
| 161 | 1994 Apr. 27 | F | 13.6 | 2007 Nov. 30 | T0 | 15 | lTL | — | — | 487.11 ± 29.43 | 355.79 | 23.63 ± 0.53 |
| 165 | 1995 Aug. 30 | F | 12.3 | 2007 Dec. 3 | T0 | 34-20 | rflL | — | — | 1148.04 ± 47.51 | 607.43 | 42.39 ± 7.68 |

TABLE 6-continued

Clinical and biochemical profiles of AIS patients with Cobb's angles less than 45°.

| Patient ID | Date of Birth | Gender | Age | Collection Date | Time point (mths) | Cobb's Angle Pre-op | Curve Type | Date of surgery | Family history | [OPN] (ng/ml) | [sCD44] (ng/ml) | [HA] (ng/ml) |
|---|---|---|---|---|---|---|---|---|---|---|---|---|
| 168 | 1992 Apr. 24 | F | 14.2 | 2006 Jun. 26 | T0 | 16-18 | rflL | — | — | 810.21 ± 28.48 | 244.4 | 103.10 ± 10.39 |
|  |  |  | 14.6 | 2006 Nov. 21 | T5 | 17-16 | rflL | — | — | 582.52 ± 23.29 | 338.03 | 99.20 ± 18.18 |
|  |  |  | 15.5 | 2007 Oct. 1 | T16 | 14-16 | rflTL | — | — | 441.81 ± 7.29 | 333.4 | 126.96 ± 1.45 |
| 176 | 1992 Oct. 24 | F | 13.8 | 2006 Jul. 3 | T0 | 29 | rT | — | — | 503.88 ± 35.81 | 331.65 | 91.50 ± 21.99 |
|  |  |  | 14.2 | 2007 Jan. 15 | T6 | 27 | rT | — | — | 675.38 ± 44.20 | 305.92 | 193.26 ± 2.38 |
| 183 | 1991 Sep. 13 | M | 14.8 | 2006 May 7 | T0 | 17 | rL | — | — | 733.99 ± 17.33 | 550.24 | 72.91 ± 10.68 |
|  |  |  | 15.4 | 2007 Jun. 2 | T13 | 7-19 | rflL | — | — | 781.03 ± 3.27 | 531.96 | 69.83 ± 7.07 |
| 200 | 1992 Jul. 29 | M | 15.2 | 2007 Oct. 30 | T0 | 23-24 | rflL | — | — | 972.10 ± 4.92 | 401.94 | 88.41 ± 10.08 |
| 201 | 1992 Nov. 27 | F | 13.7 | 2008 Jul. 12 | T0 | 10-17 | rflL | — | Sister | 782.77 ± 2.63 | 498.93 | 142.57 ± 44.69 |
| 225 | 1994 May 9 | F | 12.2 | 2006 Jul. 24 | T0 | 15-19 | rITrTL | — | — | 406.67 ± 3.40 | 617.37 | 248.10 ± 24.21 |
|  |  |  | 12.8 | 2007 Feb. 27 | T7 | 13-18 | ITrL | — | — | 651.89 ± 21.69 | 524.9 | 47.95 ± 3.60 |
| 234 | 1990 Jul. 16 | M | 16.2 | 2006 Oct. 13 | T0 | 26 | rT | — | — | 840.88 ± 1.98 | 491.26 | 89.04 ± 5.66 |
| 235 | 1991 Oct. 29 | M | 15 | 2006 Oct. 13 | T0 | 20 | ITL | — | — | 586.25 ± 0.32 | 403.8 | 181.655 ± 48.71 |
|  |  |  | 16 | 2007 Oct. 11 | T12 | 18 | ITL | — | — | 523.39 ± 9.76 | 428.29 | 188.63 ± 6.83 |
| 240 | 1993 Oct. 4 | F | 13.2 | 2006 Dec. 11 | T0 | 17-23 | rflL | — | Mother, brother, cousin | 525.88 ± 7.74 | 428.83 | 71.91 ± 4.23 |
| 242 | 1989 Sep. 12 | F | 17.3 | 2007 Jan. 12 | T0 | 6 | ITL | — | Sister | 590.13 ± 6.00 | 435.59 | 80.24 ± 3.69 |
| 244 | 1990 Oct. 20 | F | 16.2 | 2007 Jan. 19 | T0 | 27-29 | rflL | — | — | 735.26 ± 4.42 | 510.44 | 73.81 ± 6.20 |
|  |  |  | 17.3 | 2008 Feb. 13 | T13 | NA | NA | — | — | 1293.68 ± 36.92 | 449.1 | 44.51 ± 4.81 |
| 245 | 1992 Jan. 27 | F | 15.0 | 2007 Jan. 22 | T0 | 31-35 | rflL | — | — | 496.26 ± 3.54 | 333.97 | 70.41 ± 0.88 |
|  |  |  | 15.8 | 2007 Nov. 14 | T10 | 28-35 | rflL | — | — | 363.60 ± 2.97 | 562.52 | 54.98 ± 5.08 |
| 247 | 1994 Dec. 18 | F | 12.1 | 2007 Jan. 26 | T0 | 9 | rflL | — | Mother, sister | 1148.31 ± 2.17 | 371.29 | 164.68 ± 23.99 |
|  |  |  | 12.8 | 2007 Oct. 9 | T9 | 9 | rL | — | — | 806.91 ± 16.69 | 393.27 | 141.16 ± 2.62 |
| 248 | 1997 Jun. 16 | F | 9.6 | 2007 Jan. 26 | T0 | 9 | rL | — | Mother, sister | 1010.38 ± 5.14 | 443.83 | 142.95 ± 4.69 |
|  |  |  | 10.3 | 2007 Oct. 9 | T9 | 3 | ITL | — | — | 841.24 ± 18.47 | 490.2 | 158.10 ± 33.95 |
| 249 | 1991 Mar. 25 | F | 15.9 | 2007 Feb. 2 | T0 | 31 | ITL | — | — | 534.09 ± 7.74 | 459.52 | 74.98 ± 0.08 |
|  |  |  | 16.4 | 2007 Aug. 3 | T6 | NA | ITL | — | — | 340.44 ± 12.89 | 499.97 | 132.91 ± 37.20 |
|  |  |  | 16.9 | 2008 Feb. 1 | T12 | 36 | ITL | — | — | 579.65 ± 8.62 | 413.67 | 98.93 ± 19.98 |
| 250 | 1992 May 8 | F | 14.7 | 2007 Feb. 2 | T0 | 32 | ITL | — | Uncle | 688.35 ± 9.46 | 587.17 | 74.40 ± 3.75 |
|  |  |  | 15.4 | 2007 Oct. 15 | T8 | 21 | ITL | — | — | 612.19 ± 22.36 | 540.29 | 150.73 |
| 251 | 1991 Sep. 5 | F | 15.4 | 2007 Feb. 2 | T0 | 40-30 | rflL | — | — | 1146.66 ± 7.34 | 437.25 | 80.50 ± 5.24 |
| 253 | 1992 Oct. 18 | M | 14.3 | 2007 Feb. 27 | T0 | 31 | rT | — | — | 634.83 ± 0.90 | 486.03 | 184.50 ± 20.76 |
| 254 | 1991 Dec. 11 | F | 15.2 | 2007 Mar. 9 | T0 | 28 | ITL | — | — | 701.23 ± 1.92 | 362.22 | 72.85 ± 2.66 |
|  |  |  | 15.9 | 2007 Nov. 12 | T8 | 15 | ITL | — | — | 548.26 ± 25.55 | 538.63 | 83.17 ± 0.07 |
| 256 | 1996 Mar. 19 | F | 11.0 | 2007 Mar. 9 | T0 | 11 | ITL | — | — | 575.73 ± 5.49 | 530.67 | 97.73 ± 3.00 |
| 257 | 1995 Apr. 15 | F | 11.9 | 2007 Mar. 9 | T0 | 6 | ITL | — | Mother | 995.77 ± 8.22 | 468.59 | 94.49 ± 8.02 |
|  |  |  | 12.5 | 2007 Oct. 16 | T7 | NA | NA | — | — | 879.54 ± 20.53 | 421.24 | 102.11 ± 5.69 |
| 258 | 1990 Jun. 24 | M | 16.8 | 2007 Mar. 9 | T0 | 14 | rT | — | — | 876.44 ± 9.21 | 564.15 | 89.36 ± 4.66 |
|  |  |  | 17.3 | 2007 Sep. 2 | T8 | NA | NA | — | — | 520.58 ± 8.52 | 483.28 | 175.81 ± 53.68 |
| 259 | 1994 Jul. 7 | F | 12.7 | 2007 Mar. 16 | T0 | 8 | ITL | — | — | 1095.11 ± 7.88 | 397.45 | 85.33 ± 4.07 |
|  |  |  | 13.5 | 2007 Oct. 15 | T7 | 11 | ITL | — | — | 1050.58 ± 5.08 | 466.58 | 139.86 ± 15.48 |
| 260 | 1994 Jul. 7 | M | 12.7 | 2007 Mar. 16 | T0 | 6 | rflL | — | — | 1084.13 ± 1.82 | 480.1 | 127.84 ± 8.13 |
|  |  |  | 13.5 | 2007 Oct. 5 | T7 | 4 | ITL | — | — | 494.25 ± 22.05 | 401.01 | 188.45 ± 31.29 |

TABLE 6-continued

Clinical and biochemical profiles of AIS patients with Cobb's angles less than 45°.

| Patient ID | Date of Birth | Gender | Age | Collection Date | Time point (mths) | Cobb's Angle Pre-op | Curve Type | Date of surgery | Family history | [OPN] (ng/ml) | [sCD44] (ng/ml) | [HA] (ng/ml) |
|---|---|---|---|---|---|---|---|---|---|---|---|---|
| 261 | 1997 Jun. 19 | F | 9.7 | 2007 Mar. 16 | T0 | 21 | IL | — | — | 745.79 ± 22.70 | 568.33 | 122.95 ± 2.89 |
|  |  |  | 10.3 | 2007 Oct. 17 | T7 | 10 | ITL | — | — | 1150.38 ± 5.64 | 506.72 | 206.45 ± 14.75 |
|  |  |  | 10.4 | 2008 Feb. 6 | T11 | 5 | ITL | — | — | 852.44 ± 31.69 | 432.45 | 142.48 ± 27.89 |
| 263 | 1994 Oct. 13 | F | 12.4 | 2007 Mar. 20 | T0 | 7-12 | rTIL | — | Uncle | 989.52 ± 4.54 | 617.16 | 74.05 ± 5.38 |
| 264 | 1992 May 24 | F | 14.8 | 2007 Mar. 20 | T0 | 23-30 | rTIL | — | — | 579.22 ± 9.53 | 580.38 | 100.39 ± 2.76 |
| 265 | 1993 May 4 | F | 13.9 | 2007 Mar. 20 | T0 | 23 | IL | — | — | 696.52 ± 8.57 | 491.96 | 105.88 ± 7.86 |
|  |  |  | 14.5 | 2007 Nov. 13 | T8 | 11-14. | rTIL | — | — | 848.34 ± 8.38 | 531.14 | 106.80 ± 1.16 |
| 266 | 1991 Jan. 25 | F | 16.2 | 2007 Apr. 2 | T0 | 34 | rTL | — | — | 728.63 ± 5.47 | 462.66 | 78.08 ± 1.06 |
|  |  |  | 16.8 | 2007 Nov. 15 | T7 | 34 | rTL | — | — | 392.63 ± 9.28 | 349.34 | 73.67 ± 3.30 |
| 267 | 1994 May 14 | F | 12.9 | 2007 Apr. 2 | T0 | 5 | rTL | — | — | 809.78 ± 2.39 | 579.14 | 70.57 ± 2.92 |
|  |  |  | 13.5 | 2007 Nov. 15 | T7 | 5 | rTL | — | — | 925.13 ± 23.50 | 827.31 | 59.18 ± 8.22 |
| 268 | 1994 Aug. 17 | F | 12.6 | 2007 Apr. 4 | T0 | 12-4 | rTIL | — | Mother | 750.67 ± 17.49 | 385.93 | 107.96 ± 12.28 |
| 271 | 1994 Nov. 17 | F | 12.4 | 2007 Apr. 13 | T0 | 23 | rTIL | — | — | 925.40 ± 10.01 | 482.89 | 87.43 ± 12.34 |
|  |  |  | 12.9 | 2007 Oct. 15 | T6 | 24 | rTIL | — | — | 1087.79 ± 22.62 | 423.61 | 186.49 ± 10.22 |
| 272 | 1994 Apr. 14 | F | 13.0 | 2007 Apr. 13 | T0 | 22-24 | rTIL | — | Aunt | 634.87 ± 15.77 | 531.54 | 86.12 ± 1.03 |
|  |  |  | 13.6 | 2007 Dec. 5 | T8 | 14-15 | rTIL | — | — | 515.84 ± 13.88 | 594.47 | 30.80 ± 7.99 |
| 273 | 1991 Jun. 30 | F | 15.8 | 2007 Apr. 13 | T0 | 25 | rTIL | — | — | 455.86 ± 7.52 | 548.8 | 91.21 ± 10.34 |
| 274 | 1990 Feb. 28 | F | 17.1 | 2007 Apr. 17 | T0 | 11-22 | rTIL | — | — | 856.81 ± 23.09 | 461.61 | 103.50 ± 8.99 |
| 275 | 1996 Apr. 8 | F | 11.0 | 2007 Apr. 19 | T0 | 27-1. | rTIL | — | — | 943.57 ± 8.27 | 469.65 | 66.73 ± 5.64 |
|  |  |  | 11.5 | 2007 Oct. 15 | T6 | 26-19 | rTIlTL | — | — | 339.71 ± 8.66 | 513.42 | 159.78 ± 30.24 |
| 276 | 1994 Sep. 26 | F | 13.1 | 2007 Oct. 15 | T6 | 19-19 | rTIL | — | — | 430.84 ± 16.02 | 431.09 | 234.52 ± 26.95 |
| 277 | 1994 Nov. 2 | F | 12.4 | 2007 Apr. 19 | T0 | 12 | IL | — | — | 724.67 ± 0.64 | 394.65 | 96.43 ± 0.04 |
|  |  |  | 13.0 | 2007 Nov. 14 | T7 | 15-13 | rTIL | — | — | 634.03 ± 28.77 | 659.6 | 127.07 ± 4.00 |
| 278 | 1992 Jun. 8 | M | 14.9 | 2007 May 4 | T0 | 22.14 | rTIL | — | Mother | 1045.58 ± 1.10 | 364.31 | 106.88 ± 8.57 |
|  |  |  | 15.3 | 2007 Oct. 23 | T5 | 26-28 | rTIL | — | — | 1118.55 ± 3.48 | 457.48 | 234.68 ± 24.37 |
| 279 | 1998 Sep. 22 | F | 8.7 | 2007 May 30 | T0 | 19 | rT | — | — | 978.20 ± 17.94 | 442.08 | 85.62 ± 0.14 |
|  |  |  | 9.2 | 2007 Oct. 5 | T5 | 8 | rT | — | — | 851.57 ± 67.60 | 573.28 | 64.64 |
| 280 | 1992 Dec. 18 | F | 14.4 | 2007 May 30 | T0 | 19 | rTIL | — | Grand-parents | 839.91 ± 4.88 | 415.23 | 82.19 ± 6.30 |
|  |  |  | 14.9 | 2007 Nov. 2 | T6 | 24 | rT | — | — | 930.08 ± 11.55 | 468.35 | 63.88 ± 1.83 |
| 281 | 1994 Oct. 17 | F | 12.6 | 2007 Jun. 1 | T0 | 11 | rTL | — | — | 991.09 ± 2.95 | 522.65 | 151.89 ± 1.15 |
|  |  |  | 13.1 | 2007 Nov. 9 | T5 | 9 | ITTL | — | — | 655.22 ± 54.74 | 505.44 | 112.65 ± 14.80 |
| 282 | 1997 Sep. 30 | F | 9.7 | 2007 Jun. 13 | T0 | 20 | rT | — | — | 732.03 ± 19.20 | 547.53 | 138.06 ± 12.04 |
|  |  |  | 10.3 | 2008 Jan. 30 | T7 | NA | NA | — | — | 1196.46 ± 21.91 | 487.63 | 129.70 ± 7.80 |
| 286 | 1994 Jun. 1 | F | 13.3 | 2007 Sep. 17 | T0 | 28 | ITL | — | — | 499.69 ± 1.97 | 400.19 | 130.85 ± 3.82 |
| 287 | 1991 Nov. 15 | F | 15.8 | 2007 Sep. 18 | T0 | 11 | rTIL | — | — | 602.68 ± 0.65 | 418.92 | 190.43 |
| 288 | 1996 May 13 | M | 11.3 | 2007 Sep. 18 | T0 | 20 | IL | — | — | 927.74 ± 4.10 | 533.37 | 55.21 ± 10.16 |
| 289 | 1992 Oct. 23 | F | 14.9 | 2007 Sep. 18 | T0 | 18 | rT | — | — | 509.91 ± 5.91 | 362.72 | 81.33 ± 11.16 |
| 290 | 1993 Oct. 2 | F | 14.0 | 2007 Sep. 18 | T0 | 22 | rTL | — | Aunts | 498.69 ± 46.68 | 507.71 | 127.53 ± 8.29 |
| 291 | 1992 Jul. 10 | F | 20.9 | 2007 Sep. 21 | T0 | 25-31 | rTIL | — | — | 637.03 ± 7.11 | 467.8 | 154.54 ± 1.72 |
| 292 | 1994 Jan. 23 | F | 13.7 | 2007 Sep. 21 | T0 | 20 | ITL | — | Grand-mother | 691.71 ± 37.30 | 581.43 | 76.54 ± 1.66 |
| 293 | 1993 Apr. 3 | F | 14.5 | 2007 Sep. 21 | T0 | 16 | rT | — | — | 494.81 ± 7.56 | 359.48 | 166.11 |
| 295 | 1991 Aug. 9 | M | 16.1 | 2007 Sep. 26 | T0 | 11-8 | rTIL | — | — | 838.72 ± 39.67 | 405.48 | 159.20 ± 22.89 |
| 296 | 1992 Apr. 4 | F | 15.5 | 2007 Sep. 28 | T0 | 15-18 | ITrL | — | — | 761.74 ± 25.61 | 494.27 | 237.77 |
| 297 | 1997 Jul. 13 | M | 10.2 | 2007 Sep. 28 | T0 | 20 | IT | — | Uncle | 768.08 ± 6.70 | 515.45 | 100.00 ± 9.41 |

TABLE 6-continued

Clinical and biochemical profiles of AIS patients with Cobb's angles less than 45°.

| Patient ID | Date of Birth | Gender | Age | Collection Date | Time point (mths) | Cobb's Angle | Pre-op Curve Type | Date of surgery | Family history | [OPN] (ng/ml) | [sCD44] (ng/ml) | [HA] (ng/ml) |
|---|---|---|---|---|---|---|---|---|---|---|---|---|
| 298 | 1994 Nov. 9 | F | 12.9 | 2007 Sep. 28 | T0 | 18-21 | rfTfL | — | — | 750.91 ± 16.94 | 348.87 | 290.06 ± 38.15 |
| 299 | 1990 Mar. 21 | F | 17.5 | 2007 Oct. 3 | T0 | 33-43 | rfTfL | — | — | 625.36 ± 6.80 | 306.11 | 135.94 ± 1.36 |
| 301 | 1995 Feb. 6 | F | 12.7 | 2007 Oct. 9 | T0 | 13 | IT | — | Grand-mother | 948.83 ± 11.23 | 578.58 | 150.57 ± 4.40 |
| 302 | 1993 May 7 | F | 14.4 | 2007 Oct. 9 | T0 | 14.-12 | rfTfL | — | — | 873.77 ± 2.17 | 373.31 | 230.66 ± 10.50 |
| 303 | 1991 Mar. 29 | F | 16.5 | 2007 Oct. 15 | T0 | 14 | ITL | — | — | 767.96 ± 29.04 | 458.27 | 192.45 ± 10.19 |
| 304 | 1991 Oct. 25 | F | 16.0 | 2007 Oct. 16 | T0 | 25 | IT | — | Brother, father, all paternal family | 493.39 ± 34.21 | 446.06 | 185.69 ± 12.07 |
| 305 | 1992 Feb. 24 | F | 15.7 | 2007 Oct. 19 | T0 | 23 | ITL | — | Mother | 533.91 ± 18.09 | 364.52 | 123.23 ± 15.87 |
| 306 | 1994 Sep. 22 | F | 13.1 | 2007 Oct. 19 | T0 | 13-18 | rfTfL | — | Mother | 1016.54 ± 23.75 | 623.32 | 216.02 ± 19.04 |
| 307 | 1994 Jan. 25 | M | 13.7 | 2007 Oct. 24 | T0 | 8-11-11. | ITrTfL | — | — | 1328.92 ± 1.50 | 569.35 | 165.08 ± 16.63 |
| 308 | 1997 May 22 | F | 10.4 | 2007 Oct. 26 | T0 | 8 | rfTL | — | Aunts | 430.39 ± 5.44 | 519.72 | 133.63 ± 11.13 |
| 309 | 1996 Apr. 10 | F | 11.5 | 2007 Oct. 26 | T0 | 10 | ITL | — | Mother, cousins | 536.77 ± 9.30 | 485.45 | 285.92 ± 25.08 |
| 311 | 1993 May 7 | F | 14.5 | 2007 Oct. 26 | T0 | 17 | ITL | — | — | 493.18 ± 23.85 | 546.9 | 110.66 ± 9.59 |
| 313 | 1993 Jun. 4 | F | 14.4 | 2007 Oct. 26 | T0 | 20-18 | rfTfL | — | Cousin | 536.22 ± 4.65 | 379.49 | 99.52 ± 2.41 |
| 314 | 1993 Mar. 11 | F | 14.6 | 2007 Oct. 29 | T0 | 24 | rL | — | Mother | 939.67 ± 37.16 | 549.66 | 78.11 ± 7.22 |
| 315 | 1993 Dec. 16 | F | 13.9 | 2007 Oct. 31 | T0 | 14 | ITL | — | — | 537.59 ± 1.16 | 481.91 | 142.26 ± 23.98 |
| 316 | 1992 Oct. 7 | M | 15.1 | 2007 Oct. 31 | T0 | 28 | rT | — | — | 636.17 ± 2.31 | 576.05 | 94.21 ± 5.42 |
| 318 | 1997 May 25 | F | 10.4 | 2007 Oct. 15 | T0 | 11 | rfTfL | — | Mother | 1151.62 ± 33.64 | 634.57 | 112.13 ± 23.16 |
| 319 | 1993 Jun. 28 | F | 14.4 | 2007 Nov. 6 | T0 | 22 | ITL | — | Cousin | 518.10 ± 27.77 | 667.02 | 79.46 ± 6.89 |
| 320 | 1993 Sep. 24 | F | 14.1 | 2007 Nov. 9 | T0 | 15 | rT | — | — | 452.54 ± 10.01 | 765.38 | 134.09 ± 21.38 |
| 321 | 1992 Jul. 4 | F | 15.3 | 2007 Nov. 9 | T0 | 16 | ITL | — | — | 470.02 ± 16.75 | 377.13 | 110.37 ± 12.77 |
| 322 | 1996 Jun. 1 | F | 11.4 | 2007 Nov. 9 | T0 | 4 | rfTfL | — | — | 565.20 ± 48.73 | 492.94 | 95.12 ± 7.44 |
| 324 | 1991 Apr. 20 | F | 16.6 | 2007 Nov. 9 | T0 | 19-19 | rfTfL | — | — | 659.93 ± 14.39 | 562.52 | 98.61 ± 6.25 |
| 325 | 1994 Mar. 26 | F | 13.6 | 2007 Nov. 9 | T0 | 21 | rfTfL | — | Mother, grand-parents | 761.48 ± 3.82 | 846.66 | 89.91 ± 12.48 |
| 326 | 1994 Feb. 2 | M | 13.8 | 2007 Nov. 13 | T0 | 13 | ITL | — | — | 1451.37 ± 77.12 | 617.35 | 240.72 ± 27.74 |
| 328 | 1994 Sep. 24 | F | 12.8 | 2007 Nov. 14 | T0 | 11 | ITL | — | — | 580.55 ± 24.91 | 876.97 | 174.59 |
| 329 | 1996 May 29 | F | 11.5 | 2007 Nov. 14 | T0 | 6 | ITL | — | Mother | 877.16 ± 27.08 | 953.41 | 289.12 ± 4.88 |
| 330 | 1994 Feb. 5 | F | 13.8 | 2007 Nov. 16 | T0 | 12 | ITL | — | — | 1403.38 ± 20.98 | 465.43 | 279.56 |
| 332 | 1992 Jan. 26 | M | 15.8 | 2007 Nov. 23 | T0 | 24 | ITL | — | — | 864.14 ± 43.84 | 699.27 | 175.34 ± 30.44 |
| 333 | 1993 Oct. 21 | F | 14.1 | 2007 Nov. 23 | T0 | 30 | ITL | — | Cousin | 564.09 ± 7.37 | 762.16 | 143.10 ± 30.54 |
| 334 | 1993 Aug. 7 | F | 14.3 | 2007 Nov. 23 | T0 | 29-27 | rfTfL | — | — | 896.91 ± 29.60 | 727.33 | 155.95 ± 38.28 |
| 335 | 1996 Jan. 16 | F | 11.9 | 2007 Nov. 23 | T0 | 28-27 | rfTfL | — | — | 1192.08 ± 14.98 | 839.56 | 162.32 ± 0.67 |
| 337 | 1991 Sep. 4 | M | 16.2 | 2007 Nov. 28 | T0 | 24 | IL | — | Sister | 914.93 ± 10.71 | 788.28 | 114.15 ± 25.71 |
| 338 | 1994 Dec. 31 | F | 12.9 | 2007 Nov. 30 | T0 | 10 | ITL | — | Aunt | 539.94 ± 1.35 | 301.42 | 38.44 ± 5.53 |
| 339 | 1992 Mar. 17 | F | 15.7 | 2007 Nov. 30 | T0 | 25 | ITL | — | Grand-father | 747.48 ± 9.20 | 444.12 | 253.92 |
| 340 | 1995 May 21 | F | 12.5 | 2007 Nov. 30 | T0 | 30 | ITL | — | — | 746.48 ± 45.11 | 498.56 | 259.46 |
| 341 | 1996 Feb. 11 | F | 11.8 | 2007 Nov. 30 | T0 | 15-14 | rfTfL | — | Cousin | 947.50 ± 31.38 | 662.73 | 75.40 ± 1.41 |
| 342 | 1993 Dec. 1 | F | 14.0 | 2007 Dec. 7 | T0 | 16 | ITL | — | — | 993.33 ± 55.93 | 376.73 | 19.57 ± 5.63 |
| 343 | 1993 Jun. 29 | M | 14.4 | 2007 Dec. 7 | T0 | 15 | rfTfL | — | Grand-mother | 996.61 ± 25.86 | 541.76 | 43.48 ± 2.96 |
| 344 | 1996 Mar. 26 | F | 11.7 | 2007 Dec. 7 | T0 | 10 | ITL | — | — | 637.78 ± 7.73 | 702.48 | 26.94 ± 5.89 |
| 345 | 1993 Apr. 12 | F | 14.6 | 2007 Dec. 7 | T0 | 30 | ITL | — | Cousin | 722.43 ± 18.56 | 429.44 | 31.74 ± 1.77 |
| 346 | 1996 Oct. 11 | F | 11.2 | 2007 Dec. 7 | T0 | 18-17 | rfTfL | — | — | 576.26 ± 24.83 | 436.35 | 29.25 ± 2.56 |
| 347 | 1997 Apr. 7 | F | 10.7 | 2007 Dec. 11 | T0 | 5-6. | rfTfTfL | — | Sister | 1272.11 ± 18.19 | 425.98 | 41.20 ± 4.60 |

TABLE 6-continued

Clinical and biochemical profiles of AIS patients with Cobb's angles less than 45°.

| Patient ID | Date of Birth | Gender | Age | Collection Date | Time point (mths) | Cobb's Angle | Pre-op Curve Type | Date of surgery | Family history | [OPN] (ng/ml) | [sCD44] (ng/ml) | [HA] (ng/ml) |
|---|---|---|---|---|---|---|---|---|---|---|---|---|
| 348 | 1995 Jun. 10 | M | 12.5 | 2007 Dec. 11 | T0 | 10 | rTL | — | Sister | 776.87 ± 50.77 | 384.51 | 27.13 ± 1.84 |
| 350 | 1995 Feb. 22 | F | 12.8 | 2007 Dec. 13 | T0 | 25 | rTL | — | — | 1020.59 ± 46.63 | 488.19 | 32.35 ± 2.16 |
| 351 | 1992 May 19 | F | 15.6 | 2007 Dec. 13 | T0 | 14 | rTL | — | Father | 557.14 ± 25.67 | 475.23 | 20.16 ± 2.76 |
| 352 | 1996 Apr. 13 | M | 11.7 | 2007 Dec. 13 | T0 | 14 | rTL | — | Father | 1339.62 ± 39.88 | 566.82 | 97.02 |
| 353 | 1993 Aug. 12 | M | 14.3 | 2007 Dec. 13 | T0 | 24 | rT | — | — | 1569.33 ± 43.27 | 607.43 | 105.59 ± 95.83 |
| 354 | 1994 Jun. 7 | F | 13.5 | 2007 Dec. 13 | T0 | 8 | rT | — | — | 608.88 ± 6.80 | 431.16 | 69.78 ± 40.24 |
| 355 | 1993 Aug. 8 | F | 14.3 | 2007 Dec. 13 | T0 | 27 | TTL | — | — | 691.05 ± 37.53 | 378.46 | 24.41 ± 12.43 |
| 356 | 1995 May 17 | F | 12.6 | 2007 Dec. 13 | T0 | 19 | TTL | — | — | 824.89 ± 1.39 | 467.45 | 43.63 |
| 358 | 1997 Feb. 27 | F | 10.9 | 2008 Jan. 11 | T0 | 18 | rTL | — | — | 554.86 ± 8.43 | 387.21 | 116.04 ± 22.53 |
| 359 | 1995 Nov. 8 | F | 13.0 | 2008 Jan. 15 | T0 | 14 | TTL | — | — | 709.63 ± 3.85 | 485.94 | 195.32 ± 34.14 |
| 360 | 1992 May 24 | F | 15.6 | 2008 Jan. 15 | T0 | 14 | TTL | — | Mother | 466.35 ± 12.61 | 335.02 | 157.17 ± 7.22 |
| 361 | 1996 Jun. 29 | F | 11.5 | 2008 Jan. 15 | T0 | 23 | rTL | — | Aunt | 899.31 ± 10.09 | 441.72 | 81.52 ± 1.47 |
| 362 | 1997 Aug. 21 | F | 10.4 | 2008 Jan. 16 | T0 | 11 | TTL | — | Grand-mother | 471.73 ± 21.57 | 437.35 | 110.36 ± 7.42 |
| 363 | 1993 May 24 | F | 14.6 | 2008 Jan. 16 | T0 | 20-24-19 | TTrTTTL | — | Mother, grand-mother, aunt | 743.10 ± 15.01 | 353.53 | 161.77 ± 25.40 |
| 364 | 1995 Mar. 24 | F | 12.8 | 2008 Jan. 16 | T0 | 10 | TTL | — | Mother, grand-mother, aunt | 767.06 ± 11.17 | 460.75 | 160.24 ± 26.97 |
| 365 | 1999 Jul. 26 | F | 9.3 | 2008 Jan. 16 | T0 | 5 | rTL | — | Mother, grand-mother, aunt | 883.48 ± 2.32 | 403.41 | 127.81 ± 23.58 |
| 368 | 1996 Jul. 12 | F | 11.5 | 2008 Jan. 18 | T0 | 14 | rTL | — | — | 1206.06 ± 43.70 | 415.24 | 136.62 ± 28.94 |
| 369 | 1992 May 21 | F | 15.7 | 2008 Jan. 18 | T0 | 25 | rTL | — | — | 454.71 ± 13.34 | 431.44 | 132.25 ± 19.69 |
| 370 | 1994 Dec. 1 | F | 13.1 | 2008 Jan. 18 | T0 | 18-15 | rTL | — | — | 855.36 ± 10.35 | 395.7 | 140.53 ± 2.77 |
| 371 | 1992 Feb. 4 | F | 16.0 | 2008 Jan. 18 | T0 | 26-20 | rTTL | — | — | 740.05 ± 5.38 | 487.74 | 112.07 ± 3.13 |
| 372 | 1991 Jun. 21 | F | 16.6 | 2008 Jan. 21 | T0 | 23-21 | rTTL | — | Aunt, cousin | 436.58 ± 40.88 | 395.61 | 170.65 ± 13.44 |
| 374 | 1992 May 26 | F | 15.7 | 2008 Jan. 21 | T0 | 25 | TL | — | — | 498.50 ± 28.07 | 401.4 | 77.69 ± 6.60 |
| 375 | 1992 Oct. 21 | F | 15.3 | 2008 Jan. 22 | T0 | 31-55 | rTTL | — | — | 475.88 ± 0.00 | 385.69 | 130.95 ± 3.80 |
| 376 | 1993 May 18 | F | 14.7 | 2008 Jan. 22 | T0 | 16 | rTL | — | — | 554.83 ± 44.65 | 387.81 | 73.78 ± 0.15 |
| 377 | 1995 Jan. 31 | F | 13.0 | 2008 Jan. 22 | T0 | 27 | TTL | — | — | 739.47 ± 8.03 | 384.16 | 79.40 ± 1.15 |
| 379 | 1996 Sep. 14 | F | 11.4 | 2008 Jan. 25 | T0 | 5,-5 | TTrTrTL | — | — | 1404.12 ± 66.84 | 659.32 | 78.73 ± 2.62 |
| 381 | 1992 Jan. 11 | M | 16.0 | 2008 Jan. 25 | T0 | 24 | rT | — | — | 782.27 ± 1.42 | 505.65 | 283.01 ± 26.97 |
| 382 | 1993 Oct. 21 | F | 14.2 | 2008 Jan. 25 | T0 | 28-25 | rTTL | — | Cousin | 998.95 ± 9.12 | 327.82 | 77.64 ± 12.98 |
| 383 | 1994 Nov. 20 | F | 13.2 | 2008 Jan. 25 | T0 | 30-27 | rTTL | — | — | 900.32 ± 24.08 | 401.79 | 83.98 ± 7.31 |
| 384 | 1992 Feb. 9 | M | 16.0 | 2008 Jan. 29 | T0 | 25-19 | rTrT | — | — | 479.70 ± 36.72 | 444.82 | 134.93 ± 7.83 |
| 386 | 1994 Sep. 2 | F | 13.4 | 2008 Feb. 1 | T0 | 25-14 | TTrTTL | — | — | 732.99 ± 28.62 | 637.86 | 129.78 ± 2.15 |
| 387 | 1994 Apr. 11 | F | 13.8 | 2008 Feb. 1 | T0 | 14-15 | rTTL | — | — | 853.05 ± 70.97 | 373.81 | 146.21 ± 6.37 |
| 388 | 1995 Nov. 24 | F | 12.2 | 2008 Feb. 1 | T0 | 34 | rT | — | — | 963.01 ± 40.86 | 485.02 | 66.49 ± 7.43 |
| 389 | 1997 Apr. 13 | F | 10.8 | 2008 Feb. 4 | T0 | 14 | TTL | — | Father | 689.25 ± 35.56 | 435.9 | 67.38 ± 15.52 |
| 390 | 1994 Apr. 28 | F | 13.8 | 2008 Feb. 4 | T0 | 28-26 | rTTL | — | Father | 930.28 ± 18.25 | 368.83 | 56.32 ± 0.12 |
| 391 | 1994 Jul. 1 | F | 13.6 | 2008 Feb. 5 | T0 | 37 | rTL | — | — | 540.38 ± 9.17 | 501.81 | 49.99 ± 7.23 |
| 392 | 1998 Nov. 25 | F | 9.2 | 2008 Feb. 5 | T0 | 16 | rTL | — | Brother | 661.55 ± 38.23 | 412.14 | 77.84 ± 23.22 |
| 393 | 1993 Sep. 30 | M | 14.3 | 2008 Feb. 5 | T0 | 26 | rT | — | Brother | 1235.01 ± 29.98 | 488.02 | 106.86 ± 17.43 |
| 395 | 1995 May 24 | F | 12.7 | 2008 Feb. 8 | T0 | 11 | rT | — | Mother | 716.48 ± 30.93 | 496.45 | 82.74 ± 2.92 |
| 397 | 1999 Feb. 20 | F | 9.0 | 2008 Feb. 8 | T0 | 10 | rTL | — | Mother, grand-mother | 751.57 ± 2.34 | 543.59 | 85.71 ± 21.81 |

TABLE 6-continued

Clinical and biochemical profiles of AIS patients with Cobb's angles less than 45°.

| Patient ID | Date of Birth | Gender | Age | Collection Date | Time point (mths) | Cobb's Angle Pre-op | Curve Type | Date of surgery | Family history | [OPN] (ng/ml) | [sCD44] (ng/ml) | [HA] (ng/ml) |
|---|---|---|---|---|---|---|---|---|---|---|---|---|
| 398 | 1997 Sep. 16 | F | 10.4 | 2008 Feb. 8 | T0 | 16 | rTL | — | Mother, grand-mother | 872.92 ± 8.46 | 526.34 | 98.45 ± 6.33 |
| 399 | 2000 Sep. 28 | M | 7.4 | 2008 Feb. 8 | T0 | 22-20 | rTlTL | — | — | 444.55 ± 43.23 | 481.5 | 74.45 ± 10.16 |
| 400 | 1994 May 25 | F | 13.7 | 2008 Feb. 8 | T0 | 12 | rTL | — | Mother, aunt | 1492.58 ± 30.46 | 477.59 | 135.22 ± 2.80 |
| 401 | 1994 Feb. 17 | F | 14.0 | 2008 Feb. 18 | T0 | 28-21 | rTlTL | — | — | 691.24 ± 23.14 | 316.38 | 50.01 ± 1.95 |
| 402 | 1991 Jul. 15 | F | 16.6 | 2008 Feb. 14 | T0 | 19-12 | rTlTL | — | — | 423.93 ± 1.08 | 314.48 | 36.64 ± 2.04 |
| 403 | 1995 Feb. 21 | F | 13.0 | 2008 Feb. 14 | T0 | 13-13 | rTlTL | — | Sister | 1216.81 ± 131.72 | 354.37 | 52.43 ± 15.76 |
| 1264 | 1997 Sep. 22 | F | 15.2 | 2005 Apr. 18 | T0 | 40 | rTL | 2005 Apr. 18 | — | 616.12 | 578.96 | 65.92 |
| 1276 | 1997 Sep. 23 | F | 15.2 | 2005 May 16 | T0 | 42 | lT | 2005 May 16 | — | 817.56 | 450.13 | 107.62 ± 12.96 |
| 1364 | 1997 Sep. 24 | M | 14.9 | 2006 Apr. 24 | T0 | 44 | lTL | 2006 Apr. 24 | Sister, aunt | 1668.06 | 407.4 | 80.85 ± 6.90 |
| 1365 | 1990 May 11 | F | 15.9 | 2006 Apr. 26 | T0 | 23-53 | lTrL | 2006 Apr. 26 | — | 947.35 | 642.66 | 63.18 ± 5.41 |
| 1366 | 1993 Apr. 6 | F | 13.1 | 2006 May 1 | T0 | 36 | NA | 2006 May 1 | — | 1317.97 | 323.04 | 89.70 ± 20.57 |
| 1373 | 1991 Oct. 7 | F | 14.6 | 2006 May 17 | T0 | 41-48 | rTL | 2006 May 17 | — | 1584.54 | 583.14 | 80.12 ± 18.75 |
| 1380 | 1989 Oct. 9 | F | 16.7 | 2006 Jun. 26 | T0 | 35 | rL | 2006 Jun. 26 | — | 1289.98 | 602.35 | 139.38 |
| 1384 | 1991 Jan. 17 | F | 15.5 | 2006 Jul. 3 | T0 | 41 | lTL | 2006 Jul. 3 | — | 1502.51 ± 18.63 | 194.3 | 121.65 ± 44.94 |
| 1385 | 1990 Jun. 12 | F | 15.8 | 2006 Nov. 15 | T4 | 9-4 | — | — | — | 1258.85 ± 16.20 | 448.68 | 162.01 ± 11.64 |
| 1387 | 1991 Jul. 15 | F | 16.1 | 2006 Jul. 4 | T0 | 42-23 | rTlL | 2006 Jul. 4 | — | 1098.75 | 523.52 | 102.35 |
| 1388 | 1991 Dec. 13 | F | 15.0 | 2006 Jul. 17 | T0 | 29-37-35 | rTlL | 2006 Jul. 17 | Mother | 1017.47 | 689.52 | 78.42 |
| 1409 | 1993 Feb. 11 | F | 14.6 | 2006 Jul. 19 | T0 | 38 | rTL | 2006 Jul. 19 | — | 1080.53 | 811.37 | 87.57 |
| 1433 | 1992 Jul. 3 | F | 13.6 | 2006 Sep. 26 | T0 | 40 | rT | 2006 Sep. 26 | Uncle | 499.41 ± 67.54 | 389.14 | 113.56 ± 15.03 |
| 1451 | 1995 Jan. 13 | F | 14.5 | 2007 Jan. 10 | T0 | 44 | rT | 2007 Jan. 10 | Grand-mother | 459.61 ± 17.79 | 287.42 | 263.55 ± 34.89 |
| 1478 | 1990 Aug. 6 | F | 12.2 | 2007 Mar. 14 | T0 | 42 | rT | 2007 Mar. 14 | Father | 1099.93 ± 48.11 | 290.5 | 158.45 ± 3.94 |
| 1481 | 1990 Aug. 15 | F | 16.8 | 2007 Jun. 11 | T0 | 41 | rTL | 2007 Jun. 11 | — | 619.94 ± 46.51 | 251.56 | 190.25 ± 18.46 |
| 1483 | 1989 Jun. 26 | F | 16.8 | 2007 Jun. 18 | T0 | 40 | rT | 2007 Jun. 18 | — | 748.36 ± 9.30 | 250.14 | 95.34 ± 6.52 |
| 1487 | 1990 May 30 | F | 18.0 | 2007 Jun. 19 | T0 | 37-25 | rTlL | 2007 Jun. 19 | Aunts | 489.30 ± 93.18 | 396.39 | 167.02 ± 28.62 |
|  |  |  | 17.1 | 2007 Jul. 3 | T0 | 35-58-35 | lCrTlL | 2007 Jul. 3 |  | 508.82 ± 50.08 | 281.48 | 17.75 ± 1.94 |

\* Plus-minus values are means ± standard deviations.
\*\* All patients are diagnosed with AIS
† Curve type nomenclature: r, right/l, left/T, Thoracic/L, Lumbar/TL, Thoracolumbar/C, Cervical.
‡ Certain clinical information may not have been available at the time of the study, NA.

TABLE 7

Clinical and biochemical profiles of AIS patients with Cobb's angles of 45° or more.

| Patient ID | Date of Birth | Gender | Age | Collection Date | Time point (months) | Cobb's Angle Pre-op | Curve Type | Date of Surgery | Family History | [OPN] (ng/ml) | [sCD44] (ng/ml) | [HA] (ng/ml) |
|---|---|---|---|---|---|---|---|---|---|---|---|---|
| 101 | 1988 May 22 | F | 17.1 | 2005 Jun. 10 | T0 | 47 | rT | — | — | 1047.64 | 728.42 | 221.97 ± 8.23 |
| 108 | 1989 Aug. 29 | F | 15.9 | 2005 Jul. 4 | T0 | 45 | IL | — | — | 774.45 | 704.05 | 86.15 ± 12.73 |
| | | | 17.2 | 2006 Nov. 21 | T16 | 40 | IL | — | — | 414.67 ± 55.62 | 361.83 | 172.00 ± 3.68 |
| 135 | 1987 Dec. 31 | F | 18.0 | 2006 Jan. 13 | T0 | 47-30 | rTIL | — | — | 657.01 | 839.02 | 117.48 ± 5.37 |
| 145 | 1990 Feb. 15 | M | 16.2 | 2006 Apr. 21 | T0 | 50-43 | rTITL | — | Brother | 1178.85 | 961.85 | 120.52 ± 8.59 |
| 170 | 1991 Jul. 8 | F | 14.9 | 2006 Jun. 26 | T0 | 53-22 | rTIL | 2007 August | Aunt | 480.97 ± 29.49 | 317.2 | 33.76 ± 0.92 |
| | | | 15.9 | 2007 Apr. 18 | T10 | 44-21 | rTIL | | | 540.63 ± 10.65 | 410.66 | 70.69 ± 4.67 |
| 1150 | 1992 Apr. 18 | F | 12.1 | 2004 May 11 | T0 | 84 | rT | 2004 May 11 | Mother, grand-mother | 884.02 | 874.59 | 97.74 |
| 1169 | 1989 Sep. 19 | F | 14.8 | 2004 Jun. 22 | T0 | 54-52 | rTIL | 2004 Jun. 22 | — | 776.13 | 868.43 | 101.22 ± 9.41 |
| 1192 | 1990 Oct. 16 | F | 13.9 | 2004 Sep. 8 | T0 | 59 | rT | 2004 Sep. 8 | — | 1140.09 | 596.41 | 66.97 |
| 1212 | 1991 May 6 | F | 13.5 | 2004 Nov. 22 | T0 | 54 | rT | 2004 Nov. 22 | Great-aunt | 834.47 | 796.56 | 75.57 |
| 1254 | 1991 Jul. 23 | F | 13.7 | 2005 Mar. 16 | T0 | 52-49 | rTIL | 2005 Mar. 16 | — | 1091.92 | 882.29 | 82.8 |
| 1267 | 1990 Sep. 8 | F | 14.6 | 2005 Apr. 25 | T0 | 55 | IT | 2005 Apr. 25 | — | 509.48 | 596.41 | 76.87 |
| 1282 | 1988 Dec. 29 | F | 16.5 | 2005 Jun. 6 | T0 | 49 | rT | 2005 Jun. 6 | — | 718.45 | 788.41 | 53.95 ± 16.65 |
| 1310 | 1990 May 5 | F | 15.6 | 2005 Nov. 9 | T0 | 55-42 | rTIL | 2005 Nov. 9 | — | 1042.25 | 789.32 | 132.89 |
| 1353 | 1989 Aug. 8 | F | 16.6 | 2006 Mar. 27 | T0 | 46 | IT | 2006 Mar. 27 | — | 1078.92 ± 33.32 | 262.59 | 90.88 ± 1.59 |
| | | | 17.2 | 2006 Oct. 6 | T7 | 2 | NA | | | 44.35 ± 0.50 | 342.48 | 157.74 ± 37.90 |
| 1354 | 1991 Nov. 18 | F | 14.3 | 2006 Mar. 27 | T0 | 45 | rT | 2006 Mar. 27 | — | 1378.360 | 725.138 | 61.016 |
| 1355 | 1990 Feb. 26 | M | 16.1 | 2006 Mar. 28 | T0 | 74-53 | rTIL | 2006 Mar. 28 | — | 1871.67 | 467.38 | 253.56 ± 6.84 |
| 1357 | 1990 Aug. 23 | F | 14.8 | 2005 Jun. 15 | T0 | 47-50 | rTIL | 2006 Apr. 4 | Brother | 705.92 ± 16.09 | 415.22 | 174.61 ± 74.40 |
| | | | 15.7 | 2006 Apr. 4 | T10 | 57-50 | rTIL | | | 1788.1 | 374.7 | 78.86 ± 4.78 |
| 1360 | 1996 May 9 | F | 9.9 | 2006 Apr. 10 | T0 | 53-46 | rTIL | 2006 Apr. 10 | Father, aunt | 1820.95 | 444.42 | 80.45 ± 29.61 |
| 1361 | 1989 Sep. 3 | F | 16.6 | 2006 Apr. 10 | T0 | 65-95 | rTIL | 2006 Apr. 10 | — | 1512.16 | 599.64 | 67.13 ± 10.66 |
| 1369 | 1992 Feb. 19 | F | 14.2 | 2006 May 9 | T0 | 88 | rT | 2006 May 9 | — | 1498.66 | 262.58 | 91.42 ± 8.52 |
| | | | 14.8 | 2006 Nov. 24 | T6 | 25 | NA | | | 541.43 ± 10.31 | 317.72 | 166.79 ± 35.56 |
| 1371 | 1991 Jan. 30 | F | 15.3 | 2006 May 15 | T0 | 72-59 | rTIL | 2006 May 15 | — | 1723.91 | 224.15 | 89.53 ± 18.60 |
| 1372 | 1990 Sep. 6 | F | 15.7 | 2006 May 16 | T0 | 63-45-33 | rTLILC | 2006 May 16 | Aunt | 1016.66 | 597.2 | 65.24 ± 5.40 |
| 1374 | 1989 Oct. 5 | F | 16.6 | 2006 May 29 | T0 | 45 | ITL | 2006 May 29 | — | 1698.01 | 544.71 | 70.32 ± 16.24 |
| 1378 | 1992 Dec. 14 | M | 13.5 | 2006 Jun. 5 | T0 | 70 | ITL | 2006 Jun. 5 | — | 1531.64 | 394.74 | 249.97 |
| 1381 | 1990 Oct. 3 | F | 15.7 | 2006 Jun. 27 | T0 | 66 | IT | 2006 Jun. 27 | — | 1032.61 | 626.25 | 89.25 |
| 1389 | 1995 Oct. 26 | F | 10.7 | 2006 Jul. 24 | T0 | 46-66 | rTITL | 2006 Jul. 24 | — | 899.76 ± 20.49 | 359.31 | 187.61 ± 62.69 |
| | | | 11.0 | 2006 Oct. 2 | T5 | NA | NA | | | 770.91 ± 13.31 | 533.42 | 82.67 ± 1.55 |
| 1390 | 1990 Dec. 12 | F | 15.6 | 2006 Jul. 24 | T0 | 53 | ITL | 2006 Jul. 24 | — | 1269.89 | 839.02 | 78.42 |
| 1392 | 1993 May 25 | F | 13.2 | 2006 Jul. 26 | T0 | 48 | rT | 2006 Jul. 26 | Grand-mother, aunts | 1341.80 ± 15.38 | 87.13 | 105.48 ± 0.34 |
| 1393 | 1991 May 9 | F | 15.2 | 2006 Jul. 26 | T0 | 56 | rT | 2006 Jul. 26 | — | 969.63 | 821.21 | 81.59 |
| 1395 | 1988 Oct. 25 | F | 17.8 | 2006 Aug. 8 | T0 | 84 | ITL | 2006 Aug. 8 | Aunt | 1205.3 | 450.13 | 41.8 |
| 1396 | 1995 May 27 | F | 11.3 | 2006 Aug. 14 | T0 | 74-62 | NA | 2006 Aug. 14 | — | 1624.64 ± 5.10 | 166.83 | 172.75 ± 26.23 |
| | | | 11.3 | 2006 Sep. 26 | T1 | NA | NA | | | 773.40 ± 16.42 | 342.29 | 218.18 ± 2.83 |
| 1397 | 1988 Dec. 23 | M | 17.7 | 2006 Aug. 29 | T0 | 60-58 | rTIL | 2006 Aug. 29 | Uncle | 1581.40 ± 11.23 | 440.95 | 106.21 ± 10.20 |
| | | | 17.9 | 2006 Oct. 11 | T2 | 34-23 | NA | | | 1191.01 ± 14.64 | 546.18 | 158.77 ± 21.05 |
| 1406 | 1991 Oct. 29 | F | 14.9 | 2006 Sep. 20 | T0 | 62-60 | rTIL | 2006 Sep. 20 | — | 628.36 ± 45.23 | 304.04 | 52.88 ± 0.66 |
| 1410 | 1993 Jan. 4 | F | 13.7 | 2006 Sep. 28 | T0 | 56 | rT | 2006 Sep. 28 | Mother, aunt | 1287.16 ± 3.12 | 133.56 | 119.48 ± 24.22 |
| | | | 13.8 | 2006 Nov. 21 | T2 | 23 | NA | | | 903.57 ± 52.88 | 328.75 | 141.76 ± 12.56 |
| 1416 | 1991 Jul. 10 | F | 15.4 | 2006 Nov. 15 | T0 | 56-30 | rTIL | 2006 Nov. 15 | Sister, aunt | 514.30 ± 15.49 | 233.55 | 121.42 ± 28.69 |
| 1420 | 1993 Jun. 30 | F | 13.4 | 2006 Nov. 29 | T0 | 60-48 | rTIL | 2006 Nov. 29 | Sister | 661.35 ± 21.22 | 314.01 | 127.14 ± 1.06 |
| 1422 | 1994 Jun. 27 | F | 12.4 | 2006 Dec. 6 | T0 | 60-50 | rTIL | 2006 Dec. 6 | — | 530.56 ± 6.57 | 190.55 | 61.30 ± 14.49 |

TABLE 7-continued

Clinical and biochemical profiles of AIS patients with Cobb's angles of 45° or more.

| Patient ID | Date of Birth | Gender | Age | Collection Date | Time point (months) | Cobb's Angle Pre-op | Curve Type | Date of Surgery | Family History | [OPN] (ng/ml) | [sCD44] (ng/ml) | [HA] (ng/ml) |
|---|---|---|---|---|---|---|---|---|---|---|---|---|
| 1430 | 1989 Sep. 28 | F | 17.3 | 2007 Jan. 3 | T0 | 48 | rT | 2007 Jan. 3 | — | 533.56 ± 24.89 | 228.54 | 51.29 ± 7.00 |
| 1442 | 1994 Aug. 21 | F | 12.5 | 2007 Feb. 14 | T0 | 60 | rT | 2007 Feb. 14 | — | 512.99 ± 44.58 | 163.01 | 162.44 ± 3.03 |
| 1446 | 1988 Jul. 10 | F | 18.6 | 2007 Feb. 28 | T0 | 60 | rT | 2007 Feb. 28 | — | 537.87 ± 4.70 | 332.42 | 66.44 ± 20.48 |
| 1448 | 1992 Dec. 7 | F | 14.3 | 2007 Mar. 13 | T0 | 49 | lTL | 2007 Mar. 13 | — | 588.73 ± 25.88 | 110.3 | 138.81 ± 10.07 |
| 1457 | 1993 May 30 | F | 13.9 | 2007 Apr. 10 | T0 | 50-43 | rflTL | 2007 Apr. 10 | — | 1073.67 ± 69.04 | 401.79 | 83.21 ± 0.17 |
| 1458 | 1991 Sep. 27 | F | 15.4 | 2007 Apr. 11 | T0 | 45 | rT | 2007 Apr. 11 | — | 401.08 ± 22.88 | 212.16 | 66.48 ± 0.55 |
| 1459 | 1990 Mar. 28 | F | 17.1 | 2007 Apr. 18 | T0 | 72-36 | rflL | 2007 Apr. 16 | — | 761.78 ± 11.69 | 104.61 | 42.08 ± 5.99 |
|  |  |  | 17.2 | 2007 May 18 | T1 | NA | NA |  |  | 744.34 ± 10.91 | 340.71 |  |
| 1461 | 1990 May 17 | F | 16.9 | 2007 Apr. 18 | T0 | 48 | rT | 2007 Apr. 18 | Sister | 200.53 ± 3.68 | 371.51 | 112.29 ± 27.44 |
| 1464 | 1990 Jan. 2 | F | 17.3 | 2007 Apr. 25 | T0 | 53 | rT | 2007 Apr. 25 | — | 778.26 ± 19.40 | 163.01 | 133.86 ± 4.16 |
| 1467 | 1990 Nov. 18 | F | 16.5 | 2007 May 8 | T0 | 60 | rT | 2007 May 8 | — | 453.32 ± 17.32 | 236.23 | 48.59 ± 6.73 |
| 1468 | 1991 Nov. 12 | M | 15.5 | 2007 May 14 | T0 | 69 | rTL | 2007 May 14 | Cousin | 574.80 ± 42.46 | 283.37 | 116.85 ± 14.54 |
| 1471 | 1989 Oct. 8 | F | 17.6 | 2007 May 29 | T0 | 60 | rTL | 2007 May 29 | — | 907.06 ± 34.13 | 332.42 | 66.91 ± 28.51 |
| 1474 | 1969 Jun. 24 | M | 18.0 | 2007 Jun. 4 | T0 | 54-52 | rflL | 2007 Jun. 4 | — | 1254.39 ± 4.53 | 334.72 | 71.72 ± 16.08 |
| 1477 | 1992 Oct. 17 | F | 14.6 | 2007 Jun. 6 | T0 | 62-65 | rflL | 2007 Jun. 6 | Mother, brother | 829.32 ± 15.89 | 355.03 | 150.57 ± 28.87 |
| 1484 | 1991 Apr. 27 | F | 16.2 | 2007 Jun. 26 | T0 | 60 | rT | 2007 Jun. 26 | — | 489.15 ± 20.09 | 216.67 | 88.54 ± 422 |
| 1488 | 1992 Feb. 17 | M | 15.4 | 2007 Jul. 16 | T0 | 87 | rT | 2007 Jul. 16 | Mother | 1358.23 ± 56.62 | 304.83 | 120.78 ± 13.25 |
| 1489 | 1990 Sep. 26 | M | 16.8 | 2007 Jul. 17 | T0 | 57 | rT | 2007 Jul. 17 | — | 1417.61 ± 0.00 | 146.93 | 135.42 ± 2.53 |
| 1495 | 1992 Mar. 19 | F | 15.5 | 2007 Sep. 17 | T0 | 67-39 | rT | 2007 Sep. 17 | — | 437.55 ± 14.74 | 227.82 | 32.06 ± 0.29 |
| 1498 | 1992 Nov. 5 | F | 14.9 | 2007 Sep. 18 | T0 | 51-42 | rflL | 2007 Sep. 18 | — | 557.43 ± 50.58 | 152.3 | 62.63 ± 12.90 |
| 1501 | 1989 Feb. 4 | F | 16.5 | 2005 Jul. 22 | T0 | 58 | rflL | — | — | 939.53 | 711.38 | 144.30 ± 16.14 |
|  |  |  | 17.8 | 2006 Nov. 21 | T16 | 60 | rflL |  |  | 580.11 ± 7.56 | 503.43 | 107.24 ± 7.29 |
| 1502 | 1994 Mar. 14 | F | 13.6 | 2007 Oct. 15 | T0 | 55-43 | rflL | 2007 Oct. 15 | — | 856.14 ± 4.95 | 388.19 | 152.27 ± 5.09 |
|  |  |  | 13.8 | 2007 Dec. 5 | T2 | NA | NA |  |  | 1089.57 ± 22.51 | 349.14 | 55.91 ± 10.45 |
| 1506 | 1992 Jul. 7 | F | 15.3 | 2007 Nov. 6 | T0 | 65 | rT | 2007 Nov. 6 | — | 675.53 ± 13.63 | 241.98 | 85.64 ± 24.87 |
| 1517 | Nov. 20, 1990 | M | 17.2 | 2008 Feb. 13 | T0 | 50-62 | rflTL | — | — | 666.49 ± 65.68 | 328.96 | 41.3 ± 8.74 |
| 1518 | Dec. 8, 1991 | F | 16.2 | 2008 Feb. 13 | T0 | 62-62 | rflL | — | — | 672.59 ± 35.53 | 440.55 | 67.71 ± 6.81 |
| 1519 | 1993 Apr. 19 | M | 14.8 | 2008 Feb. 8 | T0 | 51 | rT | — | — | 945.23 ± 53.53 | 360.02 | 66.48 ± 1.10 |
| 1520 | 1993 Jun. 26 | F | 14.6 | 2008 Feb. 8 | T0 | 54-42 | rflTL | — | — | 752.87 ± 23.12 | 288.35 | 87.08 ± 0.36 |

\* Plus-minus values are means ± standard deviations.
\*\* All patients are diagnosed with AIS
† Curve type nomenclature: r, right/l, left/T, Thoracic/L, Lumbar/TL, Thoracolumbar/C, Cervical.
‡ Certain clinical information may not have been available at the time of the study, NA.

TABLE 8

Clinical and biochemical profiles of asymptomatic at risk children.

| Family Id | Date of Birth | Gender | Age | Collection Date | Time point (months) | Family History | [OPN] (ng/ml) | [sCD44] (ng/ml) | [HA] (ng/ml) |
|---|---|---|---|---|---|---|---|---|---|
| 1 | 1997 Sep. 2 | M | 8.8 | 2006 Jul. 10 | T0 | Mother | 439.72 ± 12.32 | 561.46 | 118.71 ± 8.74 |
| 1 | 1995 Sep. 6 | F | 10.8 | 2006 Jul. 10 | T0 | Mother | 207.88 ± 0.93 | 315.67 | 180.71 ± 19.91 |
| 2 | 1998 Feb. 8 | F | 8.7 | 2006 Oct. 3 | T0 | Mother, uncle, grand-father | 1650.21 ± 13.90 | 416.99 | 199.56 ± 55.60 |
|  |  |  | 9.2 | 2007 Apr. 19 | T6 |  | 1966.98 ± 1.96 | 459.89 | 207.57 ± 39.18 |
|  |  |  | 9.8 | 2007 Dec. 12 | T14 |  | 1816.83 ± 24.08 | 387.1 | 209.86 ± 21.38 |
| 2 | 2001 Jun. 18 | M | 5.8 | 2007 Apr. 19 | T0 | Mother, uncle, grand-father | 493.98 ± 7.26 | 463.68 | 43.99 ± 3.74 |
|  |  |  | 6.5 | 2007 Dec. 12 | T8 |  | 684.54 ± 10.06 | 438.94 | 102.21 ± 61.17 |
| 3 | 1994 Aug. 24 | F | 12.2 | 2006 Oct. 19 | T0 | Sister | 690.58 ± 2.92 | 418.18 | 220.8 |
|  |  |  | 12.6 | 2007 May 2 | T7 |  | 727.27 ± 17.36 | 467.79 | 196.82 ± 18.74 |
|  |  |  | 13.2 | 2007 Dec. 12 | T14 |  | 1212.32 ± 0.48 | 311.06 | 279.74 ± 30.33 |
| 4 | 2003 Oct. 17 | F | 3.0 | 2006 Oct. 19 | T0 | Mother | 1530.90 ± 28.42 | 478.58 | 225.02 ± 20.51 |
|  |  |  | 3.5 | 2007 Apr. 11 | T6 |  | 1021.07 ± 7.22 | 464.63 | 122.36 ± 15.35 |
|  |  |  | 4.2 | 2007 Dec. 12 | T14 |  | 1594.42 ± 23.36 | 470.05 | 332.11 |
| 5 | 2003 Jul. 17 | M | 3.2 | 2006 Oct. 19 | T0 | Mother | 905.58 ± 30.14 | 563.44 | 58.88 ± 3.86 |
|  |  |  | 3.7 | 2007 Apr. 19 | T6 |  | 1865.13 ± 7.35 | 434.93 | 128.14 ± 4.00 |
|  |  |  | 4.4 | 2007 Dec. 9 | T14 |  | 960.14 ± 26.22 | 631.93 | 32.64 ± 5.81 |
| 6 | 1998 Jul. 26 | F | 8.2 | 2006 Oct. 19 | T0 | Mother | 505.03 ± 8.92 | 564.17 | 81.86 ± 13.18 |
| 7 | 1995 Jun. 16 | F | 11.3 | 2006 Oct. 24 | T0 | Mother | 548.59 ± 6.61 | 512.92 | 80.39 ± 31.53 |
|  |  |  | 11.8 | 2007 Apr. 11 | T6 |  | 766.85 ± 5.73 | 396.69 | 103.31 ± 22.50 |
|  |  |  | 12.3 | 2007 Oct. 17 | T12 |  | 596.91 ± 35.50 | 465.36 | 122.40 ± 8.97 |
| 8 | 1996 Apr. 10 | F | 10.5 | 2006 Oct. 26 | T0 | Mother | 1109.78 ± 47.81 | 401.66 | 77.16 ± 9.72 |
|  |  |  | 11 | 2007 Apr. 11 | T6 |  | 875.81 ± 14.01 | 366.36 | 176.96 ± 4.68 |
| 9 | 1995 May 9 | F | 11.4 | 2006 Oct. 26 | T0 | Mother | 1657.97 | 440.3 | 112.58 ± 0.45 |
|  |  |  | 11.9 | 2007 Apr. 11 | T6 |  | 782.29 ± 1.47 | 429.56 | 86.57 ± 1.46 |
|  |  |  | 12.8 | 2008 Feb. 13 | T16 |  | 885.10 ± 35.98 | 255.6 | 63.42 ± 7.99 |
| 10 | 2002 Sep. 3 | F | 4.2 | 2006 Oct. 26 | T0 | Mother | 901.66 ± 12.01 | 398.27 | 158.65 ± 60.85 |
|  |  |  | 4.7 | 2007 Apr. 11 | T6 |  | 929.42 ± 3.07 | 356.88 | 167.19 ± 0.13 |
| 11 | 1992 Sep. 7 | F | 14.1 | 2006 Oct. 26 | T0 | Mother | 528.00 ± 8.83 | 469.78 | 69.05 ± 4.37 |
|  |  |  | 14.8 | 2007 Jul. 11 | T9 |  | 714.79 ± 14.44 | 383.1 | 37.97 ± 3.99 |
|  |  |  | 15.3 | 2008 Jan. 23 | T15 |  | 443.30 ± 0.58 | 472.69 | 80.27 ± 11.45 |
| 12 | 1991 Dec. 15 | F | 14.8 | 2006 Oct. 26 | T0 | Mother | 818.88 ± 0.94 | 518.03 | 134.08 ± 84.67 |
|  |  |  | 15.3 | 2007 Apr. 11 | T6 |  | 648.15 | 487.38 | 140.02 ± 50.63 |
|  |  |  | 15.9 | 2007 Nov. 14 | T13 |  | 398.28 ± 19.81 | 521.44 | 191.07 ± 8.20 |
| 12 | 1996 Feb. 23 | M | 10.7 | 2006 Oct. 26 | T0 | Mother | 1203.88 ± 55.29 | 681.23 | 85.30 ± 36.75 |
|  |  |  | 11.2 | 2007 Apr. 11 | T6 |  | 1930.95 ± 1.96 | 633.37 | 107.10 ± 15.99 |
|  |  |  | 11.8 | 2007 Nov. 14 | T13 |  | 1341.78 ± 31.57 | 687.61 | 170.54 ± 25.46 |
| 13 | 1993 Oct. 9 | F | 13.0 | 2006 Oct. 26 | T0 | Mother, grand-mother | 730.44 ± 33.95 | 397.12 | 41.87 ± 4.55 |
|  |  |  | 13.6 | 2007 May 2 | T7 |  | 420.91 ± 23.59 | 412.49 | 216.75 ± 27.71 |
|  |  |  | 14.1 | 2007 Nov. 14 | T13 |  | 943.64 ± 1.96 | 698.95 | 124.28 ± 15.03 |
| 14 | 2001 Sep. 7 | F | 5.2 | 2006 Nov. 16 | T0 | Father | 919.94 ± 11.91 | 510.08 | 45.28 ± 10.89 |
| 15 | 1997 Feb. 18 | M | 9.8 | 2006 Nov. 16 | T0 | Mother | 1629.22 ± 12.49 | 611.25 | 129.80 ± 30.80 |
|  |  |  | 10.2 | 2007 Apr. 11 | T5 |  | 1030.34 ± 6.55 | 690.56 | 146.19 ± 2.58 |
|  |  |  | 10.7 | 2007 Oct. 10 | T11 |  | 929.36 ± 11.23 | 590.8 | 135.89 ± 18.75 |
| 16 | 2002 Feb. 21 | F | 4.8 | 2006 Nov. 16 | T0 | Mother | 1834.30 ± 4.16 | 628.94 | 149.05 ± 19.17 |
|  |  |  | 5.2 | 2007 Apr. 11 | T5 |  | 909.22 ± 6.67 | 661.18 | 125.31 |
|  |  |  | 5.9 | 2007 Dec. 12 | T13 |  | 877.48 ± 23.75 | 466.59 | 70.10 ± 33.68 |
| 17 | 2000 Mar. 30 | F | 6.7 | 2006 Nov. 16 | T0 | Mother | 482.76 ± 10.64 | 678.55 | 95.92 ± 18.21 |
| 18 | 2000 Aug. 1 | F | 6.2 | 2006 Nov. 16 | T0 | Mother | 870.73 ± 21.30 | 644.62 | 146.12 ± 36.88 |
| 18 | 1997 May 5 | M | 9.5 | 2006 Nov. 16 | T0 | Mother | 1123.32 ± 7.06 | 401.66 | 112.68 ± 11.34 |
| 20 | 1998 Sep. 27 | F | 8.2 | 2006 Nov. 22 | T0 | Father | 506.21 ± 10.03 | 456.42 | 59.40 ± 30.21 |
|  |  |  | 8.8 | 2007 Jul. 11 | T8 |  | 677.71 ± 13.95 | 416.28 | 37.11 ± 6.95 |
| 21 (015) | 1998 Nov. 17 | F | 8.0 | 2006 Nov. 22 | T0 | Sister | 482.63 ± 7.58 | 458.02 | 99.16 ± 5.46 |
|  |  |  | 8.5 | 2007 May 23 | T6 |  | 511.46 | 488.33 | 151.08 |
|  |  |  | 9.0 | 2007 Nov. 14 | T12 |  | 760.00 ± 3.99 | 589.62 | 190.77 ± 5.64 |
| 21 (016) | 1991 Aug. 13 | F | 15.2 | 2006 Nov. 22 | T0 | Sister | 617.06 ± 7.65 | 511.71 | 110.15 ± 12.37 |
|  |  |  | 15.7 | 2007 May 23 | T6 |  | 619.60 ± 17.63 | 519.3 | 93.16 ± 0.39 |
|  |  |  | 16.2 | 2007 Nov. 14 | T12 |  | 685.18 ± 0.80 | 529.63 | 218.26 ± 27.22 |
| 22 | 1992 May 15 | M | 14.5 | 2006 Nov. 22 | T0 | Mother, grand-mother | 1082.23 ± 65.01 | 445.66 | 81.35 ± 14.77 |
|  |  |  | 14.9 | 2007 Apr. 11 | T5 |  | 1044.90 ± 3.21 | 432.72 | 152.54 ± 10.62 |
|  |  |  | 15.6 | 2008 Jan. 23 | T14 |  | 1010.18 ± 60.70 | 384.16 | 106.42 ± 10.80 |
| 23 (334) | 1994 Sep. 24 | F | 12.2 | 2006 Nov. 29 | T0 | Sister | 1365.94 ± 1.71 | 346.45 | 150.14 ± 2.53 |
|  |  |  | 12.6 | 2007 May 2 | T5 |  | 1856.82 ± 12.74 | 501.92 | 167.91 ± 17.19 |
|  |  |  | 13.1 | 2007 Oct. 10 | T11 |  | 947.97 ± 16.31 | 489.38 | 271.36 ± 20.40 |
| 24 | 1994 Nov. 24 | M | 12.0 | 2006 Nov. 29 | T0 | Mother, aunt | 775.28 ± 20.77 | 427.49 | 84.54 ± 0.14 |
|  |  |  | 12.5 | 2007 May 2 | T6 |  | 610.29 ± 10.86 | 436.82 | 130.53 ± 2.30 |
|  |  |  | 13.1 | 2007 Dec. 12 | T13 |  | 718.55 ± 5.97 | 355.99 | 127.92 ± 3.93 |
| 24 | 1994 Nov. 24 | F | 12 | 2006 Nov. 29 | T0 | Mother, aunt | 815.81 ± 22.25 | 473.76 | 160.63 ± 8.36 |
|  |  |  | 12.5 | 2007 May 2 | T6 |  | 673.56 ± 16.29 | 445.36 | 127.40 ± 37.13 |
|  |  |  | 13.1 | 2007 Dec. 12 | T13 |  | 1299.89 ± 28.77 | 662.73 | 276.97 |
| 25 | 1998 Jun. 5 | F | 8.4 | 2006 Nov. 29 | T0 | Mother, father | 1245.41 ± 13.75 | 441.4 | 108.75 ± 18.90 |
|  |  |  | 8.8 | 2007 Apr. 19 | T5 |  | 1766.40 ± 2.69 | 500.34 | 197.20 ± 31.62 |
|  |  |  | 9.3 | 2007 Oct. 10 | T11 |  | 944.99 ± 25.37 | 476.76 | 115.66 ± 10.09 |
| 25 | 2001 Jun. 4 | M | 5.4 | 2006 Nov. 29 | T0 | Mother, father | 1181.70 ± 50.65 | 303.75 | 157.81 ± 11.99 |
|  |  |  | 5.8 | 2007 Apr. 19 | T5 |  | 1707.51 ± 30.62 | 319.63 | 113.24 ± 2.45 |
|  |  |  | 6.3 | 2007 Oct. 10 | T11 |  | 867.79 ± 25.36 | 364.76 | 114.76 ± 33.42 |

TABLE 8-continued

Clinical and biochemical profiles of asymptomatic at risk children.

| Family Id | Date of Birth | Gender | Age | Collection Date | Time point (months) | Family History | [OPN] (ng/ml) | [sCD44] (ng/ml) | [HA] (ng/ml) |
|---|---|---|---|---|---|---|---|---|---|
| 26 | 1994 Mar. 18 | F | 12.7 | 2006 Nov. 29 | T0 | Mother | 678.95 ± 9.57 | 432.08 | 86.09 |
| 27 | 1987 Dec. 13 | F | 19 | 2006 Dec. 19 | T0 | Father | 287.27 ± 8.96 | 572.38 | 101.88 ± 13.89 |
| 28 | 2003 May 23 | F | 3.6 | 2006 Dec. 19 | T0 | Mother | 612.92 ± 3.03 | 760.08 | 45.57 ± 3.40 |
| 29 | 1990 Oct. 17 | M | 16.2 | 2006 Dec. 19 | T0 | Mother | 459.54 ± 29.16 | 488.33 | 99.03 ± 54.21 |
|  |  |  | 17.0 | 2007 Oct. 10 | T10 |  | 505.24 ± 39.04 | 441.73 | 121.53 ± 15.54 |
| 29 (652) | 1999 May 11 | F | 7.6 | 2006 Dec. 19 | T0 | Mother | 576.64 ± 20.73 | 656.77 | 114.39 |
|  |  |  | 8.4 | 2007 Oct. 10 | T10 |  | 972.66 ± 7.97 | 636.32 | 138.53 ± 16.69 |
| 29 (160) | 1996 Dec. 2 | F | 10.0 | 2006 Dec. 19 | T0 | Mother | 583.62 ± 19.18 | 600.16 | 136.79 ± 10.66 |
|  |  |  | 10.8 | 2007 Oct. 10 | T10 |  | 874.79 ± 2.17 | 535.48 | 112.73 ± 7.74 |
| 30 | 1995 Mar. 9 | M | 11.8 | 2006 Dec. 19 | T0 | Mother | 1608.98 ± 8.37 | 607.15 | 115.19 ± 6.27 |
|  |  |  | 12.3 | 2007 Jul. 4 | T7 |  | 1107.95 ± 0.53 | 504.15 | 40.04 ± 11.63 |
|  |  |  | 12.8 | 2008 Jan. 23 | T13 |  | 1578.17 ± 18.50 | 469.62 | 93.33 ± 3.68 |
| 30 | 1997 Jun. 8 | F | 9.5 | 2006 Dec. 19 | T0 | Mother | 1211.80 ± 5.47 | 586.43 | 172.18 ± 4.00 |
|  |  |  | 10.1 | 2007 Jul. 4 | T7 |  | 774.18 ± 21.15 | 534.59 | 40.03 ± 11.95 |
|  |  |  | 10.6 | 2008 Jan. 23 | T13 |  | 697.49 ± 12.25 | 473.45 | 95.89 ± 6.16 |
| 31 | 1998 Mar. 18 | F | 8.8 | 2006 Dec. 19 | T0 | Mother, aunt, grand-father | 467.80 ± 1.39 | 574.23 | 106.48 ± 29.19 |
| 31 | 1999 Nov. 3 | M | 7.1 | 2006 Dec. 19 | T0 | Mother, aunt, grand-father | 745.53 ± 40.56 | 552.66 | 98.22 ± 1.18 |
| 32 | 2004 Jun. 20 | F | 2.5 | 2006 Dec. 19 | T0 | Mother, grand-mother | 1573.79 ± 0.72 | 576.5 | 142.70 ± 0.57 |
|  |  |  | 3.1 | 2007 Jul. 4 | T7 |  | 1034.97 ± 25.55 | 494.82 | 52.38 ± 5.01 |
|  |  |  | 3.6 | 2008 Jan. 23 | T13 |  | 1237.94 ± 48.60 | 374.2 | 152.27 ± 0.32 |
| 33 | 1996 May 17 | M | 10.7 | 2007 Jan. 10 | T0 | Mother | 623.78 ± 2.66 | 649.44 | 166.16 ± 32.22 |
|  |  |  | 11.5 | 2007 Nov. 7 | T10 |  | 671.14 ± 0.27 | 634.5 | 36.87 ± 2.05 |
| 33 | 1996 Jun. 25 | F | 11.2 | 2007 Jan. 10 | T0 | Mother | 893.13 ± 34.21 | 436.86 | 92.74 ± 2.45 |
|  |  |  | 11.7 | 2007 Jul. 11 | T6 |  | 716.31 ± 27.52 | 543.59 | 37.95 ± 5.33 |
| 34 | 1996 Aug. 14 | F | 10.3 | 2006 Dec. 21 | T0 | Mother | 1135.80 ± 18.20 | 508.95 | 256.64 ± 37.18 |
|  |  |  | 10.8 | 2007 Jun. 13 | T6 |  | 594.41 ± 0.37 | 490.61 | 96.56 ± 2.45 |
|  |  |  | 11.4 | 2008 Jan. 23 | T13 |  | 978.10 ± 49.46 | 450.46 | 103.67 ± 10.95 |
| 34 | 1994 Jun. 21 | M | 12.5 | 2006 Dec. 21 | T0 | Mother | 1010.70 ± 22.34 | 416.71 | 172.33 ± 50.68 |
|  |  |  | 13.0 | 2007 Jun. 13 | T6 |  | 739.31 ± 3.43 | 499.04 | 93.55 ± 6.90 |
|  |  |  | 13.6 | 2008 Jan. 23 | T13 |  | 777.22 ± 39.78 | 448.93 | 92.70 ± 21.91 |
| 35 (605) | 1995 Mar. 31 | M | 11.8 | 2006 Dec. 21 | T0 | Mother | 1126.22 ± 46.08 | 552.37 | 163.66 ± 0.79 |
| 35 (604) | 1995 Mar. 31 | M | 11.8 | 2006 Dec. 21 | T0 | Mother | 933.16 ± 14.20 | 437.43 | 118.57 ± 6.65 |
| 35 | 1993 May 12 | F | 13.6 | 2006 Dec. 21 | T0 | Mother | 1679.45 | 436.58 | 128.45 ± 17.60 |
| 36 | 1998 Sep. 6 | M | 8.3 | 2007 Jan. 10 | T0 | Mother | 1520.81 ± 20.48 | 485.39 | 225.68 ± 85.59 |
|  |  |  | 9.2 | 2007 Nov. 14 | T10 |  | 1103.50 ± 27.07 | 899.87 | 114.96 ± 0.11 |
| 37 | 2001 Jul. 11 | F | 5.5 | 2007 Jan. 17 | T0 | Mother | 419.51 ± 10.21 | 524.02 | 35.52 ± 0.52 |
|  |  |  | 6.0 | 2007 Jul. 4 | T6 |  | 606.10 ± 14.32 | 490.91 | 209.23 |
| 38 | 1995 Jan. 19 | M | 12.0 | 2007 Jan. 17 | T0 | Mother | 435.87 ± 7.38 | 600.34 | 164.49 ± 10.01 |
| 38 | 1992 Aug. 2 | F | 14.4 | 2007 Jan. 17 | T0 | Mother | 328.67 ± 25.67 | 564.58 | 166.19 ± 2.53 |
| 39 | 1996 Jun. 8 | M | 10.6 | 2007 Jan. 24 | T0 | Mother | 437.90 ± 23.91 | 529.14 | 215.53 ± 70.15 |
|  |  |  | 11.1 | 2007 Jul. 18 | T6 |  | 617.26 ± 5.45 | 445.15 | 146.08 ± 8.82 |
| 39 | 1997 Aug. 8 | F | 9.4 | 2007 Jan. 24 | T0 | Mother | 399.82 ± 14.71 | 452.38 | 71.339 ± 22.51 |
|  |  |  | 9.9 | 2007 Jul. 18 | T6 |  | 648.28 ± 6.30 | 462.01 | 188.78 ± 12.79 |
| 40 | 1996 May 5 | F | 10.9 | 2007 Apr. 5 | T0 | Mother | 986.26 ± 9.88 | 478.27 | 99.9 |
| 40 | 1999 Apr. 23 | M | 8.0 | 2007 Apr. 5 | T0 | Mother | 851.99 ± 4.04 | 710.05 | 52.81 ± 12.17 |
| 41 | 1995 Mar. 29 | F | 12.2 | 2007 May 30 | T0 | Father | 500.68 ± 20.08 | 416.56 | 71.27 ± 0.30 |
| 42 | 1996 Jul. 3 | M | 10.8 | 2007 May 2 | T0 | Father | 391.38 ± 30.03 | 620.65 | 32.83 |
|  |  |  | 11.3 | 2007 Nov. 14 | T6 |  | 393.23 ± 4.22 | 445.78 | 167.25 ± 27.97 |
| 42 | 1992 Apr. 14 | F | 15.1 | 2007 May 2 | T0 | Father | 452.43 ± 1.68 | 519.81 | 38.46 ± 16.02 |
|  |  |  | 15.6 | 2007 Nov. 14 | T6 |  | 658.95 ± 1.62 | 938.89 | 232.91 ± 2.00 |
| 43 | 2001 Nov. 20 | F | 5.5 | 2007 May 23 | T0 | Mother | 892.70 ± 21.23 | 484.89 | 97.65 ± 30.81 |
| 44 | 1995 Sep. 11 | M | 11.6 | 2007 Jun. 13 | T0 | Mother | 1058.59 ± 6.11 | 547.8 | 41.15 ± 11.08 |
|  |  |  | 12.2 | 2007 Dec. 12 | T6 |  | 1160.10 ± 16.16 | 456.22 | 145.61 ± 51.30 |
| 45 | 1994 May 10 | F | 13.2 | 2007 Aug. 29 | T0 | Mother | 714.66 ± 6.88 | 482.12 | 120.00 ± 13.64 |
|  |  |  | 13.8 | 2008 Feb. 13 | T6 |  | 801.53 ± 42.46 | 358.64 | 134.84 ± 16.18 |
| 46 | 1999 Nov. 4 | M | 7.8 | 2007 Sep. 12 | T0 | Mother | 603.75 ± 10.96 | 569.62 | 111.95 ± 5.86 |
| 46 (980) | 1996 Apr. 15 | F | 11.4 | 2007 Sep. 13 | T0 | Mother | 504.38 ± 35.85 | 540.29 | 118.25 ± 9.11 |
| 46 (982) | 2004 Jan. 24 | F | 3.7 | 2007 Sep. 12 | T0 | Mother | 718.72 ± 78.98 | 510.97 | 153.13 ± 4.50 |
| 47 | 1996 Dec. 7 | F | 10.8 | 2007 Oct. 17 | T0 | Mother | 1010.10 ± 17.02 | 494.12 | 147.00 ± 87.36 |
| 47 | 1999 Apr. 3 | M | 8.5 | 2007 Oct. 17 | T0 | Mother | 844.83 ± 30.84 | 456.7 | 156.33 ± 50.36 |
| C6 | 1997 Feb. 6 | F | 10.3 | 2007 May 22 | T0 | Mother | 669.60 ± 4.19 | 755.65 | 133.68 ± 4.10 |
|  |  |  | 11.0 | 2008 Jan. 16 | T8 |  | 733.30 ± 11.68 | 620.67 | 250.52 ± 38.11 |
| C15 | 1997 May 27 | M | 10.0 | 2007 Jun. 6 | T0 | Brother | 441.81 ± 0.64 | 640.33 | 106.53 ± 1.88 |
|  |  |  | 10.5 | 2007 Dec. 4 | T6 |  | 444.69 ± 3.82 | 958.24 | 151.86 ± 17.41 |

\* Plus-minus values are means ± standard deviations.
† All subjects are examined before sample collection by an orthopedic surgeon to monitor possible scoliosis development.

Example 11

OPN, sCD44 and HA Levels in Non AIS Scoliotic Patients

Figure 12:
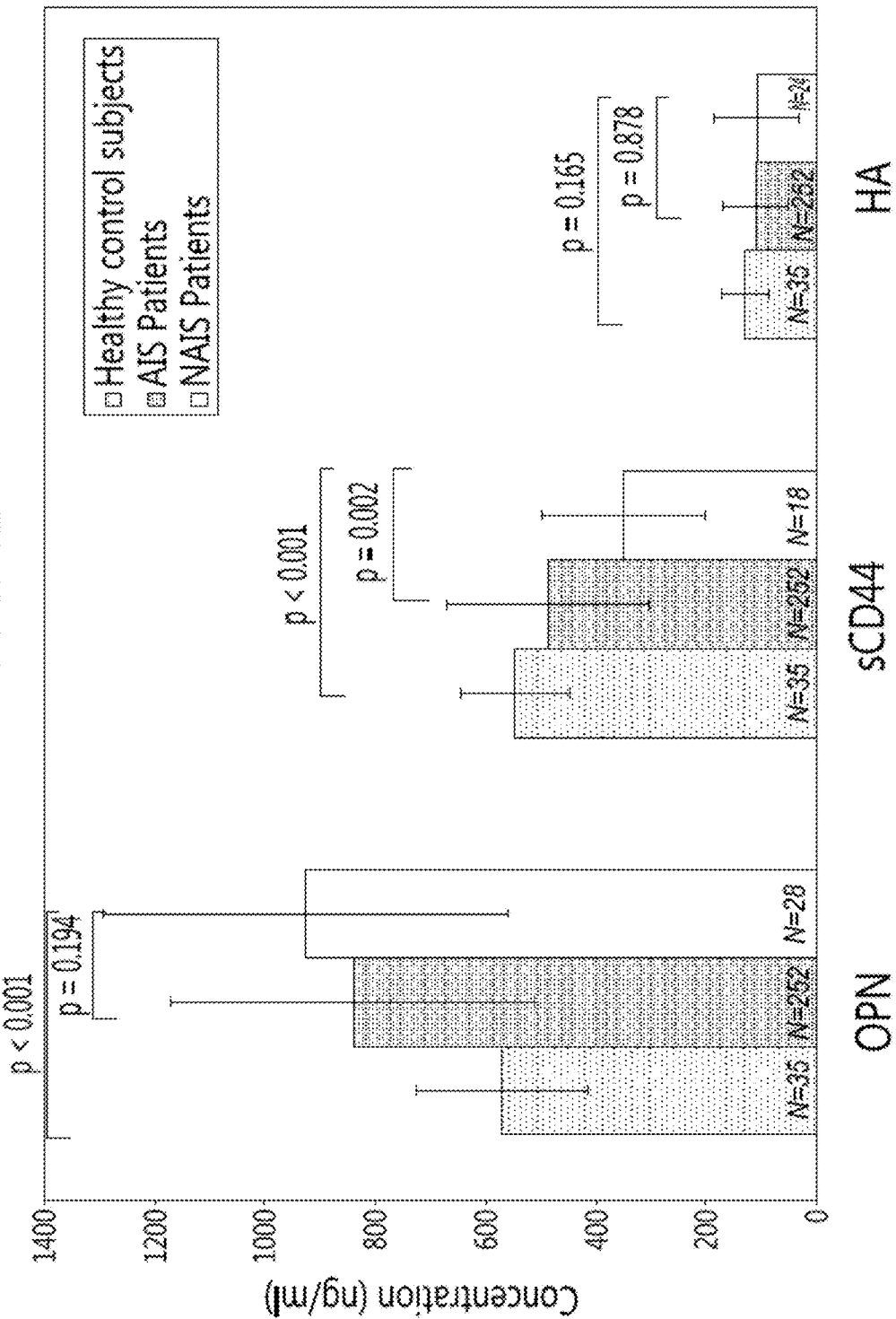
FIG. 12 compares OPN, sCD44 and HA levels in non AIS scoliotic patients (NAIS) (OPN (n=28), sCD44 (n=18), HA (n=24)), healthy controls (n=35) and AIS patients (n=252)

OPN levels were measured in non AIS scoliotic patients (NAIS patients). Results are summarized in Table 9 below. A comparison of OPN, sCD44 and HA levels in healthy, AIS and NAIS patients is also provided in FIG. 12.

TABLE 9

Biomarkers Comparison of non-AIS scoliotic Patients.

| Type of Scoliosis | Number | Mean Age (Years) | Mean Cobb Angle | Mean OPN Concentration (ng/ml) | Mean sCD44 Concentration (ng/ml) | Mean HA Concentration (ng/ml) |
|---|---|---|---|---|---|---|
| Neurological Scoloisis | 8 | 12.3 ± 3.7 | 79.4 ± 15.1 | 982 ± 452 | 274 ± 196 | 127 ± 101 |
| Congenital Scoliosis | 8 | 10.0 ± 4.4 | 51.8 ± 18.1 | 1016 ± 400 | 432 ± 79 | 123 ± 80 |
| Spondylolisthesis | 5 | 17.5 ± 2.1 | 21.0 ± 17.0 | 832 ± 125 | 386 ± 193 | 76 ± 54 |
| Kyphosis Scoliosis | 5 | 14.4 ± 2.8 | 80.2 ± 28.5 | 923 ± 393 | 352 ± 62 | 91 ± 56 |
| Other* | 2 | 15.1 | 74.5 ± 17.7 | 586 ± 52 | 240 | NA |

† Plus-minus values are means ± standard deviations
*Other scoliosis types include one neuromuscular scoliosis and one dysplasic scoliosis.

Table 10 below presents in detail biomarkers levels for non AIS scoliotic patients.

TABLE 10

Clinical and biochemical profiles of non AIS scoliotic patients.

| Patient ID | Date of Birth | Gender | Age | Collection Date | Diagnosis | Cobb's Angle Pre-op | Curve Type |
|---|---|---|---|---|---|---|---|
| 1208 | 1990 Jan. 19 | M | 17.8 | 2007 Oct. 3 | Congenital cyphose scoliosis | 72 | IT |
| 1256 | 1992 Mar. 27 | M | 13.0 | 2005 May 9 | Congenital scoliosis | 44-65 | rTIL |
| 1278 | 1998 Jul. 22 | F | 6.8 | 2005 May 30 | Congenital neurological scoliosis | 60 | IT |
| 1281 | 1985 May 21 | M | 20.1 | 2005 Aug. 1 | Spondylolisthesis | 16 | — |
| 1286 | 1990 May 8 | M | 15.1 | 2005 Jun. 15 | Dyspiasic scoliosis | 62-66 | rTIL |
| 1356 | 1993 Feb. 22 | F | 13.2 | 2006 Apr. 3 | Congenital scoliosis | 75 | rT |
| 1358 | 2003 Nov. 9 | M | 2.4 | 2006 Apr. 4 | Congenital scoliosis | 33-35 | rTIL |
| 1367 | 1993 Dec. 12 | F | 12.4 | 2006 Feb. 1 | Neurological scoliosis | 90 | ITL |
| 1368 | 1990 Jun. 21 | F | 15.9 | 2006 May 2 | Neurological cyphosis | 50 | ITL |
| 1370 | 1995 Sep. 15 | M | 10.7 | 2006 May 9 | Neurological scoliosis | 65 | rT |
| 1375 | 1992 Sep. 13 | F | 13.7 | 2006 May 30 | Congenital scoliosis | 53 | rTIL |
| 1407 | 1990 Dec. 22 | M | 16.8 | 2007 Oct. 31 | Spondylolisthesis | 9 | IL |
| 1431 | 1987 Nov. 23 | M | 19.2 | 2007 Jan. 8 | Neurological scoliosis | 90-90 | rTIT |
| 1432 | 1992 Aug. 8 | M | 14.4 | 2007 Jan. 9 | Neurological scoliosis | 64 | rT |
| 1434 | 1994 Aug. 7 | F | 12.4 | 2007 Jan. 10 | Congenital scoliosis | 79-77 | rTIL |
| 1436 | 1993 Feb. 16 | F | 13.9 | 2007 Jan. 22 | Cyphose scoliosis | 120 | — |
| 1437 | 1992 Nov. 6 | M | 14.2 | 2007 Feb. 5 | Neurolopical scoliosis | 100 | NA |
| 1455 | 1996 Dec. 14 | F | 10.3 | 2007 Apr. 3 | Congenital cyphose scoliosis | 61 | ITL |
| 1456 | 1990 Oct. 3 | F | 16.5 | 2007 Apr. 17 | Neuromuscular scoliosis | 87 | rTL |
| 1462 | 1997 Oct. 22 | F | 9.5 | 2007 Apr. 23 | Neurological scoliosis | 76 | ITL |
| 1463 | 1989 Mar. 19 | F | 18.1 | 2007 Apr. 24 | Scoliosis + Spondylolisthesis | 33 | rT |
| 1466 | 1997 Aug. 24 | F | 9.8 | 2007 May 8 | Congenital scoliosis | 39 | rL |
| 1475 | 1993 May 25 | M | 14.1 | 2007 Jun. 5 | Cyphose scoliosis | 98 | — |
| 1479 | 1996 Jan. 24 | F | 11.4 | 2007 Jun. 5 | Neurological scoliosis | 90 | rTIL |
| 1480 | 2003 Jun. 13 | F | 4.0 | 2007 Jun. 18 | Congenital scoliosis | 56 | IT |
| 1482 | 1989 Mar. 30 | F | 18.2 | 2007 Jun. 19 | spondylolisthesis gr 1 | — | NA |
| 1486 | 1993 Jan. 15 | M | 14.4 | 2007 Jun. 27 | Spondylolisthesis gr 2 | — | NA |
| 357 | 1996 Jul. 8 | F | 11.4 | 2007 Dec. 18 | Congenital scoliosis | 30-31 | rTIT |

| Patient ID | Date of Surgery | Age at Surgery | Family History | [OPN] (ng/ml) | [sCD44] (ng/ml) | [HA] (ng/ml) |
|---|---|---|---|---|---|---|
| 1208 | 2004 Nov. 8 | 14.8 | — | 1101.06 ± 31.26 | 444.81 | 82.89 ± 15.11 |
| 1256 | 2005 Mar. 29 | 13.0 | — | 1490.59 | NA | 127.74 ± 9.29 |
| 1278 | 2005 May 30 | 6.8 | — | 1401.88 | NA | 75.65 ± 5.16 |
| 1281 | 2005 Jun. 1 | 20.1 | — | 985.85 | NA | 150.30 ± 7.93 |

TABLE 10-continued

Clinical and biochemical profiles of non AIS scoliotic patients.

| | | | | | | |
|---|---|---|---|---|---|---|
| 1286 | 2005 Jun. 15 | 15.1 | — | 549.60 ± 5.06 | NA | NA |
| 1356 | 2006 Apr. 3 | 13.2 | — | 1181.85 | NA | 111.51 ± 2.30 |
| 1358 | 2006 Apr. 4 | 2.4 | — | 1530.6 | NA | 284.60 ± 69.00 |
| 1367 | 2006 May 1 | 12.4 | — | 1525.13 | NA | 350.01 ± 36.55 |
| 1368 | 2006 May 2 | 15.9 | — | 1079.23 | NA | 126.44 ± 3.63 |
| 1370 | 2006 May 9 | 10.7 | — | 1318.58 | NA | 104.06 ± 5.18 |
| 1375 | 2006 May 30 | 13.7 | Cousin | 380.08 ± 12.95 | NA | NA |
| 1407 | 2006 Sep. 25 | 15.8 | — | 818.17 ± 1.52 | 441.73 | 116.09 ± 3.88 |
| 1431 | 2007 Jan. 8 | 19.2 | — | 450.78 ± 101.56 | 275.62 | 130.30 ± 23.92 |
| 1432 | 2007 Jan. 9 | 14.4 | — | 558.47 ± 4.70 | 145.15 | 98.99 ± 13.92 |
| 1434 | 2007 Jan. 10 | 12.4 | — | 631.59 ± 7.42 | 325.95 | 44.79 ± 5.73 |
| 1436 | 2007 Jan. 22 | 13.9 | — | 220.32 ± 2.94 | 322.03 | 44.34 ± 8.37 |
| 1437 | 2007 Feb. 5 | 14.2 | — | 388.01 ± 8.22 | 225.71 | 76.96 ± 4.53 |
| 1455 | 2007 Apr. 3 | 10.3 | — | 1090.51 ± 5.57 | 323.24 | 34.79 ± 0.32 |
| 1456 | 2007 Apr. 17 | 16.5 | — | 622.46 ± 7.15 | 240.22 | NA |
| 1462 | 2007 Apr. 23 | 9.5 | — | 1118.25 ± 1.32 | 607.1 | 55.90 ± 1.82 |
| 1463 | 2007 Apr. 24 | 18.1 | — | 751.54 ± 8.69 | 284.71 | 21.56 ± 4.58 |
| 1466 | 2007 May 8 | 9.8 | — | 1110.01 ± 2.38 | 510.18 | 47.07 ± 1.48 |
| 1475 | 2007 Jun. 4 | 14.1 | — | 1123.49 ± 5.56 | 319.93 | 166.63 ± 34.63 |
| 1479 | 2007 Jun. 5 | 11.4 | — | 1098.54 ± 131.44 | 119.17 | NA |
| 1480 | 2007 Jun. 18 | 4.0 | — | 809.8 | 468.03 | 120.72 ± 40.73 |
| 1482 | 2007 Jun. 19 | 18.2 | — | 678.49 ± 18.32 | 187.48 | 46.07 ± 5.27 |
| 1486 | 2007 Jun. 27 | 14.4 | — | 924.40 ± 17.16 | 628.78 | 47.06 ± 6.84 |
| 357 | — | — | — | 996.58 ± 8.51 | 423.72 | 127.33 ± 3.13 |

\* Plus-minus values are means ± standard deviations.
† Curve type nomenclature: r, right/l, left/T, Thoracic/L, Lumbar/TL, Thoracolumbar/C, Cervical Example 12

OPN and sCD44 Levels in AIS Patients Pre and Post Operations

Figure 13:
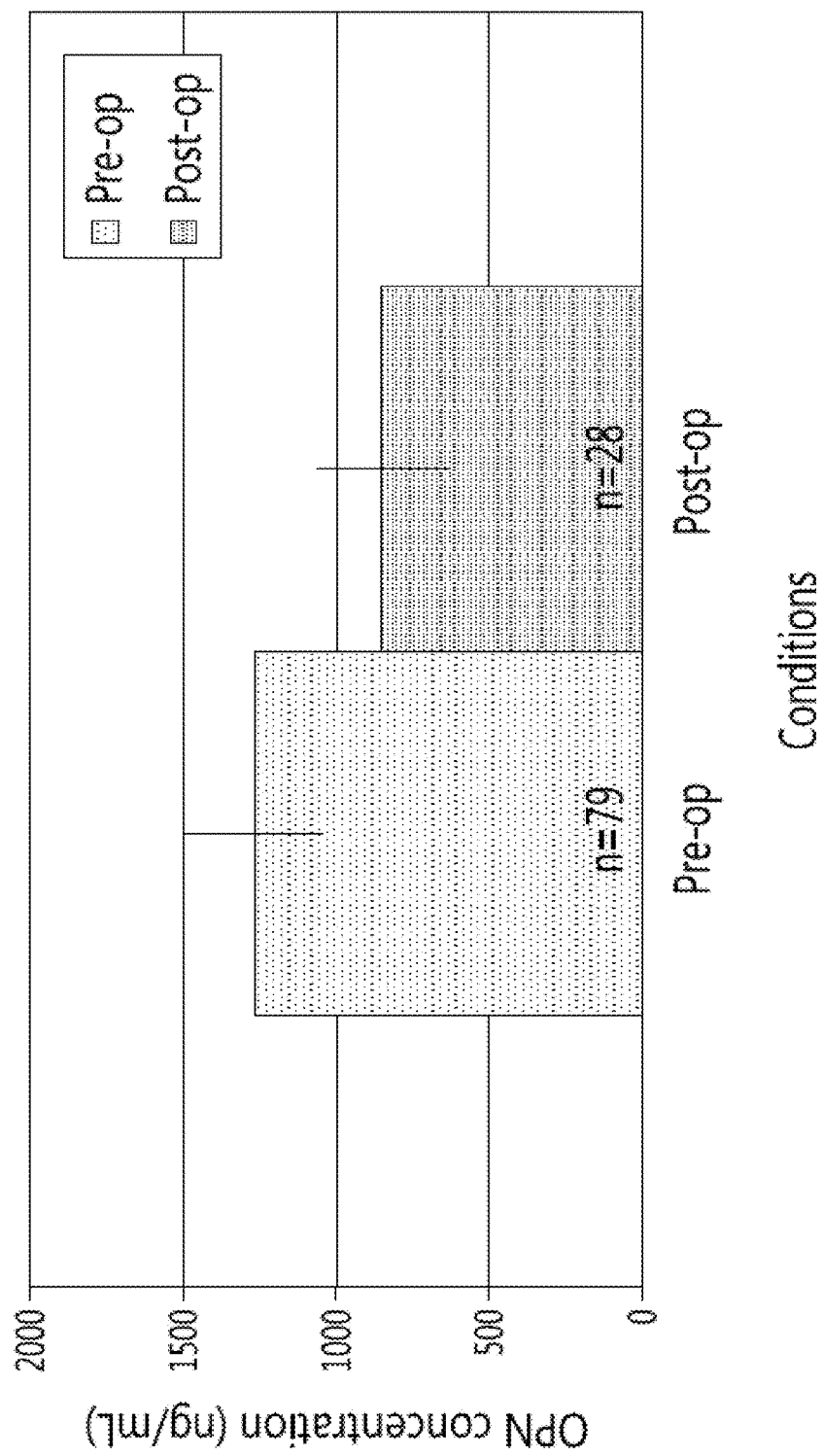
FIG. 13 presents a histogram comparison of circulating levels of OPN change in function of spine biomechanics in pre-operated AIS patients (n=79) vs. post-operated AIS patients (n=28)

OPN levels were measured in AIS patients pre (n=79) and post (N=28) operations. Interestingly, comparison of AIS patients in pre-operation vs. post operation showed a reduction in circulating OPN levels, which further support the role of OPN at the cellular level as mechanosensor (FIG. 13).

Figure 14:
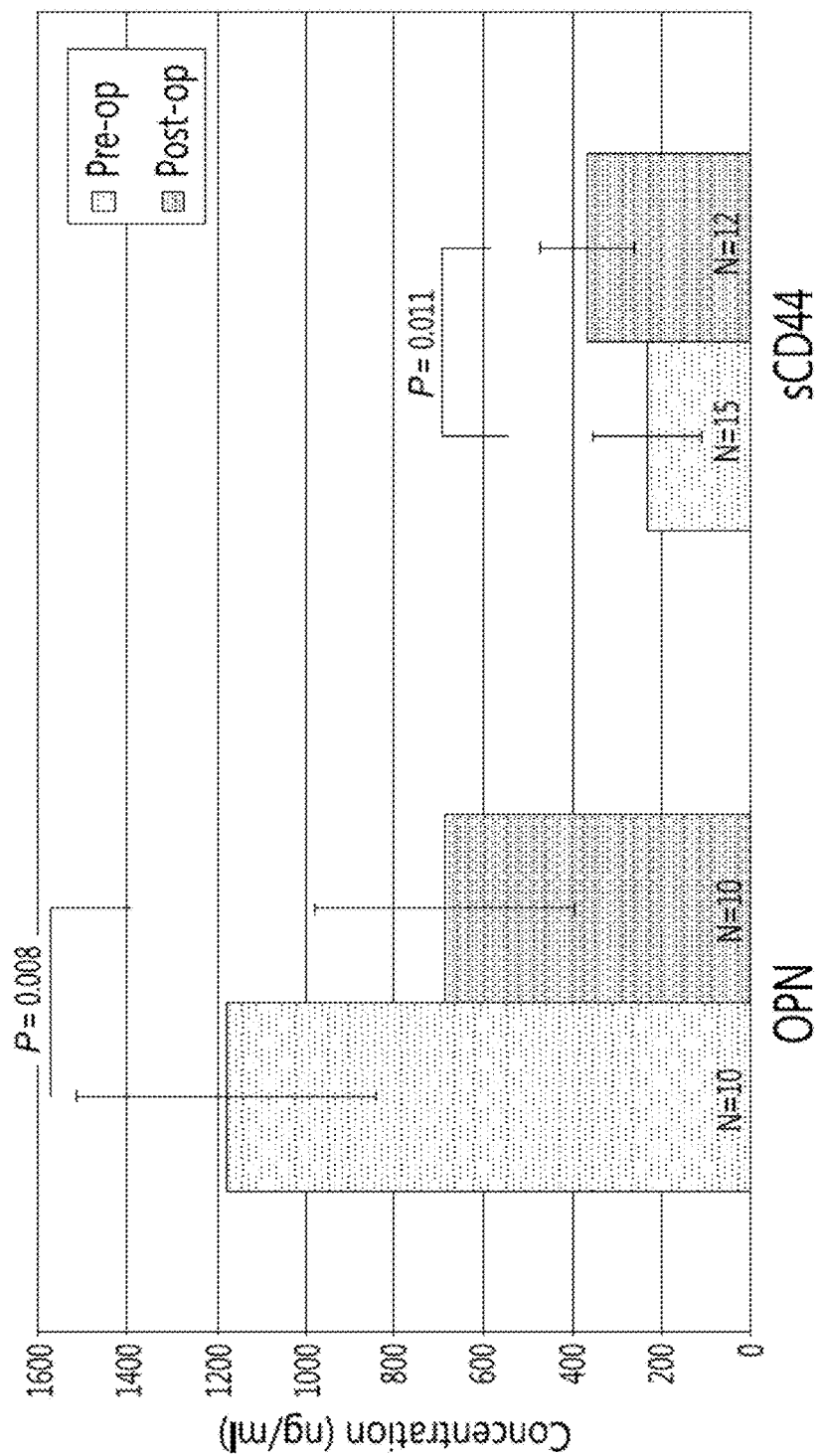
FIG. 14 presents a histogram comparison of circulating levels of OPN and sCD44 of in pre-operated AIS female (OPN (n=10); sCD44 (n=15)) vs. post-operated AIS female (OPN (n=10); sCD44 (n=12))

OPN were measured in AIS female patients pre (n=10) and post (N=10) treatment with braces. Similarly, sCD44 levels were measured in AIS female patients pre (n=15) and post (N=12) operations. Results are presented in FIG. 14.

Figure 15A:
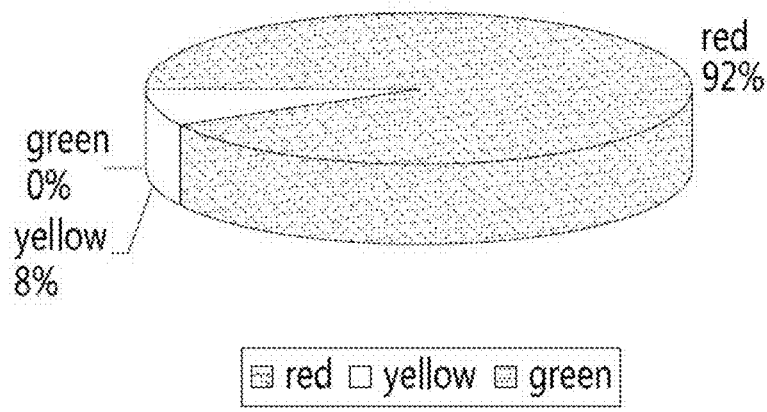
FIGS. 15A and 15B present charts distributing AIS patients across the predefined cut-off zones pre-operation (FIG. 15A) and post-operation (FIG. 15B)
Figure 15B:
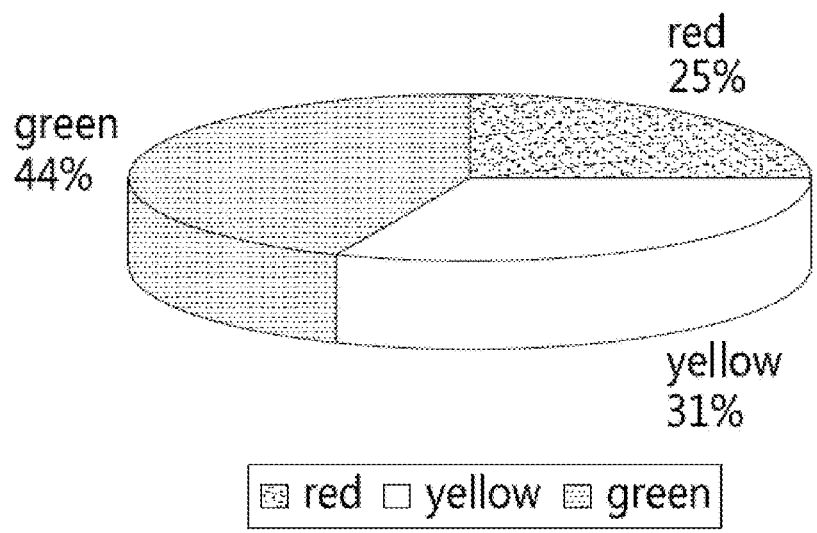

A distribution of 12 AIS patients was also performed across the predefined cut-off zones pre-operation and post-operation. FIG. 15 shows 92% of the surgically treated patients had pre-operation OPN levels in the red-zone (>800 ng/mL of plasma OPN level), while the remaining 8% were in the yellow zone (700-800 ng/mL). No patients were in the green zone representing plasma OPN levels <700 ng/mL. This also shows a strong correlation between high OPN concentrations and the progression of scoliotic curves.

Panel B of FIG. 15 show that red zone patients who were treated surgically experienced a decline in OPN concentrations in the blood. 75% of the surgically treated patients fell into the green and yellow zones (800 ng/mL or less).

Example 13

OPN Levels in AIS Patients with Various Types of Braces

OPN levels were also measured in AIS patients prior to being treated with brace (n=79) and after brace (N=28). Table 11 below also shows the effect of braces on biomarkers.

TABLE 11

Possible effects of brace treatment on biomarker concentrations.

| | | Characteristics | | | | | |
|---|---|---|---|---|---|---|---|
| Treatment | No. | Mean Age (Years) | Mean Brace Wear (Months) | Mean Cobb's Angle | Mean OPN Concentration (ng/ml) | Mean sCD44 Concentration (ng/ml) | Mean HA Concentration (ng/ml) |
| Without Brace | | | | | | | |
| Female | 193 | 14.2 ± 2.1 | — | 30.9 ± 19.3 | 809 ± 376 | 474 ± 179 | 108 ± 58 |
| Male | 36 | 14.8 ± 2.2 | — | 32.2 ± 21.1 | 1034 ± 376 | 492 ± 155 | 126 ± 62 |
| With Brace (All Female) | | | | | | | |
| All Braces Combined | 21 | 14.0 ± 1.8 | 12.0 | 21.2 ± 8.3 | 664 ± 282 | 483 ± 112 | 118 ± 60 |
| Boston | 5 | 13.0 ± 1.4 | 10.6 | 25.8 ± 4.4 | 735 ± 358 | 568 ± 184 | 150 ± 57 |
| SpineCor | 14 | 14.5 ± 1.6 | 12.7 | 20.6 ± 8.7 | 626 ± 279 | 451 ± 81 | 108 ± 62 |
| Charleston | 1 | 15.4 | 10.0 | 7.0 | 781 | 532 | 70 |

TABLE 11-continued

Possible effects of brace treatment on biomarker concentrations.

| Treatment | No. | Mean Age (Years) | Mean Brace Wear (Months) | Mean Cobb's Angle | Mean OPN Concentration (ng/ml) | Mean sCD44 Concentration (ng/ml) | Mean HA Concentration (ng/ml) |
|---|---|---|---|---|---|---|---|
| Providence Night Brace | 1 | 9.7 | 1.0 | 20.0 | 732 | 547 | 138 |
| P-value ‡ | | | | | 0.018 | 0.879 | 0.608 |

\* Plus-minus values are means ± standard deviations.
‡ Statistical analysis to compare patients with or without brace was done by bilateral unpaired Student's T-test with equal variance. A difference was considered statistically significant with a p-value < 0.05.

Figure 16A:
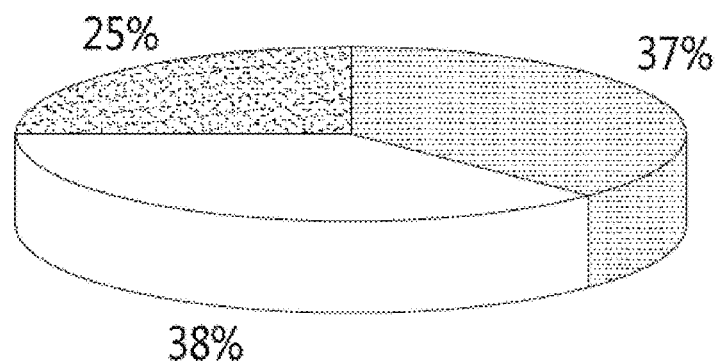
FIGS. 16A and 16B present charts distributing AIS patients across the predefined cut-off zones prior to being treated with bracing (FIG. 16A) and after bracing (FIG. 16B)
Figure 16B:
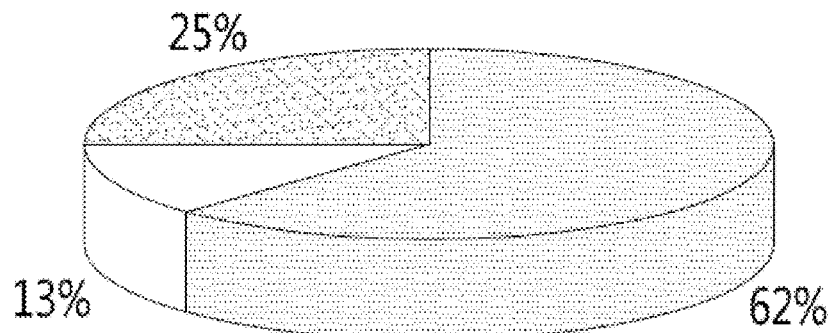

A distribution of AIS patients across the predefined cut-off zones was also performed prior to being treated with bracing and after bracing. Eight patients were tested a certain number of months after bracing, namely for each of patients #1 to 8: 7, 7, 8, 22, 22, 22 and 26 months after bracing, respectively. FIG. 16 shows that prior to being treated with bracing (Panel A), 63% of these patients were in the red and yellow zones. A significant shift towards the green zone (<700 ng/mL) was observed, which is consistent with the trend observed in surgically treated patients, as presented in FIGS. 13-15.

Example 14

Comparison of Selenium Levels in AIS Patients Vs. Healthy Subjects

Selenium concentration was reported to be significantly decreased in plasma of AIS patients (42). Selenium and more specifically Se-methylselenocystein, an organoselenium naturally occurring in diet, are used to prevent metastasis in breast cancer as chemopreventive therapy by targeting OPN transcription (43-45).

Figure 18:
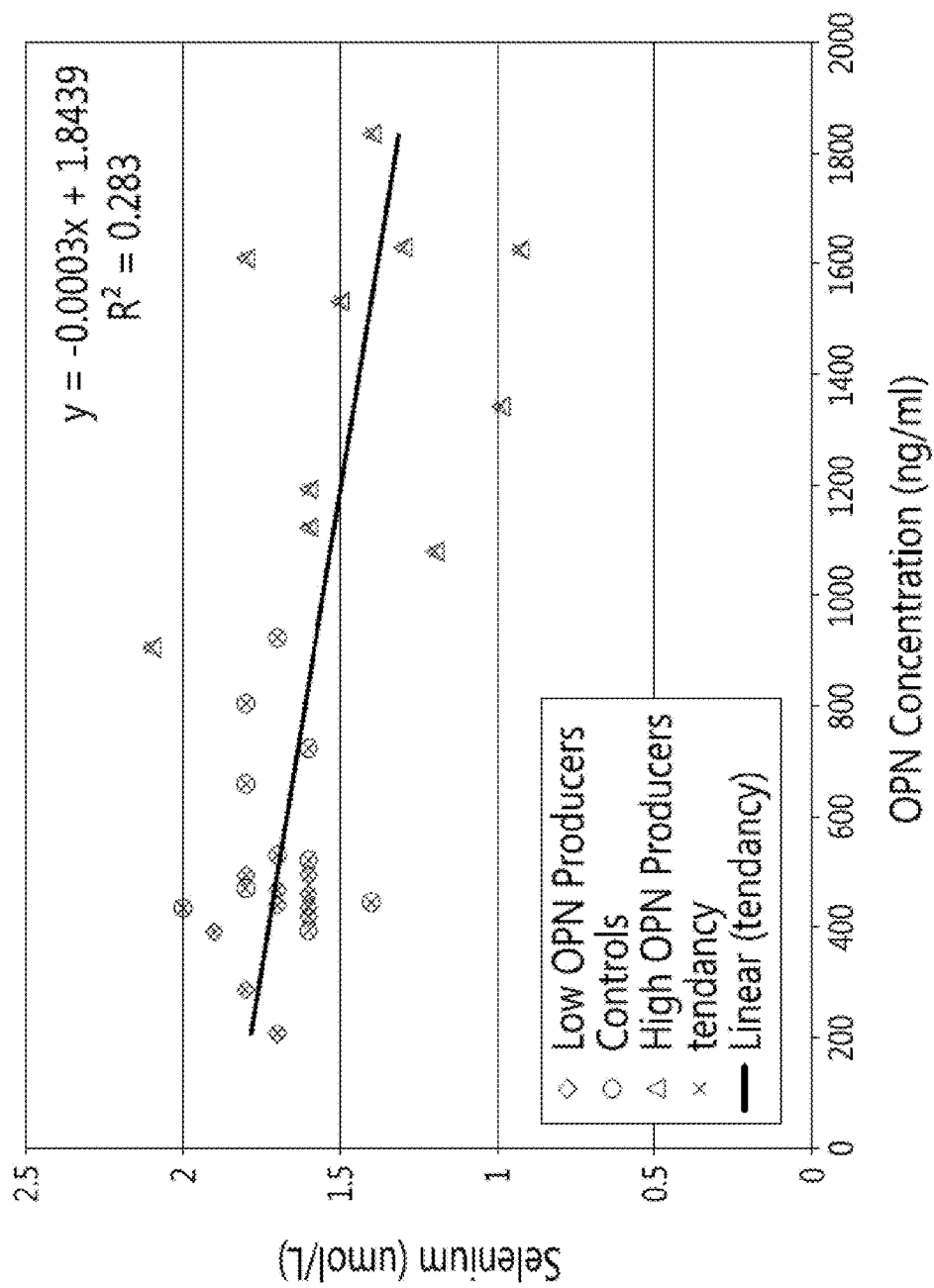
FIG. 18 presents a graph that correlates selenium levels in AIS patients with OPN levels.
Figure 19:
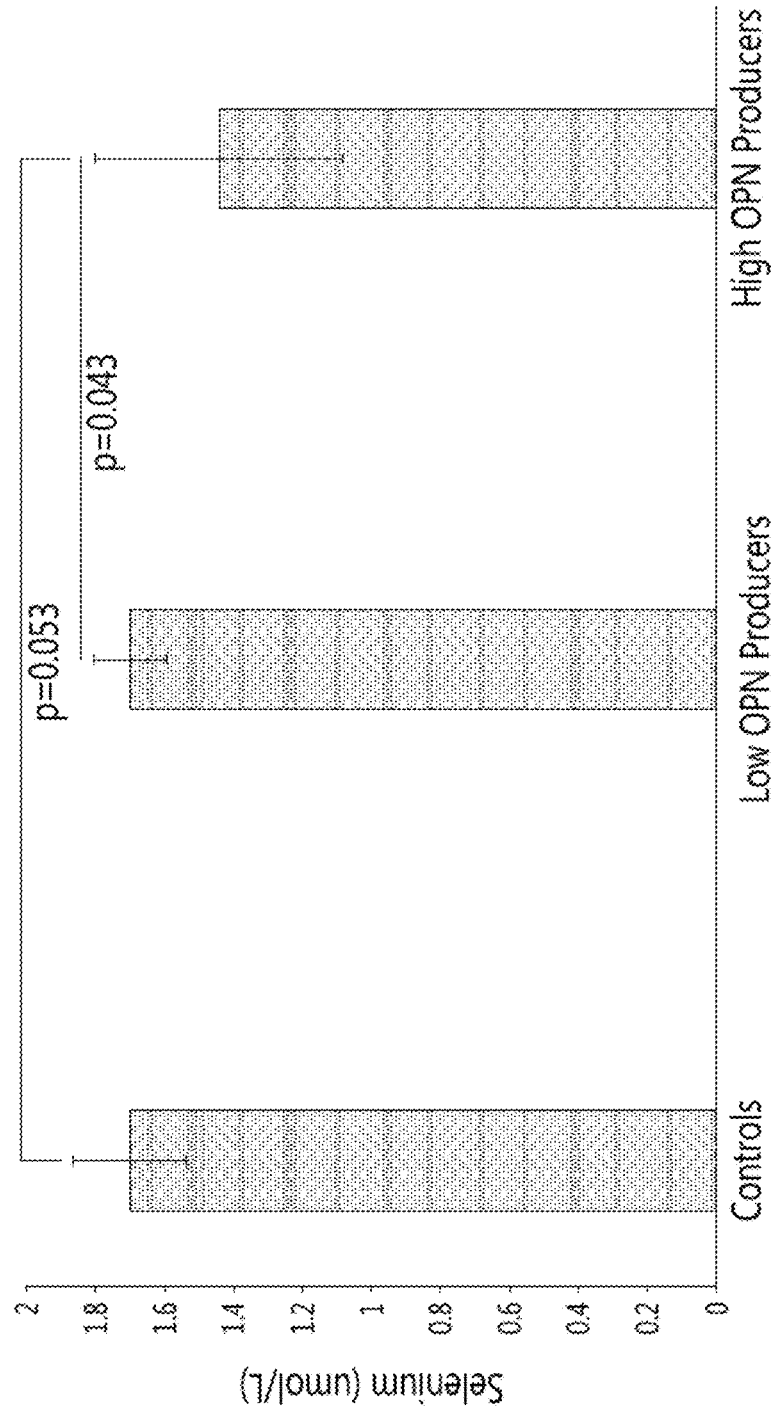
FIG. 19 presents a histogram comparing selenium levels in three categories of subjects: controls, low OPN producers and high OPN producers.

Plasma selenium concentration was thus measured in pediatric populations (AIS vs. healthy controls) to determine whether or not low selenium levels correlate with higher OPN concentrations in AIS. Plasma selenium concentrations were determined by a fluorometric method using 2,3-diaminonaphthalene (DAN) (46, 47). Results presented in FIGS. 18 and 19 show a correlation between high OPN levels and low selenium levels in scoliotic and asymptomatic at risk children.

Although the present invention has been described hereinabove by way of specific embodiments thereof, it can be modified, without departing from the spirit and nature of the subject invention as defined in the appended claims.

REFERENCES (1) Brodner W, Krepler P, Nicolakis M et al. Melatonin and adolescent idiopathic scoliosis. J Bone Joint Surg Br 2000; 82(3):399-403.
(2) Lowe T G, Edgar M, Margulies J Y et al. Etiology of idiopathic scoliosis: current trends in research. J Bone Joint Surg Am 2000; 82-A(8):1157-1168.
(3) Veldhuizen A G, Wever D J, Webb P J. The aetiology of idiopathic scoliosis: biomechanical and neuromuscular factors. Eur Spine J 2000; 9(3):178-184.
(4) Miller N H. Cause and natural history of adolescent idiopathic scoliosis. Orthop Clin North Am 1999; 30(3): 343-52, vii.
(5) Miller N H. Genetics of familial idiopathic scoliosis. Clin Orthop 2002; (401):60-64.
(6) Miller N H, Schwab D L, Sponseller P D, Manolio T A, Pugh E W, Wilson A P. Characterization of idiopathic scoliosis in a clinically well-defined population. Clin Orthop 2001; (392):349-357.
(7) Wise C A, Barnes R, Gillum J, Herring J A, Bowcock A M, Lovett M. Localization of susceptibility to familial idiopathic scoliosis. Spine 2000; 25(18):2372-2380.
(8) Moreau A, Wang D S, Forget S et al. Melatonin Signaling Dysfunction in Adolescent Idiopathic Scoliosis. Spine 2004.
(9) Denhardt D T, Noda M, O'Regan A W, Pavlin D, Berman J S. Osteopontin as a means to cope with environmental insults: regulation of inflammation, tissue remodeling, and cell survival. J Clin Invest 2001; 107(9):1055-1061.
(10) Mazzali M, Kipari T, Ophascharoensuk V, Wesson J A, Johnson R, Hughes J. Osteopontin—a molecule for all seasons. QJM 2002; 95(1):3-13.
(11) Lopez C A, Olson E S, Adams J C, Mou K, Denhardt D T, Davis R L. Osteopontin expression detected in adult cochleae and inner ear fluids. Hear Res 1995; 85(1-2): 210-222.
(12) Simoneau M, Richer N, Mercier P, Allard P, Teasdale N. Sensory deprivation and balance control in idiopathic scoliosis adolescent. Exp Brain Res 2006; 170(4):576-582.
(13) Guo X, Chau W W, Hui-Chan C W, Cheung C S, Tsang W W, Cheng J C. Balance control in adolescents with idiopathic scoliosis and disturbed somatosensory function. Spine 2006; 31(14):E437-E440.
(14) Weber B, Rosel M, Arch R, Moller P, Zoller M. Transient expression of CD44 variant isoforms in the ontogeny of the rat: ectoderm-, endoderm- and mesoderm-derived cells express different exon combinations. Differentiation 1996; 60(1):17-29.
(15) Panda D, Kundu G C, Lee B I et al. Potential roles of osteopontin and alphaVbeta3 integrin in the development of coronary artery restenosis after angioplasty. Proc Natl Acad Sci USA 1997; 94(17):9308-9313.
(16) Ruiz P, Schwarzler C, Gunthert U. CD44 isoforms during differentiation and development. Bioessays 1995; 17(1):17-24.
(17) Katagiri Y U, Sleeman J, Fujii H et al. CD44 variants but not CD44s cooperate with beta1-containing integrins to permit cells to bind to osteopontin independently of arginine-glycine-aspartic acid, thereby stimulating cell motility and chemotaxis. Cancer Res 1999; 59(1):219-226.
(18) Jalkanen S, Jalkanen M. Lymphocyte CD44 binds the COOH-terminal heparin-binding domain of fibronectin. J Cell Biol 1992; 116(3):817-825.
(19) Naujokas M F, Morin M, Anderson M S, Peterson M, Miller J. The chondroitin sulfate form of invariant chain can enhance stimulation of T cell responses through interaction with CD44. Cell 1993; 74(2):257-268.
(20) Weber G F, Ashkar S, Glimcher M J, Cantor H. Receptor-ligand interaction between CD44 and osteopontin (Eta-1). Science 1996; 271(5248):509-512.
(21) Bennett K L, Modrell B, Greenfield B et al. Regulation of CD44 binding to hyaluronan by glycosylation of variably spliced exons. J Cell Biol 1995; 131(6 Pt 1):1623-1633.
(22) Stamenkovic I, Aruffo A, Amiot M, Seed B. The hematopoietic and epithelial forms of CD44 are distinct polypeptides with different adhesion potentials for hyaluronate-bearing cells. EMBO J 1991; 10(2):343-348.
(23) Komura K, Sato S, Fujimoto M, Hasegawa M, Takehara K. Elevated levels of circulating CD44 in patients with systemic sclerosis: association with a milder subset. Rheumatology (Oxford) 2002; 41(10):1149-1154.
(24) Scott D A, Stapleton J A, Palmer R M et al. Plasma concentrations of reputed tumor-associated soluble CD44 isoforms (v5 and v6) in smokers are dose related and decline on smoking cessation. Cancer Epidemiol Biomarkers Prev 2000; 9(11):1211-1214.
(25) Wang X, Jiang H, Raso J et al. Characterization of the scoliosis that develops after pinealectomy in the chicken and comparison with adolescent idiopathic scoliosis in humans. Spine 1997; 22(22):2626-2635.
(26) von Gall C, Lewy A, Schomerus C et al. Transcription factor dynamics and neuroendocrine signalling in the mouse pineal gland: a comparative analysis of melatonin-deficient C57BL mice and melatonin-proficient C3H mice. Eur J Neurosci 2000; 12(3):964-972.
(27) Aherrahrou Z, Axtner S B, Kaczmarek P M et al. A locus on chromosome 7 determines dramatic up-regulation of osteopontin in dystrophic cardiac calcification in mice. Am J Pathol 2004; 164(4):1379-1387.
(28) Machida M, Dubousset J, Yamada T et al. Experimental scoliosis in melatonin-deficient C57BL/6J mice without pinealectomy. J Pineal Res 2006; 41(1):1-7.
(29) Scoliosis Research Society. Morbidity & Mortality Committee annual report 1997.
(30) Mishima R, Takeshima F, Sawai T et al. High plasma osteopontin levels in patients with inflammatory bowel disease. J Clin Gastroenterol 2007; 41(2):167-172.
(31) Ang C, Chambers A F, Tuck A B, Winquist E, Izawa J I. Plasma osteopontin levels are predictive of disease stage in patients with transitional cell carcinoma of the bladder. BJU Int 2005; 96(6):803-805.
(32) Wong C K, Lit L C, Tam L S, Li E K, Lam C W. Elevation of plasma osteopontin concentration is correlated with disease activity in patients with systemic lupus erythematosus. Rheumatology (Oxford) 2005; 44(5):602-606.
(33) Kim J, Ki S S, Lee S D et al. Elevated plasma osteopontin levels in patients with hepatocellular carcinoma. Am J Gastroenterol 2006; 101(9):2051-2059.
(34) Wynne-Davies R. Familial (idiopathic) scoliosis. A family survey. J Bone Joint Surg Br 1968; 50(1):24-30.
(35) De George F V, Fisher R L. Idiopathic scoliosis: genetic and environmental aspects. J Med Genet 1967; 4(4):251-257.
(36) Lein M, Jung K, Weiss S, Schnorr D, Loening S A. Soluble CD44 variants in the serum of patients with urological malignancies. Oncology 1997; 54(3):226-230.
(37) Karjalainen J M, Tammi R H, Tammi M I et al. Reduced level of CD44 and hyaluronan associated with unfavorable prognosis in clinical stage I cutaneous melanoma. Am J Pathol 2000; 157(3):957-965.
(38) Schlosser W, Gansauge F, Schlosser S, Gansauge S, Beger H G. Low serum levels of CD44, CD44v6, and neopterin indicate immune dysfunction in chronic pancreatitis. Pancreas 2001; 23(4):335-340.
(39) Sjoberg S, Fogelstrand L, Hulthe J, Fagerberg B, Krettek A. Circulating soluble CD44 is higher among women than men and is not associated with cardiovascular risk factors or subclinical atherosclerosis. Metabolism 2005; 54(2):139-141.
(40) Jenkins R H, Thomas G J, Williams J D, Steadman R. Myofibroblastic differentiation leads to hyaluronan accumulation through reduced hyaluronan turnover. J Biol Chem 2004; 279(40):41453-41460.
(41) Lien Y H, Fu J, Rucker R B, Scheck M, Abbott U, Stern R. Collagen, proteoglycan and hyaluronidase activity in cultures from normal and scoliotic chicken fibroblasts. Biochim Biophys Acta 1990; 1034(3):318-325.
(42) Dastych M, Cienciala J. Idiopathic scoliosis and concentrations of zinc, copper, and selenium in blood plasma. Biol Trace Elem Res 2002; 89(2):105-110.
(43) El-Bayoumy K, Sinha R. Molecular chemoprevention by selenium: a genomic approach. Mutat Res 2005; 591(1-2):224-236.
(44) Unni E, Kittrell F S, Singh U, Sinha R. Osteopontin is a potential target gene in mouse mammary cancer chemoprevention by Se-methylselenocysteine. Breast Cancer Res 2004; 6(5):R586-R592.
(45) He Y T, Liu D W, Ding L Y, Li Q, Xiao Y H. Therapeutic effects and molecular mechanisms of anti-fibrosis herbs and selenium on rats with hepatic fibrosis. World J Gastroenterol 2004; 10(5):703-706.
(46) Sheehan T M, Gao M. Simplified fluorometric assay of total selenium in plasma and urine. Clin Chem 1990; 36(12):2124-2126.
(47) Ando M, Takizawa M, Suwabe S, Yamato S, Shimada K. Determination of selenium in human serum by liquid chromatography/electron capture atmospheric pressure chemical ionization mass spectrometry after acid digestion and derivatization using 2,3-diaminonaphthalene. Eur J Mass Spectrom (Chichester, Eng) 2003; 9(6):619-622.
(48) Uchio E, Matsuura N, Kadonosono K, Ohno S, Uede T. Tear osteopontin levels in patients with allergic conjunctival diseases. Graefes Arch Clin Exp Ophthalmol, 2002; 240(11): 924-8.
(49) Buck et al. Design Strategies and Performance of Custom DNA Sequencing primers. Biotechniques 1999; 27:528-536.
(50) Ponta, H, Sherman L, Herrlich, P A. CD44: from Adhesion molecules to signalling regulators. Nature Reviews. 2004; 4:33-45.
(51) Garrett, K. A., P. D. Esker, and A. H. Sparks. 2007. Introduction to the R Programming Environment. The Plant Health Instructor. DOI:10.1094/PHI-A-2007-1226-02.
(52) Ihaka R, Gentleman R. A language for data analysis and graphics. Journal of Computational and Graphical Statistics 1996, 5(3):299-314.
(53) Goodison S, and Tarin D. Clinical Implications Of Anomalous Cd44 Gene Expression In Neoplasia. Frontiers in Bioscience 1998, 3, e89-109.
(54) Ito T, Hashimoto Y, Tanaka E, Kan T, Tsunoda S, Sato F, Higashiyama M, Okumura T, Shimada Y. An Inducible Short-Hairpin RNAVector against Osteopontin Reduces Metastatic Potential of Human Esophageal Squamous Cell Carcinoma In vitro and In vivo Clin Cancer Res 2006; 12(4) 1308-1316.

(55) Kadkol S S, Lin A Y, Barak V, Kalickman I, Leach L, Valyi-Nagy K, Majumdar D, Setty S, Maniotis A J, Folberg R, Pe'er J. Osteopontin Expression and Serum Levels in Metastatic Uveal Melanoma—A Pilot Study Invest Ophthalmol Vis Sci. 2006; 47(3): 802-806.
(56) Guarino V, Faviana P, Salvatore G, Castellone M D, Cirafici A, De Falco V, Celetti A, Giannini R, Basolo F, Melillo R M, Santoro M. Osteopontin Is Overexpressed in Human Papillary Thyroid Carcinomas and Enhances Thyroid Carcinoma Cell Invasiveness. The Journal of Clinical Endocrinology & Metabolism. 2005 90(9):5270-5278.
(57) Ponta et al, Nat Rev Mol Cell Biol. 2003 January; 4(1):33-45. Review.

The invention claimed is:

1. A composition for aiding in the treatment of scoliosis, comprising:
   (i) a biological fluid sample from a human subject, wherein said human subject is (a) a pediatric subject diagnosed with adolescent idiopathic scoliosis or (b) an asymptomatic subject having at least one family member diagnosed with adolescent idiopathic scoliosis, wherein said biological fluid sample is blood, plasma or serum; and
   (ii) a detectably-labeled antibody specific for the detection of osteopontin (OPN).

2. The composition of claim 1, further comprising at least one reagent for the detection of said detectably-labeled antibody.

3. The composition of claim 1, further comprising (iii) a detectably-labeled antibody specific for the detection of sCD44.

4. The composition of claim 3, further comprising at least one reagent for the detection of said detectably-labeled antibodies in (ii) and (iii).

5. The composition of claim 3, wherein the subject is a pediatric subject diagnosed with adolescent idiopathic scoliosis.

6. The composition of claim 5, wherein the sample is a plasma sample.

7. The composition of claim 3, wherein the subject is an asymptomatic subject having at least one family member diagnosed with adolescent idiopathic scoliosis.

8. The composition of claim 7, wherein the sample is a plasma sample.

9. The composition of claim 1, wherein the subject is a pediatric subject diagnosed with adolescent idiopathic scoliosis.

10. The composition of claim 9, wherein the sample is a plasma sample.

11. The composition of claim 1, wherein the subject is an asymptomatic subject having at least one family member diagnosed with adolescent idiopathic scoliosis.

12. The composition of claim 11, wherein the sample is a plasma sample.

13. The composition of claim 1, wherein the sample is a plasma sample.

* * * * *